(12) United States Patent
Famili et al.

(10) Patent No.: US 7,751,981 B2
(45) Date of Patent: Jul. 6, 2010

(54) **ARTICLES OF MANUFACTURE AND METHODS FOR MODELING *SACCHAROMYCES CEREVISIAE* METABOLISM**

(75) Inventors: Imandokht Famili, San Diego, CA (US); Jochen Förster, Copenhagen V (DK); Pengcheng Fu, Honolulu, HI (US); Jens B. Nielsen, Charlottenlund (DK); Bernhard O. Palsson, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 577 days.

(21) Appl. No.: 10/263,901

(22) Filed: Oct. 2, 2002

(65) Prior Publication Data
US 2003/0228567 A1 Dec. 11, 2003

Related U.S. Application Data

(60) Provisional application No. 60/344,447, filed on Oct. 26, 2001.

(51) Int. Cl.
*G01N 33/48* (2006.01)
*G06G 7/48* (2006.01)
(52) U.S. Cl. ............................. 702/19; 702/20; 703/11
(58) Field of Classification Search ..................... None
See application file for complete search history.

(56) References Cited

U.S. PATENT DOCUMENTS

| | | | |
|---|---|---|---|
| 5,273,038 A | 12/1993 | Beavin et al. | |
| 5,556,762 A | 9/1996 | Pinilla et al. | |
| 5,639,949 A | 6/1997 | Ligon et al. | |
| 5,689,633 A | 11/1997 | Cotner et al. | |
| 5,914,891 A | 6/1999 | Arkin et al. | |
| 5,930,154 A | 7/1999 | Thalhammer-Reyero | |
| 5,947,899 A | 9/1999 | Scollan et al. | |
| 6,132,969 A | 10/2000 | Stoughton et al. | |
| 6,165,709 A | 12/2000 | Friend et al. | |
| 6,200,803 B1 | 3/2001 | Roberts | |
| 6,221,597 B1 | 4/2001 | Roberts | |
| 6,303,302 B1 | 10/2001 | Rupp et al. | |
| 6,326,140 B1 | 12/2001 | Rine et al. | |
| 6,329,139 B1 | 12/2001 | Nova et al. | |
| 6,351,712 B1 | 2/2002 | Stoughton et al. | |
| 6,370,478 B1 | 4/2002 | Stoughton et al. | |
| 6,379,964 B1 | 4/2002 | del Cardayre et al. | |
| 6,500,710 B2 | 12/2002 | Nakagawa | |
| 6,902,692 B2 | 6/2005 | Carper | |
| 6,983,227 B1 | 1/2006 | Thalhammer-Reyero | |
| 7,127,379 B2 | 10/2006 | Palsson et al. | |
| 2002/0012939 A1 | 1/2002 | Palsson | |
| 2002/0051998 A1 | 5/2002 | Schmidt-Dannert et al. | |
| 2002/0168654 A1 | 11/2002 | Maranas et al. | |
| 2003/0059792 A1 | 3/2003 | Palsson et al. | |
| 2003/0113761 A1 | 6/2003 | Tan | |
| 2003/0224363 A1 | 12/2003 | Park et al. | |
| 2003/0233218 A1 | 12/2003 | Schilling | |
| 2004/0009466 A1 | 1/2004 | Maranas et al. | |
| 2004/0029149 A1 | 2/2004 | Palsson et al. | |
| 2004/0072723 A1 | 4/2004 | Palsson et al. | |
| 2006/0147899 A1 | 7/2006 | Famili et al. | |
| 2007/0111294 A1 | 5/2007 | Burgard et al. | |
| 2008/0176327 A1 | 7/2008 | Palsson et al. | |

FOREIGN PATENT DOCUMENTS

| | | |
|---|---|---|
| WO | WO 92/09300 | 6/1992 |
| WO | WO 00/46405 A2 | 8/2000 |
| WO | WO 01/57775 | 8/2001 |
| WO | WO 02/055995 | 7/2002 |
| WO | WO 02/061115 | 8/2002 |
| WO | WO 03/106998 | 12/2003 |

OTHER PUBLICATIONS

Covert et al., Trends in Biochemical Sciences, vol. 26, pp. 179-186, 2001.*
Ball et al., Nucleic Acids Research, vol. 28, No. 1, pp. 77-80, 2000.*
MIPS, website: Comprehensive Yeast Genome Database— Pathways, 1998, printed from http://mips.gsf.de/proj/yeast/pathways/, on Jun. 8, 2008.*
Michael Hoppert , 2004, printed from <www.isis.org.uk/WITBRL.php+michael+hoppert+compartment&hl=en&ct=clnk&cd=3 &gl=us> on Nov. 23, 2008.*
Edwards & Palsson, "The *Escherichia coli* MG1655 in silico metabolic genotype: Its definition, characteristics, and capabilities", *PNAS*, 97(10):5528-5533 (2000).
Pramanik & Keasling, "Stoichiometric Model of *Escherichia coli* Metabolism: Incorporation of Growth-Rate Dependent Biomass Composition and Mechanistic Energy Requirements", *Biotechnology & Bioengineering*, Wiley & Sons, Inc., Hoboken, NJ, US, 56(4):398-421 (1997).
Schilling et al., "Toward Metabolic Phenomics: Analysis of Genomic Data Using Flux Balances", *Biotechnology Progress*, 15(5):288-295 (1999).
Akutsu, "Genetic Network Interference Algorithm," Mathematical Science (Sur-Kagaku) Science 37(6):40-46 (1999). (Original and English translation submitted herewith).

(Continued)

*Primary Examiner*—Shubo (Joe) Zhou
(74) *Attorney, Agent, or Firm*—DLA Piper LLP (US)

(57) ABSTRACT

The invention provides an in silico model for determining a *S. cerevisiae* physiological function. The model includes a data structure relating a plurality of *S. cerevisiae* reactants to a plurality of *S. cerevisiae* reactions, a constraint set for the plurality of *S. cerevisiae* reactions, and commands for determining a distribution of flux through the reactions that is predictive of a *S. cerevisiae* physiological function. A model of the invention can further include a gene database containing information characterizing the associated gene or genes. The invention further provides methods for making an in silico *S. cerevisiae* model and methods for determining a *S. cerevisiae* physiological function using a model of the invention.

36 Claims, 10 Drawing Sheets

OTHER PUBLICATIONS

Adamowicz et al., "Nutritional complementation of oxidative glucose metabolism in *Escherichia coli* via pyrroloquinoline quinone-dependent glucose dehydrogenase and the Entner-Doudoroff pathway," *Appl. Environ. Microbiol.* 57(7):2012-2015 (1991).

Alberty, "Calculation of Biochemical Net Reactions and Pathways by Using Matrix Operations," *Biophys. J.* 71(1):507-515 (1996).

Alm "Genomic-sequence comparison of two unrelated isolates of the human gastric pathogen *Helicobacter pylori*," *Nature* 397(6715):176-80 (1999).

Alon et al., "Broad patterns of gene expression revealed by clustering analysis of tumor and normal colon tissues probed by oligonucleotide arrays," *Proc. Natl. Acad. Sci. U.S.A.*, 96(12):6745-6750 (1999).

Alter, et al., "Singular value decomposition for genome-wide expression data processing and modeling," *Proc Natl Acad Sci U.S.A.*, 97(18):10101-10106 (2000).

Altschul, et al., "Gapped BLAST and PSI-BLAST: A New Generation of Protein Database Search Programs," *Nucleic Acids Res.* 25(17):3389-3402 (1997).

Alves, et al., "Systemic properties of ensembles of metabolic networks: application of graphical and statistical methods to simple unbranched pathways," *Bioinformatics*, 16(6):534-547 (2000).

Andre, "An overview of membrane transport proteins in *Saccharomyces cerevisiae*," *Yeast*, 11(16):1575-1611 (1995).

Anonymous, "The yeast genome directory" *Nature*, 387(6632 Suppl):5 (1997).

Appel, et al., "A new generation of information retrieval tools for biologists: the example of the ExPASy WWW server," *Trends Biochem. Sci.* 19(6):258-260 (1994).

Arigoni, et al., "A Genome-Based Approach for the Identification of Essential Bacterial Genes," *Nature Biotechnology*, 16(9):851-856 (1998).

Aristidou and Penttila, "Metabolic engineering applications to renewable resource utilization," *Curr. Opin. in Biotech.* 11(2)187-198 (2000).

Attanoos, et al., "Ileostomy polyps, adenomas, and adenocarcinomas," *Gut*, 37(6):840-844 (1995).

Baba, et al., "Construction of *Escherichia coli* K-12 in-frame, single-gene knockout mutants: the Keio collection," *Mol. Syst. Biol*, 2:2006-2008 (2006).

Bailey, "Complex Biology With No Parameters," *Nat Biotechnol*, 19(6):503-504 (2001).

Bailey, and Elkan "Fitting a mixture model by expectation maximization to discover motifs in biopolymers," *Proc. Intl. Conf. Intell. Syst. Mol. Biol.* 2:28-36 (1994).

Bailey and Gribskov, "Combining evidence using p-values: application to sequence homology searches," *Bioinformatics*, 14(1):48-54 (1998).

Bairoch and Apweiler, "The SWISS-PROT Protein Sequence database and its supplement TrEMBL in 2000," *Nucleic Acids Res.* 28(1):45-48 (2000).

Baltz, et al., "DNA Sequence Sampling of the *Streptococcus pneumonia* Genome to Identify Novel Targets for Antibiotic Development," *Microb. Drug Resist.*, 4(1):1-9 (1998).

Ban, et al., "Thymine and uracil catabolism in *Escherichia coli*," *J Gen Microbiol*, 73(2):267-272 (1972).

Bansal, "Integrating co-regulated gene-groups and pair-wise genome comparisons to automate reconstruction of microbial pathways," *Bioinformatics and Bioengineering Conference*, 209-216 (2001).

Bard, et al., "Sterol mutants of *Saccharomyces cerevisiae*: chromatographic analyses," *Lipids*, 12(8):645-654 (1977).

Baxevanis, "The Molecular Biology Database Collection: 2002 update," *Nucleic Acids Res.* 30:1-12 (2002).

Beard, et al., "Energy Balance for Analysis of Complex Metabolic Networks," *Biophys. J.* 83(1):79-86 (2002).

Beckers, et al., "Large-Scale Mutational Analysis for the Annotation of the Mouse Genome," *Curr. Opin. Chem. Biol.* 6(1)17-23 (2002).

Benjamini and Hochberg, "Controlling the false discovery rate: a practical and powerful approach to multiple testing," *Journal of the Royal Statistical Society, Series B (Methodological)*, 57:289-300 (1995).

Benson, et al., "GenBank," *Nucleic Acids Res.* 28(1):15-18 (2000).

Berry, "Improving production of aromatic compounds in *Escherichia coli* by metabolic engineering," *Trends Biotechnol.* 14(7):250-256 (1996).

Bialy, "Living on the Edges," Nat Biotechnol, 19(2):111-112 (2001).

Bianchi and Zanella, *Blood Cells, Mol. Dis.* 15:47-53 (2000).

Biaudet et al., "Micado—A network-oriented database for microbial genomes," *Comput. Appl. Biosci.* 13(4):431-438 (1997).

Birkholz, "Fumarate reductase of *Helicobacter pylori*—an immunogenic protein," *J Med Microbiol*, 41(1):56-62 (1994).

Birner, et al., "Roles of phosphatidylethanolamine and of its several biosynthetic pathways in *Saccharomyces cerevisiae*," *Mol.Biol. Cell.* 12(4):997-1007 (2001).

Blackstock and Weir, "Proteomics: quantitative and physical mapping of cellular proteins," *Trends Biotechnol.* 17(3):121-127 (1999).

Blattner et al., "The Complete Genome Sequence of *Escherichia coli* K-12," *Science*, 277(5331):1453-1474 (1997).

Bochner, "New technologies to assess genotype-phenotype relationships," *Nat. Rev. Genet.* 4(4):309-314 (2003).

Boles, et al., "Identification and characterization of MAE 1, the *Saccharomyces cerevisiae* structural gene encoding mitochondrial malic enzyme," *J. Bacteriol.* 180(11):2875-2882 (1998).

Boles, et al., "A family of hexosephosphate mutases in *Saccharomyces cerevisia*," *Eur J Biochem*, 220(1):83-96 (1994).

Boles, et al., "Characterization of a glucose-repressed pyruvate kinase (Pyk2p) in *Saccharomyces cerevisiae* that is catalytically insensitive to fructose-1,6-bisphosphate," *J. Bacteriol.* 179(9):2987-2993 (1997).

Bonarius, et al., "Flux Analysis of Underdetermined Metabolic Networks: The Quest for the Missing Constraints," *Trends Biotechnol*, 15(8):308-314 (1997).

Bonarius, et al., "Metabolic flux analysis of hybridoma cells in different culture media using mass balances," *Biotechnol Bioeng*, 50(3):299-318 (1996).

Bono, et al., "Reconstruction of amino acid biosynthesis pathways from the complete genome sequence," *Genome Research*, 8(3):203-210 (1998).

Bottomley, et al., "Cloning, sequencing, expression, purification and preliminary characterization of a type II dehydroquinase from *Helicobacter pylori*," *Biochem. J.* 319(Pt 2):559-565 (1996).

Bourot and Karst, "Isolation and characterization of the *Saccharomyces cerevisiae* SUT1 gene involved in sterol uptake," *Gene*, 165(1):97-102 (1995).

Burgard, and Maranas, "Probing the Performance Limits of the *Escherichia coli* Metabolic Network Subject to Gene Additions or Deletions," *Biotechnol. Bioeng.* 74(5):364-375 (2001).

Burgard and Maranas, "Review of the Enzymes and Metabolic Pathways (EMP) Database," *Metab. Eng.* 3(3):193-194(2) (2001).

Burgard, et al., "Minimal reaction sets for *Escherichia coli* metabolism under different growth requirements and uptake environments," *Biotechnol. Prog.* 17(5):791-797 (2001).

Burgard, et al., "Optknock: a bilevel programming framework for identifying gene knockout strategies for microbial strain optimization," *Biotechnol. Bioeng.* 84(6):647-657 (2003).

Burns, "Acetyl-CoA carboxylase activity in *Helicobacter pylori* and the requirement of increased $CO_2$ for growth," *Microbiology*, 141(Pt 12):3113-3118 (1995).

Callis, "Regulation of Protein Degradation," *Plant Cell* 7:845-857 (1995).

Carrier and Keasling, "Investigating Autocatalytic Gene Expression Systems through Mechanistic Modeling," *J. Theor. Biol.* 201(1):25-36 (1999).

Chadha et al., "Hybrid process for ethanol production from rice straw," *Acta. Microbiol. Immunol. Hung.* 42(1):53-59 (1995).

Chadha, et al., "Simultaneous saccharification and fermentation of rice straw into ethanol," *Acta. Microbiol. Immunol. Hung.* 42(1):71-75 (1995).

Chalker, et al., "Systematic identification of selective essential genes in *Helicobacter pylori* by genome prioritization and allelic replacement mutagenesis," *J. Bacteriol.* 183(4):1259-1268 (2001).

Chartrain, et al., "Metabolic engineering and directed evotion for the production of pharmaceuticals," *Curr. Opin. Biotech.* 11(2):209-214 (2000).

Chen, et al., "Characterization of the respiratory chain of *Helicobacter pylori*," *FEMS Immunol. Med. Microbiol.* 24(2):169-174 (1999).
Cherry, et al., "SGD: *Saccharomyces* Genome Database," *Nucleic Acids Res.* 26(1):73-79 (1998).
Christensen and Nielsen, "Metabolic network analysis. A powerful tool in metabolic engineering," *Adv. Biochem. Eng. Biotechnol.* 66:209-231 (2000).
Ciriacy and Breitenbach, "Physiological effects of seven different blocks in glycolysis in *Saccharomyces cerevisiae*," *J. Bacteriol.* 139(1):152-160 (1979).
Clarke, "Complete set of steady states for the general stoichiometric dynamical system," *J. Chem. Phys.* 75(10):4970-4979 (1981).
Clarke, "Stoichiometric network analysis," *Cell Biophys,* 12:237-253 (1988).
Clarke, "Stability of Complex Reaction Networks," *Adv. Chem. Physics* 43:1-125 (1980).
Clifton and Fraenkel, "Mutant studies of yeast phosphofructokinase," *Biochemistry,* 21(8):1935-1942 (1982).
Clifton, et al., "Glycolysis mutants in *Saccharomyces cerevisiae,*" *Genetics*, 88(1):1-11 (1978).
Compan and Touati, "Anaerobic activation of arcA transcription in *Escherichia coli*: roles of Fnr and ArcA," *Mol. Microbiol.* 11(5):955-964 (1994).
Costanzo et al., "YPD, PombePD and WormPD: model organism vols. of the BioKnowledge library, an integrated resource for protein information," *Nucleic Acids Res.* 29(1):75-9 (2001).
Cotter et al., "Aerobic regulation of cytochrome d oxidase (cydAB) operon expression in *Escherichia coli*: roles of Fnr and ArcA in repression and activation," *Mol. Microbiol.* 25(3):605-615 (1997).
Cover and Blaser, "*Helicobacter pylori* infection, a paradigm for chronic mucosal inflammation: pathogenesis and implications for eradication and prevention," *Adv. Intern. Med.* 41:85-117 (1996).
Covert and Palsson, "Constraints-based models: regulation of gene expression reduces the steady-state solution space" *J. Theor. Biol.* 216 (2003).
Covert and Palsson, "Transcriptional regulation in constraints-based metabolic models of *Escherichia coli*," *J. Biol. Chem.* 277(31):28058-28064 (2002).
Covert, et al., "Regulation of Gene Expression in Flux Balance Models of Metabolism," *J. Theor. Biol.* 213(1):73-88 (2001).
Covert and Palsson, "Aerobic regulation of cytochrome d oxidase (cydAB) operon expression in *Escherichia coli*: roles of Fnr and ArcA in repression and activation," *J. Theor. Biol.* 216 (2003).
Cupp and McAlister-Henn, "Cloning and Characterization of the gene encoding the IDH1 subunit of NAD(+)-dependent isocitrate dehydrogenase from *Saccharomyces cerevisiae*," *J. Biol. Chem.* 267(23):16417-16423 (1992).
Dafoe, et al., "In Silico Knowledge Discovery Biomedical databases," Proceedings of the SPIE Fifth Workshop on Neutral Networks, San Francisco, Nov. 7-10, 1993.
D'Haeseleer, et al., "Genetic network inference: from co-expression clustering to reverse engineering," *Bioinformatics* 16(8):707-726 (2000).
Danchin, "Comparison Between the *Escherichia coli* and *Bacillus subtilis* Genomes Suggests That a Major Function of Polynucleotide Phosphorylase is to Synthesize CDP," *DNA Res.,* 4(1):9-18 (1997).
Dandekar, et al., "Pathway Alignment: Application to the Comparative Analysis of Glycolytic Enzymes," *Biochem J,* 343(Pt 1):115-124 (1999).
Dantigny, et al., "Transition rate kinetics from ethanol oxidation to glucose utilisation within a structured model of baker's yeast," *Appl. Microbiol. Biotechnol.* 36:352-357 (1991).
Datsenko and Wanner, "One-step inactivation of chromosomal genes in *Escherichia coli* K-12 using PCR products," *Proc. Natl. Acad. Sci. U.S.A.,* 97(12):6640-6645 (2000).
Daum, et al., "Biochemistry, cell biology and molecular biology of lipids of *Saccharomyces cerevisiae,*" *Yeast* 14(16):1471-1510 (1998).
Daum, et al., "Systematic analysis of yeast strains with possible defects in lipid metabolism," *Yeast,* 15(7):601-614 (1999).
Dauner, et al., "*Bacillus subtilis* Metabolism and Energetics in Carbon-Limited and Excess-Carbon Chemostat Culture," *J Bacteriol,* 183(24):7308-7317 (2001).

Dauner, et al., "Metabolic Flux Analysis with a Comprehensive Isotopomer Model in *Bacillus subtilis,*" *Biotechnol Bioeng,* 76(2):144-156 (2001).
Dauner and Sauer, "Stoichiometric Growth Model for Riboflavin-Producing *Bacillus subtilis,*" *Biotechnol. Bioeng.* 76(1):132-143 (2001).
de Jong, "Modeling and simulation of genetic regulatory systems: a literature review," *J. Comput. Biol.* 9(1):67-103 (2002).
De Reuse, et al., "The *Helicobacter pylori* ureC gene codes for a phosphoglucosamine mutase," *J. Bacteriol.* 179(11):3488-3493 (1997).
Delgado and Liao, "Identifying Rate-Controlling Enzymes in Metabolic Pathways without Kinetic Parameters," *Biotechnol. Prog.* 7:15-20 (1991).
Demain et al., "Cellulase, clostridia, and ethanol," *Microbiol. Mol. Biol.* 69(1):124-154 (2005).
Department of Energy, *Breaking the Biological Barriers to Cellulosic Ethanol* (2006).
DeRisi, et al., "Use of cDNA microarray to analyse gene expression patters in human cancer," *Nat. Gene.* 14:457-460 (1996).
DeRisi, et al., "Exploring the Metabolic and Genetic Control of Gene Expression on a Genomic Scale," *Science* 278(5338):680-686 (1997).
Devine, "The *Bacillus subtilis* Genome Project: Aims and Progress," *Trends Biotechnol.* 13(6):210-216 (1995).
Dickson, "Sphingolipid functions in *Saccharomyces cerevisiae*: comparison to mammals," *Ann. Rev. Biochem.* 67:27-48 (1998).
Dickson, et al., "Serine palmitoyltransferase," *Methods Enzymol.* 311:3-9 (2000).
DiRusso and Black, "Long-chain fatty acid transport in bacteria and yeast. Paradigms for defining the mechanism underlying this protein-mediated process," *Mol. Cell. Biochem.* 192(1-2):41-52 (1999).
Dooley, et al., "An all D-amino acid opiod peptide with central analgesic activity from a combinatorial library," *Science* 266(5193):2019-2022 (1994).
Duarte, et al., "Reconstruction and validation of *Saccharomyces cerevisiae* iND750, a fully compartmentalized genome-scale metabolic model," *Genome. Res.* 14(7):1298-1309 (2004).
Edwards, et al., "Characterizing the Metabolic Phenotype: A Phenotype Phase Plane Analysis," *Biotech. Bioeng.* 77(1):27-36 (2002).
Edwards and Palsson, "How Will Bioinformatics Influence Metabolic Engineering," *Biotechnol Bioeng*, 58(2-3):162-169 (1998).
Edwards and Palsson, "Systems properties of the Haemophilus influenzae Rd metabolic genotype," *J. Biol. Chem.* 274(25):17410-17416 (1999).
Edwards and Palsson, "Metabolic flux balance analysis and the in silico analysis of *Escherichia colia* K-12 gene deletions," *BMC Bioinformatics* 1:1-10 (2000).
Edwards, et al., "In Silico Predictions of *Escherichia coli* metabolic capabilities are Consistent with Experimental Data," *Nat. Biotechnol.* 19(2):125-130 (2001).
Edwards, et al., "Genomically Based Comparative Flux Balance Analysis of *Escherichia coli* and Haemophilus Influenza," Abstract of Papers, *Am. Chem. Soc.* 213(1-3):BIOT 50:13-17 (1997).
Edwards et al., BMES/EMBS Conference, Proceedings of the First Joint, vol. 2, p. 1217 (1999).
Eisen, et al., "Cluster analysis and display of genome-wide expression patterns," *Proc. Natl. Acad. Sci. U.S.A.,* 95:14863-14868 (1998).
Eisenberg, et al., "Protein Function in the Post-Genomic Era," *Nature* 405(6788):823-826 (2000).
Ermolaeva, et al., "Prediction of Operons in Microbial Genomes," *Nucl Acids Res.* 29(5):1216-1221 (2001).
Everett, et al., "Pendred Syndrome is Caused by Mutations in a Putative Sulphate Transporter Gene (PDS)," *Nat Genet,* 17:411-422 (1997).
Feist and Palsson, "The growing scope of applications of genome-scale metabolic reconstructions using *Escherichia coli,*" *Nat. Biotech.* 26(6):659-667 (2008).
Fell and Small, "Fat Synthesis in Adipose Tissue. An Examination of Stoichiometric Constraints," *Biochem. J.* 238(3):781-786 (1986).
Fiehn, "Metabolomics—the link between genotypes and phenotypes," *Plant Mol. Biol.* 48(1-2):155-171 (2002).

Finel, "Does NADH play a central role in energy metabolism in *Helicobacter pylori?*," *Trends Biochem. Sci.* 23(11):412-413 (1998).
Fiorelli, et al., "Chronic non-spherocytic haemolytic disorders associated with glucose-6-phosphate dehydrogenase variants," *Bailliere's Clinical Haematology*, 13:39-55 (2000).
Fleischmann, "Whole-genome random sequencing and assembly of *Haemophilus influenzae* Rd," *Science*, 269(5223):496-512 (1995).
Flikweert, et al., "Pyruvate decarboxylase: an indispensable enzyme for growth of *Saccharomyces cerevisiae* on glucose," *Yeast* 12(3):247-257 (1996).
Forst, "Network genomics—A Novel approach for the analysis of biological systems in the post-genomic era," *Mol. Biol. Rpts.* 29(3):265-280 (2002).
Forster, et al., "Large-scale evaluation of in silico gene deletions in *Saccharomyces cerevisiae*," *Omics*, 7(2)193-202 (2003).
Fotheringham, "Engineering biosynthetic pathways: new routes to chiral amino acids," *Curr. Opin. Chem. Biology* 4(1):120-124 (2000).
Fraenkel,"The accumulation of glucose 6-phosphate from glucose and its effect in an *Escherichia coli* mutant lacking phosphoglucose isomerase and glucose 6-phosphate dehydrogenase," *J. Biol. Chem.* 243(24):6451-6457 (1968).
Fraser, et al., "Microbial genome sequencing," *Nature*, 406:799-803 (2000).
Fromont-Racine, et al., "Toward a functional analysis of the yeast genome through exhaustive two-hybrid screens," *Nat Genet*, 16(3):277-282 (1997).
Fukuachi,et al., "Isolation, overexpression and disruption of a *Saccharomyces cerevisiae* YNK gene encoding nucleoside diphosphate kinase," *Genes*, 129(1):141-146 (1993).
Gaasterland and Selkov, "Reconstruction of Metabolic Networks Using Incomplete Information," *Proc. Int. Conf. Intell. Syst. Mol. Biol.* 3:127-135 (1995).
Galperin and Brenner, "Using Metabolic Pathway Databases for Functional Annotation," *Trends Genet.* 14(8):332-333 (1998).
Gancedo and Delgado, "Isolation and characterization of a mutant from *Saccharomyces cerevisiae* lacking fructose 1,6-bisphosphatase," *Eur. J. Biochem.* 139:651-655 (1984).
Gangloff, et al., "Molecular cloning of the yeast mitochondrial aconitase gene (ACO1) and evidence of a synergistic regulation of expression by glucose plus glutamate," *Mol. Cell. Biol.* 10(7):3551-3561 (1990).
Ge, et al., "Cloning and functional characterization of *Helicobacter pylori* fumarate reductase operon comprising three structural genes coding for subunits C, A and B," *Gene*, 204(1-2):227-234 (1997).
Glasner, et al., "ASAP, a systematic annotation package for community analysis of genomes," *Nucleic Acids Res.* 31(1):147-151 (2003).
Goffeau, "Four years of post-genomic life with 6000 yeast genes," *FEBS Lett*, 480(1):37-41 (2000).
Gombert and Nielsen, "Mathematical modeling of metabolism," *Curr. Opin. Biotech.* 11(2):180-186 (2000).
Goryanin, et al., "Mathematical simulation and analysis of cellular metabolism and regulation," *Bioinformatics*, 15(9):749-758 (1999).
Goto, et al., "LIGAND database for enzymes, compounds and reactions," *Nucleic Acids Res.* 27(1):377-379 (1999).
Goto, et al., "LIGAND: chemical database for enzyme reactions," *Bioinformatics*, 14(7):591-599 (1998).
Grewal, et al., "Computer Modelling of the Interaction Between Human Choriogonadotropin and Its Receptor," *Protein Engineering*, 7(2):205-211 (1994).
Griffin, et al., "Complementary profiling of gene expression at the transcriptome and proteome levels in *Saccharomyces cerevisiae*," *Mol Cell Proteomics*, 1:323-333 (2002).
Grundy, et al., "Regulation of the *Bacillus subtilis* acetate kinase gene by CcpA." *J. Bacteriol.* 175(22):7348-7355 (1993).
Guardia, et al., "Cybernetic modeling and regulation of metabolic pathways in multiple steady states of hybridoma cells," *Biotech. Progress* 16(5):847-853 (2000).
Guelzim et al., "Topological and causal structure of the yeast transcriptional regulatory network," *Nat Genet* 31(1):60-63 (2002).
Guetsova et al., "The isolation and characterization of *Saccharomyces cerevisiae* mutants that constitutively express purine biosynthetic genes," *Genetics* 147(2):383-397 (1997).

Hardison, et al., "Globin Gene Server: A Prototype E-Mail Database Server Featuring Extensive Multiple Alignments and Data Compilation for Electronic Genetic Analysis," *Genomics* 21(2):344-353 (1994).
Hartig, et al., "Differentially regulated malate synthase genes participate in carbon and nitrogen metabolism of *S. cerevisiae*," *Nucleic Acids Res.* 20(21):5677-5686 (1992).
Hasty, et al., "Computational Studies of Gene Regulatory Networks: In Numero Molecular Biology," *Nat. Rev. Genet.* 2(4):268-279 (2001).
Hata, et al., "Characterization of a *Saccharomyces cerevisiae* mutant, N22, defective in ergosterol synthesis and preparation of [28-14C]ergosta-5,7-dien-3 beta-ol with the mutant," *J. Biochem.*, 94(2):501-510 (1983).
Hatzimanikatis, et al., "Analysis and Design of Metabolic Reaction Networks Via Mixed-Interger linear Optimization," *AIChE Journal*, 42(5):1277-1292 (1996).
Hazell, et al., "How *Helicobacter pylori* works: an overview of the metabolism of *Helicobacter pylori*," *Helicobacter*. 2(1):1-12 (1997).
Heijnen, et al., "Application of balancing methods in modeling the penicillin fermentation," *Microbiol. Biochem.* 21:1-48 (1979).
Heinisch, et al., "Investigation of two yeast genes encoding putative isoenzymes of phosphoglycerate mutase," *Yeast* 14(3):203-213 (1998).
Heinrich, et al., "Metabolic regulation and mathematical models," *Prog. Biophys. Mol. Biol.* 32(1):1-82 (1997).
Henriksen, et al., "Growth energetics and metabolism fluxes in continuous cultures of *Penicillium chrysogenum*," *J. of Biotechnol.* 45(2):149-164 (1996).
Heyer, et al., "Exploring expression data: identification and analysis of coexpressed genes," *Genome Res.* 9(11):1106-1115 (1999).
Holter, et al., "Dynamic modeling of gene expression data," *Proc. Natl. Acad. Sci. U.S.A.*, 98(4):1693-1698 (2001).
Holter, et al., "Fundamental patterns underlying gene expression profiles: simplicity from complexity," *Proc Natl Acad Sci U.S.A.*, 97:8409-9414 (2000).
Houghten, R, "Generation and use of synthetic peptide combinatorial libraries for basic research and drug discovery," *Nature*, 354(6348):84-86 (1991).
Hughes, et al., "Functional discovery via a compendium of expression profiles," *Cell*, 102(1):109-126 (2000).
Hughes, et al., "*Helicobacter pylori* porCDAB and oorDABC genes encode distinct pyruvate: flavodoxin and 2-oxoglutarate:acceptor oxidoreductases which mediate electron transport to NADP," *J. Bacterio.l*, 180(5):1119-1128 (1998).
Ideker, et al., "Integrated Genomic and Proteomic Analyses of a Systematically Perturbed Metabolic Network," *Science*, 292(5518):929-934 (2001).
Ince and Knowles, "Ethylene formation by cell-free extracts of *Escherichia coli*," *Arch. Microbiol.* 146(2):151-158 (1986).
Ishii, et al., "DBTBS: a database of *Bacillus subtilis* promoters and transcription factors," *Nucleic Acids Res*, 29(1):278-280 (2001).
Iyer, et al., "Genomic binding sites of the yeast cell-cycle transcription factors SBF and MBF," *Nature* 409(6819):533-538 (2001).
Jamshidi, et al., "Dynamic simulation of the human red blood cell metabolic network," *Bioinformatics*, 17(3):286-287 (2001).
Jamshidi, et al., "In silico model-driven assessment of the effects of single nucleotide polymorphins (SNPs) on human red blood cell-metabolism," *Gen. Res.* 12(11):1687-1692 (2002).
Jenkins and Nunn, "Genetic and molecular characterization of the genes involved in short-chain fatty acid degradation in *Escherichia coli*: the ato system," *J. Bacteriol.* 169(1):42-52 (1987).
Jenssen, et al., "A Literature Network of Human Genes for High-Throughput Analysis of Gene Expression," *Nat. Genet.*, 28(1):21-28 (2001).
Jorgensen, et al., "Metabolic flux distributions in *Penicillium chrysogenum* during fed-batch cultivations." *Biotechnol. Bioeng.* 46(2):117-131 (1995).
Joshi and Palsson, "Metabolic dynamics in the human red cell. Part I—A comprehensive kinetic model," *J. Theor. Biol.* 141(4):515-528 (1989).

Juty, et al., "Simultaneous Modeling of Metabolic, Genetic, and Product-Interaction Networks," *Brief. Bioinform.* 2(3):223-232 (2001).

Kanehisa, M and Goto, S, "Kyoto Encyclopedia of Genes and Genomes database (KEGG)," *Nucleic Acids Res*, 28(1):27-30 (2000).

Karp, "An ontology for biological function based on molecular interactions," . *Bioinformatics*, 16(3):269-285 (2000).

Karp, "Metabolic Databases," *Trends Biochem. Sci.* Elsevier Publication, Cambridge, 23(3):114-116 (1998).

Karp, et al., "Eco Cyc: encyclopedia of *Escherichia coli* genes and metabolism," *Nucleic Acids Res.* 27(1):55-58 (1999).

Karp, et al., "EcoCyc: Encyclopedia of *Escherichia coli* genes and metabolism," *Nucleic Acids Res.* 27(1):43-50 (1997).

Karp, et al., "HinCyc: A knowledge base of the complete genome and metabolic pathways of H. influenzae," *Proc Int Conf Intell Syst Mol Biol*, 4:116-124 (1996).

Karp, et al., "Integrated pathway-genome databases and their role in drug discovery," *Trends Biotechnol.* 17(7):275-281 (1999).

Karp, et al., "The EcoCyc and MetaCyc databases," *Nucleic Acids Res.* 28(1):56-59 (2000).

Kather, et al., "Another unusual type of citric acid cycle enzyme in *Helicobacter pylori*: the malate:quinone oxidoreductase," *J. Bacteriol.* 182(11):3204-3209 (2000).

Kaufman, et al., "Towards a logical analysis of the immune response," *J. Theor. Biology* 114(4):527-561 (1985).

Keating, et al., "An ethanologenic yeast exhibiting unusual metabolism in the fermentation of lignocellulosic hexose sugars," *J. Ind. Microbiol. Biotechnol.* 31(5):235-244 (2004).

Kelly, "The physiology and metabolism of the human gastric pathogen *Helicobacter pylori*," *Adv. Microb. Physiol.* 40:137-189 (1998).

Kim et al., "*Saccharomyces cerevisiae* contains two functional citrate synthase genes," *Mol. Cell. Biol.* 6(6):1936-1942 (1986).

Kirkman, et al., "Red cell NADP+ and NADPH in glucose-6-phosphate dehydrogenase deficiency," *Journal of Clinical Investigation*, 55(4):875-878 (1975).

Kremling, et al., "The organization of metabolic reaction networks. III. Application for diauxic growth on glucose and lactose," *Metab. Eng.* 3(4):362-379 (2001).

Kunst, et al., "The Complete Genome Sequence of the Gram-positive Bacterium *Bacillus subtilus*," *Nature*, 390(6557):249-256 (1997).

Kunst and Devine, "The project of sequencing the entire *Bacillus substilis* genome," *Res. Microb.* 142:905-912 (1991).

Lacroute, "Regulation of pyrimidine biosynthesis in *Saccharomyces cerevisiae*" *J. Bacteriol.* 95(3):824-832 (1968).

Latif and Rajoka, "Production of ethanol and xylitol from corn cobs by yeasts," *Bioresour. Technol.* 77(1):57-63 (2001).

Lee, et al., "Incorporating qualitative knowledge in enzyme kinetic models using fuzzy logic," *Biotech. Bioeng.* 62(6):722-729 (1999).

Lendenmann and Egli, "Is *Escherichia coli* growing in glucose-limited chemostat culture able to utilize other sugars without lag?," *Microbiology* 141(Pt 1):71-78 (1995).

Leyva-Vasquez and Setlow, "Cloning and nucleotide sequences of the genes encoding triose phosphate isomerase, phosphoglycerate mutase, and enolase from *Bacillus subtilis*," *J. Bacteriol.* 176(13):3903-3910 (1994).

Li, and Wong, "Model-based analysis of oligonucleotide arrays: expression index computation and outlier detection," *Proc. Natl. Acad. Sci. U.S.A.*, 98(1):31-36 (2001).

Liao, et al., "Pathway Analysis, Engineering, and Physiological Considerations for Redirecting Central Metabolism," *Biotechnol. Bioeng.* 52(1):129-140 (1996).

Liao and Oh "Toward predicting metabolic fluxes in metabolically engineered strains," *Metab. Eng.* 1(3):214-223 (1999).

Link, et al., "Methods for generating precise deletions and insertions in the genome of wild-type *Escherichia coli*: Application to open reading frame characterization," *J. Bacteriol.* 179(20):6228-6237 (1997).

Loftus, et al., "Isolation, characterization, and disruption of the yeast gene encoding cytosolic NADP-specific isocitrate dehydrogenase," *Biochemistry*, 33(32):9661-9667 (1994).

Lopez, et al., "The yeast inositol monophosphatase is a lithium- and sodium-sensitive enzyme encoded by a non-essential gene pair," *Mol. Microbiol.* 31(4):1255-1264 (1999).

Lynd, et al., "Biocommodity Enginering," *Biotech. Progress* 15:777-793 (1999).

Mahadevan and Schilling, "The effects of alternate optimal solutions in constraint-based genome-scale metabolic models," *Metab. Eng.* 5(4):264-276 (2003).

Maier, et al., "Hydrogen uptake hydrogenase in *Helicobacter pylori*," *FEMS Microbiol Lett*, 141(1):71-76 (1996).

Majewski and Domach "Simple Constrained-Optimization View of Acete Overflow in *E. Coli*," *Biotechnol. Bioeng.* 35(7):732-738 (1990).

Marcelli, et al., "The respiratory chain of *Helicobacter pylori*: identification of cytochromes and the effects of oxygen on cytochrome and menaquinone levels," *FEMS Microbiol Lett*, 138(1):59-64 (1996).

Marshall and Warren, "Unidentified curved bacilli in the stomach of patients with gastritis and peptic ulceration," *Lancet*, 1(8390):1311-1315 (1984).

McAdams and Arkin, "Stochastic mechanisms in gene expression," *Proc. of the Nat. Acad. Sci. USA* 94(3):814-819 (1997).

McAdams and Arkin, "Simulation of Prokaryotic Genetic Circuits," *Ann. Rev. Biophys. Biomol. Struc.* 27:199-224 (1998).

McAdams and Arkin, "It's a noisy business! Genetic regulation at the nanomolar scale," *Trends. Gene.* 15(2):65-69 (1999).

McAdams and Shapiro, "Circuit simulation of genetic networks." *Science* 269(5224):650-656 (1995).

McAlister-Henn, L and Thompson, L, "Isolation and expression of the gene encoding yeast mitochondrial malate dehydrogenase," *J. Bacteriol.* 169(11):5157-5166 (1987).

McGee, "*Helicobacter pylori* rocF is required for arginase activity and acid protection in vitro but is not essential for colonization of mice or for urease activity," *J. Bacteriol.* 165(1):65-76 (1998).

Meldrum, "Automation for genomics, part one: preparation for sequencing," *Genome Res.* 10(8):1081-1092 (2000).

Mendes, P and Kell, D, "Non-linear optimization of biochemical pathways: Applications to metabolic engineering and parameter estimation," Bioinformatics, 14(10):869-883 (1998).

Mendz, et al., "Characterisation of glucose transport in *Helicobacter pylori*," *Biochim Biophys Acta*, 1244(2-3):269-276 (1995).

Mendz, et al., "Characterization of fumarate transport in *Helicobacter pylori*," *J. Membr. Biol.* 165(1):65-76 (1998).

Mendz et al., "De novo synthesis of pyrimidine nucleotides by *Helicobacter pylori*," *J. Appl. Bacteriol.* 77(1):1-8 (1994).

Mendz, et al., "Fumarate reductase: a target for therapeutic intervention against *Helicobacter pylori*," *Arch. Biochem. Biophys.* 321(1):153-159 (1995).

Mendz, et al., "Glucose utilization and lactate production by *Helicobacter pylori*," *J Gen Microbiol*, 139(12):3023-3028 (1993).

Mendz, et al., "In situ characterization of *Helicobacter pylori* arginase," *Biochim Biophys Acta*, 1388(2):465-477 (1998).

Mendz, et al., "Purine metabolism and the microaerophily of *Helicobacter pylori*," *Arch. Microbiol.* 168(6):448-456 (1997).

Mendz, et al., "The Entner-Doudoroff pathway in *Helicobacter pylori*," *Arch Biochem Biophys*, 312(2):349-356 (1994).

Mendz and Hazell, "Aminoacid utilization by *Helicobacter pylori*," *Int. J. Biochem. Cell. Biol.* 27(10):1085-1093 (1995).

Mendz, G and Hazell, S, "Fumarate catabolism in *Helicobacter pylori*," *Biochem Mol Biol Int*, 31(2):325-332 (1993).

Mendz and Hazell, "Glucose phosphorylation in *Helicobacter pylori*," *Arch. Biochem. Biophys.* 300(1):522-525 (1993).

Mendz, et al., "Pyruvate metabolism in *Helicobacter pylori*," *Arch. Microbiol.* 162(3):187-192 (1994).

Mendz, et al., "Salvage synthesis of purine nucleotides by *Helicobacter pylori*," *J. Appl. Bacteriol.* 77(6):674-681 (1994).

Mewes, et al., "MIPS: A database for genomes and protein sequences," *Nucleic Acids Res.* 30(1):31-34 (2002).

Mitchell, "The GLN1 locus of *Saccharomyces cerevisiae* encodes glutamine synthetase," *Genetics* 111(2):243-258 (1985).

Moszer, "The Complete Genome of *Bacillus subtilis*: From Sequence Annotation to Data Management and Analysis," *FEBS Lett.* 430(1-2):28-36 (1998).

Moszer, et al., "SubtiList: the reference database for the *Bacillus subtilis* genome," *Nucleic Acids Res.* 30(1):62-65 (2002).

Mulquiney and Kuchel, "Model of 2,3-bisphoglycerate metabolism in the human erythrocyte based on detailed enzyme kinetic equations: computer simulation and metabolic control analysis," *Biochem. J.* 342(Pt 3):597-604 (1999).

Murray and Greenberg, "Expression of yeast INM1 encoding inositol monophosphatase is regulated by inositol, carbon source and growth stage and is decreased by lithium and valproate," *Mol. Microbiol.* 36(3):651-661 (2000).

Nedenskov, "Nutritional requirements for growth of *Helicobacter pylori*," *Appl. Environ. Microbiol.* 60(9):3450-3453 (1994).

Nissen et al., "Expression of a cytoplasmic transhydrogenase in *Saccharomyces cerevisiae* results in formation of 2-oxoglutarate due to depletion of the NADPH pool," *Yeast* 18(1):19-32 (2001).

Nissen et al., "Flux distributions in anaerobic, glucose-limited continuous cultures of *Saccharomyces cerevisiae*," *Microbiology*, 143(Pt 1):203-218 (1997).

Ogasawara, "Systematic function analysis of *Bacillus subtilis* genes," *Res. Microbiol.* 151(2):129-134 (2000).

Ogata, et al., "KEGG: Kyoto Encyclopedia of Genes and Genomes," *Nucleic Acids Res.* 27(1):29-34 (1999).

Oh and Liao, "Gene expression profiling by DNA microarrays and metabolic fluxes in *Escherichia coli*," *Biotech. Prog.* 16:278-286 (2000).

Olsson, et al., "Separate and simultaneous enzymatic hydrolysis and fermentation of wheat hemicellulose with recombinant xylose utilizing *Saccharomyces cerevisiae*," *Appl. Biochem. Biotechnol.* 129-132:117-129 (2006).

Ostergaard, et al., "Increasing galactose consumption by *Saccharomyces cerevisiae* through metabolic engineering of the GAL gene regulatory network," *Nat. Biotech.* 18:1283-1286 (2000).

Otto, et al., "A mathematical model for the influence of fructose 6-phosphate, ATP, potassium, ammonium and magnesium on the phosphofructokinase from rat erythrocytes," *Eur. J. Biochem.* 49(1):169-178 (1974).

Ouzounis and Karp "Global Properties of the Metabolic Map of *Escherichia coli*," *Genome Res.* 10(4):568-576 (2000).

Overbeek, et al., "WIT: Integrated System for High-Throughput Genome Sequence Analysis and Metabolic Reconstruction" *Nucleic Acids Res.* 28(1):123-125 (2000).

Overkamp, et al., "In vivo analysis of the mechanisms for oxidation of cytosolic NADH by *Saccharomyces cerevisiae* mitochondria," *J. Bacteriol.* 182(10):2823-2830 (2000).

Ozcan, et al., "Glucose uptake and catabolite repression in dominant HTR1 mutants of *Saccharomyces cerevisiae*," *J. Bacteriol.* 175(17):5520-5528 (1993).

Pallotta, et al., "*Saccharomyces cerevisiae* mitochondria can synthesise FMN and FAD from externally added riboflavin and export them to the extramitochondrial phase," *FEBS Lett.* 428(3):245-249 (1998).

Palmieri, et al., "Identification and functions of new transporters in yeast mitochondria," *Biochem. Biophys. Acta.* 1459(2-3):363-369 (2000).

Palmieri, et al., "Identification of the yeast ACR1 gene product as a succinate-fumarate transporter essential for growth on ethanol or acetate," *FEBS Lett.* 417(1):114-118 (1997).

Palmieri, et al., "Identification of the yeast mitochondrial transporter for oxaloacetate and sulfate," *J Biol Chem*, 274(32):22184-22190 (1999).

Palmieri, et al., "Yeast mitochondrial carriers: bacterial expression, biochemical identification and metabolic significance," *J. Bioenerg. Biomembr.*, 32(1):67-77 (2000).

Palsson, "The Challenges of in Silico Biology," *Nat. Biotechnol.* 18(11):1147-1150 (2000).

Palsson, "What Lies Beyond Bioinformatics," *Nat. Biotechnol.* 15:3-4 (1997).

Papin et al., "The genome-scale metabolic extreme pathway structure in *Haemophilus influenzae* shows significant network redundancy," *J Theor Biol*, 215(1):67-82 (2002).

Parks, "Metabolism of sterols in yeast," *CRC Crit. Rev. Microbiol.* 6(4):301-341 (1978).

Parks et al., "Use of sterol mutants as probes for sterol functions in the yeast, *Saccharomyces cerevisiae*," *Crit. Rev. Biochem. Mol. Biol.* 34(6):399-404 (1999).

Patel and West, ",Degradation of the pyrimidine bases uracil and thymine by *Escherichia coli* B" Microbios. 49(199):107-113 (1987).

Paulsen, et al., "Unified inventory of established and putative transporters encoded within the complete genome of *Saccharomyces cerevisiae*," *FEBS Lett.* 430(1-2):116-125 (1998).

Pearson, et al., "Comparison of DNA Sequences With Protein Sequences," *Genomics* 46(1):24-36 (1997).

Pennisi, "Laboratory Workhouse Decoded," *Science*, 277(5331):1432-1434 (1997).

Persson, et al., "Phosphate permeases of *Saccharomyces cerevisiae*: structure, function and regulation," *Biochim. Biophys. Acta.* 1422(3):255-272 (1999).

Peterson, et al., "The Comprehensive Microbial Resource," *Nucleic Acids Res.* 29(1):123-125 (2001).

Pharkya, et al., "Exploring the overproduction of amino acids using the bilevel optimization framework OptKnock," *Biotechnol. Bioeng.* 84(7):887-899 (2003).

Phelps, et al., "Metabolomics and microarrays for improved understanding of phenotypic characteristics controlled by both genomics and environmental constraints," *Curr. Opin. Biotechnol.* 13(1):20-24 (2002).

Pieper and Reineke, "Engineering bacteria for bioremediation," *Curr. Opin. Biotech.* 11(3):262-270 (2000).

Pitson, et al., "The tricarboxylic acid cycle of *Helicobacter pylori*," *Eur. J. Biochem.* 260(1):258-267 (1999).

Price, et al., "Determination of redundancy and systems properties of the metabolic network of *Helicobacter pylori* using genome-scale extreme pathway analysis," *Genome Res*, 12(5):760-769 (2002).

Price, et al., "Genome-scale models of microbial cells: evaluating the consequences of constraints," *Nat. Rev. Microbiol.* 2(11):886-897 (2004).

Price, et al., "Network-based analysis of metabolic regulation in the human red blood cell," *J. Theor. Biol.* 225(2):185-194 (2003).

Przybyla-Zawislak, et al., "Genes of succinyl-CoA ligase from *Saccharomyces cerevisiae*," *Eur. J. Biochem.* 258(2):736-743 (1998).

Qian, et al., "Ethanol production from dilute-Acid softwood hydrolysate by co-culture," *Appl. Biochem. Biotechnol.* 134(3):273-284 (2006).

Raclot, et al., "Selective release of human adipocyte fatty acids according to molecular structure," *Biochem. J.* 324 (Pt3):911-915 (1997).

Reed, et al., "An expanded genome-scale model of *Escherichia coli* K-12 (iJR904 GSM/GPR)," *Genome Biol*, 4(9):R54 (2003).

Reed and Palsson, "Thirteen years of building constraint-based in silico models of *Escherichia coli*" *J. Bacteriol.* 185(9):2692-2699 (2003).

Regenberg et al., "Substrate specificity and gene expression of the amino-acid permeases in *Saccharomyces cerevisiae*," *Curr. Genet.* 36(6):317-328 (1999).

Remize, et al., "Engineering of the pyruvate dehydrogenase bypass in *Saccharomyces cerevisiae*: role of the cytosolic Mg(2+) and mitochondrial K(+) acetaldehyde dehydrogenases Ald6p and Ald4p in acetate formation during alcoholic fermentation," *Appl. Environ. Microbiol.* 66(8):3151-3159 (2000).

Ren, et al., "Genome-wide location and function of DNA binding proteins," *Science*, 290(5500):2306-2309 (2000).

Rao and Arkin "Control motifs for intracellular regulatory networks," *Ann. Rev. Biomed. Engin.* 3:391-419 (2001).

Repetto and Tzagoloff, "In vivo assembly of yeast mitochondrial alpha-ketoglutarate dehydrogenase complex," *Mol. Cell. Biol.* 11(8):3931-3939 (1991).

Reynolds and Penn, "Characteristics of *Helicobacter pylori* growth in a defined medium and determination of its amino acid requirements," *Microbiology* 140(Pt 10):2649-2656 (1994).

Rhee, et al., "Activation of gene expression by a ligand-induced conformational change of a protein-DNA complex," *J. Biol. Chem.* 273(18):11257-11266 (1998).

Romero and Karp, "Nutrient-Related Analysis of Pathway/Genome Databases," *Pac Symp. Biocomput.* 471-482 (2001).

Saier, "Genome sequencing and informatics: new tools for biochemical discoveries," *Plant Physiol.* 117(4):1129-1133 (1998).

Salgado, et al., "RegulonDB (version 3.2): transcriptional regulation and operon organization in *Escherichia coli* K-12," *Nucleic Acids Res.* 29(1):72-74 (2001).

Salmon, et al., "Global gene expression profiling in *Escherichia coli* K12. The effects of oxygen availability and FNR," *J. Biol. Chem.* 278(32):29837-29855 (2003).

Sauer, et al., "Metabolic Capacity of *Bacillus subtilis* for the Production of Purine Nucleosides, Riboflavin, and Folic Acid," *Biotechnol. Bioeng.* 59(2):227-238 (1998).

Sauer, et al., "Metabolic flux ratio analysis of genetic and environmental modulations of *Escherichia coli* central carbon metabolism," *J Bacteriol*, 181(21):6679-6688 (1999).

Sauer and Bailey, "Estimation of P-to-O Ratio in *Bacillus subtilis* and Its Influence on Maximum Riboflavin Yield," *Biotechnol. Bioeng.* 64(6):750-754 (1999).

Sauer, "Evolutionary Engineering of Industrially Important Microbial Phenotypes," *Adv. Biochem. Eng. Biotechnol.* 73:129-169 (2001).

Savageau, "Biochemical systems analysis. I. Some mathematical properties of the rate law for the component enzymatic reactions," *J. Theor. Biol.* 25(3):365-369 (1969).

Savageau, "Development of fractal kinetic theory for enzyme-catalysed reactions and implications for the design of biochemical pathways," *Biosystems* 47(1-2):9-36 (1998).

Savinell and Palsson, "Network Analysis of Intermediary Metabolism using Linear Optimization. II. Interpretation of Hybridoma Cell Metabolism," *J. Theor. Biol.* 154:455-473 (1992).

Savinell and Palsson, "Network Analysis of Intermediary Metabolism using Linear Optimization. I. Development of Mathematical Formalism," *J. Theor. Biol.* 154:421-454 (1992).

Schaaff-Gerstenschlager and Zimmermann, "Pentose-phosphate pathway in *Saccharomyces cerevisiae*: analysis of deletion mutants for transketolase, transaldolase, and glucose 6-phosphate dehydrogenase," *Curr. Genet.* 24(5):373-376 (1993).

Schaff, et al., "The Virtual cell" *Proc. Pac. Symp. Biocomput.* 228-239 (1999).

Schena, et al., "Quantitative monitoring of gene expression patterns with a complementary DNA microarray," *Science* 270(5235):467-470 (1995).

Schilling and Palsson, "The Underlying Pathway Structure of Biochemical Reaction Networks," *Proc. Natl. Acad. Sci. U.S.A.* 95(8):4193-4198 (1998).

Schilling, et al., "Metabolic Pathway Analysis: Basic Concepts and Scientific Applications in the Post-genomic Era," *Biotechol. Prog.* 15(3):296-303 (1999).

Schilling, et al., "Theory for the Systematic Definition of Metabolic Pathways and Their Use in Interpreting Metabolic Function from a Pathway-Oriented Perspective," *J. Theor. Biol*, 203(3):229-248 (2000).

Schilling and Palsson, "Assessment of the Metabolic Capabilities of *Haemophilus influenzae* Rd Through a Genome-scale Pathway Analysis," *J. Theor. Biol.* 203(3):249-283 (2000).

Schilling, et al., "Combining Pathway Analysis with Flux Balance Analysis for the Comprehensive Study of Metabolic Systems," *Biotechnol. Bioeng.* 71(4):286-306 (2000-2001).

Schilling, et al., "Genome-scale metabolic model of *Helicobacter pylori* 26695," *J. Bacteriol.* 184(16):4582-4593 (2002).

Schneider, et al., "The *Escherichia coli* gabDTPC operon: specific gamma-aminobutyrate catabolism and nonspecific induction," *J. Bacteriol.* 184(24):6976-6986 (2002).

Schuster, et al., "A general definition of metabolic pathways useful for systematic organization and analysis of complex metabolic networks," *Nat. Biotechnol.* 18(3):326-332 (2000).

Schuster, et al., "Detection of elementary flux modes in biochemical networks: a promising tool for pathway analysis and metabolic engineering," *Trends Biotechnol* 17(2):53-60 (1999).

Schuster, et al., "Exploring the pathway structure of metabolism: decomposition into subnetworks and application to *Mycoplasma pneumoniae*," *Bioinformatics* 18(2):351-361 (2002).

Schuster and Hilgetag, "On elementary flux modes in biochemical reaction systems at steady state," *J. Biol. Syst.* 2(2):165-182 (1994).

Schwikowski, et al., "A network of protein-protein interactions in yeast," *Nat. Biotechnol.* 18(12):1257-1261 (2000).

Scott, et al., "The Pendred Syndrome Gene Encodes a Chloride-Iodide Transport Protein," *Nat. Genet*, 21(4):440-443 (1999).

Sedivy and Fraenkel, "Fructose bisphosphatase of *Saccharomyces cerevisiae*. Cloning, disruption and regulation of the FBP1 structural gene," *J. Mol. Biol.* 186(2):307-319 (1985).

Selkov, et al., "A reconstruction of the metabolism of *Methanococcus jannaschii* from sequence data," *Gene.* 197(1-2):GC11-26 (1997).

Selkov, et al., "Functional Analysis of Gapped Microbial Genomes: Amino Acid Metabolism of *Thiobacillus ferroxidans*," *Proc. Natl. Acad. Sci. U.S.A.* 97(7):3509-3514 (2000).

Selkov et al., "MPW: the metabolic pathways database," *Nucleic Acids Res*, 26(1):43-45 (1998).

Selkov, et al., "The metabolic pathway collection from EMP: the enzymes and metabolic pathways database," *Nucleic Acids Res.* 24(1):26-28 (1996).

Shen-Orr, et al., "Network motifs in the transcriptional regulation network of *Escherichia coli*," *Nat. Gene.* 31(1):64-68 (2002).

Sherlock, et al., "The physiology of L-methionine catabolism to the secondary metabolite ethylene by *Escherichia coli*," *Curr. Opin. Immunol.* 12:201-205 (2000).

Shipston and Bunch "The physiology of L-methionine catabolism to the secondary metabolite ethylene by *Escherichia coli*," *J. Gen. Microbiol.* 135(6), 1489-1497 (1989).

Silve, et al., The immunosuppressant SR 31747 blocks cell proliferation by inhibiting a steroid isomerase in *Saccharomyces cerevisiae, Mol. Cell. Biol.* 16(6):2719-2727 (1996).

Skouloubris, et al., "The *Helicobacter pylori* UreI protein is not involved in urease activity but is essential for bacterial survival in vivo," *Infect. Immun.* 66(9):4517-4521 (1998).

Smith, et al., "Functional analysis of the genes of yeast chromosome V by genetic footprinting," *Science*, 274(5295):2069-2074 (1996).

Somogyi and Sniegoski, "Modeling the complexity of genetic networks: understanding the multigenic and pleitropic regulation," *Complexity* 1(6):45-63 (1996).

Sorlie, et al., "Gene expression patterns of breast carcinomas distinguish tumor subclasses with clinical implications," *Proc. Natl. Acad. Sci. U.S.A.*, 98(19):10869-10874 (2001).

Stark, et al., "Amino acid utilisation and deamination of glutamine and asparagine by *Helicobacter pylori*," *J. Med. Microbiol.*, 46(9):793-800 (1997).

Stephanopoulos, "Metabolic engineering," *Curr. Opin. Biotechnol.* 5(2):196-200 (1994).

Stephanopoulos, "Metabolic Engineering," *Biotechnol. Bioeng.* 58(2-3):119-120 (1998).

Summers, et al., "*Saccharomyces cerevisiae* cho2 mutants are deficient in phospholipid methylation and cross-pathway regulation of inositol synthesis" *Gene.* 120(4):909-922 (1988).

Swartz, "A PURE approach to constructive biology," *Nat. Biotechnol.* 19(8):732-733 (2001).

Syvanen, "Accessing genetic variation: Genotyping single nucleotide polymorphisms," *Nat. Rev. Gene.* 2(12):930-942 (2001).

Szambelan, et al., "Use of *Zymomonas mobilis* and *Saccharomyces cerevisiae* mixed with *Kluyveromyces fragilis* for improved ethanol production from Jerusalem artichoke tubers," *Biotechnol. Lett.* 26(10):845-848 (2004).

Tamayo, et al., "Interpreting patterns of gene expression with self-organizing maps: methods and application to hematopoietic differentiation," *Proc. Natl. Acad. Sci. U.S.A.* 96(6):2907-2912 (1999).

Tanaka and Zerez, "Red cell enzymopathies of the glycolytic pathway," *Semin. Hematol.* 27(2):165-185 (1990).

Taniguchi and Tanaka, "Clarification of interactions among microorganisms and development of co-culture system for production of useful substances," *Adv. Biochem. Eng. Biotechnol.* 90:35-62 (2004).

Tandeitnik, et al., "Modeling of biological neurons by artificial neural networks," *Nineteenth Convention of Electrical and Electronics Engineers in Israel*, Jerusalem, Israel, New York, NY USA, pp. 239-242 (1996).

Tao, et al., "Engineering a homo-ethanol pathway in *Escherichia coli*: increased glycolytic flux and levels of expression of glycolytic genes during xylose fermentation," *J. Bacteriol.* 183(10):2979-2988 (2001).

ter Linde, et al., "Genome-wide transcriptional analysis of aerobic and anaerobic chemostat cultures of *Saccharomyces cerevisiae*," *J. Bacteriol.* 181(24):7409-7413 (1999).

Thieffry and Thomas, "Dynamical behavior of biological regulatory networks II. Immunity control in bacteriophage lambda," *Bull. Math. Biology.* 57(2):277-297 (1995).

Thomas, "Boolean Formalization of Genetic Control Circuits," *J. Theor. Biol.* 42(3):563-585 (1973).

Thomas, "Logical Analyses of Systems Comprising Feedback Loops," *J. Theor. Biol.* 73(4):631-656 (1978).

Thomas and Surdin-Kerjan, "Metabolism of sulfur amino acids in *Saccharomyces cerevisiae*," *Microbiol. Mol. Biol. Rev.* 61(4):503-532 (1997).

Tomb, et al., "The complete genome sequence of the gastric pathogen *Helicobacter pylori*," *Nature* 388(6642):539-547 (1997).

Tomita, et al., "E-Cell: Software Environment for Whole-Cell Simulation," *Bioinformatics* 15(1):72-84 (1999).

Trotter, et al., "A genetic screen for aminophospholipid transport mutants identifies the phosphatidylinositol 4-kinase, STT4p, as an essential component in phosphatidylserine metabolism," *J. Biol. Chem.* 273(21):13189-13196 (1998).

Uetz, et al., "A comprehensive analysis of protein-protein interactions in *Saccharomyces cerevisiae*," *Nature* 403(6770):623-627 (2000).

Van den Berg and Steensma, "ACS2, a *Saccharomyces cerevisiae* gene encoding acetyl-coenzyme A synthetase, essential for growth on glucose," *Eur. J. Biochem.* 231(3):704-713 (1995).

van Dijken, et al., "Alcoholic fermentation by 'non-fermentative' yeasts," *Yeast* 2(2):123-127 (1986).

van Dijken, et al., "Kinetics of growth and sugar consumption in yeasts," *Antonie Van Leeuwenhoek*, 63(3-4):343-352 (1993).

Vanrolleghem, et al., "Validation of a Metabolic Network for *Saccharomyces cerevisiae* Using Mixed Substrate Studies," *Biotechnol. Prog.* 12(4):434-448 (1996).

Varma and Palsson, "Metabolic capabilities of *Escherichia coli*. II: Optimal Growth Patterns," *J. Theor. Biol.* 165:503-522 (1993).

Varma and Palsson, "Metabolic capabilities of *Escherichia coli*: I. Synthesis of Biosynthetic Precursors and Cofactors," *J. Theor. Biol.* 165:477-502 (1993).

Varma and Palsson, "Parametric sensitivity of stoichiometric flux balance models applied to wild-type *Escherichia coli* metabolism," *Biotechnol. Bioeng.* 45(1):69-79 (1995).

Varma and Palsson, "Predictions for Oxygen Supply Control to Enhance Population Stability of Engineered Production Strains," *Biotechnol. Bioeng.* 43(4):275-285 (1994).

Varma and Palsson, "Stoichiometric flux balance models quantitatively predict growth and metabolic by-product secretion in wild-type *Escherichia coli* W3110," *Appl. Environ. Microbiol.* 60(10):3724-3731 (1994).

Varma, et al., "Metabolic Flux Balancing: Basic Concepts, Scientific and Practical Use," *Biotechnology* 12:994-998 (1994).

Varma, et al., "Biochemical Production Capabilities of *Escherichia coli*," *Biotechnol. Bioeng.* 42(1):59-73 (1993).

Varma, et al., "Stoichiometric Interpretation of *Escherichia coli* Glucose Catabolism Under Various Oxygenation Rates," *Appl. Environ. Microbiol.* 59(8):2465-2473 (1993).

Varner and Ramkrishna, "Mathematical Models of Metabolic Pathways," *Curr. Opin. Biotechnol.* 10(2):146-150 (1999).

Varner, "Large-scale prediction of phenotype: concept," *Biotech. Bioeng.* 69(6):664-678 (2000).

Vaseghi, et al., "In vivo Dynamics of the pentose phosphate pathway in *Saccharomyces cerevisiae*," *Metab. Eng.* 1:128-140 (1999).

Velculescu, et al., "Analysing uncharted transcriptomes with SAGE," *Trends Genet.* 16(10):423-425 (2000).

Venter, et al., "Shotgun sequencing of the human genome," *Science* 280(5369):1540-1542 (1998).

Verduyn, "Physiology of yeasts in relation to biomass yields," *Antonie Van Leeuwenhoek*, 60(3-4):325-353 (1999).

Verduyn, et al., "A theoretical evaluation of growth yields of yeasts," *Antonie Van Leeuwenhoek*, 59(1):49-63 (1991).

Verduyn, et al., "Energetics of *Saccharomyces cerevisiae* in anaerobic glucose-limited chemostat cultures," *J. Gen. Microbiol.* 136:405-412 (1990).

Vissing, et al., "Paradoxically Enhanced Glucose Production During Exercise in Humans with Blocked Glycolysis Caused by Muscle Phosphofructokinase Deficiency," *Neurology*, 47(3):766-771 (1996).

Vo, et al., "Reconstruction and functional characterization of the human mitochondrial metabolic network abased on proteomic and biochemical dataz," *J. Biol. Chem.* 279(38):39532-39540 (2004).

Wang, et al., "Computer-aided baker's yeast fermentations," *Biotechnol. Bioeng.* 19(1):69-86 (1977).

Wang, et al., "Computer control of bakers' yeast production," *Biotechnol. Bioeng.* 21:975-995 (1979).

Waterston and Sulston, "The Human Genome Project: reaching the finish line," *Science*,282(5386):53-54 (1998).

Wen et al., "Large-scale temporal gene expression mapping of central nervous system development," *Proc. Natl. Acad. Sci. U.S.A.*, 95(1):334-339 (1998).

Wiback and Palsson, "Extreme pathway analysis of human red blood cell metabolism," *Biophys. J.* 83:808-818 (2002).

Wieczorke, et al., "Concurrent knock-out of at least 20 transporter genes is required to block uptake of hexoses in *Saccharomyces cerevisiae*," *FEBS Lett.* 464(3):123-128 (1999).

Wills and Melham, "Pyruvate carboxylase deficiency in yeast: a mutant affecting the interaction between the glyoxylate and Krebs cycles," *Arch. Biochem. Biophys.* 236(2):782-791 (1985).

Wingender, et al., "The TRANSFAC system on gene expression regulation," *Nucleic Acid Res.* 29(1):281-283 (2001).

Winzeler, et al., "Functional characterization of the *S. cerevisiae* genome by gene deletion and parallel analysis," *Science*, 285(5429):901-906 (1999).

Wong, P. et al., "Mathematical Model of the Lac Operon: Inducer Exclusion, Catabolite Repression, and Diauxic Growth on Glucose and Lactose," *Biotechnol. Prog.* 13(2):132-143 (1997).

Xie and Wang, "Energy Metabolism and ATP Balance in Animal Cell Cultivation Using a Stoichiometrically Based Reaction Network," *Biotech. Bioengineer.* 52:591-601 (1996).

Xie and Wang, "Material Balance Studies on Animal Cell Metabolism Using a Stoichiometrically Based Reaction Network," *Biotech. Bioengineer.* 52:579-590 (1996).

Xie and Wang, "Integrated Approaches to the Design of Media and Feeding Strategies for Fed-Batch Cultures of Animal Cells," *Trends Biotechnol.* 15(3):109-113 (1997).

Yamada, et al., "Effects of common polymorphisms on the properties of recombinant human methylenetetrahydrofolate reductase," *Proc. Natl. Acad. Sci. U.S.A.*, 98(26):14853-14858 (2001).

Yeung, et al., "Reverse engineering gene networks using singular value decomposition and robust regression," *Proc. Natl. Acad. Sci. U.S.A.*, 99(9):6163-6168 (2002).

Yeung, et al., "Model-based clustering and data transformations for gene expression data," *Bioinformatics* 17(10):977-87 (2001).

Yoshida, et al., "Combined transcriptome and proteome analysis as a powerful approach to study genes under glucose repression in *Bacillus subtilis*," *Nucleic Acids Res.* 29(3):683-692 (2001).

Zanella and Bianchi, "Red cell pyruvate kinase deficiency: from genetics to clinical manifestations," *Bailliere's Best Pract. Res. Clin. Haematol.* 13(1):57-81 (2000).

Zeng, et al., "Use of respiratory quotient as a control parameter for optimum oxygen supply and scale-up of 2,3-butanediol production under microaerobic conditions," *Biotechnol. Bioeng.* 44(9):1107-1114 (1994).

Zhu, J and Zhang, M, "SCPD: a promoter database of the yeast *Saccharomyces cerevisiae*," *Bioinformatics* 15(7-8):607-611 (1999).

Zigova, "Effect of R and pre-seed conditions on biomass and galactosyl transferase production during fed-batch culture of *S. cerevisiae* BT150," *J. Biotechnol.* 80(1):55-62 (2000).

Zweytick, et al., "Biochemical characterization and subcellular localization of the sterol C-24(28) reductase, erg4p, from the yeast *Saccharomyces cerevisiae*," *FEBS Lett.* 470(1):83-87 (2000).

URL affymetrix.com, Affymetrix protocol for *E. coli* Antisense Genome. (As printed on Sep. 18, 2009).

URL affymetrix.com/products/arrays/specific/ecoli antisense.affx. (As printed on Sep. 18, 2009).

URL asap.ahabs.wisc.edu/annotation/php/logon.php, The ASAP website.(As printed on Sep. 17, 2009).

URL ca.expasy.org/sprot/, protein database SWISS-PROT. (As printed on Jun. 15, 2009).

URL chem.qmw.ac.uk/iubmb/enzyme/, Enzyme Nomenclature database maintained by G.P. Moss of Queen Mary and Westfield College in the United Kingdom. (As printed on Sep. 18, 2009).

URL dchip.org, dChip software. (As printed on Jun. 15, 2009).

URL Dictionary.com pp. 1-2 (2004), Matrix.(As printed on Nov. 12, 2004).

URL ecocyc.panbio.com/ecocyc/ecocyc.html, EcoCyc. (As printed on Sep. 18, 2009).

URL enzobio.com/lifesci_index.htm, Enzo BioArray Terminal Labeling Kit protocol. (As printed on Sep. 18, 2009).

URL genetics.wisc.edu/, *E. coli* Genome Project at the University of Wisconsin. (As printed on Sep. 18, 2009).

URL genome.ad.jp/kegg/, Kyoto Encyclopedia of Genes and Genomes database (KEGG). (As printed on Sep. 18, 2009).

URL Genome.jp Website, KEGG *Bacillus subtillis*, 1-7 (2005). (As printed on Sep. 18, 2009).

URL genome.tugraz.at/Software/Genesis/Description.html, "Genesis" software. (As printed Sep. 18, 2009).

URL igweb.integratedgenomics.com/MPW/, Metabolic pathways database (MPW). (As printed on Sep. 18, 2009).

URL integratedgenomics.com, ERGO from Integrated Genomics. (As printed on Sep. 18, 2009).

URL mips.gsf.de/proj/yeast/pathways/ on Jun. 6, 2008, MIPS, website: Comprehensive Yeast Genome Database—Pathways (1998). (As printed on Sep. 18, 2009).

URL ncbi.nlm.gov, Genbank genome database. (As printed on Jun. 15, 2009).

URL ncbi.nlm.nih.gov/entrez/query.fcgi?db=Genome, The NCBI Entrez Genome database. (As printed on Sep. 18, 2009).

URL ncbi.nlm.nih.gov/LocusLink/, LocusLink database maintained by the NCBI.

URL ncbi.nlm.nih.gov/Taxonomy/taxonomyhome.html/. (As printed on Sep. 18, 2009).

URL nslij-genetics.org/search_omim.html, Online Mendelian Inheritance in Man database, Center for Medical Genetics, Johns Hopkins University (Baltimore, MD) and National Center for Biotechnology Information, National Library of Medicine (Bethesda, MD). (As printed Sep. 18, 2009).

URL qiagen.com, Qiagen RNeasy Mini Kit. (As printed Sep. 18, 2009).

URL rana.lbl.gov/EisenSoftware.htm, "Cluster" software. (As printed Sep. 18, 2009).

URL genome-www.stanford.edu/~sherlock/cluster.html, "XCluster" software. (As printed Sep. 18, 2009).

URL systembiology.ucsd.edu. (As printed Sep. 18, 2009).

URL tigr.org, ,The Institute for Genome Research, J Craig Venter Institute. (As printed Sep. 18, 2009).

URL tula.cifn.unam.mx:8850/regulondb/regulon_intro.frameset. (As printed Sep. 18, 2009).

URL workbench.sdsc.edu/, Biology Workbench. (As printed Sep. 18, 2009).

URL 216.190.101.28/IGwit/ or wit.mcs.anl.gov/WIT/, What is There (WIT). (As printed Sep. 18, 2009).

\* cited by examiner

Figure 2

$$
\begin{array}{c}
\phantom{x} \\
B \\
C \\
D \\
E \\
F \\
G \\
A_{external} \\
E_{external}
\end{array}
\begin{bmatrix}
R_1 & R_2 & R_3 & R_4 & R_5 & R_6 & V_{growth} & A_{xt} & E_{xt} \\
0 & 1 & -1 & 0 & 0 & 0 & 0 & 0 & 0 \\
0 & 0 & 0 & 1 & -1 & 0 & 0 & 0 & 0 \\
0 & 0 & 0 & 0 & 1 & 0 & -1 & 0 & 0 \\
0 & 0 & 0 & 0 & 1 & -1 & 0 & 0 & 0 \\
0 & 0 & 2 & 0 & 0 & 0 & -1 & 0 & 0 \\
1 & -1 & 0 & -1 & 0 & 0 & 0 & 0 & 0 \\
-1 & 0 & 0 & 0 & 0 & 0 & 0 & -1 & 0 \\
0 & 0 & 0 & 0 & 0 & 1 & 0 & 0 & -1
\end{bmatrix}
\begin{bmatrix}
R_1 \\ R_2 \\ R_3 \\ R_4 \\ R_5 \\ R_6 \\ V_{growth} \\ A_{xt} \\ E_{xt}
\end{bmatrix}
=
\begin{bmatrix}
0 \\ 0 \\ 0 \\ 0 \\ 0 \\ 0 \\ 0 \\ 0
\end{bmatrix}
$$

| Mass Balance | Flux Constraints |
|---|---|
| B: $R_2 - R_3 = 0$ | $0 \leq R_1 \leq \infty$ |
| C: $R_4 - R_5 = 0$ | $-\infty \leq R_2 \leq \infty$ |
| D: $R_5 - V_{growth} = 0$ | $0 \leq R_3 \leq \infty$ |
| E: $R_5 - R_6 = 0$ | $0 \leq R_4 \leq \infty$ |
| F: $2 R_3 - V_{growth} = 0$ | $0 \leq R_5 \leq \infty$ |
| G: $R_1 - R_2 - R_4 = 0$ | $0 \leq R_6 \leq \infty$ |
| $A_{external}$: $-A_{xt} - R_1 = 0$ | $0 \leq V_{growth} \leq \infty$ |
| $E_{external}$: $R_6 - E_{xt} = 0$ | $Y_1 \leq A_{xt} \leq Y_1$ |
|  | $-\infty \leq E_{xt} \leq \infty$ |
|  | $Y_1 = $ const. |

| Objective Function |
|---|
| $Z = V_{growth}$ |

ARTICLES OF MANUFACTURE AND METHODS FOR MODELING *SACCHAROMYCES CEREVISIAE* METABOLISM

This application claims priority under 35 U.S.C. §119(e) to U.S. Provisional Application No. 60/344,447 filed Oct. 26, 2001, which is incorporated herein by reference in its entirety.

This invention was made with United States Government support under grant NIH ROIHL59234 awarded by the National Institutes of Health. The U.S. Government has certain rights in this invention.

BACKGROUND OF THE INVENTION

This invention relates generally to analysis of the activity of a chemical reaction network and, more specifically, to computational methods for simulating and predicting the activity of *Saccharomyces cerevisiae* (*S. cerevisiae*) reaction networks.

*Saccharomyces cerevisiae* is one of the best-studied microorganisms and in addition to its significant industrial importance it serves as a model organism for the study of eukaryotic cells (Winzeler et al. *Science* 285: 901-906 (1999)). Up to 30% of positionally cloned genes implicated in human disease have yeast homologs.

The first eukaryotic genome to be sequenced was that of *S. cerevisiae*, and about 6400 open reading frames (or genes) have been identified in the genome. *S. cerevisiae* was the subject of the first expression profiling experiments and a compendium of expression profiles for many different mutants and different growth conditions has been established. Furthermore, a protein-protein interaction network has been defined and used to study the interactions between a large number of yeast proteins.

*S. cerevisiae* is used industrially to produce fuel ethanol, technical ethanol, beer, wine, spirits and baker's yeast, and is used as a host for production of many pharmaceutical proteins (hormones and vaccines). Furthermore, *S. cerevisiae* is currently being exploited as a cell factory for many different bioproducts including insulin.

Genetic manipulations, as well as changes in various fermentation conditions, are being considered in an attempt to improve the yield of industrially important products made by *S. cerevisiae*. However, these approaches are currently not guided by a clear understanding of how a change in a particular parameter, or combination of parameters, is likely to affect cellular behavior, such as the growth of the organism, the production of the desired product or the production of unwanted by-products. It would be valuable to be able to predict how changes in fermentation conditions, such as an increase or decrease in the supply of oxygen or a media component, would affect cellular behavior and, therefore, fermentation performance. Likewise, before engineering the organism by addition or deletion of one or more genes, it would be useful to be able to predict how these changes would affect cellular behavior.

However, it is currently difficult to make these sorts of predictions for *S. cerevisiae* because of the complexity of the metabolic reaction network that is encoded by the *S. cerevisiae* genome. Even relatively minor changes in media composition can affect hundreds of components of this network such that potentially hundreds of variables are worthy of consideration in making a prediction of fermentation behavior. Similarly, due to the complexity of interactions in the network, mutation of even a single gene can have effects on multiple components of the network. Thus, there exists a need for a model that describes *S. cerevisiae* reaction networks, such as its metabolic network, which can be used to simulate many different aspects of the cellular behavior of *S. cerevisiae* under different conditions. The present invention satisfies this need, and provides related advantages as well.

SUMMARY OF THE INVENTION

The invention provides a computer readable medium or media, including: (a) a data structure relating a plurality of reactants in *S. cerevisiae* to a plurality of reactions in *S. cerevisiae*, wherein each of the *S. cerevisiae* reactions includes a reactant identified as a substrate of the reaction, a reactant identified as a product of the reaction and a stoichiometric coefficient relating the substrate and the product, (b) a constraint set for the plurality of *S. cerevisiae* reactions, and (c) commands for determining at least one flux distribution that minimizes or maximizes an objective function when the constraint set is applied to the data representation, wherein at least one flux distribution is predictive of a physiological function of *S. cerevisiae*. In one embodiment, at least one of the cellular reactions in the data structure is annotated to indicate an associated gene and the computer readable medium or media further includes a gene database including information characterizing the associated gene. In another embodiment, at least one of the cellular reactions in the data structure is annotated with an assignment of function within a subsystem or a compartment within the cell.

The invention also provides a method for predicting physiological function of *S. cerevisiae*, including: (a) providing a data structure relating a plurality of *S. cerevisiae* to a plurality of *S. cerevisiae* reactions, wherein each of the *S. cerevisiae* reactions includes a reactant identified as a substrate of the reaction, a reactant identified as a product of the reaction and a stoichiometric coefficient relating the substrate and the product; (b) providing a constraint set for the plurality of *S. cerevisiae* reactions; (c) providing an objective function, and (d) determining at least one flux distribution that minimizes or maximizes the objective function when the constraint set is applied to the data structure, thereby predicting a *S. cerevisiae* physiological function. In one embodiment, at least one of the *S. cerevisiae* reactions in the data structure is annotated to indicate an associated gene and the method predicts a *S. cerevisiae* physiological function related to the gene.

Also provided by the invention is a method for making a data structure relating a plurality of *S. cerevisiae* reactants to a plurality of *S. cerevisiae* reactions in a computer readable medium or media, including: (a) identifying a plurality of *S. cerevisiae* reactions and a plurality of reactants that are substrates and products of the reactions; (b) relating the plurality of reactants to the plurality of reactions in a data structure, wherein each of the reactions includes a reactant identified as a substrate of the reaction, a reactant identified as a product of the reaction and a stoichiometric coefficient relating the substrate and the product; (c) determining a constraint set for the plurality of *S. cerevisiae* reactions; (d) providing an objective function; (e) determining at least one flux distribution that minimizes or maximizes the objective function when the constraint set is applied to the data structure, and (f) if at least one flux distribution is not predictive of a physiological function of *S. cerevisiae*, then adding a reaction to or deleting a reaction from the data structure and repeating step (e), if at least one flux distribution is predictive of a physiological function of the eukaryotic cell, then storing the data structure in a computer readable medium or media. The invention further provides a data structure relating a plurality of *S.*

*cerevisiae* reactants to a plurality of reactions, wherein the data structure is produced by the method.

BRIEF DESCRIPTION OF THE DRAWINGS

FIG. 2 shows the stoichiometric matrix (S) for the hypothetical metabolic network shown in FIG. 1.

FIG. 3 shows mass balance constraints and flux constraints (reversibility constraints) that can be placed on the hypothetical metabolic network shown in FIG. 1. ($\infty$, infinity; $Y_1$, uptake rate value)

FIG. 9 shows the utilization of glucose at varying dilution rates in anaerobic chemostat culture. The data-point at the dilution rate of 0.0 is extrapolated from the experimental results. The shaded area or the infeasible region contains a set of stoichiometric constraints that cannot be balanced simultaneously with growth demands. The model produces the optimal glucose uptake rate for a given growth rate on the line of optimal solution (indicated by Model (optimal)). Imposition of additional constraints drives the solution towards a region where more glucose is needed (i.e. region of alternative sub-optimal solution). At the optimal solution, the in silico model does not secrete pyruvate and acetate. The maximum difference between the model and the experimental points is 8% at the highest dilution rate. When the model is forced to produce these by-products at the experimental level (Model (forced)), the glucose uptake rate is increased and becomes closer to the experimental values. FIGS. 9B and 9C show the secretion rate of anaerobic by-products in chemostat culture. (q, secretion rate; D, dilution rate).

FIG. 10A shows biomass yield ($Y_x$), and secretion rates of ethanol (Eth), and glycerol (Gly). FIG. 10B shows $CO_2$ secretion rate ($q_{CO2}$) and respiratory quotient (RQ; i.e. $q_{CO2}/q_{O2}$) of the aerobic glucose-limited continuous culture of *S. cerevisiae*. (exp, experimental).

DETAILED DESCRIPTION OF THE INVENTION

Figure 1:
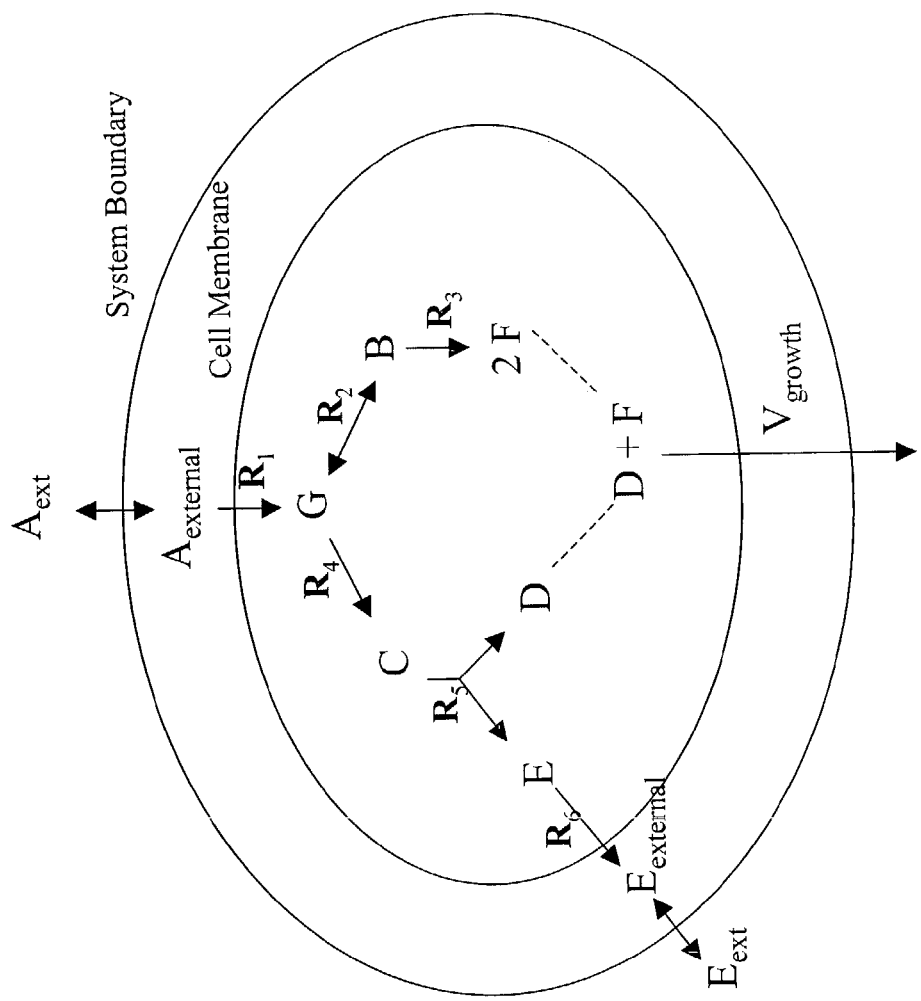
FIG. 1 shows a schematic representation of a hypothetical metabolic network.

The present invention provides an in silico model of the baker's and brewer's yeast, *S. cerevisiae*, that describes the interconnections between the metabolic genes in the *S. cerevisiae* genome and their associated reactions and reactants. The model can be used to simulate different aspects of the cellular behavior of *S. cerevisiae* under different environmental and genetic conditions, thereby providing valuable information for industrial and research applications. An advantage of the model of the invention is that it provides a holistic approach to simulating and predicting the metabolic activity of *S. cerevisiae*.

As an example, the *S. cerevisiae* metabolic model can be used to determine the optimal conditions for fermentation performance, such as for maximizing the yield of a specific industrially important enzyme. The model can also be used to calculate the range of cellular behaviors that *S. cerevisiae* can display as a function of variations in the activity of one gene or multiple genes. Thus, the model can be used to guide the organismal genetic makeup for a desired application. This ability to make predictions regarding cellular behavior as a consequence of altering specific parameters will increase the speed and efficiency of industrial development of *S. cerevisiae* strains and conditions for their use.

The *S. cerevisiae* metabolic model can also be used to predict or validate the assignment of particular biochemical reactions to the enzyme-encoding genes found in the genome, and to identify the presence of reactions or pathways not indicated by current genomic data. Thus, the model can be used to guide the research and discovery process, potentially leading to the identification of new enzymes, medicines or metabolites of commercial importance.

The models of the invention are based on a data structure relating a plurality of *S. cerevisiae* reactants to a plurality of *S. cerevisiae* reactions, wherein each of the *S. cerevisiae* reactions includes a reactant identified as a substrate of the reaction, a reactant identified as a product of the reaction and a stoichiometric coefficient relating the substrate and the product.

As used herein, the term "*S. cerevisiae* reaction" is intended to mean a conversion that consumes a substrate or forms a product that occurs in or by a viable strain of *S. cerevisiae*. The term can include a conversion that occurs due to the activity of one or more enzymes that are genetically encoded by a *S. cerevisiae* genome. The term can also include a conversion that occurs spontaneously in a *S. cerevisiae* cell. Conversions included in the term include, for example, changes in chemical composition such as those due to nucleophilic or electrophilic addition, nucleophilic or electrophilic substitution, elimination, isomerization, deamination, phosphorylation, methylation, glycolysation, reduction, oxidation or changes in location such as those that occur due to a transport reaction that moves a reactant within the same compartment or from one cellular compartment to another. In the case of a transport reaction, the substrate and product of the reaction can be chemically the same and the substrate and product can be differentiated according to location in a particular cellular compartment. Thus, a reaction that transports a chemically unchanged reactant from a first compartment to a second compartment has as its substrate the reactant in the first compartment and as its product the reactant in the second compartment. It will be understood that when used in reference to an in silico model or data structure, a reaction is intended to be a representation of a chemical conversion that consumes a substrate or produces a product.

As used herein, the term "S. cerevisiae reactant" is intended to mean a chemical that is a substrate or a product of a reaction that occurs in or by a viable strain of S. cerevisiae. The term can include substrates or products of reactions performed by one or more enzymes encoded by S. cerevisiae gene(s), reactions occurring in S. cerevisiae that are performed by one or more non-genetically encoded macromolecule, protein or enzyme, or reactions that occur spontaneously in a S. cerevisiae cell. Metabolites are understood to be reactants within the meaning of the term. It will be understood that when used in reference to an in silico model or data structure, a reactant is intended to be a representation of a chemical that is a substrate or a product of a reaction that occurs in or by a viable strain of S. cerevisiae.

As used herein the term "substrate" is intended to mean a reactant that can be converted to one or more products by a reaction. The term can include, for example, a reactant that is to be chemically changed due to nucleophilic or electrophilic addition, nucleophilic or electrophilic substitution, elimination, isomerization, deamination, phosphorylation, methylation, reduction, oxidation or that is to change location such as by being transported across a membrane or to a different compartment.

As used herein, the term "product" is intended to mean a reactant that results from a reaction with one or more substrates. The term can include, for example, a reactant that has been chemically changed due to nucleophilic or electrophilic addition, nucleophilic or electrophilic substitution, elimination, isomerization, deamination, phosphorylation, methylation, reduction or oxidation or that has changed location such as by being transported across a membrane or to a different compartment.

As used herein, the term "stoichiometric coefficient" is intended to mean a numerical constant correlating the number of one or more reactants and the number of one or more products in a chemical reaction. Typically, the numbers are integers as they denote the number of molecules of each reactant in an elementally balanced chemical equation that describes the corresponding conversion. However, in some cases the numbers can take on non-integer values, for example, when used in a lumped reaction or to reflect empirical data.

As used herein, the term "plurality," when used in reference to S. cerevisiae reactions or reactants is intended to mean at least 2 reactions or reactants. The term can include any number of S. cerevisiae reactions or reactants in the range from 2 to the number of naturally occurring reactants or reactions for a particular strain of S. cerevisiae. Thus, the term can include, for example, at least 10, 20, 30, 50, 100, 150, 200, 300, 400, 500, 600 or more reactions or reactants. The number of reactions or reactants can be expressed as a portion of the total number of naturally occurring reactions for a particular strain of S. cerevisiae such as at least 20%, 30%, 50%, 60%, 75%, 90%, 95% or 98% of the total number of naturally occurring reactions that occur in a particular strain of S. cerevisiae.

As used herein, the term "data structure" is intended to mean a physical or logical relationship among data elements, designed to support specific data manipulation functions. The term can include, for example, a list of data elements that can be added combined or otherwise manipulated such as a list of representations for reactions from which reactants can be related in a matrix or network. The term can also include a matrix that correlates data elements from two or more lists of information such as a matrix that correlates reactants to reactions. Information included in the term can represent, for example, a substrate or product of a chemical reaction, a chemical reaction relating one or more substrates to one or more products, a constraint placed on a reaction, or a stoichiometric coefficient.

As used herein, the term "constraint" is intended to mean an upper or lower boundary for a reaction. A boundary can specify a minimum or maximum flow of mass, electrons or energy through a reaction. A boundary can further specify directionality of a reaction. A boundary can be a constant value such as zero, infinity, or a numerical value such as an integer and non-integer.

As used herein, the term "activity," when used in reference to a reaction, is intended to mean the rate at which a product is produced or a substrate is consumed. The rate at which a product is produced or a substrate is consumed can also be referred to as the flux for the reaction.

As used herein, the term "activity," when used in reference to S. cerevisiae is intended to mean the rate of a change from an initial state of S. cerevisiae to a final state of S. cerevisiae. The term can include, the rate at which a chemical is consumed or produced by S. cerevisiae, the rate of growth of S. cerevisiae or the rate at which energy or mass flow through a particular subset of reactions.

The invention provides a computer readable medium, having a data structure relating a plurality of S. cerevisiae reactants to a plurality of S. cerevisiae reactions, wherein each of the S. cerevisiae reactions includes a reactant identified as a substrate of the reaction, a reactant identified as a product of the reaction and a stoichiometric coefficient relating the substrate and the product.

The plurality of S. cerevisiae reactions can include reactions of a peripheral metabolic pathway. As used herein, the term "peripheral," when used in reference to a metabolic pathway, is intended to mean a metabolic pathway that includes one or more reactions that are not a part of a central metabolic pathway. As used herein, the term "central," when used in reference to a metabolic pathway, is intended to mean a metabolic pathway selected from glycolysis, the pentose phosphate pathway (PPP), the tricarboxylic acid (TCA) cycle and the electron transfer system (ETS), associated anapleurotic reactions, and pyruvate metabolism.

A plurality of S. cerevisiae reactants can be related to a plurality of S. cerevisiae reactions in any data structure that represents, for each reactant, the reactions by which it is consumed or produced. Thus, the data structure, which is referred to herein as a "reaction network data structure," serves as a representation of a biological reaction network or system. An example of a reaction network that can be represented in a reaction network data structure of the invention is the collection of reactions that constitute the metabolic reactions of S. cerevisiae.

The methods and models of the invention can be applied to any strain of S. cerevisiae including, for example, strain CEN.PK113.7D or any laboratory or production strain. A strain of S. cerevisiae can be identified according to classification criteria known in the art. Classification criteria include, for example, classical microbiological characteristics, such as those upon which taxonomic classification is traditionally based, or evolutionary distance as determined for example by comparing sequences from within the genomes of organisms, such as ribosome sequences.

The reactants to be used in a reaction network data structure of the invention can be obtained from or stored in a compound database. As used herein, the term "compound database" is intended to mean a computer readable medium or media containing a plurality of molecules that includes substrates and products of biological reactions. The plurality of molecules can include molecules found in multiple organisms, thereby constituting a universal compound database. Alternatively, the plurality of molecules can be limited to those that occur in a particular organism, thereby constituting an organism-specific compound database. Each reactant in a compound database can be identified according to the chemical species and the cellular compartment in which it is present. Thus, for example, a distinction can be made between glucose in the extracellular compartment versus glucose in the cytosol. Additionally each of the reactants can be specified as a metabolite of a primary or secondary metabolic pathway. Although identification of a reactant as a metabolite of a primary or secondary metabolic pathway does not indicate any chemical distinction between the reactants in a reaction, such a designation can assist in visual representations of large networks of reactions.

As used herein, the term "compartment" is intended to mean a subdivided region containing at least one reactant, such that the reactant is separated from at least one other reactant in a second region. A subdivided region included in the term can be correlated with a subdivided region of a cell. Thus, a subdivided region included in the term can be, for example, the intracellular space of a cell; the extracellular space around a cell; the periplasmic space; the interior space of an organelle such as a mitochondrium, endoplasmic reticulum, Golgi apparatus, vacuole or nucleus; or any subcellular space that is separated from another by a membrane or other physical barrier. Subdivided regions can also be made in order to create virtual boundaries in a reaction network that are not correlated with physical barriers. Virtual boundaries can be made for the purpose of segmenting the reactions in a network into different compartments or substructures.

As used herein, the term "substructure" is intended to mean a portion of the information in a data structure that is separated from other information in the data structure such that the portion of information can be separately manipulated or analyzed. The term can include portions subdivided according to a biological function including, for example, information relevant to a particular metabolic pathway such as an internal flux pathway, exchange flux pathway, central metabolic pathway, peripheral metabolic pathway, or secondary metabolic pathway. The term can include portions subdivided according to computational or mathematical principles that allow for a particular type of analysis or manipulation of the data structure.

The reactions included in a reaction network data structure can be obtained from a metabolic reaction database that includes the substrates, products, and stoichiometry of a plurality of metabolic reactions of *S. cerevisiae*. The reactants in a reaction network data structure can be designated as either substrates or products of a particular reaction, each with a stoichiometric coefficient assigned to it to describe the chemical conversion taking place in the reaction. Each reaction is also described as occurring in either a reversible or irreversible direction. Reversible reactions can either be represented as one reaction that operates in both the forward and reverse direction or be decomposed into two irreversible reactions, one corresponding to the forward reaction and the other corresponding to the backward reaction.

Reactions included in a reaction network data structure can include intra-system or exchange reactions. Intra-system reactions are the chemically and electrically balanced inter-conversions of chemical species and transport processes, which serve to replenish or drain the relative amounts of certain metabolites. These intra-system reactions can be classified as either being transformations or translocations. A transformation is a reaction that contains distinct sets of compounds as substrates and products, while a translocation contains reactants located in different compartments. Thus, a reaction that simply transports a metabolite from the extracellular environment to the cytosol, without changing its chemical composition is solely classified as a translocation, while a reaction such as the phosphotransferase system (PTS) which takes extracellular glucose and converts it into cytosolic glucose-6-phosphate is a translocation and a transformation.

Exchange reactions are those which constitute sources and sinks, allowing the passage of metabolites into and out of a compartment or across a hypothetical system boundary. These reactions are included in a model for simulation purposes and represent the metabolic demands placed on *S. cerevisiae*. While they may be chemically balanced in certain cases, they are typically not balanced and can often have only a single substrate or product. As a matter of convention the exchange reactions are further classified into demand exchange and input/output exchange reactions.

The metabolic demands placed on the *S. cerevisiae* metabolic reaction network can be readily determined from the dry weight composition of the cell which is available in the published literature or which can be determined experimentally. The uptake rates and maintenance requirements for *S. cerevisiae* can be determined by physiological experiments in which the uptake rate is determined by measuring the depletion of the substrate. The measurement of the biomass at each point can also be determined, in order to determine the uptake rate per unit biomass. The maintenance requirements can be determined from a chemostat experiment. The glucose uptake rate is plotted versus the growth rate, and the y-intercept is interpreted as the non-growth associated maintenance requirements. The growth associated maintenance requirements are determined by fitting the model results to the experimentally determined points in the growth rate versus glucose uptake rate plot.

Input/output exchange reactions are used to allow extracellular reactants to enter or exit the reaction network represented by a model of the invention. For each of the extracellular metabolites a corresponding input/output exchange reaction can be created. These reactions can either be irreversible or reversible with the metabolite indicated as a substrate with a stoichiometric coefficient of one and no products produced by the reaction. This particular convention is adopted to allow the reaction to take on a positive flux value (activity level) when the metabolite is being produced or removed from the reaction network and a negative flux value when the metabolite is being consumed or introduced into the reaction network. These reactions will be further constrained during the course of a simulation to specify exactly which metabolites are available to the cell and which can be excreted by the cell.

A demand exchange reaction is always specified as an irreversible reaction containing at least one substrate. These reactions are typically formulated to represent the production of an intracellular metabolite by the metabolic network or the aggregate production of many reactants in balanced ratios such as in the representation of a reaction that leads to biomass formation, also referred to as growth. As set forth in the Examples, the biomass components to be produced for growth include L-Alanine, L-Arginine, L-Asparagine, L-Aspartate, L-Cysteine, L-Glutamine, L-Glutamate, Glycine, L-Histidine, L-Isoleucine, L-Leucine, L-Lysine, L-Methionine, L-Phenylalanine, L-Proline, L-Serine, L-Threonine, L-Tryptophan, L-Tyrosine, L-Valine, AMP, GMP, CMP, UMP, dAMP, dCMP, dTMP, dGMP, Glycogen, alpha,alpha-Trehalose, Mannan, beta-D-Glucan, Triacylglycerol, Ergosterol, Zymosterol, Phosphatidate, Phosphatidylcholine, Phosphatidylethanolamine, Phosphatidyl-D-myo-inositol, Phosphatidylserine, ATP, Sulfate, ADP and Orthophosphate, with exemplary values shown in Table 1.

TABLE 1

Cellular components of *S. cerevisiae* (mmol/gDW).

| ALA | 0.459 | CMP | 0.05 |
|---|---|---|---|
| ARG | 0.161 | dAMP | 0.0036 |
| ASN | 0.102 | dCMP | 0.0024 |
| ASP | 0.297 | dGMP | 0.0024 |
| CYS | 0.007 | DTMP | 0.0036 |
| GLU | 0.302 | TAGLY | 0.007 |
| GLN | 0.105 | ERGOST | 0.0007 |
| GLY | 0.290 | ZYMST | 0.015 |
| HIS | 0.066 | PA | 0.0006 |
| ILE | 0.193 | PINS | 0.005 |
| LEU | 0.296 | PS | 0.002 |
| LYS | 0.286 | PE | 0.005 |
| MET | 0.051 | PC | 0.006 |
| PHE | 0.134 | GLYCOGEN | 0.519 |
| PRO | 0.165 | TRE | 0.023 |
| SER | 0.185 | Mannan | 0.809 |
| THR | 0.191 | 13GLUCAN | 1.136 |
| TRP | 0.028 | SLF | 0.02 |
| TYR | 0.102 | ATP | 23.9166 |
| VAL | 0.265 | ADP | 23.9166 |
| AMP | 0.051 | PI | 23.9456 |
| GMP | 0.051 | Biomass | 1 |
| UMP | 0.067 | | |

A demand exchange reaction can be introduced for any metabolite in a model of the invention. Most commonly, these reactions are introduced for metabolites that are required to be produced by the cell for the purposes of creating a new cell such as amino acids, nucleotides, phospholipids, and other biomass constituents, or metabolites that are to be produced for alternative purposes. Once these metabolites are identified, a demand exchange reaction that is irreversible and specifies the metabolite as a substrate with a stoichiometric coefficient of unity can be created. With these specifications, if the reaction is active it leads to the net production of the metabolite by the system meeting potential production demands. Examples of processes that can be represented as a demand exchange reaction in a reaction network data structure and analyzed by the methods of the invention include, for example, production or secretion of an individual protein; production or secretion of an individual metabolite such as an amino acid, vitamin, nucleoside, antibiotic or surfactant; production of ATP for extraneous energy requiring processes such as locomotion; or formation of biomass constituents.

In addition to these demand exchange reactions that are placed on individual metabolites, demand exchange reactions that utilize multiple metabolites in defined stoichiometric ratios can be introduced. These reactions are referred to as aggregate demand exchange reactions. An example of an aggregate demand reaction is a reaction used to simulate the concurrent growth demands or production requirements associated with cell growth that are placed on a cell, for example, by simulating the formation of multiple biomass constituents simultaneously at a particular cellular growth rate.

A hypothetical reaction network is provided in FIG. 1 to exemplify the above-described reactions and their interactions. The reactions can be represented in the exemplary data structure shown in FIG. 2 as set forth below. The reaction network, shown in FIG. 1, includes intrasystem reactions that occur entirely within the compartment indicated by the shaded oval such as reversible reaction $R_2$ which acts on reactants B and G and reaction $R_3$ which converts one equivalent of B to two equivalents of F. The reaction network shown in FIG. 1 also contains exchange reactions such as input/output exchange reactions $A_{xt}$ and $E_{xt}$, and the demand exchange reaction, $V_{growth}$, which represents growth in response to the one equivalent of D and one equivalent of F. Other intrasystem reactions include $R_1$ which is a translocation and transformation reaction that translocates reactant A into the compartment and transforms it to reactant G and reaction $R_6$ which is a transport reaction that translocates reactant E out of the compartment.

A reaction network can be represented as a set of linear algebraic equations which can be presented as a stoichiometric matrix S, with S being an m×n matrix where m corresponds to the number of reactants or metabolites and n corresponds to the number of reactions taking place in the network. An example of a stoichiometric matrix representing the reaction network of FIG. 1 is shown in FIG. 2. As shown in FIG. 2, each column in the matrix corresponds to a particular reaction n, each row corresponds to a particular reactant m, and each $S_{mn}$ element corresponds to the stoichiometric coefficient of the reactant m in the reaction denoted n. The stoichiometric matrix includes intra-system reactions such as $R_2$ and $R_3$ which are related to reactants that participate in the respective reactions according to a stoichiometric coefficient having a sign indicative of whether the reactant is a substrate or product of the reaction and a value correlated with the number of equivalents of the reactant consumed or produced by the reaction. Exchange reactions such as $-E_{xt}$ and $-A_{xt}$ are similarly correlated with a stoichiometric coefficient. As exemplified by reactant E, the same compound can be treated separately as an internal reactant (E) and an external reactant ($E_{external}$) such that an exchange reaction ($R_6$) exporting the compound is correlated by stoichiometric coefficients of $-1$ and 1, respectively. However, because the compound is treated as a separate reactant by virtue of its compartmental location, a reaction, such as $R_5$, which produces the internal reactant (E) but does not act on the external reactant ($E_{external}$) is correlated by stoichiometric coefficients of 1 and 0, respectively. Demand reactions such as $V_{growth}$ can also be included in the stoichiometric matrix being correlated with substrates by an appropriate stoichiometric coefficient.

As set forth in further detail below, a stoichiometric matrix provides a convenient format for representing and analyzing a reaction network because it can be readily manipulated and used to compute network properties, for example, by using linear programming or general convex analysis. A reaction network data structure can take on a variety of formats so long as it is capable of relating reactants and reactions in the manner exemplified above for a stoichiometric matrix and in a manner that can be manipulated to determine an activity of one or more reactions using methods such as those exemplified below. Other examples of reaction network data structures that are useful in the invention include a connected graph, list of chemical reactions or a table of reaction equations.

A reaction network data structure can be constructed to include all reactions that are involved in *S. cerevisiae* metabolism or any portion thereof. A portion of *S. cerevisiae* metabolic reactions that can be included in a reaction network data structure of the invention includes, for example, a central metabolic pathway such as glycolysis, the TCA cycle, the PPP or ETS; or a peripheral metabolic pathway such as amino acid biosynthesis, amino acid degradation, purine biosynthesis, pyrimidine biosynthesis, lipid biosynthesis, fatty acid metabolism, vitamin or cofactor biosynthesis, transport processes and alternative carbon source catabolism. Examples of individual pathways within the peripheral pathways are set forth in Table 2, including, for example, the cofactor biosynthesis pathways for quinone biosynthesis, riboflavin biosynthesis, folate biosyntheis, coenzyme A biosynthesis, NAD biosynthesis, biotin biosynthesis and thiamin biosynthesis.

Depending upon a particular application, a reaction network data structure can include a plurality of S. cerevisiae reactions including any or all of the reactions listed in Table 2. Exemplary reactions that can be included are those that are identified as being required to achieve a desired S. cerevisiae specific growth rate or activity including, for example, reactions identified as ACO1, CDC19, CIT1, DAL7, ENO1, FBA1, FBP1, FUM1, GND1, GPM1, HXK1, ICL1, IDH1, IDH2, IDP1, IDP2, IDP3, KGD1, KGD2, LPD1, LSC1, LSC2, MDH1, MDH2, MDH3, MLS1, PDC1, PFK1, PFK2, PGI1, PGK1, PGM1, PGM2, PYC1, PYC2, PYK2, RKI1, RPE1, SOL1, TAL1, TDH1, TDH2, TDH3, TKL1, TPI1, ZWF1 in Table 2. Other reactions that can be included are those that are not described in the literature or genome annotation but can be identified during the course of iteratively developing a S. cerevisiae model of the invention including, for example, reactions identified as MET6_2, MNADC, MNADD1, MNADE, MNADF_1, MNADPHPS, MNADG1, MNADG2, MNADH, MNPT1.

TABLE 2

| Locus # | E.C. # | Gene | Gene Description | Reaction | Rxn Name |
|---|---|---|---|---|---|
| Carbohydrate Metabolism Glycolysis/Gluconeogenesis | | | | | |
| YCL040W | 2.7.1.2 | GLK1 | Glucokinase | GLC + ATP -> G6P + ADP | glk1_1 |
| YCL040W | 2.7.1.2 | GLK1 | Glucokinase | MAN + ATP -> MAN6P + ADP | glk1_2 |
| YCL040W | 2.7.1.2 | GLK1 | Glucokinase | bDGLC + ATP -> bDG6P + ADP | glk1_3 |
| YFR053C | 2.7.1.1 | HXK1 | Hexokinase I (PI) (also called Hexokinase A) | bDGLC + ATP -> G6P + ADP | hxk1_1 |
| YFR053C | 2.7.1.1 | HXK1 | Hexokinase I (PI) (also called Hexokinase A) | GLC + ATP -> G6P + ADP | hxk1_2 |
| YFR053C | 2.7.1.1 | HXK1 | Hexokinase I (PI) (also called Hexokinase A) | MAN + ATP -> MAN6P + ADP | hxk1_3 |
| YFR053C | 2.7.1.1 | HXK1 | Hexokinase I (PI) (also called Hexokinase A) | ATP + FRU -> ADP + F6P | hxk1_4 |
| YGL253W | 2.7.1.1 | HXK2 | Hexokinase II (PII) (also called Hexokinase B) | bDGLC + ATP -> G6P + ADP | hxk2_1 |
| YGL253W | 2.7.1.1 | HXK2 | Hexokinase II (PII) (also called Hexokinase B) | GLC + ATP -> G6P + ADP | hxk2_2 |
| YGL253W | 2.7.1.1 | HXK2 | Hexokinase II (PII) (also called Hexokinase B) | MAN + ATP -> MAN6P + ADP | hxk2_3 |
| YGL253W | 2.7.1.1 | HXK2 | Hexokinase II (PII) (also called Hexokinase B) | ATP + FRU -> ADP + F6P | hxk2_4 |
| YBR196C | 5.3.1.9 | PGI1 | Glucose-6-phosphate isomerase | G6P <-> F6P | pgi1_1 |
| YBR196C | 5.3.1.9 | PGI1 | Glucose-6-phosphate isomerase | G6P <-> bDG6P | pgi1_2 |
| YBR196C | 5.3.1.9 | PGI1 | Glucose-6-phosphate isomerase | bDG6P <-> F6P | pgi1_3 |
| YMR205C | 2.7.1.11 | PFK2 | phosphofructokinase beta subunit | F6P + ATP -> FDP + ADP | pfk2 |
| YGR240C | 2.7.1.11 | PFK1 | phosphofructokinase alpha subunit | F6P + ATP -> FDP + ADP | pfk1_1 |
| YGR240C | 2.7.1.11 | PFK1 | phosphofructokinase alpha subunit | ATP + TAG6P -> ADP + TAG16P | pfk1_2 |
| YGR240C | 2.7.1.11 | PFK1 | phosphofructokinase alpha subunit | ATP + S7P -> ADP + S17P | pfk1_3 |
| YKL060C | 4.1.2.13 | FBA1 | fructose-bisphosphate aldolase | FDP <-> T3P2 + T3P1 | fba1_1 |
| YDR050C | 5.3.1.1 | TPI1 | triosephosphate isomerase | T3P2 <-> T3P1 | tpi1 |
| YJL052W | 1.2.1.12 | TDH1 | Glyceraldehyde-3-phosphate dehydrogenase 1 | T3P1 + PI + NAD <-> NADH + 13PDG | tdh1 |
| YJR009C | 1.2.1.12 | TDH2 | glyceraldehyde 3-phosphate dehydrogenase | T3P1 + PI + NAD <-> NADH + 13PDG | tdh2 |
| YGR192C | 1.2.1.12 | TDH3 | Glyceraldehyde-3-phosphate dehydrogenase 3 | T3P1 + PI + NAD <-> NADH + 13PDG | tdh3 |
| YCR012W | 2.7.2.3 | PGK1 | phosphoglycerate kinase | 13PDG + ADP <-> 3PG + ATP | pgk1 |
| YKL152C | 5.4.2.1 | GPM1 | Phosphoglycerate mutase | 13PDG <-> 23PDG | gpm1_1 |
| YKL152C | 5.4.2.1 | GPM1 | Phosphoglycerate mutase | 3PG <-> 2PG | gpm1_2 |
| YDL021W | 5.4.2.1 | GPM2 | Similar to GPM1 (phosphoglycerate mutase) | 3PG <-> 2PG | gpm2 |
| YOL056W | 5.4.2.1 | GPM3 | phosphoglycerate mutase | 3PG <-> 2PG | gpm3 |
| YGR254W | 4.2.1.11 | ENO1 | enolase I | 2PG <-> PEP | eno1 |
| YHR174W | 4.2.1.11 | ENO2 | enolase | 2PG <-> PEP | eno2 |
| YMR323W | 4.2.1.11 | ERR1 | Protein with similarity to enolases | 2PG <-> PEP | eno3 |
| YPL281C | 4.2.1.11 | ERR2 | enolase related protein | 2PG <-> PEP | eno4 |
| YOR393W | 4.2.1.11 | ERR1 | enolase related protein | 2PG <-> PEP | eno5 |
| YAL038W | 2.7.1.40 | CDC19 | Pyruvate kinase | PEP + ADP -> PYR + ATP | cdc19 |
| YOR347C | 2.7.1.40 | PYK2 | Pyruvate kinase, glucose-repressed isoform | PEP + ADP -> PYR + ATP | pyk2 |
| YER178w | 1.2.4.1 | PDA1 | pyruvate dehydrogenase (lipoamide) alpha chain precursor, E1 component, alpha unit | PYRm + COAm + NADm -> NADHm + CO2m + ACCOAm | pda1 |
| YBR221c | 1.2.4.1 | PDB1 | pyruvate dehydrogenase (lipoamide) beta chain precursor, E1 component, beta unit | | |
| YNL071w | 2.3.1.12 | LAT1 | dihydrolipoamide S-acetyltransferase, E2 component | | |
| Citrate cycle (TCA cycle) | | | | | |
| YNR001C | 4.1.3.7 | CIT1 | Citrate synthase, Nuclear encoded mitochondrial protein. | ACCOAm + OAm -> COAm + CITm | cit1 |
| YCR005C | 4.1.3.7 | CIT2 | Citrate synthase, non-mitochondrial citrate synthase | ACCOA + OA -> COA + CIT | cit2 |
| YPR001W | 4.1.3.7 | cit3 | Citrate synthase, Mitochondrial isoform of citrate synthase | ACCOAm + OAm -> COAm + CITm | cit3 |
| YLR304C | 4.2.1.3 | aco1 | Aconitase, mitochondrial | CITm <-> ICITm | aco1 |
| YJL200C | 4.2.1.3 | YJL200C | aconitate hydratase homolog | CITm <-> ICITm | aco2 |
| YNL037C | 1.1.1.41 | IDH1 | Isocitrate dehydrogenase (NAD+) mito, subunit1 | ICITm + NADm -> CO2m + NADHm + AKGm | idh1 |
| YOR136W | 1.1.1.41 | IDH2 | Isocitrate dehydrogenase (NAD+) mito, subunit2 | | |
| YDL066W | 1.1.1.42 | IDP1 | Isocitrate dehydrogenase (NADP+) | ICITm + NADPm -> NADPHm + OSUCm | idp1_1 |

TABLE 2-continued

| Locus # | E.C. # | Gene | Gene Description | Reaction | Rxn Name |
|---|---|---|---|---|---|
| YLR174W | 1.1.1.42 | IDP2 | Isocitrate dehydrogenase (NADP+) | ICIT + NADP -> NADPH + OSUC | idp2_1 |
| YNL009W | 1.1.1.42 | IDP3 | Isocitrate dehydrogenase (NADP+) | ICIT + NADP -> NADPH + OSUC | idp3_1 |
| YDL066W | 1.1.1.42 | IDP1 | Isocitrate dehydrogenase (NADP+) | OSUCm -> CO2m + AKGm | idp1_2 |
| YLR174W | 1.1.1.42 | IDP2 | Isocitrate dehydrogenase (NADP+) | OSUC -> CO2 + AKG | idp2_2 |
| YNL009W | 1.1.1.42 | IDP3 | Isocitrate dehydrogenase (NADP+) | OSUC -> CO2 + AKG | idp3_2 |
| YIL125W | 1.2.4.2 | kgd1 | alpha-ketoglutarate dehydrogenase complex, E1 component | AKGm + NADm + COAm -> CO2m + NADHm + SUCCOAm | kgd1a |
| YDR148C | 2.3.1.61 | KGD2 | Dihydrolipoamide S-succinyltransferase, E2 component | | |
| YGR244C | 6.2.1.4/ 62.1.5 | LSC2 | Succinate-CoA ligase (GDP-forming) | ATPm + SUCCm + COAm <-> ADPm + PIm + SUCCOAm | lsc2 |
| YOR142W | 6.2.1.4/ 6.2.1.5 | LSC1 | succinate-CoA ligase alpha subunit | ATPm + ITCm + COAm <-> ADPm + PIm + ITCCOAm | lsc1 |

Electron Transport System, Complex II

| YKL141w | 1.3.5.1 | SDH3 | succinate dehydrogenase cytochrome b | SUCCm + FADm <-> FUMm + FADH2m | sdh3 |
|---|---|---|---|---|---|
| YKL148c | 1.3.5.1 | SDH1 | succinate dehydrogenase cytochrome b | | |
| YLL041c | 1.3.5.1 | SDH2 | Succinate dehydrogenase (ubiquinone) iron-sulfur protein subunit | | |
| YDR178w | 1.3.5.1 | SDH4 | succinate dehydrogenase membrane anchor subunit | | |
| YLR164w | 1.3.5.1 | YLR164w | strong similarity to SDH4P | | |
| YMR118c | 1.3.5.1 | YMR118c | strong similarity to succinate dehydrogenase | | |
| YJL045w | 1.3.5.1 | YJL045w | strong similarity to succinate dehydrogenase flavoprotein | | |
| YEL047c | 1.3.99.1 | YEL047c | soluble fumarate reductase, cytoplasmic | FADH2m + FUM -> SUCC + FADm | frds1 |
| YJR051W | 1.3.99.1 | osm1 | Mitochondrial soluble fumarate reductase involved in osmotic regulation | FADH2m + FUMm -> SUCCm + FADm | osm1 |
| YPL262W | 4.2.1.2 | FUM1 | Fumaratase | FUMm <-> MALm | fum1_1 |
| YPL262W | 4.2.1.2 | FUM1 | Fumaratase | FUM <-> MAL | fum1_2 |
| YKL085W | 1.1.1.37 | MDH1 | mitochondrial malate dehydrogenase | MALm + NADm <-> NADHm + OAm | mdh1 |
| YDL078C | 1.1.1.37 | MDH3 | MALATE DEHYDROGENASE, PEROXISOMAL | MAL + NAD <-> NADH + OA | mdh3 |
| YOL126C | 1.1.1.37 | MDH2 | malate dehydrogenase, cytoplasmic | MAL + NAD <-> NADH + OA | mdh2 |

Anaplerotic Reactions

| YER065C | 4.1.3.1 | ICL1 | isocitrate lyase | ICIT -> GLX + SUCC | icl1 |
|---|---|---|---|---|---|
| YPR006C | 4.1.3.1 | ICL2 | Isocitrate lyase, may be nonfunctional | ICIT -> GLX + SUCC | icl2 |
| YIR031C | 4.1.3.2 | dal7 | Malate synthase | ACCOA + GLX -> COA + MAL | dal7 |
| YNL117W | 4.1.3.2 | MLS1 | Malate synthase | ACCOA + GLX -> COA + MAL | mls1 |
| YKR097W | 4.1.1.49 | pck1 | phosphoenolpyruvate carboxykinase | OA + ATP -> PEP + CO2 + ADP | pck1 |
| YLR377C | 3.1.3.11 | FBP1 | fructose-1,6-bisphosphatase | FDP -> F6P + PI | fbp1 |
| YGL062W | 6.4.1.1 | PYC1 | pyruvate carboxylase | PYR + ATP + CO2 -> ADP + OA + PI | pyc1 |
| YBR218C | 6.4.1.1 | PYC2 | pyruvate carboxylase | PYR + ATP + CO2 -> ADP + OA + PI | pyc2 |
| YKL029C | 1.1.1.38 | MAE1 | mitochondrial malic enzyme | MALm + NADPm -> CO2m + NADPHm + PYRm | mae1 |

Pentose phosphate cycle

| YNL241C | 1.1.1.49 | zwf1 | Glucose-6-phosphate-1-dehydrogenase | G6P + NADP <-> D6PGL + NADPH | zwf1 |
|---|---|---|---|---|---|
| YNR034W | 3.1.1.31 | SOL1 | Possible 6-phosphogluconolactonase | D6PGL -> D6PGC | sol1 |
| YCR073W-A | 3.1.1.31 | SOL2 | Possible 6-phosphogluconolactonase | D6PGL -> D6PGC | sol2 |
| YHR163W | 3.1.1.31 | SOL3 | Possible 6-phosphogluconolactonase | D6PGL -> D6PGC | sol3 |
| YGR248W | 3.1.1.31 | SOL4 | Possible 6-phosphogluconolactonase | D6PGL -> D6PGC | sol4 |
| YGR256W | 1.1.1.44 | GND2 | 6-phosphogluconate dehydrogenase | D6PGC + NADP -> NADPH + CO2 + RL5P | gnd2 |
| YHR183W | 1.1.1.44 | GND1 | 6-phosphogluconate dehydrogenase | D6PGC + NADP -> NADPH + CO2 + RL5P | gnd1 |
| YJL121C | 5.1.3.1 | RPE1 | ribulose-5-P 3-epimerase | RL5P <-> X5P | rpe1 |
| YOR095C | 5.3.1.6 | RKI1 | ribose-5-P isomerase | RL5P <-> R5P | rki1 |
| YBR117C | 2.2.1.1 | TKL2 | transketolase | R5P + X5P <-> T3P1 + S7P | tkl2_1 |
| YBR117C | 2.2.1.1 | TKL2 | transketolase | X5P + E4P <-> F6P + T3P1 | tkl2_2 |
| YPR074C | 2.2.1.1 | TKL1 | transketolase | R5P + X5P <-> T3P1 + S7P | tkl1_1 |
| YPR074C | 2.2.1.1 | TKL1 | transketolase | X5P + E4P <-> F6P + T3P1 | tkl1_2 |
| YLR354C | 2.2.1.2 | TAL1 | transaldolase | T3PI + S7P <-> E4P + F6P | tal1_1 |
| YGR043C | 2.2.1.2 | YGR043C | transaldolase | T3PI + S7P <-> E4P + F6P | tal1_2 |
| YCR036W | 2.7.1.15 | RBK1 | Ribokinase | RIB + ATP -> R5P + ADP | rbk1_1 |
| YCR036W | 2.7.1.15 | RBK1 | Ribokinase | DRIB + ATP -> DR5P + ADP | rbk1_2 |
| YKL127W | 5.4.2.2 | pgm1 | phosphoglucomutase | R1P <-> R5P | pgm1_1 |
| YKL127W | 5.4.2.2 | pgm1 | phosphoglucomutase 1 | G1P <-> G6P | pgm1_2 |
| YMR105C | 5.4.2.2 | pgm2 | phosphoglucomutase | R1P <-> R5P | pgm2_1 |
| YMR105C | 5.4.2.2 | pgm2 | Phosphoglucomutase | G1P <-> G6P | pgm2_2 |

Mannose

| YER003C | 5.3.1.8 | PMI40 | mannose-6-phosphate isomerase | MAN6P <-> F6P | pmi40 |
|---|---|---|---|---|---|
| YFL045C | 5.4.2.8 | SEC53 | phosphomannomutase | MAN6P <-> MAN1P | sec53 |

TABLE 2-continued

| Locus # | E.C. # | Gene | Gene Description | Reaction | Rxn Name |
|---|---|---|---|---|---|
| YDL055C | 2.7.7.13 | PSA1 | mannose-1-phosphate guanyltransferase, GDP-mannose pyrophosphorylase | GTP + MANIP -> PPI + GDPMAN | psa1 |
| Fructose | | | | | |
| YIL107C | 2.7.1.105 | PFK26 | 6-Phosphofructose-2-kinase | ATP + F6P -> ADP + F26P | pfk26 |
| YOL136C | 2.7.1.105 | pfk27 | 6-phosphofructo-2-kinase | ATP + F6P -> ADP + F26P | pfk27 |
| YJL155C | 3.1.3.46 | FBP26 | Fructose-2,6-biphosphatase | F26P -> F6P + PI | fbp26 |
| — | 2.7.1.56 | — | 1-Phosphofructokinase (Fructose 1-phosphate kinase) | FIP + ATP -> FDP + ADP | frc3 |
| Sorbose | S c does not metabolize sorbitol, erythritol, mannitol, xylitol, ribitol, arabinitol, galactinol | | | | |
| YJR159W | 1.1.1.14 | SOR1 | sorbitol dehydrogenase (L-iditol 2-dehydrogenase) | SOT + NAD -> FRU + NADH | sor1 |
| Galactose metabolism | | | | | |
| YBR020W | 2.7.1.6 | gal1 | galactokinase | GLAC + ATP -> GAL1P + ADP | gal1 |
| YBR018C | 2.7.7.10 | gal7 | galactose-1-phosphate uridyl transferase | UTP + GAL1P <-> PPI + UDPGAL | gal7 |
| YBR019C | 5.1.3.2 | gal10 | UDP-glucose 4-epimerase | UDPGAL <-> UDPG | gal10 |
| YHL012W | 2.7.7.9 | YHL012W | UTP--Glucose 1-Phosphate Uridylyltransferase | G1P + UTP <-> UDPG + PPI | ugp1_2 |
| YKL035W | 2.7.7.9 | UGP1 | Uridinephosphoglucose pyrophosphorylase | G1P + UTP <-> UDPG + PPI | ugp1_1 |
| YBR184W | 3.2.1.22 | YBR184W | Alpha-galactosidase (melibiase) | MELI -> GLC + GLAC | mel1_1 |
| YBR184W | 3.2.1.22 | YBR184W | Alpha-galactosidase (melibiase) | DFUC -> GLC + GLAC | mel1_2 |
| YBR184W | 3.2.1.22 | YBR184W | Alpha-galactosidase (melibiase) | RAF -> GLAC + SUC | mel1_3 |
| YBR184W | 3.2.1.22 | YBR184W | Alpha-galactosidase (melibiase) | GLACL <-> MYOI + GLAC | mel1_4 |
| YBR184W | 3.2.1.22 | YBR184W | Alpha-galactosidase (melibiase) | EPM <-> MAN + GLAC | mel1_5 |
| YBR184W | 3.2.1.22 | YBR184W | Alpha-galactosidase (melibiase) | GGL <-> GL + GLAC | mel1_6 |
| YBR184W | 3.2.1.22 | YBR184W | Alpha-galactosidase (melibiase) | MELT <->SOT + GLAC | mel1_7 |
| YBR299W | 3.2.1.20 | MAL32 | Maltase | MLT -> 2 GLC | mal32a |
| YGR287C | 3.2.1.20 | YGR287C | putative alpha glucosidase | MLT -> 2 GLC | mal32b |
| YGR292W | 3.2.1.20 | MAL12 | Maltase | MLT -> 2 GLC | mal12a |
| YIL172C | 3.2.1.20 | YIL172C | putative alpha glucosidase | MLT -> 2 GLC | mal12b |
| YJL216C | 3.2.1.20 | YJL216C | probable alpha-glucosidase (MALTase) | MLT -> GLC | mal12c |
| YJL221C | 3.2.1.20 | FSP2 | homology to maltase(alpha-D-glucosidase) | MLT -> 2 GLC | fsp2a |
| YJL221C | 3.2.1.20 | FSP2 | homology to maltase(alpha-D-glucosidase) | 6DGLC -> GLAC + GLC | fsp2b |
| YBR018C | 2.7.7.12 | GAL7 | UDPglucose--hexose-1-phosphate uridylyltransferase | UDPG + GAL1P <-> G1P + UDPGAL | unkrx10 |
| Trehalose | | | | | |
| YBR126C | 2.4.1.15 | TPS1 | trehalose-6-P synthetase, 56 kD synthase subunit of trehalose-6-phosphate synthase\/phosphatase complex | UDPG + G6P -> UDP + TRE6P | tps1 |
| YML100W | 2.4.1.15 | tsl1 | trehalose-6-P synthetase, 123 kD regulatory subunit of trehalose-6-phosphate synthase\/phosphatase complex\, homologous to TPS3 gene product | UDPG + G6P -> UDP + TRE6P | tsl1 |
| YMR261C | 2.4.1.15 | TPS3 | trehalose-6-P synthetase, 115 kD regulatory subunit of trehalose-6-phosphate synthase\/phosphatase complex | UDPG + G6P -> UDP + TRE6P | tps3 |
| YDR074W | 3.1.3.12 | TPS2 | Trehalose-6-phosphate phosphatase | TRE6P -> TRE + PI | tps2 |
| YPR026W | 3.2.1.28 | ATH1 | Acid trehalase | TRE -> 2 GLC | ath1 |
| YBR001C | 3.2.1.28 | NTH2 | Neutral trehalase, highly homologous to Nth1p | TRE -> 2 GLC | nth2 |
| YDR001C | 3.2.1.28 | NTH1 | neutral trehalase | TRE -> 2 GLC | nth1 |
| Glycogen Metabolism (sucrose and sugar metabolism) | | | | | |
| YEL011W | 2.4.1.18 | glc3 | Branching enzyme, 1,4-glucan-6-(1,4-glucano)-transferase | GLYCOGEN + PI -> G1P | glc3 |
| YPR160W | 2.4.1.1 | GPH1 | Glycogen phosphorylase | GLYCOGEN + PI -> G1P | gph1 |
| YFR015C | 2.4.1.11 | GSY1 | Glycogen synthase (UDP-gluocse--starch glucosyltransferase) | UDPG -> UDP + GLYCOGEN | gsy1 |
| YLR258W | 2.4.1.11 | GSY2 | Glycogen synthase (UDP-gluocse--starch glucosyltransferase) | UDPG -> UDP + GLYCOGEN | gsy2 |
| Pyruvate Metabolism | | | | | |
| YAL054C | 6.2.1.1 | acs1 | acetyl-coenzyme A synthetase | ATPm + ACm + COAm -> AMPm + PPIm + ACCOAm | acs1 |
| YLR153C | 6.2.1.1 | ACS2 | acetyl-coenzyme A synthetase | ATP + AC + COA -> AMP + PPI + ACCOA | acs2 |
| YDL168W | 1.2.1.1 | SFA1 | Formaldehyde dehydrogenase/long-chain alcohol dehydrogenase | FALD + RGT + NAD <-> FGT + NADH | sfa1_1 |
| YJL068C | 3.1.2.12 | — | S-Formylglutathione hydrolase | FGT <-> RGT + FOR | unkrx11 |
| YGR087C | 4.1.1.1 | PDC6 | pyruvate decarboxylase | PYR -> CO2 + ACAL | pdc6 |
| YLR134W | 4.1.1.1 | PDC5 | pyruvate decarboxylase | PYR -> CO2 + ACAL | pdc5 |
| YLR044C | 4.1.1.1 | pdc1 | pyruvate decarboxylase | PYR -> CO2 + ACAL | pdc1 |
| YBL015W | 3.1.2.1 | ACH1 | acetyl CoA hydrolase | COA + AC -> ACCOA | ach1_1 |
| YBL015W | 3.1.2.1 | ACH1 | acetyl CoA hydrolase | COAm + ACm -> ACCOAm | ach1_2 |
| YDL131W | 4.1.3.21 | LYS21 | probable homocitrate synthase, mitochondrial isozyme precursor | ACCOA + AKG -> HCIT + COA | lys21 |
| YDL182W | 4.1.3.21 | LYS20 | homocitrate synthase, cytosolic isozyme | ACCOA + AKG -> HCIT + COA | lys20 |
| YDL182W | 4.1.3.21 | LYS20 | Homocitrate synthase | ACCOAm + AKGm -> HCITm + COAm | lys20a |
| YGL256W | 1.1.1.1 | adh4 | alcohol dehydrogenase isoenzyme IV | ETH + NAD <-> ACAL + NADH | adh4 |
| YMR083W | 1.1.1.1 | adh3 | alcohol dehydrogenase isoenzyme III | ETHm + NADm <-> ACALm + NADHm | adh3 |
| YMR303C | 1.1.1.1 | adh2 | alcohol dehydrogenase II | ETH + NAD <-> ACAL + NADH | adh2 |

TABLE 2-continued

| Locus # | E.C. # | Gene | Gene Description | Reaction | Rxn Name |
|---|---|---|---|---|---|
| YBR145W | 1.1.1.1 | ADH5 | alcohol dehydrogenase isoenzyme V | ETH + NAD <-> ACAL + NADH | adh5 |
| YOL086C | 1.1.1.1 | adh1 | Alcohol dehydrogenase | ETH + NAD <-> ACAL + NADH | adh1 |
| YDL168W | 1.1.1.1 | SFA1 | Alcohol dehydrogenase I | ETH + NAD <-> ACAL + NADH | sfa1_2 |
| | | | Glyoxylate and dicarboxylate metabolism | | |
| | | | Glyoxal Pathway | | |
| YML004C | 4.4.1.5 | GLO1 | Lactoylglutathione lyase, glyoxalase I | RGT + MTHGXL <-> LGT | glo1 |
| YDR272W | 3.1.2.6 | GLO2 | Hydroxyacylglutathione hydrolase | LGT -> RGT + LAC | glo2 |
| YOR040W | 3.1.2.6 | GLO4 | glyoxalase II (hydroxyacylglutathione hydrolase) | LGTm -> RGTm + LACm | glo4 |
| | | | Energy Metabolism | | |
| | | | Oxidative Phosphorylation | | |
| YBR011C | 3.6.1.1 | ipp1 | Inorganic pyrophosphatase | PPI -> 2 PI | ipp1 |
| YMR267W | 3.6.1.1 | ppa2 | mitochondrial inorganic pyrophosphatase | PPIm -> 2 PIm | ppa2 |
| | 1.2.2.1 | FDNG | Formate dehydrogenase | FOR + Qm -> QH2m + CO2 + 2 HEXT | fdng |
| YML120C | 1.6.5.3 | NDI1 | NADH dehydrogenase (ubiquinone) | NADHm + Qm -> QH2m + NADm | ndi1 |
| YDL085W | 1.6.5.3 | NDH2 | Mitochondrial NADH dehydrogenase that catalyzes the oxidation of cytosolic NADH | NADH + Qm -> QH2m + NAD | ndh2 |
| YMR145C | 1.6.5.3 | NDH1 | Mitochondrial NADH dehydrogenase that catalyzes the oxidation of cytosolic NADH | NADH + Qm -> QH2m + NAD | ndh1 |
| YHR042W | 1.6.2.4 | NCP1 | NADPH--ferrihemoprotein reductase | NADPH + 2 FERIm -> NADP + 2 FEROm | ncp1 |
| YKL141w | 1.3.5.1 | SDH3 | succinate dehydrogenase cytochrome b | FADH2m + Qm <-> FADm + QH2m | fad |
| YKL148c | 1.3.5.1 | SDH1 | succinate dehydrogenase cytochrome b | | |
| YLL041c | 1.3.5.1 | SDH2 | succinate dehydrogenase cytochrome b | | |
| YDR178w | 1.3.5.1 | SDH4 | succinate dehydrogenase cytochrome b | | |
| | | | Electron Transport System, Complex III | | |
| YEL024W | 1.10.2.2 | RIP1 | ubiquinol-cytochrome c reductase iron-sulfur subunit | O2m + 4 FEROm + 6 Hm -> 4 FERIm | cyto |
| Q0105 | 1.10.2.2 | CYTB | ubiquinol-cytochrome c reductase cytochrome b subunit | | |
| YOR065W | 1.10.2.2 | CYT1 | ubiquinol-cytochrome c reductase cytochrome c1 subunit | | |
| YBL045C | 1.10.2.2 | COR1 | ubiquinol-cytochrome c reductase core subunit 1 | | |
| YPR191W | 1.10.2.2 | QCR1 | ubiquinol-cytochrome c reductase core subunit 2 | | |
| YPR191W | 1.10.2.2 | QCR2 | ubiquinol-cytochrome c reductase | | |
| YFR033C | 1.10.2.2 | QCR6 | ubiquinol-cytochrome c reductase subunit 6 | | |
| YDR529C | 1.10.2.2 | QCR7 | ubiquinol-cytochrome c reductase subunit 7 | | |
| YJL166W | 1.10.2.2 | QCR8 | ubiquinol-cytochrome c reductase subunit 8 | | |
| YGR183C | 1.10.2.2 | QCR9 | ubiquinol-cytochrome c reductase subunit 9 | | |
| YHR001W-A | 1.10.2.2 | QCR10 | ubiquinol-cytochrome c reductase subunit 10 | | |
| | | | Electron Transport System, Complex IV | | |
| Q0045 | 1.9.3.1 | COX1 | cytochrome c oxidase subunit I | QH2m + 2 FERIm + 15 Hm -> Qm + 2 FEROm | cytr |
| Q0250 | 1.9.3.1 | COX2 | cytochrome c oxidase subunit I | | |
| Q0275 | 1.9.3.1 | COX3 | cytochrome c oxidase subunit I | | |
| YDL067C | 1.9.3.1 | COX9 | cytochrome c oxidase subunit I | | |
| YGL187C | 1.9.3.1 | COX4 | cytochrome c oxidase subunit I | | |
| YGL191W | 1.9.3.1 | COX13 | cytochrome c oxidase subunit I | | |
| YHR051W | 1.9.3.1 | COX6 | cytochrome c oxidase subunit I | | |
| YIL111W | 1.9.3.1 | COX5B | cytochrome c oxidase subunit I | | |
| YLR038C | 1.9.3.1 | COX12 | cytochrome c oxidase subunit I | | |
| YLR395C | 1.9.3.1 | COX8 | cytochrome c oxidase subunit I | | |
| YMR256C | 1.9.3.1 | COX7 | cytochrome c oxidase subunit I | | |
| YNL052W | 1.9.3.1 | COX5A | cytochrome c oxidase subunit I | | |
| | | | ATP Synthase | | |
| YBL099W | 3.6.1.34 | ATP1 | F1F0-ATPase complex, F1 alpha subunit | ADPm + PIm -> ATPm + 3 Hm | atp1 |
| YPL271W | 3.6.1.34 | ATP15 | F1F0-ATPase complex, F1 epsilon subunit | | |
| YDL004W | 3.6.1.34 | ATP16 | F-type H+-transporting ATPase delta chain | | |
| Q0085 | 3.6.1.34 | ATP6 | F1F0-ATPase complex, FO A subunit | | |
| YBR039W | 3.6.1.34 | ATP3 | F1F0-ATPase complex, F1 gamma subunit | | |
| YBR127C | 3.6.1.34 | VMA2 | H+-ATPase V1 domain 60 KD subunit, vacuolar | | |
| YPL078C | 3.6.1.34 | ATP4 | F1F0-ATPase complex, F1 delta subunit | | |
| YDR298C | 3.6.1.34 | ATP5 | F1F0-ATPase complex, OSCP subunit | | |
| YDR377W | 3.6.1.34 | ATP17 | ATP synthase complex, subunit f | | |
| YJR121W | 3.6.1.34 | ATP2 | F1F0-ATPase complex, F1 beta subunit | | |
| YKL016C | 3.6.1.34 | ATP7 | F1F0-ATPase complex, FO D subunit | | |
| YLR295C | 3.6.1.34 | ATP14 | ATP synthase subunit h | | |
| Q0080 | 3.6.1.34 | ATP8 | F-type H+-transporting ATPase subunit 8 | | |
| Q0130 | 3.6.1.34 | ATP9 | F-type H+-transporting ATPase subunit c | | |
| YOL077W-A | 3.6.1.34 | ATP19 | ATP synthase k chain, mitochondrial | | |
| YPR020W | 3.6.1.34 | ATP20 | subunit G of the dimeric form of mitochondrial F1F0-ATP synthase | | |

TABLE 2-continued

| Locus # | E.C. # | Gene | Gene Description | Reaction | Rxn Name |
|---|---|---|---|---|---|
| YLR447C | 3.6.1.34 | VMA6 | V-type H+-transporting ATPase subunit AC39 | | |
| YGR020C | 3.6.1.34 | VMA7 | V-type H+-transporting ATPase subunit F | | |
| YKL080W | 3.6.1.34 | VMA5 | V-type H+-transporting ATPase subunit C | | |
| YDL185W | 3.6.1.34 | TFP1 | V-type H+-transporting ATPase subunit A | | |
| YBR127C | 3.6.1.34 | VMA2 | V-type H+-transporting ATPase subunit B | | |
| YOR332W | 3.6.1.34 | VMA4 | V-type H+-transporting ATPase subunit E | | |
| YEL027W | 3.6.1.34 | CUP5 | V-type H+-transporting ATPase proteolipid subunit | | |
| YHR026W | 3.6.1.34 | PPA1 | V-type H+-transporting ATPase proteolipid subunit | | |
| YPL234C | 3.6.1.34 | TFP3 | V-type H+-transporting ATPase proteolipid subunit | | |
| YMR054W | 3.6.1.34 | STV1 | V-type H+-transporting ATPase subunit I | | |
| YOR270C | 3.6.1.34 | VPH1 | V-type H+-transporting ATPase subunit I | | |
| YEL051W | 3.6.1.34 | VMA8 | V-type H+-transporting ATPase subunit D | | |
| YHR039C-A | 3.6.1.34 | VMA10 | vacuolar ATP synthase subunit G | | |
| YPR036W | 3.6.1.34 | VMA13 | V-type H+-transporting ATPase 54 kD subunit | | |
| | | | Electron Transport System, Complex IV | | |
| Q0045 | 1.9.3.1 | COX1 | cytochrome-c oxidase subunit I | 4 FEROm + O2m + 6 Hm -> 4 FERIm | cox1 |
| Q0275 | 1.9.3.1 | COX3 | Cytochrome-c oxidase subunit III, mitochondrially-coded | | |
| Q0250 | 1.9.3.1 | COX2 | cytochrome-c oxidase subunit II | | |
| YDL067C | 1.9.3.1 | COX9 | Cytochrome-c oxidase | | |
| YGL187C | 1.9.3.1 | COX4 | cytochrome-c oxidase chain IV | | |
| YGL191W | 1.9.3.1 | COX13 | cytochrome-c oxidase chain VIa | | |
| YHR051W | 1.9.3.1 | COX6 | cytochrome-c oxidase subunit VI | | |
| YIL111W | 1.9.3.1 | COX5b | cytochrome-c oxidase chain Vb | | |
| YLR038C | 1.9.3.1 | COX12 | cytochrome-c oxidase, subunit VIB | | |
| YLR395C | 1.9.3.1 | COX8 | cytochrome-c oxidase chain VIII | | |
| YMR256C | 1.9.3.1 | COX7 | cytochrome-c oxidase, subunit VII | | |
| YNL052W | 1.9.3.1 | COX5A | cytochrome-c oxidase chain V.A precursor | | |
| YML054C | 1.1.2.3 | cyb2 | Lactic acid dehydrogenase | 2 FERIm + LLACm -> PYRm + 2 FEROm | cyb2 |
| YDL174C | 1.1.2.4 | DLD1 | mitochondrial enzyme D-lactate ferricytochrome c oxidoreductase | 2 FERIm + LACm -> PYRm + 2 FEROm | dld1 |
| | | | Methane metabolism | | |
| YPL275W | 1.2.1.2 | YPL275W | putative formate dehydrogenase/putative pseudogene | FOR + NAD -> CO2 + NADH | tfo1a |
| YPL276W | 1.2.1.2 | YPL276W | putative formate dehydrogenase/putative pseudogene | FOR + NAD -> CO2 + NADH | tfo1b |
| YOR388C | 1.2.1.2 | FDH1 | Protein with similarity to formate dehydrogenases | FOR + NAD -> CO2 + NADH | fdh1 |
| | | | Nitrogen metabolism | | |
| YBR208C | 6.3.4.6 | DUR1 | urea amidolyase containing urea carboxylase/allophanate hydrolase | ATP + UREA + CO2 <-> ADP + PI + UREAC | dur1 |
| YBR208C | 3.5.1.54 | DUR1 | Allophanate hydrolase | UREAC -> 2 NH3 + 2 CO2 | dur2 |
| YJL126W | 3.5.5.1 | NIT2 | nitrilase | ACNL -> INAC + NH3 | nit2 |
| | | | Sulfur metabolism (Cystein biosynthesis maybe) | | |
| YJR137C | 1.8.7.1 | ECM17 | Sulfite reductase | H2SO3 + 3 NADPH <-> H2S + 3 NADP | ecm17 |
| | | | Lipid Metabolism<br>Fatty acid biosynthesis | | |
| YER015W | 6.2.1.3 | FAA2 | Long-chain-fatty-acid--CoA ligase, Acyl-CoA synthetase | ATP + LCCA + COA <-> AMP + PPI + ACOA | faa2 |
| YIL009W | 6.2.1.3 | FAA3 | Long-chain-fatty-acid--CoA ligase, Acyl-CoA synthetase | ATP + LCCA + COA <-> AMP + PPI + ACOA | faa3 |
| YOR317W | 6.2.1.3 | FAA1 | Long-chain-fatty-acid--CoA ligase, Acyl-CoA synthetase | ATP + LCCA + COA <-> AMP + PPI + ACOA | faa1 |
| YMR246W | 6.2.1.3 | FAA4 | Acyl-CoA synthase (long-chain fatty acid CoA ligase); contributes to activation of imported myristate | ATP + LCCA + COA <-> AMP + PPI + ACOA | faa4 |
| YKR009C | 1.1.1.- | FOX2 | 3-Hydroxyacyl-CoA dehydrogenase | HACOA + NAD <-> OACOA + NADH | fox2b |
| YIL160C | 2.3.1.16 | pot1 | 3-Ketoacyl-CoA thiolase | OACOA + COA -> ACOA + ACCOA | pot1_1 |
| YPL028W | 2.3.1.9 | erg10 | Acetyl-CoA C-acetyltransferase, ACETOACETYL-CoA THIOLASE | 2 ACCOA <-> COA + AACCOA | erg10_1 |
| YPL028W | 2.3.1.9 | erg10 | Acetyl-CoA C-acetyltransferase, ACETOACETYL-COA THIOLASE (mitoch) | 2 ACCOAm <-> COAm + AACCOAm | erg10_2 |
| | | | Fatty Acids Metabolism<br>Mitochondrial type II fatty acid synthase | | |
| YKL192C | 1.6.5.3 | ACP1 | Acyl carrier protein, component of mitochondrial type II fatty acid synthase | NADHm + Qm -> NADm + QH2m | ACP1 |
| YER061C | — | CEM1 | Beta-ketoacyl-ACP synthase, mitochondrial (3-oxoacyl-[Acyl-carrier-protein] synthase) | | |
| YOR221C | — | MCT1 | Malonyl CoA-acyl carrier protein transferase | | |
| YKL055C | — | OAR1 | 3-Oxoacyl-[acyl-carrier-protein] reductase | | |
| YKL192C/<br>YER061C/<br>YOR221C/<br>YKL055C | 1.6.5.3/-/<br>-/- | ACP1/<br>CEM1/<br>MCT1/<br>OAR1 | Type II fatty acid synthase | ACACPm + 4 MALACPm + 8 NADPHm -> 8 NADPm + C100ACPm + 4 CO2m + 4 ACPm | TypeII_1 |

TABLE 2-continued

| Locus # | E.C. # | Gene | Gene Description | Reaction | Rxn Name |
|---|---|---|---|---|---|
| YKL192C/ YER061C/ YOR221C/ YKL055C | 1.6.5.3/-/ -/- | ACP1/ CEM1/ MCT1/ OAR1 | Type II fatty acid synthase | ACACPm + 5 MALACPm + 10 NADPHm -> 10 NADPm + C120ACPm + 5 CO2m + 5 ACPm | TypeII_2 |
| YKL192C/ YER061C/ YOR221C/ YKL055C | 1.6.5.3/-/ -/- | ACP1/ CEM1/ MCT1/ OAR1 | Type II fatty acid synthase | ACACPm + 6 MALACPm + 12 NADPHm -> 12 NADPm + C140ACPm + 6 CO2m + 6 ACPm | TypeII_3 |
| YKL192C/ YER061C/ YOR221C/ YKL055C | 1.6.5.3/- -/- | ACP1/ CEM1/ MCT1/ OAR1 | Type II fatty acid synthase | ACACPm + 6 MALACPm + 11 NADPHm -> 11 NADPm + C141ACPm + 6 CO2m + 6 ACPm | TypeII_4 |
| YKL192C/ YER061C/ YOR221C/ YKL055C | 1.6.5.3/-/ -/- | ACP1/ CEM1/ MCT1/ OAR1 | Type II fatty acid synthase | ACACPm + 7 MALACPm + 14 NADPHm -> 14 NADPm + C160ACPm + 7 CO2m + 7 ACPm | TypeII_5 |
| YKL192C/ YER061C/ YOR221C/ YKL055C | 1.6.5.3/-/ -/- | ACP1/ CEM1/ MCT1/ OAR1 | Type II fatty acid synthase | ACACPm + 7 MALACPm + 13 NADPHm -> 13 NADPm + C161ACPm + 7 CO2m + 7 ACPm | TypeII_6 |
| YKL192C/ YER061C/ YOR221C/ YKL055C | 1.6.5.3/-/ -/- | ACP1/ CEM1/ MCT1/ OAR1 | Type II fatty acid synthase | ACACPm + 8 MALACPm + 16 NADPHm -> 16 NADPm + C180ACPm + 8 CO2m + 8 ACPm | TypeII_7 |
| YKL192C/ YER061C/ YOR221C/ YKL055C | 1.6.5.3/-/ -/- | ACP1/ CEM1/ MCT1/ OAR1 | Type II fatty acid synthase | ACACPm + 8 MALACPm + 15 NADPHm -> 15 NADPm + C181ACPm + 8 CO2m + 8 ACPm | TypeII_8 |
| YKL192C/ YER061C/ YOR221C/ YKL055C | 1.6.5.3/-/ -/- | ACP1/ CEM1/ MCT1/ OAR1 | Type II fatty acid synthase | ACACPm + 8 MALACPm + 14 NADPHm -> 14 NADPm + C182ACPm + 8 CO2m + 8 ACPm | TypeII_9 |
| | | | Cytosolic fatty acid synthesis | | |
| YNR016C | 6.4.1.2 6.3.4.14 | ACC1 | acetyl-CoA carboxylase (ACC)/biotin carboxylase | ACCOA + ATP + CO2 <-> MALCOA + ADP + PI | acc1 |
| YKL182w | 4.2.1.61, 1.3.1.9, 2.3.1.38, 2.3.1.39, 3.1.2.14, 2.3.1.86 | fas1 | fatty-acyl-CoA synthase, beta chain | MALCOA + ACP <-> MALACP + COA | fas1_1 |
| YPL231w | 2.3.1.85, 1.1.1.100, 2.3.1.41 | FAS2 | fatty-acyl-CoA synthase, alpha chain | | |
| YKL182w | 4.2.1.61, 1.3.1.9, 2.3.1.38; 2.3.1.39, 3.1.2.14, 2.3.1.86 | fas1 | fatty-acyl-CoA synthase, beta chain | ACCOA + ACP <-> ACACP + COA | fas1_2 |
| YER061C | 2.3.1.41 | CEM1 | 3-Oxoacyl-[acyl-carrier-protein] synthase | MALACPm + ACACPm -> ACPm + CO2m + 3OACPm | cem1 |
| YGR037C/ YNR016C/ YKL182W/ YPL231w | 6.4.1.2, 6.3.4.1, 4.2.3.1.85; 1.1.1.100; 2.3.1.41; 4.2.1.61 | ACB1/ ACC1/ fas1/ FAS2/ | b-Ketoacyl-ACP synthase (C10, 0), fatty acyl CoA synthase | ACACP + 4 MALACP + 8 NADPH -> 8 NADP + C100ACP + 4 CO2 + 4 ACP | c100sn |
| YGR037C/ YNR016C/ YKL182W/ YPL231w | 6.4.1.2, 6.3.4.1, 4.2.3.1.85; 1.1.1.100, 2.3.1.41, 4.2.1.61 | ACB1/ ACC1/ fas1/ FAS2/ | b-Ketoacyl-ACP synthase (C12, 0), fatty acyl CoA synthase | ACACP + 5 MALACP + 10 NADPH -> 10 NADP + C120ACP + 5 CO2 + 5 ACP | c120sn |
| YGR037C/ YNR016C/ YKL182W/ YPL231w | 6.4.1.2, 6.3.4.1; 4.2.3.1.85; 1.1.1.100, 2.3.1.41; 4.2.1.61 | ACB1/ ACC1/ fas1/ FAS2/ | b-Ketoacyl-ACP synthase (C14, 0) | ACACP + 6 MALACP + 12 NADPH -> 12 NADP + C140ACP + 6 CO2 + 6 ACP | c140sn |
| YGR037C/ YNR016C/ YKL182W/ YPL231w | 6.4.1.2, 6.3.4.1, 4.2.3.1.85; 1.1.1.100; 2.3.1.41; 4.2.1.61 | ACB1/ ACC1/ fas1/ FAS2/ | b-Ketoacyl-ACP synthase I (C14, 1) | ACACP + 6 MALACP + 11 NADPH -> 11 NADP + C141ACP + 6 CO2 + 6 ACP | c141sy |

TABLE 2-continued

| Locus # | E.C. # | Gene | Gene Description | Reaction | Rxn Name |
|---|---|---|---|---|---|
| YGR037C/ YNR016C/ YKL182W/ YPL231w | 6.4.1.2, 6.3.4.1, 4.2.3.1.85; 1.1.1.100, 2.3.1.41, 4.2.1.61 | ACB1/ ACC1/ fas1/ FAS2 | b-Ketoacyl-ACP synthase I (C16, 0) | ACACP + 7 MALACP + 14 NADPH -> 14 NADP + C160ACP + 7 CO2 + 7 ACP | c160sn |
| YGR037C/ YNR016C/ YKL182W/ YPL231w | 6.4.1.2; 6.3.4.1; 4.2.3.1.85; 1.1.1.100, 2.3.1.41, 4.2.1.61 | ACB1/ ACC1/ fas1/ FAS2 | b-Ketoacyl-ACP synthase I (C16, 1) | ACACP + 7 MALACP + 13 NADPH -> 13 NADP + C161ACP + 7 CO2 + 7 ACP | c161sy |
| YGR037C/ YNR016C/ YKL182W/ YPL231w | 6.4.1.2, 6.3.4.1; 42.3.1.85; 1.1.1.100, 2.3.1.41, 4.2.1.61 | ACB1/ ACC1/ fas1/ FAS2 | b-Ketoacyl-ACP synthase I (C18, 0) | ACACP + 8 MALACP + 16 NADPH -> 16 NADP + C180ACP + 8 CO2 + 8 ACP | c180sy |
| YGR037C/ YNR016C/ YKL182W/ YPL231w | 6.4.1.2, 6.3.4.1; 4.2.3.1.85, 1.1.1.100, 2.3.1.41; 4.2.1.61 | ACB1/ ACC1/ fas1/ FAS2 | b-Ketoacyl-ACP synthase I (C18, 1) | ACACP + 8 MALACP + 15 NADPH -> 15 NADP + C181ACP + 8 CO2 + 8 ACP | c181sy |
| YGR037C/ YNR016C/ YKL182W/ YPL231w | 6.4.1.2, 6.3.4.1, 4.2.3.1.85; 1.1.1.100, 2.3.1.41, 4.2.1.61 | ACB1/ ACC1/ fas1/ FAS2 | b-Ketoacyl-ACP synthase I (C18, 2) | ACACP + 8 MALACP + 14 NADPH -> 14 NADP + C182ACP + 8 CO2 + 8 ACP | c182sy |
| YKL182W | 4.2.1.61 | fas1 | 3-hydroxypalmitoyl-[acyl-carrier protein] dehydratase | 3HPACP <-> 2HDACP | fas1_3 |
| YKL182W | 1.3.1.9 | fas1 | Enoyl-ACP reductase | AACP + NAD <-> 23DAACP + NADH | fas1_4 |

Fatty acid degradation

| YGL205W/ YKR009C/ YIL160C | 1.3.3.6/ 2.3.1.18 | POX1/ FOX2/ POT3 | Fatty acid degradation | C140 + ATP + 7 COA + 7 FADm + 7 NAD -> AMP + PPI + 7 FADH2m + 7 NADH + 7 ACCOA | c140dg |
| YGL205W/ YKR009C/ YIL160C | 1.3.3.6/ 2.3.1.18 | POX1/ FOX2/ POT3 | Fatty acid degradation | C160 + ATP + 8 COA + 8 FADm + 8 NAD -> AMP + PPI + 8 FADH2m + 8 NADH + 8 ACCOA | c160dg |
| YGL205W/ YKR009C/ YIL160C | 1.3.3.6/ 2.3.1.18 | POX1/ FOX2/ POT3 | Fatty acid degradation | C180 + ATP + 9 COA + 9 FADm + 9 NAD -> AMP + PPI + 9 FADH2m + 9 NADH + 9 ACCOA | c180dg |

Phospholipid Biosynthesis

| — | — | | Glycerol-3-phosphate acyltransferase | GL3P + 0.017 C100ACP + 0.062 C120ACP + 0.1 C140ACP + 0.27 C160ACP + 0.169 C161ACP + 0.055 C180ACP + 0.235 C181ACP + 0.093 C182ACP -> AGL3P + ACP | Gat1_1 |
| — | — | | Glycerol-3-phosphate acyltransferase | GL3P + 0.017 C100ACP + 0.062 C120ACP + 0.1 C140ACP + 0.27 + C160ACP + 0.169 C161ACP + 0.055 C180ACP + 0.235 C181ACP + 0.093 C182ACP -> AGL3P + ACP | Gat2_1 |
| — | — | | Glycerol-3-phosphate acyltransferase | T3P2 + 0.017 C100ACP + 0.062 C120ACP + 0.1 C140ACP + 0.27 C160ACP + 0.169 C161ACP + 0.055 C180ACP + 0.235 C181ACP + 0.093 C182ACP -> AT3P2 + ACP | Gat1_2 |
| — | — | | Glycerol-3-phosphate acyltransferase | T3P2 + 0.017 C100ACP + 0.062 C120ACP + 0.1 C140ACP + 0.27 C160ACP + 0.169 C161ACP + 0.055 C180ACP + 0.235 C181ACP + 0.093 C182ACP -> AT3P2 + ACP | Gat2_2 |
| — | — | | Acyldihydroxyacetonephosphate reductase | AT3P2 + NADPH -> AGL3P + NADP | ADHAPR |

TABLE 2-continued

| Locus # | E.C. # | Gene | Gene Description | Reaction | Rxn Name |
|---|---|---|---|---|---|
| YDL052C | 2.3.1.51 | SLC1 | 1-Acylglycerol-3-phosphate acyltransferase | AGL3P + 0.017 C100ACP + 0.062 C120ACP + 0.100 C140ACP + 0.270 C160ACP + 0.169 C161ACP + 0.055 C180ACP + 0.235 C181ACP + 0.093 C182ACP -> PA + ACP | slc1 |
| — | 2.3.1.51 | — | 1-Acylglycerol-3-phosphate acyltransferase | AGL3P + 0.017 C100ACP + 0.062 C120ACP + 0.100 C140ACP + 0.270 C160ACP + 0.169 C161ACP + 0.055 C180ACP + 0.235 C181ACP + 0.093 C182ACP -> PA + ACP | AGAT |
| YBR029C | 2.7.7.41 | CDS1 | CDP-Diacylglycerol synthetase | PAm + CTPm <-> CDPDGm + PPIm | cds1a |
| YBR029C | 2.7.7.41 | CDS1 | CDP-Diacylglycerol synthetase | PA + CTP <-> CDPDG + PPI | cds1b |
| YER026C | 2.7.8.8 | cho1 | phosphatidylserine synthase | CDPDG + SER <-> CMP + PS | cho1a |
| YER026C | 2.7.8.8 | cho1 | Phosphatidylserine synthase | CDPDGm + SERm <-> CMPm + PSm | cho1b |
| YGR170W | 4.1.1.65 | PSD2 | phosphatidylserine decarboxylase located in vacuole or Golgi | PS -> PE + CO2 | psd2 |
| YNL169C | 4.1.1.65 | PSD1 | Phosphatidylserine Decarboxylase 1 | PSm -> PEm + CO2m | psd1 |
| YGR157W | 2.1.1.17 | CHO2 | Phosphatidylethanolamine N-methyltransferase | SAM + PE -> SAH + PMME | cho2 |
| YJR073C | 2.1.1.16 | OPI3 | Methylene-fatty-acyl-phospholipid synthase. | SAM + PMME -> SAH + PDME | opi3_1 |
| YJR073C | 2.1.1.16 | OPI3 | Phosphatidyl-N-methylethanolamine N-methyltransferase | PDME + SAM -> PC + SAH | opi3_2 |
| YLR133W | 2.7.1.32 | CKI1 | Choline kinase | ATP + CHO -> ADP + PCHO | cki1 |
| YGR202C | 2.7.7.15 | PCT1 | Cholinephosphate cytidylyltransferase | PCHO + CTP -> CDPCHO + PPI | pct1 |
| YNL130C | 2.7.8.2 | CPT1 | Diacylglycerol cholinephosphotransferase | CDPCHO + DAGLY -> PC + CMP | cpt1 |
| YDR147W | 2.7.1.82 | EKI1 | Ethanolamine kinase | ATP + ETHM -> ADP + PETHM | eki1 |
| YGR007W | 2.7.7.14 | MUQ1 | Phosphoethanolamine cytidylyltransferase | PETHM + CTP -> CDPETN + PPI | ect1 |
| YHR123W | 2.7.8.1 | EPT1 | Ethanolaminephosphotransferase. | CDPETN + DAGLY <-> CMP + PE | ept1 |
| YJL153C | 5.5.1.4 | ino1 | myo-Inositol-1-phosphate synthase | G6P -> MI1P | ino1 |
| YHR046C | 3.1.3.25 | INM1 | myo-Inositol-1(or 4)-monophosphatase | MI1P -> MYOI + PI | impa1 |
| YPR113W | 2.7.8.11 | PIS1 | phosphatidylinositol synthase | CDPDG + MYOI -> CMP + PINS | pis1 |
| YJR066W | 2.7.1.137 | tor1 | 1-Phosphatidylinositol 3-kinase | ATP + PINS -> ADP + PINSP | tor1 |
| YKL203C | 2.7.1.137 | tor2 | 1-Phosphatidylinositol 3-kinase | ATP + PINS -> ADP + PINSP | tor2 |
| YLR240W | 2.7.1.137 | vps34 | 1-Phosphatidylinositol 3-kinase | ATP + PINS -> ADP + PINSP | vps34 |
| YNL267W | 2.7.1.67 | PIK1 | Phosphatidylinositol 4-kinase (PI 4-kinase), generates PtdIns 4-P | ATP + PINS -> ADP + PINS4P | pik1 |
| YLR305C | 2.7.1.67 | STT4 | Phosphatidylinositol 4-kinase | ATP + PINS -> ADP + PINS4P | sst4 |
| YFR019W | 2.7.1.68 | FAB1 | PROBABLE PHOSPHATIDYLINOSITOL-4-PHOSPHATE 5-KINASE, 1-phosphatidylinositol-4-phosphate kinase | PINS4P + ATP -> D45PI + ADP | fab1 |
| YDR208W | 2.7.1.68 | MSS4 | Phosphatidylinositol-4-phosphate 5-kinase, required for proper organization of the actin cytoskeleton | PINS4P + ATP -> D45PI + ADP | mss4 |
| YPL268W | 3.1.4.11 | plc1 | 1-phosphatidylinositol-4,5-bisphosphate phosphodiesterase | D45PI -> TPI + DAGLY | plc1 |
| YCL004W | 2.7.8.8 | PGS1 | CDP-diacylglycerol - serine O-phosphatidyltransferase | CDPDGm + GL3Pm <-> CMPm + PGPm | pgs1 |
| — | 3.1.3.27 | | Phosphatidylglycerol phosphate phosphatase A | PGPm -> PIm + PGm | Pgpa |
| YDL142C | | CRD1 | Cardiolipin synthase | CDPDGm + PGm -> CMPm + CLm | crd1 |
| YDR284C | 2.7.8.5 | DPP1 | diacylglycerol pyrophosphate phosphatase | PA -> DAGLY + PI | dpp1 |
| YDR503C | | LPP1 | lipid phosphate phosphatase | DGPP -> PA + PI | lpp1 |

Sphingoglycolipid Metabolism

| Locus # | E.C. # | Gene | Gene Description | Reaction | Rxn Name |
|---|---|---|---|---|---|
| YDR062W | 2.3.1.50 | LCB2 | Serine C-palmitoyltransferase | PALCOA + SER -> COA + DHSPH + CO2 | lcb2 |
| YMR296C | 2.3.1.50 | LCB1 | Serine C-palmitoyltransferase | PALCOA + SER -> COA + DHSPH + CO2 | lcb1 |
| YBR265w | 1.1.1.102 | TSC10 | 3-Dehydrosphinganine reductase | DHSPH + NADPH -> SPH + NADP | tsc10 |
| YDR297W | | SUR2 | SYRINGOMYCIN RESPONSE PROTEIN 2 | SPH + O2 + NADPH -> PSPH + NADP | sur2 |
| — | | | Ceramide synthase | PSPH + C260COA -> CER2 + COA | csyna |
| — | | | Ceramide synthase | PSPH + C240COA -> CER2 + COA | csynb |
| YMR272C | | SCS7 | Ceramide hydroxylase that hydroxylates the C-26 fatty-acyl moiety of mositol-phosphorylceramide | CER2 + NADPH + O2 -> CER3 + NADP | scs7 |
| YKL004W | | AUR1 | IPS synthase, AUREOBASIDIN A RESISTANCE PROTEIN | CER3 + PINS -> IPC | aur1 |
| YBR036C | | CSG2 | Protein required for synthesis of the mannosylated sphingolipids | IPC + GDPMAN -> MIPC | csg2 |
| YPL057C | | SUR1 | Protein required for synthesis of the mannosylated sphingolipids | IPC + GDPMAN -> MIPC | sur1 |
| YDR072C | 2.-.-.- | IPT1 | MIP2C synthase, MANNOSYL DIPHOSPHORYLINOSITOL CERAMIDE SYNTHASE | MIPC + PINS -> MIP2C | ipt1 |

TABLE 2-continued

| Locus # | E.C. # | Gene | Gene Description | Reaction | Rxn Name |
|---|---|---|---|---|---|
| YOR171C | | LCB4 | Long chain base kinase, involved in sphingolipid metabolism | SPH + ATP -> DHSP + ADP | lcb4_1 |
| YLR260W | | LCB5 | Long chain base kinase, involved in sphingolipid metabolism | SPH + ATP -> DHSP + ADP | lcb5_1 |
| YOR171C | | LCB4 | Long chain base kinase, involved in sphingolipid metabolism | PSPH + ATP -> PHSP + ADP | lcb4_2 |
| YLR260W | | LCB5 | Long chain base kinase, involved in sphingolipid metabolism | PSPH + ATP -> PHSP + ADP | lcb5_2 |
| YJL134W | | LCB3 | Sphingoid base-phosphate phosphatase, putative regulator of sphingolipid metabolism and stress response | DHSP -> SPH + PI | lcb3 |
| YKR053C | | YSR3 | Sphingoid base-phosphate phosphatase, putative regulator of sphingolipid metabolism and stress response | DHSP -> SPH + PI | ysr3 |
| YDR294C | | DPL1 | Dihydrosphingosme-1-phosphate lyase | DHSP -> PETHM + C16A | dpl1 |
| | | | Sterol biosynthesis | | |
| YML126C | 4.1.3.5 | HMGS | 3-hydroxy-3-methylglutaryl coenzyme A synthase | H3MCOA + COA <-> ACCOA + AACCOA | hmgs |
| YLR450W | 1.1.1.34 | hmg2 | 3-hydroxy-3-methylglutaryl-coenzyme A (HMG-CoA) reductase isozyme | MVL + COA + 2 NADP <-> H3MCOA + 2 NADPH | hmg2 |
| YML075C | 1.1.1.34 | hmg1 | 3-hydroxy-3-methylglutaryl-coenzyme A (HMG-CoA) reductase isozyme | MVL + COA + 2 NADP <-> H3MCOA + 2 NADPH | hmg1 |
| YMR208W | 2.7.1.36 | erg12 | mevalonate kinase | ATP + MVL -> ADP + PMVL | erg12_1 |
| YMR208W | 2.7.1.36 | erg12 | mevalonate kinase | CTP + MVL -> CDP + PMVL | erg12_2 |
| YMR208W | 2.7.1.36 | erg12 | mevalonate kinase | GTP + MVL -> GDP + PMVL | erg12_3 |
| YMR208W | 2.7.1.36 | erg12 | mevalonate kinase | UTP + MVL -> UDP + PMVL | erg12_4 |
| YMR220W | 2.7.4.2 | ERG8 | 48 kDa Phosphomevalonate kinase | ATP + PMVL -> ADP + PPMVL | erg8 |
| YNR043W | 4.1.1.33 | MVD1 | Diphosphomevalonate decarboxylase | ATP + PPMVL -> ADP + PI + IPPP + CO2 | mvd1 |
| YPL117C | 5.3.3.2 | idi1 | Isopentenyl diphosphate.dimethylallyl diphosphate isomerase (IPP isomerase) | IPPP <-> DMPP | idi1 |
| YJL167W | 2.5.1.1 | ERG20 | prenyltransferase | DMPP + IPPP -> GPP + PPI | erg20_1 |
| YJL167W | 2.5.1.10 | ERG20 | Farnesyl diphosphate synthetase (FPP synthetase) | GPP + IPPP -> FPP + PPI | erg20_2 |
| YHR190W | 2.5.1.21 | ERG9 | Squalene synthase | 2 FPP + NADPH -> NADP + SQL | erg9 |
| YGR175C | 1.14.99.7 | ERG1 | Squalene monoxygenase | SQL + O2 + NADP -> S23E + NADPH | erg1 |
| YHR072W | 5.4.99.7 | ERG7 | 2,3-oxidosqualene-lanosterol cyclase | S23E -> LNST | erg7 |
| YHR007c | 1.14.14.1 | erg11 | cytochrome P450 lanosterol 14a-demethylase | LNST + RFP + O2 -> IGST + OFP | erg11_1 |
| YNL280c | 1.-.-.- | ERG24 | C-14 sterol reductase | IGST + NADPH -> DMZYMST + NADP | erg24 |
| YGR060w | 1.-.-.- | ERG25 | C-4 sterol methyl oxidase | 3 O2 + DMZYMST -> IMZYMST | erg25_1 |
| YGL001c | 5.3.3.1 | ERG26 | C-3 sterol dehydrogenase (C-4 decarboxylase) | IMZYMST -> IIMZYMST + CO2 | erg26_1 |
| YLR100C | | YLR100C | C-3 sterol keto reductase | IIMZYMST + NADPH -> MZYMST + NADP | erg11_2 |
| YGR060w | 1.-.-.- | ERG25 | C-4 sterol methyl oxidase | 3 O2 + MZYMST -> IZYMST | erg25_2 |
| YGL001c | 5.3.3.1 | ERG26 | C-3 sterol dehydrogenase (C-4 decarboxylase) | IZYMST -> IIZYMST + CO2 | erg26_2 |
| YLR100C | | YLR100C | C-3 sterol keto reductase | IIZYMST + NADPH -> ZYMST + NADP | erg11_3 |
| YML008c | 2.1.1.41 | erg6 | S-adenosyl-methionine delta-24-sterol-c-methyltransferase | ZYMST + SAM -> FEST + SAH | erg6 |
| YMR202W | | ERG2 | C-8 sterol isomerase | FEST -> EPST | erg2 |
| YLR056w | 1.-.-.- | ERG3 | C-5 sterol desaturase | EPST + O2 + NADPH -> NADP + ERTROL | erg3 |
| YMR015c | 1.14.14.- | ERG5 | C-22 sterol desaturase | ERTROL + O2 + NADPH -> NADP + ERTROL | erg5 |
| YGL012w | 1.-.-.- | ERG4 | sterol C-24 reductase | ERTEOL + NADPH -> ERGOST + NADP | erg4 |
| | | | | LNST + 3 O2 + 4 NADPH + NAD -> MZYMST + CO2 + 4 NADP + NADH | unkrxn3 |
| | | | | MZYMST + 3 O2 + 4 NADPH + NAD -> ZYMST + CO2 + 4 NADP + NADH | unkrxn4 |
| | 5.3.3.5 | | Cholestenol delta-isomerase | ZYMST + SAM -> ERGOST + SAH | cdisoa |
| | | | Nucleotide Metabolism | | |
| | | | Histidine Biosynthesis | | |
| YOL061W | 2.7.6.1 | PRS5 | ribose-phosphate pyrophosphokinase | R5P + ATP <-> PRPP + AMP | prs5 |
| YBL068W | 2.7.6.1 | PRS4 | ribose-phosphate pyrophosphokinase 4 | R5P + ATP <-> PRPP + AMP | prs4 |
| YER099C | 2.7.6.1 | PRS2 | ribose-phosphate pyrophosphokinase 2 | R5P + ATP <-> PRPP + AMP | prs2 |
| YHL011C | 2.7.6.1 | PRS3 | ribose-phosphate pyrophosphokinase 3 | R5P + ATP <-> PRPP + AMP | prs3 |
| YKL181W | 2.7.6.1 | PRS1 | ribose-phosphate pyrophosphokinase | R5P + ATP <-> PRPP + AMP | prs1 |
| YIR027C | 3.5.2.5 | dal1 | allantoinase | ATN <-> ATT | dal1 |
| YIR029W | 3.5.3.4 | dal2 | allantoicase | ATT <-> UGC + UREA | dal2 |
| YIR032C | 3.5.3.19 | dal3 | ureidoglycolate hydrolase | UGC <-> GLX + 2 NH3 + CO2 | dal3 |
| | | | Purine metabolism | | |
| YJL005W | 4.6.1.1 | CYR1 | adenylate cyclase | ATP -> cAMP + PPI | cyr1 |
| YDR454C | 2.7.4.8 | GUK1 | guanylate kinase | GMP + ATP <-> GDP + ADP | guk1_1 |

TABLE 2-continued

| Locus # | E.C. # | Gene | Gene Description | Reaction | Rxn Name |
|---|---|---|---|---|---|
| YDR454C | 2.7.4.8 | GUK1 | guanylate kinase | DGMP + ATP <-> DGDP + ADP | guk1_2 |
| YDR454C | 2.7.4.8 | GUK1 | guanylate kinase | GMP + DATP <-> GDP + DADP | guk1_3 |
| YMR300C | 2.4.2.14 | ade4 | phosphoribosylpyrophosphate amidotransferase | PRPP + GLN -> PPI + GLU + PRAM | ade4 |
| YGL234W | 6.3.4.13 | ade5,7 | glycinamide ribotide synthetase and aminoimidazole ribotide synthetase | PRAM + ATP + GLY <-> ADP + PI + GAR | ade5 |
| YDR408C | 2.1.2.2 | ade8 | glycinamide ribotide transformylase | GAR + FTHF -> THF + FGAR | ade8 |
| YGR061C | 6.3.5.3 | ade6 | 5'-phosphoribosylformyl glycinamidine synthetase | FGAR + ATP + GLN -> GLU + ADP + PI + FGAM | ade6 |
| YGL234W | 6.3.3.1 | ade5,7 | Phosphoribosylformylglycinamide cyclo-ligase | FGAM + ATP -> ADP + PI + AIR | ade7 |
| YOR128C | 4.1.1.21 | ade2 | phosphoribosylamino-imidazole-carboxylase | CAIR <-> AIR + CO2 | ade2 |
| YAR015W | 6.3.2.6 | ade1 | phosphoribosyl amino imidazolesuccinocarboxamide synthetase | CAIR + ATP + ASP <-> ADP + PI + SAICAR | ade1 |
| YLR359W | 4.3.2 2 | ADE13 | 5'-Phosphoribosyl-4-(N-succinocarboxamide)-5-aminoimidazole lyase | SAICAR <-> FUM + AICAR | ade13_1 |
| YLR028C | 2.1.2.3 | ADE16 | 5-aminoimidazole-4-carboxamide ribonucleotide (AICAR) transformylase\/IMP cyclohydrolase | AICAR + FTHF <-> THF + PRFICA | ade16_1 |
| YMR120C | 2.1.2.3 | ADE17 | 5-aminomidazole-4-carboxamide ribonucleotide (AICAR) transformylase\/IMP cyclohydrolase | AICAR + FTHF <-> THF + PRFICA | ade17_1 |
| YLR028C | 3.5.4.10 | ADE16 | 5-aminoimidazole-4-carboxamide ribonucleotide (AICAR) transformylase\/IMP cyclohydrolase | PRFICA <-> IMP | ade16_2 |
| YMR120C | 2.1.2.3 | ADE17 | IMP cyclohydrolase | PRFICA <-> IMP | ade17_2 |
| YNL220W | 6.3.4.4 | ade12 | adenylosuccinate synthetase | IMP + GTP + ASP -> GDP + PI + ASUC | ade12 |
| YLR359W | 4.3.2.2 | ADE13 | Adenylosuccinate Lyase | ASUC <-> FUM + AMP | ade13_2 |
| YAR073W | 1.1.1.205 | fun63 | putative inosine-5'-monophosphate dehydrogenase | IMP + NAD -> NADH + XMP | fun63 |
| YHR216W | 1.1.1.205 | pur5 | purine excretion | IMP + NAD -> NADH + XMP | pur5 |
| YML056C | 1.1.1.205 | IMD4 | probable inosine-5'-monophosphate dehydrogenase (IMP | IMP + NAD -> NADH + XMP | prm5 |
| YLR432W | 1.1.1.205 | IMD3 | probable inosine-5'-monophosphate dehydrogenase (IMP | IMP + NAD -> NADH + XMP | prm4 |
| YAR075W | 1.1.1.205 | YAR075W | Protein with strong similarity to inosine-5'-monophosphate dehydrogenase, frameshifted from YAR073W, possible pseudogene | IMP + NAD -> NADH + XMP | prm6 |
| YMR217W | 6.3.5.2, 6.3.4.1 | GUA1 | GMP synthase | XMP + ATP + GLN -> GLU + AMP + PPI + GMP | gua1 |
| YML035C | 3.5.4.6 | amd1 | AMP deaminase | AMP -> IMP + NH3 | amd1 |
| YGL248W | 3.1.4.17 | PDE1 | 3',5'-Cyclic-nucleotide phosphodiesterase, low affinity | cAMP -> AMP | pde1 |
| YOR360C | 3.1.4.17 | pde2 | 3',5'-Cyclic-nucleotide phosphodiesterase, high affinity | cAMP -> AMP | pde2_1 |
| YOR360C | 3.1.4.17 | pde2 | | cdAMP -> DAMP | pde2_2 |
| YOR360C | 3.1.4.17 | pde2 | | cIMP -> IMP | pde2_3 |
| YOR360C | 3.1.4.17 | pde2 | | cGMP -> GMP | pde2_4 |
| YOR360C | 3.1.4.17 | pde2 | | cCMP -> CMP | pde2_5 |
| YDR530C | 2.7.7.53 | APA2 | 5',5'''-P-1,P-4-tetraphosphate phosphorylase II | ADP + ATP -> PI + ATRP | apa2 |
| YCL050C | 2.7.7.53 | apa1 | 5',5'''-P-1,P-4-tetraphosphate phosphorylase II | ADP + GTP -> PI + ATRP | apa1_1 |
| YCL050C | 2.7.7.53 | apa1 | 5',5'''-P-1,P-4-tetraphosphate phosphorylase II | GDP + GTP -> PI + GTRP | apa1_3 |
| | | | Pyrimidine metabolism | | |
| YJL130C | 2.1.3.2 | ura2 | Aspartate-carbamoyltransferase | CAP + ASP -> CAASP + PI | ura2_1 |
| YLR420W | 3.5.2.3 | ura4 | dihydroorotase | CAASP <-> DOROA | ura4 |
| YKL216W | 1.3.3.1 | ura1 | dihydroorotate dehydrogenase | DOROA + O2 <-> H2O2 + OROA | ura1_1 |
| YKL216W | 1.3.3.1 | PYRD | Dihydroorotate dehydrogenase | DOROA + Qm <-> QH2m + OROA | ura1_2 |
| YML106W | 2.4.2.10 | URA5 | Orotate phosphoribosyltransferase 1 | OROA + PRPP <-> PPI + OMP | ura5 |
| YMR271C | 2.4.2.10 | URA10 | Orotate phosphoribosyltransferase 2 | OROA + PRPP <-> PPI + OMP | ura10 |
| YEL021W | 4.1.1.23 | ura3 | orotidine-5'-phosphate decarboxylase | OMP -> CO2 + UMP | ura3 |
| YKL024C | 2.7.4.14 | URA6 | Nucleoside-phosphate kinase | ATP + UMP <-> ADP + UDP | npk |
| YHR128W | 2.4.2.9 | fur1 | UPRTase, Uracil phosphoribosyltransferase | URA + PRPP -> UMP + PPI | fur1 |
| YPR062W | 3.5.4.1 | FCY1 | cytosine deaminase | CYTS -> URA + NH3 | fcy1 |
| — | 2.7.1.21 | | Thymidine (deoxyuridine) kinase | DU + ATP -> DUMP + ADP | tdk1 |
| — | 2.7.1.21 | | Thymidine (deoxyuridine) kinase | DT + ATP -> ADP + DTMP | tdk2 |
| YNR012W | 2.7.1.48 | URK1 | Uridine kinase | URI + GTP -> UMP + GDP | urk1_1 |
| YNR012W | 2.7.1.48 | URK1 | Cytodine kinase | CYTD + GTP -> GDP + CMP | urk1_2 |
| YNR012W | 2.7.1.48 | URK1 | Uridine kinase, converts ATP and uridine to ADP and UMP | URI + ATP -> ADP + UMP | urk1_3 |
| YLR209C | 2.4.2.4 | PNP1 | Protein with similarity to human purine nucleoside phosphorylase, Thymidine (deoxyuridine) phosphorylase, Purine nucleotide phosphorylase | DU + PI <-> URA + DR1P | deoa1 |
| YLR209C | 2.4.2.4 | PNP1 | Protein with similarity to human purine nucleoside phosphorylase, Thymidine (deoxyuridine) phosphorylase | DT + PI <-> THY + DR1P | deoa2 |
| YLR245C | 3.5.4.5 | CDD1 | Cytidine deaminase | CYTD -> URI + NH3 | cdd1_1 |
| YLR245C | 3.5.4.5 | CDD1 | Cytidine deaminase | DC -> NH3 + DU | cdd1_2 |
| YJR057W | 2.7.4.9 | cdc8 | dTMP kinase | DTMP + ATP <-> ADP + DTDP | cdc8 |
| YDR353W | 1.6.4.5 | TRR1 | Thioredoxin reductase | OTHIO + NADPH -> NADP + RTHIO | trr1 |
| YHR106W | 1.6.4.5 | TRR2 | mitochondrial thioredoxin reductase | OTHIOm + NADPHm -> NADPm + RTHIOm | trr2 |
| YBR252W | 3.6.1.23 | DUT1 | dUTP pyrophosphatase (dUTPase) | DUTP -> PPI + DUMP | dut1 |
| YOR074C | 2.1.1.45 | cdc21 | Thymidylate synthase | DUMP + METTHF -> DHF + DTMP | cdc21 |
| — | 2.7.4.14 | | Cytidylate kinase | DCMP + ATP <-> ADP + DCDP | cmka1 |

TABLE 2-continued

| Locus # | E.C. # | Gene | Gene Description | Reaction | Rxn Name |
|---|---|---|---|---|---|
| — | 2.7.4.14 | | Cytidylate kinase | CMP + ATP <-> ADP + CDP | cmka2 |
| YHR144C | 3.5.4.12 | DCD1 | dCMP deaminase | DCMP <-> DUMP + NH3 | dcd1 |
| YBL039C | 6.3.4.2 | URA7 | CTP synthase, highly homologus to URA8 CTP synthase | UTP + GLN + ATP -> GLU + CTP + ADP + PI | ura7_1 |
| YJR103W | 6.3.4.2 | URA8 | CTP synthase | UTP + GLN + ATP -> GLU + CTP + ADP + PI | ura8_1 |
| YBL039C | 6.3.4.2 | URA7 | CTP synthase, highly homologus to URA8 CTP synthase | ATP + UTP + NH3 - > ADP + PI + CTP | ura7_2 |
| YJR103W | 6.3.4.2 | URA8 | CTP synthase | ATP + UTP + NH3 -> ADP + PI + CTP | ura8_2 |
| YNL292W | 4.2.1.70 | PUS4 | Pseudouridine synthase | URA + R5P <-> PURI5P | pus4 |
| YPL212C | 4.2.1.70 | PUS1 | intranuclear protein which exhibits a nucleotide-specific intron-dependent tRNA pseudouridine synthase activity | URA + R5P <-> PURI5P | pus1 |
| YGL063W | 4.2.1.70 | PUS2 | pseudouridine synthase 2 | URA + R5P <-> PURI5P | pus2 |
| YFL001W | 4.2.1.70 | deg1 | Similar to rRNA methyltransferase (*Caenorhabditis elegans*) and hypothetical 28 K protein (alkaline endoglucanase gene 5' region) from *Bacillus* sp. | URA + R5P <-> PURI5P | deg1 |
| | | | Salvage Pathways | | |
| YML022W | 2.4.2.7 | APT1 | Adenine phosphoribosyltransferase | AD + PRPP -> PPI + AMP | apt1 |
| YDR441C | 2.4.2.7 | APT2 | similar to adenine phosphoribosyltransferase | AD + PRPP -> PPI + AMP | apt2 |
| YNL141W | 3.5.4.4 | AAH1 | adenine aminohydrolase (adenine deaminase) | ADN -> INS + NH3 | aah1a |
| YNL141W | 3.5.4.4 | AAH1 | adenine aminohydrolase (adenine deaminase) | DA -> DIN + NH3 | aah1b |
| YLR209C | 2.4.2.1 | PNP1 | Purine nucleotide phosphorylase, Xanthosine phosphorylase | DIN + PI <-> HYXN + DR1P | xapa1 |
| YLR209C | 2.4.2.1 | PNP1 | Xanthosine phosphorylase, Purine nucleotide phosphorylase | DA + PI <-> AD + DR1P | xapa2 |
| YLR209C | 2.4.2.1 | PNP1 | Xanthosine phosphorylase | DG + PI <-> GN + DR1P | xapa3 |
| YLR209C | 2.4.2.1 | PNP1 | Xanthosine phosphorylase, Purine nucleotide phosphorylase | HYXN + RIP <-> INS + PI | xapa4 |
| YLR209C | 2.4.2.1 | PNP1 | Xanthosine phosphorylase, Purine nucleotide phosphorylase | AD + RIP <-> PI + ADN | xapa5 |
| YLR209C | 2.4.2.1 | PNP1 | Xanthosine phosphorylase, Purine nucleotide phosphorylase | GN + RIP <-> PI + GSN | xapa6 |
| YLR209C | 2.4.2.1 | PNP1 | Xanthosine phosphorylase, Purine nucleotide phosphorylase | XAN + RIP <-> PI + XTSINE | xapa7 |
| YJR133W | 2.4.2.22 | XPT1 | Xanthine-guanine phosphoribosyltransferase | XAN + PRPP -> XMP + PPI | gpt1 |
| YDR400W | 3.2.2.1 | urh1 | Purine nucleosidase | GSN -> GN + RIB | pur21 |
| YDR400W | 3.2.2.1 | urh1 | Purine nucleosidase | ADN -> AD + RIB | pur11 |
| YJR105W | 2.7.1.20 | YJR105W | Adenosine kinase | ADN + ATP -> AMP + ADP | prm2 |
| YDR226W | 2.7.4.3 | adk1 | cytosolic adenylate kinase | ATP + AMP <-> 2 ADP | adk1_1 |
| YDR226W | 2.7.4.3 | adk1 | cytosolic adenylate kinase | GTP + AMP <-> ADP + GDP | adk1_2 |
| YDR226W | 2.7.4.3 | adk1 | cytosolic adenylate kinase | ITP + AMP <-> ADP + IDP | adk1_3 |
| YER170W | 2.7.4.3 | ADK2 | Adenylate kinase (mitochondrial GTP: AMP phosphotransferase | ATPm + AMPm <-> 2 ADPm | adk2_1 |
| YER170W | 2.7.4.3 | adk2 | Adenylate kinase (mitochondrial GTP: AMP phosphotransferase | GTPm + AMPm <-> ADPm + GDPm | adk2_2 |
| YER170W | 2.7.4.3 | adk2 | Adenylate kinase (mitochondrial GTP: AMP phosphotransferase) | ITPm + AMPm <-> ADPm + IDPm | adk2_3 |
| YGR180C | 1.17.4.1 | RNR4 | ribonucleotide reductase, small subunit (alt), beta chain | | |
| YIL066C | 1.17.4.1 | RNR3 | Ribonucleotide reductase (ribonucleoside-diphosphate reductase) large subunit, alpha chain | ADP + RTHIO -> DADP + OTHIO | rnr3 |
| YJL026W | 1.17.4.1 | rnr2 | small subunit of ribonucleotide reductase, beta chain | | |
| YKL067W | 2.7.4.6 | YNK1 | Nucleoside-diphosphate kinase | UDP + ATP <-> UTP + ADP | ynk1_1 |
| YKL067W | 2.7.4.6 | YNK1 | Nucleoside-diphosphate kinase | CDP + ATP <-> CTP + ADP | ynk1_2 |
| YKL067W | 2.7.4.6 | YNK1 | Nucleoside-diphosphate kinase | DGDP + ATP <-> DGTP + ADP | ynk1_3 |
| YKL067W | 2.7.4.6 | YNK1 | Nucleoside-diphosphate kinase | DUDP + ATP <-> DUTP + ADP | ynk1_4 |
| YKL067W | 2.7.4.6 | YNK1 | Nucleoside-diphosphate kinase | DCDP + ATP <-> DCTP + ADP | ynk1_5 |
| YKL067W | 2.7.4.6 | YNK1 | Nucleoside-diphosphate kinase | DTDP + ATP <-> DTTP + ADP | ynk1_6 |
| YKL067W | 2.7.4.6 | YNK1 | Nucleoside-diphosphate kinase | DADP + ATP <-> DATP + ADP | ynk1_7 |
| YKL067W | 2.7.4.6 | YNK1 | Nucleoside diphosphate kinase | GDP + ATP <-> GTP + ADP | ynk1_8 |
| YKL067W | 2.7.4.6 | YNK1 | Nucleoside diphosphate kinase | IDP + ATP <-> ITP + IDP | ynk1_9 |
| — | 2.7.4.11 | | Adenylate kinase, dAMP kinase | DAMP + ATP <-> DADP + ADP | dampk |
| YNL141W | 3.5.4.2 | AAH1 | Adenine deaminase | AD -> NH3 + HYXN | yicp |
| — | 2.7.1.73 | | Inosine kinase | INS + ATP -> IMP + ADP | gsk1 |
| — | 2.7.1.73 | | Guanosine kinase | GSN + ATP -> GMP + ADP | gsk2 |
| YDR399W | 2.4.2.8 | HPT1 | Hypoxanthine phosphoribosyltransferase | HYXN + PRPP -> PPI + IMP | hpt1_1 |
| YDR399W | 2.4.2.8 | HPT1 | Hypoxanthine phosphoribosyltransferase | GN + PRPP -> PPI + GMP | hpt1_2 |
| — | 2.4.2.3 | | Uridine phosphorylase | URI + PI <-> URA + RIP | udp |
| YKL024C | 2.1.4.- | URA6 | Uridylate kinase | UMP + ATP <-> UDP + ADP | pyrh1 |
| YKL024C | 2.1.4.- | URA6 | Uridylate kinase | DUMP + ATP <-> DUDP + ADP | pyrh2 |
| — | 3.2.2.10 | | CMP glycosylase | CMP -> CYTS + R5P | cmpg |
| YHR144C | 3.5.4.13 | DCD1 | dCTP deaminase | DCTP -> DUTP + NH3 | dcd |
| — | 3.1.3.5 | | 5'-Nucleotidase | DUMP -> DU + PI | usha1 |
| — | 3.1.3.5 | | 5'-Nucleotidase | DTMP -> DT + PI | usha2 |

TABLE 2-continued

| Locus # | E.C. # | Gene | Gene Description | Reaction | Rxn Name |
|---|---|---|---|---|---|
| — | 3.1.3.5 | | 5'-Nucleotidase | DAMP -> DA + PI | usha3 |
| — | 3.1.3.5 | | 5'-Nucleotidase | DGMP -> DG + PI | usha4 |
| — | 3.1.3.5 | | 5'-Nucleotidase | DCMP -> DC + PI | usha5 |
| — | 3.1.3.5 | | 5'-Nucleotidase | CMP -> CYTD + PI | usha6 |
| — | 3.1.3.5 | | 5'-Nucleotidase | AMP -> PI + ADN | usha7 |
| — | 3.1.3.5 | | 5'-Nucleotidase | GMP -> PI + GSN | usha8 |
| — | 3.1.3.5 | | 5'-Nucleotidase | IMP -> PI + INS | usha9 |
| — | 3.1.3.5 | | 5'-Nucleotidase | XMP -> PI + XTSINE | usha12 |
| — | 3.1.3.5 | | 5'-Nucleotidase | UMP -> PI + URI | usha11 |
| YER070W | 1.17.4.1 | RNR1 | Ribonucleoside-diphosphate reductase | ADP + RTHIO -> DADP + OTHIO | rnr1__1 |
| YER070W | 1.17.4.1 | RNR1 | Ribonucleoside-diphosphate reductase | GDP + RTHIO -> DGDP + OTHIO | rnr1__2 |
| YER070W | 1.17.4.1 | RNR1 | Ribonucleoside-diphosphate reductase | CDP + RTHIO -> DCDP + OTHIO | rnr1__3 |
| YER070W | 1.17.4.1 | RNR1 | Ribonucleoside-diphosphate reductase | UDP + RTHIO -> OTHIO + DUDP | rnr1__4 |
| — | 1.17.4.2 | | Ribonucleoside-triphosphate reductase | ATP + RTHIO -> DATP + OTHIO | nrdd1 |
| — | 1.17.4.2 | | Ribonucleoside-triphosphate reductase | GTP + RTHIO -> DGTP + OTHIO | nrdd2 |
| — | 1.17.4.2 | | Ribonucleoside-triphosphate reductase | CTP + RTHIO -> DCTP + OTHIO | nrdd3 |
| — | 1.17.4.2 | | Ribonucleoside-triphosphate reductase | UTP + RTHIO -> OTHIO + DUTP | nrdd4 |
| — | 3.6.1.- | | Nucleoside triphosphatase | GTP -> GSN + 3 PI | mutt1 |
| — | 3.6.1.- | | Nucleoside triphosphatase | DGTP -> DG + PI | mutt2 |
| YML035C | 3.2.2.4 | AMD1 | AMP deaminase | AMP -> AD + R5P | amn |
| YBR284W | 3.2.2.4 | YBR284W | Protein with similarity to AMP deaminase | AMP -> AD + R5P | amn1 |
| YJL070C | 3.2.2.4 | YJL070C | Protein with similarity to AMP deaminase | AMP -> AD + R5P | amn2 |
| | | | Amino Acid Metabolism Glutamate Metabolism (Aminosugars met) | | |
| YMR250W | 4.1.1.15 | GAD1 | Glutamate decarboxylase B | GLU -> GABA + CO2 | btn2 |
| YGR019W | 2.6.1.19 | uga1 | Aminobutyrate aminotransaminase 2 | GABA + AKG -> SUCCSAL + GLU | uga1 |
| YBR006w | 1.2.1.16 | YBR006w | Succinate semialdehyde dehydrogenase-NADP | SUCCSAL + NADP -> SUCC + NADPH | gabda |
| YKL104C | 2.6.1.16 | GFA1 | Glutamine_fructose-6-phosphate amidotransferase (glucoseamine-6-phosphate synthase) | F6P + GLN -> GLU + GA6P | gfa1 |
| YFL017C | 2.3.1.4 | GNA1 | Glucosamine-phosphate N-acetyltransferase | ACCOA + GA6P <-> COA + NAGA6P | gna1 |
| YEL058W | 5.4.2.3 | PCM1 | Phosphoacetylglucosamine Mutase | NAGA1P <-> NAGA6P | pcm1a |
| YDL103C | 2.7.7.23 | QRI1 | N-Acetylglucosamine-1-phosphate-uridyltransferase | UTP + NAGA1P <-> UDPNAG + PPI | qrt1 |
| YBR023C | 2.4.1.16 | chs3 | chitin synthase 3 | UDPNAG -> CHIT + UDP | chs3 |
| YBR038W | 2.4.1.16 | CHS2 | chitin synthase 2 | UDPNAG -> CHIT + UDP | chs2 |
| YNL192W | 2.4.1.16 | CHS1 | chitin synthase 2 | UDPNAG -> CHIT + UDP | chs1 |
| YHR037W | 1.5.1.12 | put2 | delta-1-pyrroline-5-carboxylate dehydrogenase | GLUGSALm + NADPm -> NADPHm + GLUm P5Cm + NADm -> NADHm + GLUm | put2__1 put2 |
| YDL171C | 1.4.1.14 | GLT1 | Glutamate synthase (NADH) | AKG + GLN + NADH -> NAD + 2 GLU | glt1 |
| YDL215C | 1.4.1.4 | GDH2 | glutamate dehydrogenase | GLU + NAD -> AKG + NH3 + NADH | gdh2 |
| YAL062W | 1.4.1.4 | GDH3 | NADP-linked glutamate dehydrogenase | AKG + NH3 + NADPH <-> GLU + NADP | gdh3 |
| YOR375C | 1.4.1.4 | GDH1 | NADP-specific glutamate dehydrogenase | AKG + NH3 + NADPH <-> GLU + NADP | gdh1 |
| YPR035W | 6.3.1.2 | gln1 | glutamine synthetase | GLU + NH3 + ATP -> GLN + ADP + PI | gln1 |
| YEL058W | 5.4.2.3 | PCM1 | Phosphoglucosamine mutase | GA6P <-> GA1P | pcm1b |
| — | 3.5.1.2 | | Glutaminase A | GLN -> GLU + NH3 | glnasea |
| — | 3.5.1.2 | | Glutaminase B | GLN -> GLU + NH3 | glnaseb |
| | | | Glucosamine | | |
| — | 5.3.1.10 | | Glucosamine-6-phosphate deaminase | GA6P -> F6P + NH3 | nagb |
| | | | Arabinose | | |
| YBR149W | 1.1.1.117 | ARA1 | D-arabinose 1-dehydrogenase (NAD(P)+) | ARAB + NAD -> ARABLAC + NADH | ara1__1 |
| YBR149W | 1.1.1.117 | ARA1 | D-arabmose 1-dehydrogenase (NAD(P)+) | ARAB + NADP -> ARABLAC + NADPH | ara1__2 |
| | | | Xylose | | |
| YGR194C | 2.7.1.17 | XKS1 | Xylulokinase | XUL + ATP -> X5P + ADP | xks1 |
| | | | Mannitol | | |
| — | 1.1.1.17 | | Mannitol-1-phosphate 5-dehydrogenase | MNT6P + NAD <-> F6P + NADH | mtld |
| | | | Alanine and Aspartate Metabolism | | |
| YKL106W | 2.6.1.1 | AAT1 | Asparate transaminase | OAm + GLUm <-> ASPm + AKGm | aat1__1 |
| YLR027C | 2.6.1.1 | AAT2 | Asparate transaminase | OA + GLU <->ASP + AKG | aat2__1 |
| YAR035W | 2.3.1.7 | YAT1 | Carnitine O-acetyltransferase | COAm + ACARm -> ACCOAm + CARm | yat1 |
| YML042W | 2.3.1.7 | CAT2 | Carnitine O-acetyltransferase | ACCOA + CAR -> COA + ACAR | cat2 |
| YDR111C | 2.6.1.2 | YDR111C | putative alanine transaminase | PYR + GLU <-> AKG + ALA | alab |
| YLR089C | 2.6.1.2 | YLR089C | alanine aminotransferase, mitochondrial precursor (glutamic--) | PYRm + GLUm <-> AKGm + ALAm | cfx2 |
| YPR145W | 6.3.5.4 | ASN1 | asparagine synthetase | ASP + ATP + GLN -> GLU + ASN + AMP + PP1 | asn1 |
| YGR124W | 6.3.5.4 | ASN2 | asparagine synthetase | ASP + ATP + GLN -> GLU + ASN + AMP + PP1 | asn2 |

TABLE 2-continued

| Locus # | E.C. # | Gene | Gene Description | Reaction | Rxn Name |
|---|---|---|---|---|---|
| YLL062C | 2.1.1.10 | MHT1 | Putative cobalamin-dependent homocysteine S-methyltransferase, Homocysteine S-methyltransferase | SAM + HCYS -> SAH + MET | mht1 |
| YPL273W | 2.1.1.10 | SAM4 | Putative cobalamin-dependent homocysteine S-methyltransferase | SAM + HCYS -> SAH + MET | sam4 |

Asparagine

| Locus # | E.C. # | Gene | Gene Description | Reaction | Rxn Name |
|---|---|---|---|---|---|
| YCR024c | 6.1.1.22 | YCR024c | asn-tRNA synthetase, mitochondrial | ATPm + ASPm + TRNAm -> AMPm + PP1m + ASPTRNAm | rnas |
| YHR019C | 6.1.1.23 | DED81 | asn-tRNA synthetase | ATP + ASP + TRNA -> AMP + PPI + ASPTRNA | ded81 |
| YLR155C | 3.5.1.1 | ASP3-1 | Asparaginase, extracellular | ASN -> ASP + NH3 | asp3_1 |
| YLR157C | 3.5.1.1 | ASP3-2 | Asparaginase, extracellular | ASN -> ASP + NH3 | asp3_2 |
| YLR158C | 3.5.1.1 | ASP3-3 | Asparaginase, extracellular | ASN -> ASP + NH3 | asp3_3 |
| YLR160C | 3.5.1.1 | ASP3-4 | Asparaginase, extracellular | ASN -> ASP + NH3 | asp3_4 |
| YDR321W | 3.5.1.1 | asp1 | Asparaginase | ASN -> ASP + NH3 | asp1 |

Glycine, serine and threonine metabolism

| Locus # | E.C. # | Gene | Gene Description | Reaction | Rxn Name |
|---|---|---|---|---|---|
| YER081W | 1.1.1.95 | ser3 | Phosphoglycerate dehydrogenase | 3PG + NAD -> NADH + PHP | ser3 |
| YIL074C | 1.1.1.95 | ser33 | Phosphoglycerate dehydrogenase | 3PG + NAD -> NADH + PHP | ser33 |
| YOR184W | 2.6.1.52 | ser1 | phosphoserine transaminase | PHP + GLU -> AKG + 3PSER | ser1_1 |
| YGR208W | 3.1.3.3 | ser2 | phosphoserine phosphatase | 3PSER -> PI + SER | ser2 |
| YBR263W | 2.1.2.1 | SHM1 | Glycine hydroxymethyltransferase | THFm + SERm <-> GLYm + METTHFm | shm1 |
| YLR058C | 2.1.2.1 | SHM2 | Glycine hydroxymethyltransferase | THF + SER <-> GLY + METTHF | shm2 |
| YFL030W | 2.6.1.44 | YFL030W | Putative alanine glyoxylate aminotransferase (serine pyruvate aminotransferase) | ALA + GLX <-> PYR + GLY | agt |
| YDR019C | 2.1.2.10 | GCV1 | glycine cleavage T protein (T subunit of glycine decarboxylase complex | GLYm + THFm + NADm -> METTHFm + NADHm + CO2 + NH3 | gcv1_1 |
| YDR019C | 2.1.2.10 | GCV1 | glycine cleavage T protein (T subunit of glycine decarboxylase complex | GLY + THF + NAD-> METTHF + NADH + CO2 + NH3 | gcv1_2 |
| YER052C | 2.7.2.4 | hom3 | Aspartate kinase, Aspartate kinase I, II, III | ASP + ATP -> ADP + BASP | hom3 |
| YDR158W | 1.2.1.11 | hom2 | aspartic beta semi-aldehyde dehydrogenase, Aspartate semialdehyde dehydrogenase | BASP + NADPH -> NADP + PI + ASPSA | hom2 |
| YJR139C | 1.1.1.3 | hom6 | Homoserine dehydrogenase I | ASPSA + NADH -> NAD + HSER | hom6_1 |
| YJR139C | 1.1.1.3 | hom6 | Homoserine dehydrogenase I | ASPSA + NADPH -> NADP + HSER | hom6_2 |
| YHR025W | 2.7.1.39 | thr1 | homoserine kinase | HSER + ATP -> ADP + PHSER | thr1 |
| YCR053W | 4.2.99.2 | thr4 | threonine synthase | PHSER -> PI + THR | thr4_1 |
| YGR155W | 4.2.1.22 | CYS4 | Cystathionine beta-synthase | SER + HCYS -> LLCT | cys4 |
| YEL046C | 4.1.2.5 | GLY1 | Threonine Aldolase | GLY + ACAL -> THR | gly1 |
| YMR189W | 1.4.4.2 | GCV2 | Glycine decarboxylase complex (P-subunit), glycine synthase (P-subunit), Glycine cleavage system (P-subunit) | GLYm + LIPOm <-> SAPm + CO2m | gcv2 |
| YCL064C | 4.2.1.16 | cha1 | threonine deaminase | THR -> NH3 + OBUT | cha1_1 |
| YER086W | 4.2.1.16 | ilv1 | L-Serine dehydratase | THRm -> NH3m + OBUTm | ilv1 |
| YCL064C | 4.2.1.13 | cha1 | catabolic serine (threonine) dehydratase | SER -> PYR + NH3 | cha1_2 |
| YIL167W | 4.2.1.13 | YIL167W | catabolic serine (threonine) dehydratase | SER -> PYR + NH3 | sdl1 |
| — | 1.1.1.103 | | Threonine dehydrogenase | THR + NAD -> GLY + AC + NADH | tdh1c |

Methionine metabolism

| Locus # | E.C. # | Gene | Gene Description | Reaction | Rxn Name |
|---|---|---|---|---|---|
| YFR055W | 4.4.1.8 | YFR055W | Cystathionine-b-lyase | LLCT -> HCYS + PYR + NH3 | metc |
| YER043C | 3.3.1.1 | SAH1 | putative S-adenosyl-L-homocysteine hydrolase | SAH -> HCYS + ADN | sah1 |
| YER091C | 2.1.1.14 | met6 | vitamin B12-(cobalamin)-independent isozyme of methionine synthase (also called N5-methyltetrahydrofolate homocysteine methyltransferase or 5-methyltetrahydropteroyl triglutamate homocysteine methyltransferase) | HCYS + MTHPTGLU -> THPTGLU + MET | met6 |
| — | 2.1.1.13 | | Methionine synthase | HCYS + MTHF -> THF + MET | met6_2 |
| YAL012W | 4.4.1.1 | cys3 | cystathionine gamma-lyase | LLCT -> CYS + NH3 + OBUT | cys3 |
| YNL277W | 2.3.1.31 | met2 | homoserine O-trans-acetylase | ACCOA + HSER <-> COA + OAHSER | met2 |
| YLR303W | 4.2.99.10 | MET17 | O-Acetylhomoserine (thiol)-lyase | OAHSER + METH -> MET + AC | met17_1 |
| YLR303W | 4.2.99.8 | MET17 | O-Acetylhomoserine (thiol)-lyase | OAHSER + H2S -> AC + HCYS | met17_2 |
| YLR303W | 4.2.99.8, 4.2.99.10 | met17 | O-acetylhomoserine sulfhydrylase (OAH SHLase), converts O-acetylhomoserine into homocysteine | OAHSER + H2S -> AC + HCYS | met17_3 |
| YML082W | 4.2.99.9 | YML082W | putative cystathionine gamma-synthase | OSLHSER <-> SUCC + OBUT + NH4 | met17h |
| YDR502C | 2.5.1.6 | sam2 | S-adenosylmethionine synthetase | MET + ATP -> PPI + PI + SAM | sam2 |
| YLR180W | 2.5.1.6 | sam1 | S-adenosylmethionine synthetase | MET + ATP -> PPI + PI + SAM | sam1 |
| YLR172C | 2.1.1.98 | DPH5 | Diphthine synthase | SAM + CALH -> SAH + DPTH | dph5 |

Cysteine Biosynthesis

| Locus # | E.C. # | Gene | Gene Description | Reaction | Rxn Name |
|---|---|---|---|---|---|
| YJR010W | 2.7.7.4 | met3 | ATP sulfurylase | SLF + ATP -> PPI + APS | met3 |
| YKL001C | 2.7.1.25 | met14 | adenylylsulfate kinase | APS + ATP -> ADP + PAPS | met14 |
| YFR030W | 1.8.1.2 | met10 | sulfite reductase | H2SO3 + 3 NADPH <-> H2S + 3 NADP | met10 |
| — | 2.3.1.30 | | Serine transacetylase | SER + ACCOA -> COA + ASER | cys1 |
| YGR012W | 4.2.99.8 | YGR012W | putative cysteine synthase (O-acetylserine sulfhydrylase) (O- | ASER + H2S -> AC + CYS | sul11 |
| YOL064C | 3.1.3.7 | MET22 | 3'–5' Bisphosphate nucleotidase | PAP -> AMP + PI | met22 |

TABLE 2-continued

| Locus # | E.C. # | Gene | Gene Description | Reaction | Rxn Name |
|---|---|---|---|---|---|
| YPR167C | 1.8.99.4 | MET16 | PAPS Reductase | PAPS + RTHIO -> OTHIO + H2SO3 + PAP | met16 |
| YCL050C | 2.7.7.5 | apa1 | diadenosine 5',5'''-P1,P4-tetraphosphate phosphorylase I | ADP + SLF <-> PI + APS | apa1_2 |
| Branched Chain Amino Acid Metabolism (Valine, Leucine and Isoleucine) | | | | | |
| YHR208W | 2.6.1.42 | BAT1 | Branched chain amino acid aminotransferase | OICAPm + GLUm <-> AKGm + LEUm | bat1_1 |
| YHR208W | 2.6.1.42 | BAT1 | Branched chain amino acid aminotransferase | OMVALm + GLUm <-> AKGm + ILEm | bat1_2 |
| YJR148W | 2.6.1.42 | BAT2 | branched-chain amino acid transaminase, highly similar to mammalian ECA39, which is regulated by the oncogene myc | OMVAL + GLU <-> AKG + ILE | bat2_1 |
| YJR148W | 2.6.1.42 | BAT2 | Branched chain amino acid aminotransferase | OIVAL + GLU <-> AKG + VAL | bat2_2 |
| YJR148W | 2.6.1.42 | BAT2 | branched-chain amino acid transaminase, highly similar to mammalian ECA39, which is regulated by the oncogene myc | OICAP + GLU <-> AKG + LEU | bat2_3 |
| YMR108W | 4.1.3.18 | ilv2 | Acetolactate synthase, large subunit | OBUTm + PYRm -> ABUTm + CO2m | ilv2_1 |
| YCL009C | 4.1.3.18 | ILV6 | Acetolactate synthase, small subunit | | |
| YMR108W | 4.1.3.18 | ilv2 | Acetolactate synthase, large subunit | 2 PYRm -> CO2m + ACLACm | ilv2_2 |
| YCL009C | 4.1.3.18 | ILV6 | Acetolactate synthase, small subunit | | |
| YLR355C | 1.1.1.86 | ilv5 | Keto-acid reductoisomerase | ACLACm + NADPHm -> NADPm + DHVALm | ilv5_1 |
| YLR355C | 1.1.1.86 | ilv5 | Keto-acid reductoisomerase | ABUTm + NADPHm -> NADPm + DHMVAm | ilv5_2 |
| YJR016C | 4.2.1.9 | ilv3 | Dihydroxy acid dehydratase | DHVALm -> OIVALm | ilv3_1 |
| YJR016C | 4.2.1.9 | ilv3 | Dihydroxy acid dehydratase | DHMVAm -> OMVALm | ilv3_2 |
| YNL104C | 4.1.3.12 | LEU4 | alpha-isopropylmalate synthase (2-Isopropylmalate Synthase) | ACCOAm + OIVALm -> COAm + IPPMALm | leu4 |
| YGL009C | 4.2.1.33 | leu1 | Isopropylmalate isomerase | CBHCAP <-> IPPMAL | leu1_1 |
| YGL009C | 4.2.1.33 | leu1 | isopropylmalate isomerase | PPMAL <-> IPPMAL | leu1_2 |
| YCL018W | 1.1.1.85 | leu2 | beta-IPM (isopropylmalate) dehydrogenase | IPPMAL + NAD -> NADH + OICAP + CO2 | leu2 |
| Lysine biosynthesis/degradation | | | | | |
| — | 4.2.1.79 | | 2-Methylcitrate dehydratase | HCITm <-> HACNm | lys3 |
| YDR234W | 4.2.1.36 | lys4 | Homoaconitate hydratase | HICITm <-> HACNm | lys4 |
| YIL094C | 1.1.1.155 | LYS12 | Homoisocitrate dehydrogenase (Strathern 1.1.1.87) | HICITm + NADm <-> OXAm + CO2m + NADHm | lys12 |
| — | | | non-enzymatic | OXAm <-> CO2m + AKAm | lys12b |
| — | 2.6.1.39 | | 2-Aminoadipate transaminase | AKA + GLU <-> AMA + AKG | amit |
| YBR115C | 1.2.1.31 | lys2 | L-Aminoadipate-semialdehyde dehydrogenase, large subunit | AMA + NADPH + ATP -> AMASA + NADP + AMP + PPI | lys2_1 |
| YGL154C | 1.2.1.31 | lys5 | L-Aminoadipate-semialdehyde dehydrogenase, small subunit | | |
| YBR115C | 1.2.1.31 | lys2 | L-Aminoadipate-semialdehyde dehydrogenase, large subunit | AMA + NADH + ATP -> AMASA + NAD + AMP + PPI | lys2_2 |
| YGL154C | 1.2.1.31 | lys5 | L-Aminoadipate-semialdehyde dehydrogenase, small subunit | | |
| YNR050C | 1.5.1.10 | lys9 | Saccharopine dehydrogenase (NADP+, L-glutamate forming) | GLU + AMASA + NADPH <-> SACP + NADP | lys9 |
| YIR034C | 1.5.1.7 | lys1 | Saccharopine dehydrogenase (NAD+, L-lysine forming) | SACP + NAD <-> LYS + AKG + NADH | lys1a |
| YDR037W | 6.1.1.6 | krs1 | lysyl-tRNA synthetase, cytosolic | ATP + LYS + LTRNA -> AMP + PPI + LLTRNA | krs1 |
| YNL073W | 6.1.1.6 | msk1 | lysyl-tRNA synthetase, mitochondrial | ATPm + LYSm + LTRNAm -> AMPm + PPIm + LLTRNAm | msk1 |
| YDR368W | 1.1.1.- | YPRI | similar to aldo-keto reductase | | |
| Arginine metabolism | | | | | |
| YMR062C | 2.3.1.1 | ECM40 | Amino-acid N-acetyltransferase | GLUm + ACCOAm -> COAm + NAGLUm | ecm40_1 |
| YER069W | 2.7.2.8 | arg5 | Acetylglutamate kinase | NAGLUm + ATPm -> ADPm + NAGLUPm | arg6 |
| YER069W | 1.2.1.38 | arg5 | N-acetyl-gamma-glutamyl-phosphate reductase and acetylglutamate kinase | NAGLUPm + NADPHm -> NADPm + PIm + NAGLUSm | arg5 |
| YOL140W | 2.6.1.11 | arg8 | Acetylornithine aminotransferase | NAGLUSm + GLUm -> AKGm + NAORNm | arg8 |
| YMR062C | 2.3.1.35 | ECM40 | Glutamate N-acetyltransferase | NAORNm + GLUm -> ORNm + NAGLUm | ecm40_2 |
| YJL130C | 6.3.5.5 | ura2 | carbamoyl-phosphate synthetase, aspartate transcarbamylase, and glutamine amidotransferase | GLN + 2 ATP + CO2 -> GLU + CAP + 2 ADP + PI | ura2_2 |
| YJR109C | 6.3.5.5 | CPA2 | carbamyl phosphate synthetase, large chain | GLN + 2 ATP + CO2 -> GLU + CAP + 2 ADP + PI | cpa2 |
| YOR303W | 6.3.5.5 | cpa1 | Carbamoyl phosphate synthetase, samll chain, arginine specific | | |

TABLE 2-continued

| Locus # | E.C. # | Gene | Gene Description | Reaction | Rxn Name |
|---|---|---|---|---|---|
| YJL088W | 2.1.3.3 | arg3 | Ornithine carbamoyltransferase | ORN + CAP -> CITR + PI | arg3 |
| YLR438W | 2.6.1.13 | car2 | Ornithine transaminase | ORN + AKG -> GLUGSAL + GLU | car2 |
| YOL058W | 6.3.4.5 | arg1 | arginosuccinate synthetase | CITR + ASP + ATP <-> AMP + PPI + ARGSUCC | arg1 |
| YHR018C | 4.3.2.1 | arg4 | argininosuccinate lyase | ARGSUCC <-> FUM + ARG | arg4 |
| YKL184W | 4.1.1.17 | spe1 | Ornithine decarboxylase | ORN -> PTRSC + CO2 | spe1 |
| YOL052C | 4.1.1.50 | spe2 | S-adenosylmethionine decarboxylase | SAM <-> DSAM + CO2 | spe2 |
| YPR069C | 2.5.1.16 | SPE3 | putrescine aminopropyltransferase (spermidine synthase) | PTRSC + SAM -> SPRMD + 5MTA | spe3 |
| YLR146C | 2.5.1.22 | SPE4 | Spermine synthase | DSAM + SPRMD -> 5MTA + SPRM | spe4 |
| YDR242W | 3.5.1.4 | AMD2 | Amidase | GBAD -> GBAT + NH3 | amd2_1 |
| YMR293C | 3.5.1.4 | YMR293C | Probable Amidase | GBAD -> GBAT + NH3 | amd |
| YPL111W | 3.5.3.1 | car1 | arginase | ARG -> ORN + UREA | car1 |
| YDR341C | 6.1.1.19 | YDR341C | arginyl-tRNA synthetase | ATP + ARG + ATRNA -> AMP + PPI + ALTRNA | atrna |
| YHR091C | 6.1.1.19 | MSR1 | arginyl-tRNA synthetase | ATP + ARG + ATRNA -> AMP + PPI + ALTRNA | msr1 |
| YHR068W | 1.5.99.6 | DYS1 | deoxyhypusine synthase | SPRMD + Qm -> DAPRP + QH2m | dys1 |
| Histidine metabolism | | | | | |
| YER055C | 2.4.2.17 | his1 | ATP phosphoribosyltransferase | PRPP + ATP -> PPI + PRBATP | his1 |
| YCL030C | 3.6.1.31 | his4 | phosphoribosyl-AMP cyclohydrolase/phosphoribosyl-ATP pyrophosphohydrolase/histidinol dehydrogenase | PRBATP -> PPI + PRBAMP | his4_1 |
| YCL030C | 3.5.4.19 | his4 | histidinol dehydrogenase | PRBAMP -> PRFP | his4_2 |
| YIL020C | 5.3.1.16 | his6 | phosphoribosyl-5-amino-1-phosphoribosyl-4-imidazolecarboxiamide isomerase | PRFP -> PRLP | his6 |
| YOR202W | 4.2.1.19 | his3 | imidazoleglycerol-phosphate dehydratase | DIMGP -> IMACP | his3 |
| YIL116W | 2.6.1.9 | his5 | histidinol-phosphate aminotransferase | IMACP + GLU -> AKG + HISOLP | his5 |
| YFR025C | 3.1.3.15 | his2 | Histidinolphosphatase | HISOLP -> PI + HISOL | his2 |
| YCL030C | 1.1.1.23 | his4 | phosphoribosyl-AMP cyclohydrolase/phosphoribosyl-ATP pyrophosphohydrolase/histidinol dehydrogenase | HISOL + 2 NAD -> HIS + 2 NADH | his4_3 |
| YBR248C | 2.4.2.- | his7 | glutamine amidotransferase cyclase | PRLP + GLN -> GLU + AICAR + DIMGP | his7 |
| YPR033C | 6.1.1.21 | hts1 | histidyl-tRNA synthetase | ATP + HIS + HTRNA -> AMP + PPI + HHTRNA | hts1 |
| YBR034C | 2.1.1.- | hmt1 | hnRNP arginine N-methyltransferase | SAM + HIS -> SAH + MHIS | hmt1 |
| YCL054W | 2.1.1.- | spb1 | putative RNA methyltransferase | | |
| YML110C | 2.1.1.- | coq5 | ubiquinone biosynthesis methyltransferase COQ5 | | |
| YOR201C | 2.1.1.- | pet56 | rRNA (guanosine-2'-O-)-methyltransferase | | |
| YPL266W | 2.1.1.- | dim1 | dimethyladenosine transferase | | |
| Phenylalanine, tyrosine and tryptophan biosynthesis (Aromatic Amino Acids) | | | | | |
| YBR249C | 4.1.2.15 | ARO4 | 3-deoxy-D-arabino-heptulosonate 7-phosphate (DAHP) synthase isoenzyme | E4P + PEP -> PI + 3DDAH7P | aro4 |
| YDR035W | 4.1.2.15 | ARO3 | DAHP synthase\; a.k.a. phospho-2-dehydro-3-deoxyheptonate aldolase, phenylalanine-inhibited\; phospho-2-keto-3-deoxyheptonate aldolase\; 2-dehydro-3-deoxyphosphoheptonate aldolase\, 3-deoxy-D-arabine-heptulosonate-7-phosphate synthase | E4P + PEP -> PI + 3DDAH7P | aro3 |
| YDR127W | 4.6.1.3 | aro1 | pentafunctional arom polypeptide (contains: 3-dehydroquinate synthase, 3-dehydroquinate dehydratase (3-dehydroquinase), shikimate 5-dehydrogenase, shikimate kinase, and epsp synthase) | 3DDAH7P -> DQT + PI | aro1_1 |
| YDR127W | 4.2.1.10 | aro1 | 3-Dehydroquinate dehydratase | DQT -> DHSK | aro1_2 |
| YDR127W | 1.1.1.25 | aro1 | Shikimate dehydrogenase | DHSK + NADPH -> SME + NADP | aro1_3 |
| YDR127W | 2.7.1.71 | aro1 | Shikimate kinase I, II | SME + ATP -> ADP + SME5P | aro1_4 |
| YDR127W | 2.5.1.19 | aro1 | 3-Phosphoshikimate-1-carboxyvinyltransferase | SME5P + PEP -> 3PSME + PI | aro1_5 |
| YGL148W | 4.6.1.4 | aro2 | Chorismate synthase | 3PSME -> PI + CHOR | aro2 |
| YPR060C | 5.4.99.5 | aro7 | Chorismate mutase | CHOR -> PHEN | aro7 |
| YNL316C | 4.2.1.51 | pha2 | prephenate dehydratase | PHEN -> CO2 + PHPYR | pha2 |
| YHR137W | 2.6.1.- | ARO9 | putative aromatic amino acid aminotransferase II | PHPYR + GLU <-> AKG + PHE | aro9_1 |
| YBR166C | 1.3.1.13 | tyr1 | Prephenate dehydrogenase (NADP+) | PHEN + NADP -> 4HPP + CO2 + NADPH | tyr1 |
| YGL202W | 2.6.1.- | ARO8 | aromatic amino acid aminotransferase I | 4HPP + GLU -> AKG + TYR | aro8 |
| YHR137W | 2.6.1.- | ARO9 | aromatic amino acid aminotransferase II | 4HPP + GLU -> AKG + TYR | aro9_2 |
| — | 1.3.1.12 | | Prephanate dehydrogenase | PHEN + NAD -> 4HPP + CO2 + NADH | tyra2 |
| YER090W | 4.1.3.27 | trp2 | Anthranilate synthase | CHOR + GLN -> GLU + PYR + AN | trp2_1 |
| YKL211C | 4.1.3.27 | trp3 | Anthranilate synthase | CHOR + GLN -> GLU + PYR + AN | trp3_1 |
| YDR354W | 2.4.2.18 | trp4 | anthranilate phosphoribosyl transferase | AN + PRPP -> PPI + NPRAN | trp4 |
| YDR007W | 5.3.1.24 | trp1 | n-(5'-phosphoribosyl)-anthranilate isomerase | NPRAN -> CPAD5P | trp1 |
| YKL211C | 4.1.1.48 | trp3 | Indoleglycerol phosphate synthase | CPAD5P -> CO2 + IGP | trp3_2 |
| YGL026C | 4.2.1.20 | trp5 | tryptophan synthetase | IGP + SER -> T3PI + TRP | trp5 |
| YDR256C | 1.11.1.6 | CTA1 | catalase A | 2 H2O2 -> O2 | cta1 |
| YGR088W | 1.11.1.6 | CTT1 | cytoplasmic catalase T | 2 H2O2 -> O2 | ctt1 |

TABLE 2-continued

| Locus # | E.C. # | Gene | Gene Description | Reaction | Rxn Name |
|---|---|---|---|---|---|
| YKL106W | 2.6.1.1 | AAT1 | Asparate aminotransferase | 4HPP + GLU <-> AKG + TYR | aat1_2 |
| YLR027C | 2.6.1.1 | AAT2 | Asparate aminotransferase | 4HPP + GLU <-> AKG + TYR | aat2_2 |
| YMR170C | 1.2.1.5 | ALD2 | Cytosolic aldeyhde dehydrogenase | ACAL + NAD -> NADH + AC | ald2 |
| YMR169C | 1.2.1.5 | ALD3 | strong similarity to aldehyde dehydrogenase | ACAL + NAD -> NADH + AC | ald3 |
| YOR374W | 1.2.1.3 | ALD4 | mitochondrial aldehyde dehydrogenase | ACALm + NADm -> NADHm + ACm | ald4_1 |
| YOR374W | 1.2.1.3 | ALD4 | mitochondrial aldehyde dehydrogenase | ACALm + NADPm -> NADPHm + ACm | ald4_2 |
| YER073W | 1.2.1.3 | ALD5 | mitochondrial Aldehyde Dehydrogenase | ACALm + NADPm -> NADPHm + ACm | ald5_1 |
| YPL061W | 1.2.1.3 | ALD6 | Cytosolic Aldehyde Dehydrogenase | ACAL + NADP -> NADPH + AC | ald6 |
| YJR078W | 1.13.11.11 | YJR078W | Protein with similarity to indoleamine 2,3-dioxygenases, which catalyze conversion of tryptophan and other indole derivatives into kynurenines, Tryptophan 2,3-dioxygenase | TRP + O2 -> FKYN | tdo2 |
| — | 3.5.1.9 | | Kynurenine formamidase | FKYN -> FOR + KYN | kfor |
| YLR231C | 3.7.1.3 | YLR231C | probable kynureninase (L-kynurenine hydrolase) | KYN -> ALA + AN | kynu_1 |
| YBL098W | 1.14.13.9 | YBL098W | Kynurenine 3-hydroxylase, NADPH-dependent flavin monooxygenase that catalyzes the hydroxylation of kynurenine to 3-hydroxykynurenine in tryptophan degradation and nicotinic acid synthesis, Kynurenine 3-monooxygenase | KYN + NADPH + O2 -> HKYN + NADP | kmo |
| YLR231C | 3.7.1.3 | YLR231C | probable kynureninase (L-kynurenine hydrolase) | HKYN -> HAN + ALA | kynu_2 |
| YJR025C | 1.13.11.6 | BNA1 | 3-hydroxyanthranilate 3,4-dioxygenase (3-HAO) (3-hydroxyanthranilic acid dioxygenase) (3-hydroxyanthranilatehydroxyanthranilic acid dioxygenase) (3-hydroxyanthranilate oxygenase) | HAN + O2 -> CMUSA | bna1 |
| — | 4.1.1.45 | | Picolinic acid decarboxylase | CMUSA -> CO2 + AM6SA | aaaa |
| — | 1.2.1.32 | | | AM6SA + NAD -> AMUCO + NADH | aaab |
| — | 1.5.1.- | | | AMUCO + NADPH -> AKA + NADP + NH4 | aaac |
| — | 1.3.11.27 | | 4-Hydroxyphenylpyruvate dioxygenase | 4HPP + O2 -> HOMOGEN + CO2 | tyrdega |
| — | 1.13.11.5 | | Homogentisate 1,2-dioxygenase | HOMOGEN + O2 -> MACAC | tyrdegb |
| — | 5.2.1.2 | | Maleyl-acetoacetate isomerase | MACAC -> FUACAC | tyrdegc |
| — | 3.7.1.2 | | Fumarylacetoacetase | FUACAC -> FUM + ACTAC | trydegd |
| YDR268w | 6.1.1.2 | MSW1 | tryptophanyl-tRNA synthetase, mitochondrial | ATPm + TRPm + TRNAm -> AMPm + PPIm + TRPTRNAm | msw1 |
| YDR242W | 3.5.1.4 | AMD2 | putative amidase | PAD -> PAC + NH3 | amd2_2 |
| YDR242W | 3.5.1.4 | AMD2 | putative amidase | IAD -> IAC + NH3 | amd2_3 |
| — | 2.6.1.29 | | Diamine transaminase | SPRMD + ACCOA -> ASPERMD + COA | spra |
| — | 1.5.3.11 | | Polyamine oxidase | ASPERMD + O2 -> APRUT + APROA + H2O2 | sprb |
| — | 1.5.3.11 | | Polyamine oxidase | APRUT + O2 -> GABAL + APROA + H2O2 | sprc |
| — | 2.6.1.29 | | Diamine transaminase | SPRM + ACCOA -> ASPRM + COA | sprd |
| — | 1.5.3.11 | | Polyamine oxidase | ASPRM + O2 -> ASPERMD + APROA + H2O2 | spre |
| | | | Proline biosynthesis | | |
| YDR300C | 2.7.2.11 | pro1 | gamma-glutamyl kinase, glutamate kinase | GLU + ATP -> ADP + GLUP | pro1 |
| YOR323C | 1.2.1.41 | PRO2 | gamma-glutamyl phosphate reductase | GLUP + NADH -> NAD + PI + GLUGSAL | pro2_1 |
| YOR323C | 1.2.1.41 | pro2 | gamma-glutamyl phosphate reductase | GLUP + NADPH -> NADP + PI + GLUGSAL | pro2_2 |
| — | | | spontaneous conversion (Strathern) | GLUGSAL <-> P5C | gps1 |
| — | | | spontaneous conversion (Strathern) | GLUGSALm <-> P5Cm | gps2 |
| YER023W | 1.5.1.2 | pro3 | Pyrroline-5-carboxylate reductase | P5C + NADPH -> PRO + NADP | pro3_1 |
| YER023W | 1.5.1.2 | pro3 | Pyrroline-5-carboxylate reductase | PHC + NADPH -> HPRO + NADP | pro3_3 |
| YER023W | 1.5.1.2 | pro3 | Pyrroline-5-carboxylate reductase | PHC + NADH -> HPRO + NAD | pro3_4 |
| YLR142W | 1.5.3.- | PUT1 | Proline oxidase | PROm + NADm -> P5Cm + NADHm | pro3_5 |
| | | | Metabolism of Other Amino Acids beta-Alanine metabolism | | |
| | 1.2.1.3 | | aldehyde dehydrogenase, mitochondrial 1 | GABALm + NADm -> GABAm + NADHm | ald1 |
| YER073W | 1.2.1.3 | ALD5 | mitochondrial Aldehyde Dehydrogenase | LACALm + NADm <-> LLACm + NADHm | ald5_2 |
| | | | Cyanoamino acid metabolism | | |
| YJL126W | 3.5.5.1 | NIT2 | NITRILASE | APROP -> ALA + NH3 | nit2_1 |
| YJL126W | 3.5.5.1 | NIT2 | NITRILASE | ACYBUT -> GLU + NH3 | nit2_2 |
| | | | Proteins, Peptides and Aminoacids Metabolism | | |
| YLR195C | 2.3.1.97 | nmt1 | Glycylpeptide N-tetradecanoyltransferase | TCOA + GLP -> COA + TGLP | nmt1 |
| YDL040C | 2.3.1.88 | nat1 | Peptide alpha-N-acetyltransferase | ACCOA + PEPD -> COA + APEP | nat1 |
| YGR147C | 2.3.1.88 | NAT2 | Peptide alpha-N-acetyltransferase | ACCOA + PEPD -> COA + APEP | nat2 |

TABLE 2-continued

| Locus # | E.C. # | Gene | Gene Description | Reaction | Rxn Name |
|---|---|---|---|---|---|
| | | | Glutathione Biosynthesis | | |
| YJL101C | 6.3.2.2 | GSH1 | gamma-glutamylcysteine synthetase | CYS + GLU + ATP -> GC + PI + ADP | gsh1 |
| YOL049W | 6.3.2.3 | GSH2 | Glutathione Synthetase | GLY + GC + ATP -> RGT + PI + ADP | gsh2 |
| YBR244W | 1.11.1.9 | GPX2 | Glutathione peroxidase | 2 RGT + H2O2 <-> OGT | gpx2 |
| YIR037W | 1.11.1.9 | HYR1 | Glutathione peroxidase | 2 RGT + H2O2 <-> OGT | hyr1 |
| YKL026C | 1.11.1.9 | GPX1 | Glutathione peroxidase | 2 RGT + H2O2 <-> OGT | gpx1 |
| YPL091W | 1.6.4.2 | GLR1 | Glutathione oxidoreductase | NADPH + OGT -> NADP + RGT | glr1 |
| YLR299W | 2.3.2.2 | ECM38 | gamma-glutamyltranspeptidase | RGT + ALA -> CGLY + ALAGLY | ecm38 |
| | | | Metabolism of Complex Carbohydrates | | |
| | | | Starch and sucrose metabolism | | |
| YGR032W | 2.4.1.34 | GSC2 | 1,3-beta-Glucan synthase | UDPG -> 13GLUCAN + UDP | gsc2 |
| YLR342W | 2.4.1.34 | FKS1 | 1,3-beta-Glucan synthase | UDPG -> 13GLUCAN + UDP | fks1 |
| YGR306W | 2.4.1.34 | FKS3 | Protein with similarity to Fks1p and Gsc2p | UDPG -> 13GLUCAN + UDP | fks3 |
| YDR261C | 3.2.1.58 | exg2 | Exo-1,3-b-glucanase | 13GLUCAN -> GLC | exg2 |
| YGR282C | 3.2.1.58 | BGL2 | Cell wall endo-beta-1,3-glucanase | 13GLUCAN -> GLC | bgl2 |
| YLR300W | 3.2.1.58 | exg1 | Exo-1,3-beta-glucanase | 13GLUCAN -> GLC | exg1 |
| YOR190W | 3.2.1.58 | spr1 | sporulation-specific exo-1,3-beta-glucanase | 13GLUCAN -> GLC | spr1 |
| | | | Glycoprotein Biosynthesis/Degradation | | |
| YMR013C | 2.7.1.108 | sec59 | Dolichol kinase | CTP + DOL -> CDP + DOLP | sec59 |
| YPR183W | 2.4.1.83 | DPM1 | Dolichyl-phosphate beta-D-mannosyltransferase | GDPMAN + DOLP -> GDP + DOLMANP | dpm1 |
| YAL023C | 2.4.1.109 | PMT2 | Dolichyl-phosphate-mannose--protein mannosyltransferase | DOLMANP -> DOLP + MANNAN | pmt2 |
| YDL093W | 2.4.1.109 | PMT5 | Dolichyl-phosphate-mannose--protein mannosyltransferase | DOLMANP -> DOLP + MANNAN | pmt5 |
| YDL095W | 2.4.1.109 | PMT1 | Dolichyl-phosphate-mannose--protein mannosyltransferase | DOLMANP -> DOLP + MANNAN | pmt1 |
| YGR199W | 2.4.1.109 | PMT6 | Dolichyl-phosphate-mannose--protein mannosyltransferase | DOLMANP -> DOLP + MANNAN | pmt6 |
| YJR143C | 2.4.1.109 | PMT4 | Dolichyl-phosphate-mannose--protein mannosyltransferase | DOLMANP -> DOLP + MANNAN | pmt4 |
| YOR321W | 2.4.1.109 | PMT3 | Dolichyl-phosphate-mannose--protein mannosyltransferase | DOLMANP -> DOLP + MANNAN | pmt3 |
| YBR199W | 2.4.1.131 | KTR4 | Glycolipid 2-alpha-mannosyltransferase | MAN2PD + 2 GDPMAN -> 2 GDP + 2MANPD | ktr4 |
| YBR205W | 2.4.1.131 | KTR3 | Glycolipid 2-alpha-mannosyltransferase | MAN2PD + 2 GDPMAN -> 2 GDP + 2MANPD | ktr3 |
| YDR483W | 2.4.1.131 | kre2 | Glycolipid 2-alpha-mannosyltransferase | MAN2PD + 2 GDPMAN -> 2 GDP + 2MANPD | kre2 |
| YJL139C | 2.4.1.131 | yur1 | Glycolipid 2-alpha-mannosyltransferase | MAN2PD + 2 GDPMAN -> 2 GDP + 2MANPD | yur1 |
| YKR061W | 2.4.1.131 | KTR2 | Glycolipid 2-alpha-mannosyltransferase | MAN2PD + 2 GDPMAN -> 2 GDP + 2MANPD | ktr2 |
| YOR099W | 2.4.1.131 | KTR1 | Glycolipid 2-alpha-mannosyltransferase | MAN2PD + 2 GDPMAN -> 2 GDP + 2MANPD | ktr1 |
| YPL053C | 2.4.1.131 | KTR6 | Glycolipid 2-alpha-mannosyltransferase | MAN2PD + 2 GDPMAN -> 2 GDP + 2MANPD | ktr6 |
| | | | Aminosugars metabolism | | |
| YER062C | 3.1.3.21 | HOR2 | DL-glycerol-3-phosphatase | GL3P -> GL + PI | hor2 |
| YIL053W | 3.1.3.21 | RHR2 | DL-glycerol-3-phosphatase | GL3P -> GL + PI | rhr2 |
| YLR307W | 3.5.1.41 | CDA1 | Chitin Deacetylase | CHIT -> CHITO + AC | cda1 |
| YLR308W | 3.5.1.41 | CDA2 | Chitin Deacetylase | CHIT -> CHITO + AC | cda2 |
| | | | Metabolism of Complex Lipids | | |
| | | | Glycerol (Glycerolipid metabolism) | | |
| YFL053W | 2.7.1.29 | DAK2 | dihydroxyacetone kinase | GLYN + ATP -> T3P2 + ADP | dak2 |
| YML070W | 2.7.1.29 | DAK1 | putative dihydroxyacetone kinase | GLYN + ATP -> T3P2 + ADP | dak1 |
| YDL022W | 1.1.1.8 | GPD1 | glycerol-3-phosphate dehydrogenase (NAD) | T3P2 + NADH -> GL3P + NAD | gpd1 |
| YOL059W | 1.1.1.8 | GPD2 | glycerol-3-phosphate dehydrogenase (NAD) | T3P2 + NADH -> GL3P + NAD | gpd2 |
| YHL032C | 2.7.1.30 | GUT1 | glycerol kinase | GL + ATP -> GL3P + ADP | gut1 |
| YIL155C | 1.1.99.5 | GUT2 | glycerol-3-phosphate dehydrogenase | GL3P + FADm -> T3P2 + FADH2m | gut2 |
| | | | | DAGLY + 0.017 C100ACP + 0.062 C120ACP + 0.100 C140ACP + 0.270 C160ACP + 0.169 C161ACP + 0.055 C180ACP + 0.235 C181ACP + 0.093 C182ACP -> TAGLY + ACP | daga |
| | | | Metabolism of Cofactors, Vitamins, and Other Substances | | |
| | | | Thiamine (Vitamin B1) metabolism | | |
| YOR143C | 2.7.6.2 | THI80 | Thiamin pyrophosphokinase | ATP + THIAMIN -> AMP + TPP | thi80__1 |
| YOR143C | 2.7.6.2 | THI80 | Thiamin pyrophosphokinase | ATP + TPP -> AMP + TPPP | thi80__2 |

TABLE 2-continued

| Locus # | E.C. # | Gene | Gene Description | Reaction | Rxn Name |
|---|---|---|---|---|---|
| | | | thiC protein | AIR -> AHM | thic |
| YOL055C | 2.7.1.49 | THI20 | Bipartite protein consisting of N-terminal hydroxymethylpyrimidine phosphate (HMP-P) kinase domain, needed for thiamine biosynthesis, fused to C-terminal Pet18p-like domain of indeterminant function | AHM + ATP -> AHMP + ADP | thi20 |
| YPL258C | 2.7.1.49 | THI21 | Bipartite protein consisting of N-terminal hydroxymethylpyrimidine phosphate (HMP-P) kinase domain, needed for thiamine biosynthesis, fused to C-terminal Pet18p-like domain of indeterminant function | AHM + ATP -> AHMP + ADP | thi21 |
| YPR121W | 2.7.1.49 | THI22 | Bipartite protein consisting of N-terminal hydroxymethylpyrimidine phosphate (HMP-P) kinase domain, needed for thiamine biosynthesis, fused to C-terminal Pet18p-like domain of indeterminant function | AHM + ATP -> AHMP + ADP | thi22 |
| YOL055C | 2.7.4.7 | THI20 | HMP-phosphate kinase | AHMP + ATP -> AHMPP + ADP | thid |
| — | | | Hypothetical | T3PI + PYR -> DTP | unkrxn1 |
| — | | | thiG protein | DTP + TYR + CYS -> THZ + HBA + CO2 | thig |
| — | | | thiE protein | DTP + TYR + CYS -> THZ + HBA + CO2 | thie |
| — | | | thiF protein | DTP + TYR + CYS -> THZ + HBA + CO2 | thif |
| — | | | thiH protein | DTP + TYR + CYS -> THZ + HBA + CO2 | thih |
| YPL214C | 2.7.1.50 | THI6 | Hydroxyethylthiazole kinase | THZ + ATP -> THZP + ADP | thim |
| YPL214C | 2.5.1.3 | THI6 | TMP pyrophosphorylase, hydroxyethylthiazole kinase | THZP + AHMPP -> THMP + PPI | thi6 |
| | 2.7.4.16 | | Thiamin phosphate kinase | THMP + ATP <-> TPP + ADP | thi1 |
| | 3.1.3.- | | (DL)-glycerol-3-phosphatase 2 | THMP -> THIAMIN + PI | unkrxn8 |
| | | | Riboflavin metabolism | | |
| YBL033C | 3.5.4.25 | rib1 | GTP cyclohydrolase II | GTP -> D6RP5P + FOR + PPI | rib1 |
| YBR153W | 3.5.4.26 | RIB7 | HTP reductase, second step in the riboflavin biosynthesis pathway | D6RP5P -> A6RP5P + NH3 | ribd1 |
| YBR153W | 1.1.1.193 | rib7 | Pyrimidine reductase | A6RP5P + NADPH -> A6RP5P2 + NADP | rib7 |
| — | | | Pyrimidine phosphatase | A6RP5P2 -> A6RP + PI | prm |
| — | | | 3,4 Dihydroxy-2-butanone-4-phosphate synthase | RL5P -> DB4P + FOR | ribb |
| YBR256C | 2.5.1.9 | RIB5 | Riboflavin biosynthesis pathway enzyme, 6,7-dimethyl-8-ribityllumazine synthase, apha chain | DB4P + A6RP -> D8RL + PI | rib5 |
| YOL143C | 2.5.1.9 | RIB4 | Riboflavin biosynthesis pathway enzyme, 6,7-dimethyl-8-ribityllumazine synthase, beta chain | | |
| YAR071W | 3.1.3.2 | pho11 | Acid phosphatase | FMN -> RIBFLAV + PI | pho11 |
| YDR236C | 2.7.1.26 | FMN1 | Riboflavin kinase | RIBFLAV + ATP -> FMN + ADP | fmn1_1 |
| YDR236C | 2.7.1.26 | FMN1 | Riboflavin kinase | RIBFLAVm + ATPm -> FMNm + ADPm | fmn1_2 |
| YDL045C | 2.7.7.2 | FAD1 | FAD synthetase | FMN + ATP -> FAD + PPI | fad1 |
| | 2.7.7.2 | | FAD synthetase | FMNm + ATPm -> FADm + PPIm | fad1b |
| | | | Vitamin B6 (Pyridoxine) Biosynthesis metabolism | | |
| — | 2.7.1.35 | | Pyridoxine kinase | PYRDX + ATP -> P5P + ADP | pdxka |
| — | 2.7.1.35 | | Pyridoxine kinase | PDLA + ATP -> PDLA5P + ADP | pdxkb |
| — | 2.7.1.35 | | Pyridoxine kinase | PL + ATP -> PL5P + ADP | pdxkc |
| YBR035C | 1.4.3.5 | PDX3 | Pyridoxine 5'-phosphate oxidase | PDLA5P + O2 -> PL5P + H2O2 + NH3 | pdx3_1 |
| YBR035C | 1.4.3.5 | PDX3 | Pyridoxine 5'-phosphate oxidase | P5P + O2 <-> PL5P + H2O2 | pdx3_2 |
| YBR035C | 1.4.3.5 | PDX3 | Pyridoxine 5'-phosphate oxidase | PYRDX + O2 <-> PL + H2O2 | pdx3_3 |
| YBR035C | 1.4.3.5 | PDX3 | Pyridoxine 5'-phosphate oxidase | PL + O2 + NH3 <-> PDLA + H2O2 | pdx3_4 |
| YBR035C | 1.4.3.5 | PDX3 | Pyridoxine 5'-phosphate oxidase | PDLA5P + O2 -> PL5P + H2O2 + NH3 | pdx3_5 |
| YOR184W | 2.6.1.52 | ser1 | Hypothetical transaminase/phosphoserine transaminase | OHB + GLU <-> PHT + AKG | ser1_2 |
| YCR053W | 4.2.99.2 | thr4 | Threonine synthase | PHT -> 4HLT + PI | thr4_2 |
| | 3.1.3.- | | Hypothetical Enzyme | PDLA5P -> PDLA + PI | hor2b |
| | | | Pantothenate and CoA biosynthesis | | |
| — | | | | 3 MALCOA -> CHCOA + 2 COA + 2 CO2 | bio1 |
| — | 2.3.1.47 | | 8-Amino-7-oxononanoate synthase | ALA + CHCOA <-> CO2 + COA + AONA | biof |
| YNR058W | 2.6.1.62 | BIO3 | 7,8-diamino-pelargonic acid aminotransferase (DAPA) aminotransferase | SAM + AONA <-> SAMOB + DANNA | bio3 |
| YNR057C | 6.3.3.3 | BIO4 | dethiobiotin synthetase | CO2 + DANNA + ATP <-> DTB + PI + ADP | bio4 |
| YGR286C | 2.8.1.6 | BIO2 | Biotin synthase | DTB + CYS <-> BT | bio2 |
| | | | Folate biosynthesis | | |
| YGR267C | 3.5.4.16 | fol2 | GTP cyclohydrolase I | GTP -> FOR + AHTD | fol2 |
| — | 3.6.1.- | | Dihydroneopterin triphosphate pyrophosphorylase | AHTD -> PPI + DHPP | ntpa |
| YDR481C | 3.1.3.1 | pho8 | Glycerophosphatase, Alkaline phosphatase, Nucleoside triphosphatase | AHTD -> DHP + 3 PI | pho8 |

TABLE 2-continued

| Locus # | E.C. # | Gene | Gene Description | Reaction | Rxn Name |
|---|---|---|---|---|---|
| YDL100C | 3.6.1.- | YDL100C | Dihydroneopterin monophosphate dephosphorylase | DHPP -> DHP + PI | dhdnpa |
| YNL256W | 4.1.2.25 | fol1 | Dihydroneopterin aldolase | DHP -> AHHMP + GLAL | fol1_1 |
| YNL256W | 2.7.6.3 | fol1 | 6-Hydroxymethyl-7,8 dihydropterin pyrophosphokinase | AHHMP + ATP -> AMP + AHHMD | fol1_2 |
| YNR033W | 4.1.3.- | ABZ1 | Aminodeoxychorismate synthase | CHOR + GLN -> ADCHOR + GLU | abz1 |
|  | 4.--.- |  | Aminodeoxychorismate lyase | ADCHOR -> PYR + PABA | pabc |
| YNL256W | 2.5.1.15 | fol1 | Dihydropteroate synthase | PABA + AHHMD -> PPI + DHPT | fol1_3 |
| YNL256W | 2.5.1.15 | fol1 | Dihydropteroate synthase | PABA + AHHMP -> DHPT | fol1_4 |
| — | 6.3.2.12 |  | Dihydrofolate synthase | DHPT + ATP + GLU -> ADP + PI + DHF | folc |
| YOR236W | 1.5.1.3 | dfr1 | Dihydrofolate reductase | DHFm + NADPHm -> NADPm + THFm | dfr1_1 |
| YOR236W | 1.5.1.3 | dfr1 | Dihydrofolate reductase | DHF + NADPH -> NADP + THF | dfr1_2 |
| — | 6.3.3.2 |  | 5-Formyltetrahydrofolate cyclo-ligase | ATPm + FTHFm -> ADPm + PIm + MTHFm | ftfa |
| — | 6.3.3.2 |  | 5-Formyltetrahydrofolate cyclo-ligase | ATP + FTHF -> ADP + PI + MTHF | ftfb |
| YKL132C | 6.3.2.17 | RMA1 | Protein with similarity to folylpolyglutamate synthase; converts tetrahydrofolyl-[Glu(n)] + glutamate to tetrahydrofolyl-[Glu(n + 1)] | THF + ATP + GLU <-> ADP + PI + THFG | rma1 |
| YMR113W | 6.3.2.17 | FOL3 | Dihydrofolate synthetase | THF + ATP + GLU <-> ADP + PI + THFG | fol3 |
| YOR241W | 6.3.2.17 | MET7 | Folylpolyglutamate synthetase, involved in methionine biosynthesis and maintenance of mitochondrial genome | THF + ATP + GLU <-> ADP + PI + THFG | met7 |
| One carbon pool by folate [MAP: 00670] | | | | | |
| YPL023C | 1.5.1.20 | MET12 | Methylene tetrahydrofolate reductase | METTHFm + NADPHm -> NADPm + MTHFm | met12 |
| YGL125W | 1.5.1.20 | met13 | Methylene tetrahydrofolate reductase | METTHFm + NADPHm -> NADPm + MTHFm | met13 |
| YBR084W | 1.5.1.5 | mis1 | the mitochondrial trifunctional enzyme C1-tetrahydroflate synthase | METTHFm + NADPm <-> METHFm + NADPHm | mis1_1 |
| YGR204W | 1.5.1.5 | ade3 | the cytoplasmic trifunctional enzyme C1-tetrahydrofolate synthase | METTHF + NADP <-> METHF + NADPH | ade3_1 |
| YBR084W | 6.3.4.3 | mis1 | the mitochondrial trifunctional enzyme C1-tetrahydroflate synthase | THFm + FORm + ATPm -> ADPm + PIm + FTHFm | mis1_2 |
| YGR204W | 6.3.4.3 | ade3 | the cytoplasmic trifunctional enzyme C1-tetrahydrofolate synthase | THF + FOR + ATP -> ADP + PI + FTHF | ade3_2 |
| YBR084W | 3.5.4.9 | mis1 | the mitochondrial trifunctional enzyme C1-tetrahydroflate synthase | METHFm <-> FTHFm | mis1_3 |
| YGR204W | 3.5.4.9 | ade3 | the cytoplasmic trifunctional enzyme C1-tetrahydrofolate synthase | METHF <-> FTHF | ade3_3 |
| YKR080W | 1.5.1.15 | MTD1 | NAD-dependent 5,10-methylenetetrahydrafolate dehydrogenase | METTHF + NAD -> METHF + NADH | mtd1 |
| YBL013W | 2.1.2.9 | fmt1 | Methionyl-tRNA Transformylase | FTHFm + MTRNAm -> THFm + FMRNAm | fmt1 |
| Coenzyme A Biosynthesis | | | | | |
| YBR176W | 2.1.2.11 | ECM31 | Ketopentoate hydroxymethyl transferase | OIVAL + METTHF -> AKP + THF | ecm31 |
| YHR063C | 1.1.1.169 | PAN5 | Putative ketopantoate reductase (2-dehydropantoate 2-reductase) involved in coenzyme A synthesis, has similarity to Cbs2p, Ketopantoate reductase | AKP + NADPH -> NADP + PANT | pane |
| YLR355C | 1.1.1.86 | ilv5 | Ketol-acid reductoisomerase | AKPm + NADPHm -> NADPm + PANTm | ilv5_3 |
| YIL145C | 6.3.2.1 | YIL145C | Pantoate-b-alanine ligase | PANT + bALA + ATP -> AMP + PPI + PNTO | panca |
| YDR531W | 2.7.1.33 | YDR531W | Putative pantothenate kinase involved in coenzyme A biosynthesis, Pantothenate kinase | PNTO + ATP -> ADP + 4PPNTO | coaa |
| — | 6.3.2.5 |  | Phosphopantothenate-cysteine ligase | 4PPNTO + CTP + CYS -> CMP + PPI + 4PPNCYS | pchg |
| — | 4.1.1.36 |  | Phosphopantothenate-cysteine decarboxylase | 4PPNCYS -> CO2 + 4PPNTE | pcdcl |
| — | 2.7.7.3 |  | Phospho-pantethiene adenylyltransferase | 4PPNTE + ATP -> PPI + DPCOA | patrana |
| — | 2.7.7.3 |  | Phospho-pantethiene adenylyltransferase | 4PPNTEm + ATPm -> PPIm + DPCOAm | patranb |
| — | 2.7.1.24 |  | DephosphoCoA kinase | DPCOA + ATP -> ADP + COA | dphcoaka |
| — | 2.7.1.24 |  | DephosphoCoA kinase | DPCOAm + ATPm -> ADPm + COAm | dphcoakb |
| — | 4.1.1.11 |  | ASPARTATE ALPHA-DECARBOXYLASE | ASP -> CO2 + bALA | pancb |
| YPL148C | 2.7.8.7 | PPT2 | Acyl carrier-protein synthase, phosphopantetheine protein transferase for Acp1p | COA -> PAP + ACP | acps |
| NAD Biosynthesis | | | | | |
| YGL037C | 3.5.1.19 | PNC1 | Nicotinamidase | NAM <-> NAC + NH3 | nadh |
| YOR209C | 2.4.2.11 | NPT1 | NAPRTase | NAC + PRPP -> NAMN + PPI | npt1 |
|  | 1.4.3.- |  | Aspartate oxidase | ASP + FADm -> FADH2m + ISUCC | nadb |
|  | 1.4.3.16 |  | Quinolate synthase | ISUCC + T3P2 -> PI + QA | nada |
| YFR047C | 2.4.2.19 | QPT1 | Quinolate phosphoribosyl transferase | QA + PRPP -> NAMN + CO2 + PPI | nadc |

TABLE 2-continued

| Locus # | E.C. # | Gene | Gene Description | Reaction | Rxn Name |
|---|---|---|---|---|---|
| YLR328W | 2.7.7.18 | YLR328W | Nicotinamide mononucleotide (NMN) adenylyltransferase | NAMN + ATP -> PPI + NAAD | nadd1 |
| YHR074W | 6.3.5.1 | QNS1 | Deamido-NAD ammonia ligase | NAAD + ATP + NH3 -> NAD + AMP + PPI | nade |
| YJR049c | 2.7.1.23 | utr1 | NAD kinase, POLYPHOSPHATE KINASE (EC 2.7.4.1)/NAD + KINASE (EC 2.7.1.23) | NAD + ATP -> NADP + ADP | nadf_1 |
| YEL041w | 2.7.1.23 | YEL041w | NAD kinase, POLYPHOSPHATE KINASE (EC 2.7.4.1)/NAD + KINASE (EC 2.7.1.23) | NAD + ATP -> NADP + ADP | nadf_2 |
| YPL188w | 2.7.1.23 | POS5 | NAD kinase, POLYPHOSPHATE KINASE (EC 2.7.4.1)/NAD + KINASE (EC 2.7.1.23) | NAD + ATP -> NADP + ADP | nadf_5 |
|  | 3.1.2.- |  | NADP phosphatase | NADP -> NAD + PI | nadphps |
|  | 3.2.2.5 |  |  | NAD -> NAM + ADPRIB | nad1 |
|  | 2.4.2.1 |  | strong similarity to purine-nucleoside phosphorylases | ADN + PI <-> AD + RIP | nadg1 |
|  | 2.4.2.1 |  | strong similarity to purine-nucleoside phosphorylases | GSN + PI <-> GN + RIP | nadg2 |
|  |  |  | Nicotinic Acid synthesis from TRP |  |  |
| YFR047C | 2.4.2.19 | QPT1 | Quinolate phosphoribosyl transferase | QAm + PRPPm -> NAMNm + CO2m + PPIm | mnadc |
| YLR328W | 2.7.7.18 | YLR328W | NAMN adenylyl transferase | NAMNm + ATPm -> PPIm + NAADm | mnadd1 |
| YLR328W | 2.7.7.18 | YLR328W | NAMN adenylyl transferase | NMNm + ATPm -> NADm + PPIm | mnadd2 |
| YHR074W | 6.3.5.1 | QNS1 | Deamido-NAD ammonia ligase | NAADm + ATPm + NH3m -> NADm + AMPm + PPIm | mnade |
| YJR049c | 2.7.1.23 | utr1 | NAD kinase, POLYPHOSPHATE KINASE (EC 2.7.4.1)/NAD + KINASE (EC 2.7.1.23) | NADm + ATPm -> NADPm + ADPm | mnadf_1 |
| YPL188w | 2.7.1.23 | POS5 | NAD kinase, POLYPHOSPHATE KINASE (EC 2.7.4.1)/NAD + KINASE (EC 2.7.1.23) | NADm + ATPm -> NADPm + ADPm | mnadf_2 |
| YEL041w | 2.7.1.23 | YEL041w | NAD kinase, POLYPHOSPHATE KINASE (EC 2.7.4.1)/NAD + KINASE (EC 2.7.1.23) | NADm + ATPm -> NADPm + ADPm | mnadf_5 |
| — | 3.1.2.- |  | NADP phosphatase | NADPm -> NADm + PIm | mnadphps |
| YLR209C | 2.4.2.1 | PNP1 | strong similarity to purine-nucleoside phosphorylases | ADNm + PIm <-> ADm + RIPm | mnadg1 |
| YLR209C | 2.4.2.1 | PNP1 | strong similarity to purine-nucleoside phosphorylases | GSNm + PIm <-> GNm + RIPm | mnadg2 |
| YGL037C | 3.5.1.19 | PNC1 | Nicotinamidase | NAMm <-> NACm + NH3m | mnadh |
| YOR209C | 2.4.2.11 | NPT1 | NAPRTase | NACm + PRPPm -> NAMNm + PPIm | mnpt1 |
|  | 3.2.2.5 |  |  | NADm -> NAMm + ADPRIBm | mnad1 |
|  |  |  | Uptake Pathways |  |  |
|  |  |  | Porphyrin and Chlorophyll Metabolism |  |  |
| YDR232W | 2.3.1.37 | hem1 | 5-Aminolevulinate synthase | SUCCOAm + GLYm -> ALAVm + COAm + CO2m | hem1 |
| YGL040C | 4.2.1.24 | HEM2 | Aminolevulinate dehydratase | 2 ALAV -> PBG | hem2 |
| YDL205C | 4.3.1.8 | HEM3 | Hydroxymethylbilane synthase | 4 PBG -> HMB + 4 NH3 | hem3 |
| YOR278W | 4.2.1.75 | HEM4 | Uroporphyrinogen-III synthase | HMB -> UPRG | hem4 |
| YDR047W | 4.1.1.37 | HEM12 | Uroporphyrinogen decarboxylase | UPRG -> 4 CO2 + CPP | hem12 |
| YDR044W | 1.3.3.3 | HEM13 | Coproporphyrinogen oxidase, aerobic | O2 + CPP -> 2 CO2 + PPHG | hem13 |
| YER014W | 1.3.3.4 | HEM14 | Protoporphyrinogen oxidase | O2 + PPHGm -> PPIXm | hem14 |
| YOR176W | 4.99.1.1 | HEM15 | Ferrochelatase | PPIXm -> PTHm | hem15 |
| YGL245W | 6.1.1.17 | YGL245W | glutamyl-tRNA synthetase, cytoplasmic | GLU + ATP -> GTRNA + AMP + PPI | unrxn10 |
| YOL033W | 6.1.1.17 | MSE1 |  | GLUm + ATPm -> GTRNAm + AMPm + PPIm | mse1 |
| YKR069W | 2.1.1.107 | met1 | uroporphyrin-III C-methyltransferase | SAM + UPRG -> SAH + PC2 | met1 |
|  |  |  | Quinone Biosynthesis |  |  |
| YKL211C | 4.1.3.27 | trp3 | anthranilate synthase Component II and indole-3-phosphate (multifunctional enzyme) | CHOR -> 4HBZ + PYR | trp3_3 |
| YER090W | 4.1.3.27 | trp2 | anthranilate synthase Component I | CHOR -> 4HBZ + PYR | trp2_2 |
| YPR176C | 2.5.1.- | BET2 | geranylgeranyltransferase type II beta subunit | 4HBZ + NPP -> N4HBZ + PPI | bet2 |
| YJL031C | 2.5.1.- | BET4 | geranylgeranyltransferase type II alpha subunit |  |  |
| YGL155W | 2.5.1.- | cdc43 | geranylgeranyltransferase type I beta subunit |  |  |
| YBR003W | 2.5.1.- | COQ1 | Hexaprenyl pyrophosphate synthetase, catalyzes the first step in coenzyme Q (ubiquinone) biosynthesis pathway | 4HBZ + NPP -> N4HBZ + PPI | coq1 |
| YNR041C | 2.5.1.- | COQ2 | para-hydroxybenzoate--polyprenyltransferase | 4HBZ + NPP -> N4HBZ + PPI | coq2 |
| YPL172C | 2.5.1.- | COX10 | protoheme IX farnesyltransferase, mitochondrial precursor | 4HBZ + NPP -> N4HBZ + PPI | cox10 |
| YDL090C | 2.5.1.- | ram1 | protein farnesyltransferase beta subunit | 4HBZ + NPP -> N4HBZ + PPI | ram1 |
| YKL019W | 2.5.1.- | RAM2 | protein farnesyltransferase alpha subunit |  |  |
| YBR002C | 2.5.1.- | RER2 | putative dehydrodolichyl diphosphate synthetase | 4HBZ + NPP -> N4HBZ + PPI | rer2 |
| YMR101C | 2.5.1.- | SRT1 | putative dehydrodolichyl diphosphate synthetase | 4HBZ + NPP -> N4HBZ + PPI | srt1 |
| YDR538W | 4.1.1.- | PAD1 | Octaprenyl-hydroxybenzoate decarboxylase | N4HBZ -> CO2 + 2NPPP | pad1_2 |
|  | 1.13.14.- |  | 2-Octaprenylphenol hydroxylase | 2NPPP + O2 -> 2N6H | ubib |
| YPL266W | 2.1.1.- | DIM1 |  | 2N6H + SAM -> 2NPMP + SAH | dim1 |
| — | 1.14.13.- |  | 2-Octaprenyl-6-methoxyphenol hydroxylase | 2NPMPm + O2m -> 2NPMBm | ubih |

TABLE 2-continued

| Locus # | E.C. # | Gene | Gene Description | Reaction | Rxn Name |
|---|---|---|---|---|---|
| YML110C | 2.1.1.- | COQ5 | 2-Octaprenyl-6-methoxy-1,4-benzoquinone methylase | 2NPMBm + SAMm -> 2NPMMBm + SAHm | coq5 |
| YGR255C | 1.14.13- | COQ6 | COQ6 monooxygenase | 2NPMMBm + O2m -> 2NMHMBm | coq6b |
| YOL096C | 2.1.1.64 | COQ3 | 3-Dimethylubiquinone 3-methyltransferase | 2NMHMBm + SAMm -> QH2m + SAHm | ubig |

Memberane Transport
Mitochondiral Membrane Transport
The followings diffuse through the inner mitochondiral membrane in a non-carrier-mediated manner:

| Locus # | E.C. # | Gene | Gene Description | Reaction | Rxn Name |
|---|---|---|---|---|---|
| | | | | O2 <-> O2m | mo2 |
| | | | | CO2 <-> CO2m | mco2 |
| | | | | ETH <-> ETHm | meth |
| | | | | NH3 <-> NH3m | mnh3 |
| | | | | MTHN <-> MTHNm | mmthn |
| | | | | THFm <-> THF | mthf |
| | | | | METTHFm <-> METTHF | mmthf |
| | | | | SERm <-> SER | mser |
| | | | | GLYm <-> GLY | mgly |
| | | | | CBHCAPm <-> CBHCAP | mcbh |
| | | | | OICAPm <-> OICAP | moicap |
| | | | | PROm <-> PRO | mpro |
| | | | | CMPm <-> CMP | mcmp |
| | | | | ACm <-> AC | mac |
| | | | | ACAR -> ACARm | macar__ |
| | | | | CARm -> CAR | mcar__ |
| | | | | ACLAC <-> ACLACm | maclac |
| | | | | ACTAC <-> ACTACm | mactc |
| | | | | SLF -> SLFm + Hm | mslf |
| | | | | THRm <-> THR | mthr |
| | | | | AKAm -> AKA | maka |
| YMR056c | | AAC1 | ADP/ATP carrier protein (MCF) | ADP + ATPm + PI -> Hm + ADPm + ATP + PIm | aac1 |
| YBL030C | | pet9 | ADP/ATP carrier protein (MCF) | ADP + ATPm + PI -> Hm + ADPm + ATP + PIm | pet9 |
| YBR085w | | AAC3 | ADP/ATP carrier protein (MCF) | ADP + ATPm + PI -> Hm + ADPm + ATP + PIm | aac3 |
| YJR077C | | MIR1 | phosphate carrier | PI <-> Hm + PIm | mir1a |
| YER053C | | YER053C | similarity to C. elegans mitochondrial phosphate carrier | PI + OHm <-> PIm | mir1d |
| YLR348C | | DIC1 | dicarboxylate carrier | MAL + SUCCm <-> MALm + SUCC | dic1__1 |
| YLR348C | | DIC1 | dicarboxylate carrier | MAL + PIm <-> MALm + PI | dic1__2 |
| YLR348C | | DIC1 | dicarboxylate carrier | SUCC + PIm -> SUCCm + PI | dic1__3 |
| | | | | MALT + PIm <-> MALTm + PI | mmlt |
| YKL120W | | OAC1 | Mitochondrial oxaloacetate carrier | OA <-> OAm + Hm | moab |
| YBR291C | | CTP1 | citrate transport protein | CIT + MALm <-> CITm + MAL | ctp1__1 |
| YBR291C | | CTP1 | citrate transport protein | CIT + PEPm <-> CITm + PEP | ctp1__2 |
| YBR291C | | CTP1 | citrate transport protein | CIT + ICITm <-> CITm + ICIT | ctp1__3 |
| | | | | IPPMAL <-> IPPMALm | mpma1R |
| | | | | LAC <-> LACm + Hm | mlac |
| | | | pyruvate carrier | PYR <-> PYRm + Hm | pyrca |
| | | | glutamate carrier | GLU <-> GLUm + Hm | gca |
| | | | | GLU + OHm -> GLUm | gcb |
| YOR130C | | ORT1 | ornithine carrier | ORN + Hm <-> ORNm | ort1 |
| YOR100C | | CRC1 | carnitine carrier | CARm + ACAR -> CAR + ACARm | crc1 |
| | | | | OIVAL <-> OIVALm | moival |
| | | | | OMVAL <-> OMVALm | momval |
| YIL134W | | FLX1 | Protein involved in transport of FAD from cytosol into the mitochondrial matrix | FAD + FMNm -> FADm + FMN | mfad |
| | | | | RIBFLAV <-> RIBFLAVm | mribo |
| | | | | DTB <-> DTBm | mdtb |
| | | | | H3MCOA <-> H3MCOAm | mmcoa |
| | | | | MVL <-> MVLm | mmvl |
| | | | | PA <-> PAm | mpa |
| | | | | 4PPNTE <-> 4PPNTEm | mppnt |
| | | | | AD <-> ADm | mad |
| | | | | PRPP <-> PRPPm | mprpp |
| | | | | DHF <-> DHFm | mdhf |
| | | | | QA <-> QAm | mqa |
| | | | | OPP <-> OPPm | mopp |
| | | | | SAM <-> SAMm | msam |
| | | | | SAH <-> SAHm | msah |
| YJR095W | | SFC1 | Mitochondrial membrane succinate-fumarate transporter, member of the mitochondrial carrier family (MCF) of membrane transporters | SUCC + FUMm -> SUCCm + FUM | sfc1 |

TABLE 2-continued

| Locus # | E.C. # | Gene | Gene Description | Reaction | Rxn Name |
|---|---|---|---|---|---|
| YPL134C | | ODC1 | 2-oxodicarboylate transporter | AKGm + OXA <-> AKG + OXAm | odc1 |
| YOR222W | | ODC2 | 2-oxodicarboylate transporter | AKGm + OXA <-> AKG + OXAm | odc2 |
| | | | Malate Aspartate Shuttle | | |
| | | | Included elsewhere | | |
| | | | Glycerol phosphate shuttle | | |
| | | | | T3P2m -> T3P2 | mt3p |
| | | | | GL3P -> GL3Pm | mgl3p |
| | | | Plasma Membrane Transport | | |
| | | | Carbohydrates | | |
| YHR092c | | HXT4 | moderate- to low-affinity glucose transporter | GLCxt -> GLC | hxt4 |
| YLR081w | | GAL2 | galactose (and glucose) permease | GLCxt -> GLC | gal2__3 |
| YOL156w | | HXT11 | low affinity glucose transport protein | GLCxt -> GLC | hxt11 |
| YDR536W | | stl1 | Protein member of the hexose transporter family | GLCxt -> GLC | stl1__1 |
| YHR094c | | hxt1 | High-affinity hexose (glucose) transporter | GLCxt -> GLC | hxt1__1 |
| YOL156w | | HXT11 | Glucose permease | GLCxt -> GLC | hxt11__1 |
| YEL069c | | HXT13 | high-affinity hexose transporter | GLCxt -> GLC | hxt13__1 |
| YDL245c | | HXT15 | Hexose transporter | GLCxt -> GLC | hxt15__1 |
| YJR158w | | HXT16 | hexose permease | GLCxt -> GLC | hxt16__1 |
| YFL011w | | HXT10 | high-affinity hexose transporter | GLCxt -> GLC | hxt10__1 |
| YNR072w | | HXT17 | Putative hexose transporter | GLCxt -> GLC | hxt17__1 |
| YMR011w | | HXT2 | high affinity hexose transporter-2 | GLCxt -> GLC | hxt2__1 |
| YHR092c | | hxt4 | High-affinity glucose transporter | GLCxt -> GLC | hxt4__1 |
| YDR345c | | hxt3 | Low-affinity glucose transporter | GLCxt -> GLC | hxt3__1 |
| YHR096c | | HXT5 | hexose transporter | GLCxt -> GLC | hxt5__1 |
| YDR343c | | HXT6 | Hexose transporter | GLCxt -> GLC | hxt6__1 |
| YDR342c | | HXT7 | Hexose transporter | GLCxt -> GLC | hxt7__1 |
| YJL214w | | HXT8 | hexose permease | GLCxt -> GLC | hxt8__4 |
| YJL219w | | HXT9 | hexose permease | GLCxt -> GLC | hxt9__1 |
| YLR081w | | gal2 | galactose permease | GLACxt + HEXT -> GLAC | gal2__1 |
| YFL011w | | HXT10 | high-affinity hexose transporter | GLACxt + HEXT -> GLAC | hxt10__4 |
| YOL156w | | HXT11 | Glucose permease | GLACxt + HEXT -> GLAC | hxt11__4 |
| YNL318c | | HXT14 | Member of the hexose transporter family | GLACxt + HEXT -> GLAC | hxt14 |
| YJL219w | | HXT9 | hexose permease | GLACxt + HEXT -> GLAC | hxt9__4 |
| YDR536W | | stl1 | Protein member of the hexose transporter family | GLACxt + HEXT -> GLAC | stl1__4 |
| YFL055w | | AGP3 | Amino acid permease for serine, aspartate, and glutamate | GLUxt + HEXT <-> GLU | agp3__3 |
| YDR536W | | stl1 | Protein member of the hexose transporter family | GLUxt + HEXT <-> GLU | stl1__2 |
| YKR039W | | gap1 | General amino acid permease | GLUxt + HEXT <-> GLU | gap8 |
| YCL025C | | AGP1 | Amino acid permease for most neutral amino acids | GLUxt + HEXT <-> GLU | gap24 |
| YPL265W | | DIP5 | Dicarboxylic amino acid permease | GLUxt + HEXT <-> GLU | dip10 |
| YDR536W | | stl1 | Protein member of the hexose transporter family | GLUxt + HEXT <-> GLU | stl1__3 |
| YHR094c | | hxt1 | High-affinity hexose (glucose) transporter | FRUxt + HEXT -> FRU | hxt1__2 |
| YFL011w | | HXT10 | high-affinity hexose transporter | FRUxt + HEXT -> FRU | hxt10__2 |
| YOL156w | | HXT11 | Glucose permease | FRUxt + HEXT -> FRU | hxt11__2 |
| YEL069c | | HXT13 | high-affinity hexose transporter | FRUxt + HEXT -> FRU | hxt13__2 |
| YDL245c | | HXT15 | Hexose transporter | FRUxt + HEXT -> FRU | hxt15__2 |
| YJR158w | | HXT16 | hexose permease | FRUxt + HEXT -> FRU | hxt16__2 |
| YNR072w | | HXT17 | Putative hexose transporter | FRUxt + HEXT -> FRU | hxt17__2 |
| YMR011w | | HXT2 | high affinity hexose transporter-2 | FRUxt + HEXT -> FRU | hxt2__2 |
| YDR345c | | hxt3 | Low-affinity glucose transporter | FRUxt + HEXT -> FRU | hxt3__2 |
| YHR092c | | hxt4 | High-affinity glucose transporter | FRUxt + HEXT -> FRU | hxt4__2 |
| YHR096c | | HXT5 | hexose transporter | FRUxt + HEXT -> FRU | hxt5__2 |
| YDR343c | | HXT6 | Hexose transporter | FRUxt + HEXT -> FRU | hxt6__2 |
| YDR342c | | HXT7 | Hexose transporter | FRUxt + HEXT -> FRU | hxt7__2 |
| YJL214w | | HXT8 | hexose permease | FRUxt + HEXT -> FRU | hxt8__5 |
| YJL219w | | HXT9 | hexose permease | FRUxt + HEXT -> FRU | hxt9__2 |
| YHR094c | | hxt1 | High-affinity hexose (glucose) transporter | MANxt + HEXT -> MAN | hxt1__5 |
| YFL011w | | HXT10 | high-affinity hexose transporter | MANxt + HEXT -> MAN | hxt10__3 |
| YOL156w | | HXT11 | Glucose permease | MANxt + HEXT -> MAN | hxt11__3 |
| YEL069c | | HXT13 | high-affinity hexose transporter | MANxt + HEXT -> MAN | hxt13__3 |
| YDL245c | | HXT15 | Hexose transporter | MANxt + HEXT -> MAN | hxt15__3 |
| YJR158w | | HXT16 | hexose permease | MANxt + HEXT -> MAN | hxt16__3 |
| YNR072w | | HXT17 | Putative hexose transporter | MANxt + HEXT -> MAN | hxt17__3 |
| YMR011w | | HXT2 | high affinity hexose transporter-2 | MANxt + HEXT -> MAN | hxt2__3 |
| YDR345c | | hxt3 | Low-affinity glucose transporter | MANxt + HEXT -> MAN | hxt3__3 |
| YHR092c | | hxt4 | High-affinity glucose transporter | MANxt + HEXT -> MAN | hxt4__3 |
| YHR096c | | HXT5 | hexose transporter | MANxt + HEXT -> MAN | hxt5__3 |
| YDR343c | | HXT6 | Hexose transporter | MANxt + HEXT -> MAN | hxt6__3 |
| YDR342c | | HXT7 | Hexose transporter | MANxt + HEXT -> MAN | hxt7__3 |
| YJL214w | | HXT8 | hexose permease | MANxt + HEXT -> MAN | hxt8__6 |
| YJL219w | | HXT9 | hexose permease | MANxt + HEXT -> MAN | hxt9__3 |
| YDR497c | | ITR1 | myo-inositol transporter | MIxt + HEXT -> MI | itr1 |
| YOL103w | | ITR2 | myo-inositol transporter | MIxt + HEXT -> MI | itr2 |
| | | | Maltase permease | MLTxt + HEXT -> MLT | mltup |

TABLE 2-continued

| Locus # | E.C. # | Gene | Gene Description | Reaction | Rxn Name |
|---|---|---|---|---|---|
| YIL162W | 3.2.1.26 | SUC2 | invertase (sucrose hydrolyzing enzyme) | SUCxt -> GLCxt + FRUxt | suc2 |
|  |  |  | sucrose | SUCxt + HEXT -> SUC | sucup |
| YBR298c |  | MAL31 | Dicarboxylates | MALxt + HEXT <-> MAL | mal31 |
|  |  |  | a-Ketoglutarate/malate translocator | MALxt + AKG <-> MAL + AKGxt | akmup |
|  |  |  | a-methylglucoside | AMGxt <-> AMG | amgup |
|  |  |  | Sorbose | SORxt <-> SOR | sorup |
|  |  |  | Arabinose (low affinity) | ARABxt <-> ARAB | arbup1 |
|  |  |  | Fucose | FUCxt + HEXT <-> FUC | fucup |
|  |  |  |  | GLTLxt + HEXT -> GLTL | gltlupb |
|  |  |  | Glucitol | GLTxt + HEXT -> GLT | gltup |
|  |  |  | Glucosamine | GLAMxt + HEXT <-> GLAM | gaup |
| YLL043W |  | FPS1 | Glycerol | GLxt <-> GL | glup |
| YKL217W |  | JEN1 | Lactate transport | LACxt + HEXT <-> LAC | lacup1 |
|  |  |  | Mannitol | MNTxt + HEXT -> MNT | mntup |
|  |  |  | Melibiose | MELIxt + HEXT -> MELI | melup_1 |
|  |  |  | N-Acetylglucosamine | NAGxt + HEXT -> NAG | nagup |
|  |  |  | Rhamnose | RMNxt + HEXT -> RMN | rmnup |
|  |  |  | Ribose | RIBxt + HEXT -> RIB | ribup |
|  |  |  | Trehalose | TRExt + HEXT -> TRE | treup_1 |
|  |  |  |  | TRExt -> AATRE6P | treup_2 |
|  |  |  |  | XYLxt <-> XYL | xylup |
|  |  |  | Amino Acids |  |  |
| YKR039W |  | gap1 | General amino acid permease | ALAxt + HEXT <-> ALA | gap1_1 |
| YPL265W |  | DIP5 | Dicarboxylic amino acid permease | ALAxt + HEXT <-> ALA | dip5 |
| YCL025C |  | AGP1 | Amino acid permease for most neutral amino acids | ALAxt + HEXT <-> ALA | gap25 |
| YOL020W |  | TAT2 | Tryptophan permease | ALAxt + HEXT <-> ALA | tat5 |
| YOR348C |  | PUT4 | Proline permease | ALAxt + HEXT <-> ALA | put4 |
| YKR039W |  | gap1 | General amino acid permease | ARGxt + HEXT <-> ARG | gap2 |
| YEL063C |  | can1 | Permease for basic amino acids | ARGxt + HEXT <-> ARG | can1_1 |
| YNL270C |  | ALP1 | Protein with strong similarity to permeases | ARGxt + HEXT <-> ARG | alp1 |
| YKR039W |  | gap1 | General amino acid permease | ASNxt + HEXT <-> ASN | gap3 |
| YCL025C |  | AGP1 | Amino acid permease for most neutral amino acids | ASNxt + HEXT <-> ASN | gap21 |
| YDR508C |  | GNP1 | Glutamine permease (high affinity) | ASNxt + HEXT <-> ASN | gnp2 |
| YPL265W |  | DIP5 | Dicarboxylic amino acid permease | ASNxt + HEXT <-> ASN | dip6 |
| YFL055W |  | AGP3 | Amino acid permease for serine, aspartate, and glutamate | ASPxt + HEXT <-> ASP | agp3_2 |
| YKR039W |  | gap1 | General amino acid permease | ASPxt + HEXT <-> ASP | gap4 |
| YPL265W |  | DIP5 | Dicarboxylic amino acid permease | ASPxt + HEXT <-> ASP | dip7 |
| YKR039W |  | gap1 | General amino acid permease | CYSxt + HEXT <-> CYS | gap5 |
| YDR508C |  | GNP1 | Glutamine permease (high affinity) | CYSxt + HEXT <-> CYS | gnp3 |
| YBR068C |  | BAP2 | Branched chain amino acid permease | CYSxt + HEXT <-> CYS | bap2_1 |
| YDR046C |  | BAP3 | Branched chain amino acid permease | CYSxt + HEXT <-> CYS | bap3_1 |
| YBR069C |  | VAP1 | Amino acid permease | CYSxt + HEXT <-> CYS | vap7 |
| YOL020W |  | TAT2 | Tryptophan permease | CYSxt + HEXT <-> CYS | tat7 |
| YKR039W |  | gap1 | General amino acid permease | GLYxt + HEXT <-> GLY | gap6 |
| YOL020W |  | TAT2 | Tryptophan permease | GLYxt + HEXT <-> GLY | tat6 |
| YPL265W |  | DIP5 | Dicarboxylic amino acid permease | GLYxt + HEXT <-> GLY | dip8 |
| YOR348C |  | PUT4 | Proline permease | GLYxt + HEXT <-> GLY | put5 |
| YKR039W |  | gap1 | General amino acid permease | GLNxt + HEXT <-> GLN | gap7 |
| YCL025C |  | AGP1 | Amino acid permease for most neutral amino acids | GLNxt + HEXT <-> GLN | gap22 |
| YDR508C |  | GNP1 | Glutamine permease (high affinity) | GLNxt + HEXT <-> GLN | gnp1 |
| YPL265W |  | DIP5 | Dicarboxylic amino acid permease | GLNxt + HEXT <-> GLN | dip9 |
| YGR191W |  | HIP1 | Histidine permease | HISxt + HEXT <-> HIS | hip1 |
| YKR039W |  | gap1 | General amino acid permease | HISxt + HEXT <-> HIS | gap9 |
| YCL025C |  | AGP1 | Amino acid permease for most neutral amino acids | HISxt + HEXT <-> HIS | gap23 |
| YBR069C |  | VAP1 | Amino acid permease | HISxt + HEXT <-> HIS | vap6 |
| YBR069C |  | TAT1 | Amino acid permease that transports valine, leucine, isleucine, tyrosine, tryptophan, and threonine | ILExt + HEXT <-> ILE | tat1_2 |
| YKR039W |  | gap1 | General amino acid permease | ILExt + HEXT <-> ILE | gap10 |
| YCL025C |  | AGP1 | Amino acid permease for most neutral amino acids | ILExt + HEXT <-> ILE | gap32 |
| YBR068C |  | BAP2 | Branched chain amino acid permease | ILExt + HEXT <-> ILE | bap2_2 |
| YDR046C |  | BAP3 | Branched chain amino acid permease | ILExt + HEXT <-> ILE | bap3_2 |
| YBR069C |  | VAP1 | Amino acid permease | ILExt + HEXT <-> ILE | vap3 |
| YBR069C |  | TAT1 | Amino acid permease that transports valine, leucine, isleucine, tyrosine, tryptophan, and threonine | LEUxt + HEXT <-> LEU | tat1_3 |
| YKR039W |  | gap1 | General amino acid permease | LEUxt + HEXT <-> LEU | gap11 |
| YCL025C |  | AGP1 | Amino acid permease for most neutral amino acids | LEUxt + HEXT <-> LEU | gap33 |
| YBR068C |  | BAP2 | Branched chain amino acid permease | LEUxt + HEXT <-> LEU | bap2_3 |
| YDR046C |  | BAP3 | Branched chain amino acid permease | LEUxt + HEXT <-> LEU | bap3_3 |
| YBR069C |  | VAP1 | Amino acid permease | LEUxt + HEXT <-> LEU | vap4 |
| YDR508C |  | GNP1 | Glutamine permease (high affinity) | LEUxt + HEXT <-> LEU | gnp7 |
| YKR039W |  | gap1 | General amino acid permease | METxt + HEXT <-> MET | gap13 |
| YCL025C |  | AGP1 | Amino acid permease for most neutral amino acids | METxt + HEXT <-> MET | gap26 |
| YDR508C |  | GNP1 | Glutamine permease (high affinity) | METxt + HEXT <-> MET | gnp4 |
| YBR068C |  | BAP2 | Branched chain amino acid permease | METxt + HEXT <-> MET | bap2_4 |
| YDR046C |  | BAP3 | Branched chain amino acid permease | METxt + HEXT <-> MET | bap3_4 |

TABLE 2-continued

| Locus # | E.C. # | Gene | Gene Description | Reaction | Rxn Name |
|---|---|---|---|---|---|
| YGR055W | | MUP1 | High-affinity methionine permease | METxt + HEXT <-> MET | mup1 |
| YHL036W | | MUP3 | Low-affinity methionine permease | METxt + HEXT <-> MET | mup3 |
| YKR039W | | gap1 | General amino acid permease | PHExt + HEXT <-> PHEN | gap14 |
| YCL025C | | AGP1 | Amino acid permease for most neutral amino acids | PHExt + HEXT <-> PHEN | gap29 |
| YOL020W | | TAT2 | Tryptophan permease | PHExt + HEXT <-> PHEN | tat4 |
| YBR068C | | BAP2 | Branched chain amino acid permease | PHExt + HEXT <-> PHEN | bap2_5 |
| YDR046C | | BAP3 | Branched chain amino acid permease | PHExt + HEXT <-> PHEN | bap3_5 |
| YKR039W | | gap1 | General amino acid permease | PROxt + HEXT <-> PRO | gap15 |
| YOR348C | | PUT4 | Proline permease | PROxt + HEXT <-> PRO | put6 |
| YBR069C | | TAT1 | Amino acid permease that transports valine, leucine, isleucine, tyrosine, tryptophan, and threonine | TRPxt + HEXT <-> TRP | tat1_6 |
| YKR039W | | gap1 | General amino acid permease | TRPxt + HEXT <-> TRP | gap18 |
| YBR069C | | VAP1 | Amino acid permease | TRPxt + HEXT <-> TRP | vap2 |
| YOL020W | | TAT2 | Tryptophan permease | TRPxt + HEXT <-> TRP | tat3 |
| YBR068C | | BAP2 | Branched chain amino acid permease | TRPxt + HEXT <-> TRP | bap2_6 |
| YDR046C | | BAP3 | Branched chain amino acid permease | TRPxt + HEXT <-> TRP | bap3_6 |
| YBR069C | | TAT1 | Amino acid permease that transports valine, leucine, isleucine, tyrosine, tryptophan, and threonine | TYRxt + HEXT <-> TYR | tat1_7 |
| YKR039W | | gap1 | General amino acid permease | TYRxt + HEXT <-> TYR | gap19 |
| YCL025C | | AGP1 | Amino acid permease for most neutral amino acids | TYRxt + HEXT <-> TYR | gap28 |
| YBR068C | | BAP2 | Branched chain amino acid permease | TYRxt + HEXT <-> TYR | bap2_7 |
| YBR069C | | VAP1 | Amino acid permease | TYRxt + HEXT <-> TYR | vap1 |
| YOL020W | | TAT2 | Tryptophan permease | TYRxt + HEXT <-> TYR | tat2 |
| YDR046C | | BAP3 | Branched chain amino acid permease | TYRxt + HEXT <-> TYR | bap3_7 |
| YKR039W | | gap1 | General amino acid permease | VALxt + HEXT <-> VAL | gap20 |
| YCL025C | | AGP1 | Amino acid permease for most neutral amino acids | VALxt + HEXT <-> VAL | gap31 |
| YDR046C | | BAP3 | Branched chain amino acid permease | VALxt + HEXT <-> VAL | bap3_8 |
| YBR069C | | VAP1 | Amino acid permease | VALxt + HEXT <-> VAL | vap5 |
| YBR068C | | BAP2 | Branched chain amino acid permease | VALxt + HEXT <-> VAL | bap2_8 |
| YFL055W | | AGP3 | Amino acid permease for serine, aspartate, and glutamate | SERxt + HEXT <-> SER | agp3_1 |
| YCL025C | | AGP1 | Amino acid permease for most neutral amino acids | SERxt + HEXT <-> SER | gap27 |
| YDR508C | | GNP1 | Glutamine permease (high affinity) | SERxt + HEXT <-> SER | gnp5 |
| YKR039W | | gap1 | General amino acid permease | SERxt + HEXT <-> SER | gap16 |
| YPL265W | | DIP5 | Dicarboxylic amino acid permease | SERxt + HEXT <-> SER | dip11 |
| YBR069C | | TAT1 | Amino acid permease that transports valine, leucine, isleucine, tyrosine, tryptophan, and threonine | THRxt + HEXT <-> THR | tat1_1 |
| YCL025C | | AGP1 | Amino acid permease for most neutral amino acids | THRxt + HEXT <-> THR | gap30 |
| YKR039W | | gap1 | General amino acid permease | THRxt + HEXT <-> THR | gap17 |
| YDR508C | | GNP1 | Glutamine permease (high affinity) | THRxt + HEXT <-> THR | gnp6 |
| YNL268W | | LYP1 | Lysine specific permease (high affinity) | LYSxt + HEXT <-> LYS | lyp1 |
| YKR039W | | gap1 | General amino acid permease | LYSxt + HEXT <-> LYS | gap12 |
| YLL061W | | MMP1 | High affinity S-methylmethionine permease | MMETxt + HEXT -> MMET | mmp1 |
| YPL274W | | SAM3 | High affinity S-adenosylmethionine permease | SAMxt + HEXT -> SAM | sam3 |
| YOR348C | | PUT4 | Proline permease | GABAxt + HEXT -> GABA | put7 |
| YDL210W | | uga4 | Amino acid permease with high specificity for GABA | GABAxt + HEXT -> GABA | uga4 |
| YBR132C | | AGP2 | Plasma membrane carnitine transporter | CARxt <-> CAR | agp2 |
| YGL077C | | HNM1 | Choline permease | CHOxt + HEXT -> MET | hnm1 |
| YNR056C | | BIO5 | transmembrane regulator of KAPA/DAPA transport | BIOxt + HEXT -> BIO | bio5a |
| YDL210W | | uga4 | Amino acid permease with high specificity for GABA | ALAVxt + HEXT -> ALAV | uga5 |
| YKR039W | | gap1 | General amino acid permease | ORNxt + HEXT <-> ORN | gap1b |
| YEL063C | | can1 | Permease for basic amino acids | ORNxt + HEXT <-> ORN | can1b |
| | | | Putrescine | PTRSCxt + HEXT -> PTRSC | ptrup |
| | | | Spermidine & putrescine | SPRMDxt + HEXT -> SPRMD | sprup1 |
| YKR093W | | PTR2 | Dipeptide | DIPEPxt + HEXT -> DIPEP | ptr2 |
| YKR093W | | PTR2 | Oligopeptide | OPEPxt + HEXT -> OPEP | ptr3 |
| YKR093W | | PTR2 | Peptide | PEPTxt + HEXT -> PEPT | ptr4 |
| YBR021W | | FUR4 | Uracil | URAxt + HEXT -> URA | uraup1 |
| | | | Nicotinamide mononucleotide transporter | NMNxt + HEXT -> NMN | nmnup |
| YER056C | | FCY2 | Cytosine purine permease | CYTSxt + HEXT -> CYTS | fcy2_1 |
| YER056C | | FCY2 | Adenine | ADxt + HEXT -> AD | fcy2_2 |
| YER056C | | FCY2 | Guanine | GNxt + HEXT <-> GN | fcy2_3 |
| YER060W | | FCY21 | Cytosine purine permease | CYTSxt + HEXT -> CYTS | fcy21_1 |
| YER060W | | FCY21 | Adenine | ADxt + HEXT -> AD | fcy21_2 |
| YER060W | | FCY21 | Guanine | GNxt + HEXT <-> GN | fcy21_3 |
| YER060W-A | | FCY22 | Cytosine purine permease | CYTSxt + HEXT -> CYTS | fcy22_1 |
| YER060W-A | | FCY22 | Adenine | ADxt + HEXT -> AD | fcy22_2 |
| YER060W-A | | FCY22 | Guanine | GNxt + HEXT <-> GN | fcy22_3 |
| YGL186C | | YGL186C | Cytosine purine permease | CYTSxt + HEXT -> CYTS | cytup1 |
| YGL186C | | YGL186C | Adenine | ADxt + HEXT -> AD | adup1 |
| YGL186C | | YGL186C | Guanine | GNxt + HEXT <-> GN | gnup |
| | | | G-system | ADNxt + HEXT -> ADN | ncgup1 |
| | | | G-system | GSNxt + HEXT -> GSN | ncgup3 |

TABLE 2-continued

| Locus # | E.C. # | Gene | Gene Description | Reaction | Rxn Name |
|---|---|---|---|---|---|
| YBL042C | | FUI1 | Uridine permease, G-system | URIxt + HEXT -> URI | uriup |
| | | | G-system | CYTDxt + HEXT -> CYTD | ncgup4 |
| | | | G-system (transports all nucleosides) | INSxt + HEXT -> INS | ncgup5 |
| | | | G-system | XTSINExt + HEXT -> XTSINE | ncgup6 |
| | | | G-system | DTxt + HEXT -> DT | ncgup7 |
| | | | G-system | DINxt + HEXT -> DIN | ncgup8 |
| | | | G-system | DGxt + HEXT -> DG | ncgup9 |
| | | | G-system | DAxt + HEXT -> DA | ncgup10 |
| | | | G-system | DCxt + HEXT -> DC | ncgup11 |
| | | | G-system | DUxt + HEXT -> DU | ncgup12 |
| | | | C-system | ADNxt + HEXT -> ADN | nccup1 |
| YBL042C | | FUI1 | Uridine permease, C-system | URIxt + HEXT -> URI | nccup2 |
| | | | C-system | CYTDxt + HEXT -> CYTD | nccup3 |
| | | | C-system | DTxt + HEXT -> DT | nccup4 |
| | | | C-system | DAxt + HEXT -> DA | nccup5 |
| | | | C-system | DCxt + HEXT -> DC | nccup6 |
| | | | C-system | DUxt + HEXT -> DU | nccup7 |
| | | | Nucleosides and deoxynucleoside | ADNxt + HEXT -> ADN | ncup1 |
| | | | Nucleosides and deoxynucleoside | GSNxt + HEXT -> GSN | ncup2 |
| YBL042C | | FUI1 | Uridine permease, Nucleosides and deoxynucleoside | URIxt + HEXT -> URI | ncup3 |
| | | | Nucleosides and deoxynucleoside | CYTDxt + HEXT -> CYTD | ncup4 |
| | | | Nucleosides and deoxynucleoside | INSxt + HEXT -> INS | ncup5 |
| | | | Nucleosides and deoxynucleoside | DTxt + HEXT -> DT | ncup7 |
| | | | Nucleosides and deoxynucleoside | DINxt + HEXT -> DIN | ncup8 |
| | | | Nucleosides and deoxynucleoside | DGxt + HEXT -> DG | ncup9 |
| | | | Nucleosides and deoxynucleoside | DAxt + HEXT -> DA | ncup10 |
| | | | Nucleosides and deoxynucleoside | DCxt + HEXT -> DC | ncup11 |
| | | | Nucleosides and deoxynucleoside | DUxt + HEXT -> DU | ncup12 |
| | | | Hypoxanthine | HYXNxt + HEXT <-> HYXN | hyxnup |
| | | | Xanthine | XANxt <-> XAN | xanup |
| | | | Metabolic By-Products | | |
| YCR032W | | BPH1 | Probable acetic acid export pump, Acetate transport | ACxt + HEXT <-> AC | acup |
| | | | Formate transport | FORxt <-> FOR | forup |
| | | | Ethanol transport | ETHxt <-> ETH | ethup |
| | | | Succinate transport | SUCCxt + HEXT <-> SUCC | succup |
| YKL217W | | JEN1 | Pyruvate lactate proton symport | PYRxt + HEXT -> PYR | jen1_1 |
| | | | Other Compounds | | |
| YHL016C | | dur3 | Urea active transport | UREAxt + 2 HEXT <-> UREA | dur3 |
| YGR121C | | MEP1 | Ammonia transport | NH3xt <-> NH3 | mep1 |
| YNL142W | | MEP2 | Ammonia transport, low capacity high affinity | NH3xt <-> NH3 | mep2 |
| YPR138C | | MEP3 | Ammonia transport, high capacity low affinity | NH3xt <-> NH3 | mep3 |
| YJL129C | | trk1 | Potassium transporter of the plasma membrane, high affinity, member of the potassium transporter (TRK) family of membrane transporters | Kxt + HEXT <-> K | trk1 |
| YBR294W | | SUL1 | Sulfate permease | SLFxt -> SLF | sul1 |
| YLR092W | | SUL2 | Sulfate permease | SLFxt -> SLF | sul2 |
| YGR125W | | YGR125W | Sulfate permease | SLFxt -> SLF | sulup |
| YML123C | | pho84 | Inorganic phosphate transporter, transmembrane protein Citrate | PIxt + HEXT <-> PI | pho84 |
| | | | | CITxt + HEXT <-> CIT | citup |
| | | | Dicarboxylates | FUMxt + HEXT <-> FUM | fumup |
| | | | Fatty acid transport | C140xt -> C140 | faup1 |
| | | | Fatty acid transport | C160xt -> C160 | faup2 |
| | | | Fatty acid transport | C161xt -> C161 | faup3 |
| | | | Fatty acid transport | C180xt -> C180 | faup4 |
| | | | Fatty acid transport | C181xt -> C181 | faup5 |
| | | | a-Ketoglutarate | AKGxt + HEXT <-> AKG | akgup |
| YLR138W | | NHA1 | Putative Na+/H+ antiporter | NAxt <-> NA + HEXT | nha1 |
| YCR028C | | FEN2 | Pantothenate | PNTOxt + HEXT <-> PNTO | fen2 |
| | | | ATP drain flux for constant maintanence requirements | ATP -> ADP + PI | atpmt |
| YCR024c-a | | PMP1 | H+-ATPase subunit, plasma membrane | ATP -> ADP + PI + HEXT | pmp1 |
| YEL017c-a | | PMP2 | H+-ATPase subunit, plasma membrane | ATP -> ADP + PI + HEXT | pmp2 |
| YGL008c | | PMA1 | H+-transporting P-type ATPase, major isoform, plasma membrane | ATP -> ADP + PI + HEXT | pma1 |
| YPL036w | | PMA2 | H+-transporting P-type ATPase, minor isoform, plasma membrane | ATP -> ADP + PI + HEXT | pma2 |
| | | | Glyceraldehyde transport | GLALxt <-> GLAL | glaltx |
| | | | Acetaldehyde transport | ACALxt <-> ACAL | acaltx |
| YLR237W | | THI7 | Thiamine transport protein | THMxt + HEXT -> THIAMIN | thm1 |
| YOR071C | | YOR071C | Probable low affinity thiamine transporter | THMxt + HEXT -> THIAMIN | thm2 |
| YOR192C | | YOR192C | Probable low affinity thiamine transporter | THMxt + HEXT -> THIAMIN | thm3 |
| YIR028W | | dal4 | | ATNxt -> ATN | dal4 |
| YJR152W | | dal5 | | ATTxt -> ATT | dal5 |
| | | | | MTHNxt <-> MTHN | mthup |
| | | | | PAPxt <-> PAP | papx |
| | | | | DTTPxt <-> DTTP | dttpx |

TABLE 2-continued

| Locus # | E.C. # | Gene | Gene Description | Reaction | Rxn Name |
|---|---|---|---|---|---|
| | | | | THYxt <-> THY + HEXT | thyx |
| | | | | GA6Pxt <-> GA6P | ga6pup |
| YGR065C | | VHT1 | H+/biotin symporter and member of the allantoate permease family of the major facilitator superfamily | BTxt + HEXT <-> BT | btup |
| | | | | AONAxt + HEXT <-> AONA | kapaup |
| | | | | DANNAxt + HEXT <-> DANNA | dapaup |
| | | | | OGTxt -> OGT | ogtup |
| | | | | SPRMxt -> SPRM | sprmup |
| | | | | PIMExt -> PIME | pimeup |
| | | | Oxygen transport | O2xt <-> O2 | o2tx |
| | | | Carbon dioxide transport | CO2xt <-> CO2 | co2tx |
| YOR011W | | AUS1 | | ERGOSTxt <-> ERGOST | ergup |
| YOR011W | | AUS1 | Putative sterol transporter | ZYMSTxt <-> ZYMST | zymup |
| | | | | RFLAVxt + HEXT -> RIBFLAV | rflup |

Standard chemical names for the acronyms used to identify the reactants in the reactions of Table 2 are provided in Table 3.

TABLE 3

| Abbreviation | Metabolite |
|---|---|
| 13GLUCAN | 1,3-beta-D-Glucan |
| 13PDG | 3-Phospho-D-glyceroyl phosphate |
| 23DAACP | 2,3-Dehydroacyl-[acyl-carrier-protein] |
| 23PDG | 2,3-Bisphospho-D-glycerate |
| 2HDACP | Hexadecenoyl-[acp] |
| 2MANPD | ("alpha"-D-mannosyl)(,2)-"beta"-D-mannosyl-diacetylchitobiosyldiphosphodolichol |
| 2N6H | 2-Nonaprenyl-6-hydroxyphenol |
| 2NMHMB | 3-Demethylubiquinone-9 |
| 2NMHMBm | 3-Demethylubiquinone-9M |
| 2NPMBm | 2-Nonaprenyl-6-methoxy-1,4-benzoquinoneM |
| 2NPMMBm | 2-Nonaprenyl-3-methyl-6-methoxy-1,4-benzoquinoneM |
| 2NPMP | 2-Nonaprenyl-6-methoxyphenol |
| 2NPMPm | 2-Nonaprenyl-6-methoxyphenolM |
| 2NPPP | 2-Nonaprenylphenol |
| 2PG | 2-Phospho-D-glycerate |
| 3DDAH7P | 2-Dehydro-3-deoxy-D-arabino-heptonate 7-phosphate |
| 3HPACP | (3R)-3-Hydroxypalmitoyl-[acyl-carrier protein] |
| 3PG | 3-Phospho-D-glycerate |
| 3PSER | 3-Phosphoserine |
| 3PSME | 5-O-(1-Carboxyvinyl)-3-phosphoshikimate |
| 4HBZ | 4-Hydroxybenzoate |
| 4HLT | 4-Hydroxy-L-threonine |
| 4HPP | 3-(4-Hydroxyphenyl)pyruvate |
| 4PPNCYS | (R)-4'-Phosphopantothenoyl-L-cysteine |
| 4PPNTE | Pantetheine 4'-phosphate |
| 4PPNTEm | Pantetheine 4'-phosphateM |
| 4PPNTO | D-4'-Phosphopantothenate |
| 5MTA | 5'-Methylthioadenosine |
| 6DGLC | D-Gal alpha 1->6D-Glucose |
| A6RP | 5-Amino-6-ribitylamino-2,4 (1H, 3H)-pyrimidinedione |
| A6RP5P | 5-Amino-6-(5'-phosphoribosylamino)uracil |
| A6RP5P2 | 5-Amino-6-(5'-phosphoribitylamino)uracil |
| AACCOA | Acetoacetyl-CoA |
| AACP | Acyl-[acyl-carrier-protein] |
| AATRE6P | alpha,alpha'-Trehalose 6-phosphate |
| ABUTm | 2-Aceto-2-hydroxybutyrateM |
| AC | Acetate |
| ACACP | Acyl-[acyl-carrier protein] |
| ACACPm | Acyl-[acyl-carrier protein]M |
| ACAL | Acetaldehyde |
| ACALm | AcetaldehydeM |
| ACAR | O-Acetylcarnitine |
| ACARm | O-AcetylcarnitineM |
| ACCOA | Acetyl-CoA |
| ACCOAm | Acetyl-CoAM |

TABLE 3-continued

| Abbreviation | Metabolite |
|---|---|
| ACLAC | 2-Acetolactate |
| ACLACm | 2-AcetolactateM |
| ACm | AcetateM |
| ACNL | 3-Indoleacetonitrile |
| ACOA | Acyl-CoA |
| ACP | Acyl-carrier protein |
| ACPm | Acyl-carrier proteinM |
| ACTAC | Acetoacetate |
| ACTACm | AcetoacetateM |
| ACYBUT | gamma-Amino-gamma-cyanobutanoate |
| AD | Adenine |
| ADCHOR | 4-amino-4-deoxychorismate |
| ADm | AdenineM |
| ADN | Adenosine |
| ADNm | AdenonsineM |
| ADP | ADP |
| ADPm | ADPM |
| ADPRIB | ADPribose |
| ADPRIBm | ADPriboseM |
| AGL3P | Acyl-sn-glycerol 3-phosphate |
| AHHMD | 2-Amino-7,8-dihydro-4-hydroxy-6-(diphosphooxymethyl)pteridine |
| AHHMP | 2-Amino-4-hydroxy-6-hydroxymethyl-7,8-dihydropteridine |
| AHM | 4-Amino-5-hydroxymethyl-2-methylpyrimidine |
| AHMP | 4-Amino-2-methyl-5-phosphomethylpyrimidine |
| AHMPP | 2-Methyl-4-amino-5-hydroxymethylpyrimidine diphosphate |
| AHTD | 2-Amino-4-hydroxy-6-(erythro-1,2,3-trihydroxypropyl)-dihydropteridine triphosphate |
| AICAR | 1-(5'-Phosphoribosyl)-5-amino-4-imidazolecarboxamide |
| AIR | Aminoimidazole ribotide |
| AKA | 2-Oxoadipate |
| AKAm | 2-OxoadipateM |
| AKG | 2-Oxoglutarate |
| AKGm | 2-OxoglutarateM |
| AKP | 2-Dehydropantoate |
| AKPm | 2-DehydropantoateM |
| ALA | L-Alanine |
| ALAGLY | R-S-Alanylglycine |
| ALAm | L-AlanineM |
| ALAV | 5-Aminolevulinate |
| ALAVm | 5-AminolevulinateM |
| ALTRNA | L-Arginyl-tRNA(Arg) |
| AM6SA | 2-Aminomuconate 6-semialdehyde |
| AMA | L-2-Aminoadipate |
| AMASA | L-2-Aminoadipate 6-semialdehyde |
| AMG | Methyl-D-glucoside |
| AMP | AMP |
| AMPm | AMPM |
| AMUCO | 2-Aminomuconate |
| AN | Anthranilate |
| AONA | 8-Amino-7-oxononanoate |

TABLE 3-continued

| Abbreviation | Metabolite |
|---|---|
| APEP | Nalpha-Acetylpeptide |
| APROA | 3-Aminopropanal |
| APROP | alpha-Aminopropionitrile |
| APRUT | N-Acetylputrescine |
| APS | Adenylylsulfate |
| ARAB | D-Arabinose |
| ARABLAC | D-Arabinono-1,4-lactone |
| ARG | L-Arginine |
| ARGSUCC | N-(L-Arginino)succinate |
| ASER | O-Acetyl-L-serine |
| ASN | L-Asparagine |
| ASP | L-Aspartate |
| ASPERMD | N1-Acetylspermidine |
| ASPm | L-AspartateM |
| ASPRM | N1-Acetylspermine |
| ASPSA | L-Aspartate 4-semialdehyde |
| ASPTRNA | L-Asparaginyl-tRNA(Asn) |
| ASPTRNAm | L-Asparaginyl-tRNA(Asn)M |
| ASUC | N6-(1,2-Dicarboxyethyl)-AMP |
| AT3P2 | Acyldihydroxyacetone phosphate |
| ATN | Allantoin |
| ATP | ATP |
| ATPm | ATPM |
| ATRNA | tRNA(Arg) |
| ATRP | P1,P4-Bis(5'-adenosyl)tetraphosphate |
| ATT | Allantoate |
| bALA | beta-Alanine |
| BASP | 4-Phospho-L-aspartate |
| bDG6P | beta-D-Glucose 6-phosphate |
| bDGLC | beta-D-Glucose |
| BIO | Biotin |
| BT | Biotin |
| C100ACP | Decanoyl-[acp] |
| C120ACP | Dodecanoyl-[acyl-carrier protein] |
| C120ACPm | Dodecanoyl-[acyl-carrier protein]M |
| C140 | Myristic acid |
| C140ACP | Myristoyl-[acyl-carrier protein] |
| C140ACPm | Myristoyl-[acyl-carrier protein]M |
| C141ACP | Tetradecenoyl-[acyl-carrier protein] |
| C141ACPm | Tetradecenoyl-[acyl-carrier protein]M |
| C160 | Palmitate |
| C160ACP | Hexadecanoyl-[acp] |
| C160ACPm | Hexadecanoyl-[acp]M |
| C161 | 1-Hexadecene |
| C161ACP | Palmitoyl-[acyl-carrier protein] |
| C161ACPm | Palmitoyl-[acyl-carrier protein]M |
| C16A | C16_aldehydes |
| C180 | Stearate |
| C180ACP | Stearoyl-[acyl-carrier protein] |
| C180ACPm | Stearoyl-[acyl-carrier protein]M |
| C181 | 1-Octadecene |
| C181ACP | Oleoyl-[acyl-carrier protein] |
| C181ACPm | Oleoyl-[acyl-carrier protein]M |
| C182ACP | Linolenoyl-[acyl-carrier protein] |
| C182ACPm | Linolenoyl-[acyl-carrier protein]M |
| CAASP | N-Carbamoyl-L-aspartate |
| CAIR | 1-(5-Phospho-D-ribosyl)-5-amino-4-imidazolecarboxylate |
| CALH | 2-(3-Carboxy-3-aminopropyl)-L-histidine |
| cAMP | 3',5'-Cyclic AMP |
| CAP | Carbamoyl phosphate |
| CAR | Carnitine |
| CARm | CarnitineM |
| CBHCAP | 3-Isopropylmalate |
| CBHCAPm | 3-IsopropylmalateM |
| cCMP | 3',5'-Cyclic CMP |
| cdAMP | 3',5'-Cyclic dAMP |
| CDP | CDP |
| CDPCHO | CDPcholine |
| CDPDG | CDPdiacylglycerol |
| CDPDGm | CDPdiacylglycerolM |
| CDPETN | CDPethanolamine |
| CLR2 | Ceramide-2 |
| CER3 | Ceramide-3 |
| CGLY | Cys-Gly |
| cGMP | 3',5'-Cyclic GMP |
| CHCOA | 6-Carboxyhexanoyl-CoA |
| CHIT | Chitin |
| CHITO | Chitosan |
| CHO | Choline |
| CHOR | Chorismate |
| cIMP | 3',5'-Cyclic IMP |
| CIT | Citrate |
| CITm | CitrateM |
| CITR | L-Citrulline |
| CLm | CardiolipinM |
| CMP | CMP |
| CMPm | CMPM |
| CMUSA | 2-Amino-3-carboxymuconate semialdehyde |
| CO2 | CO2 |
| CO2m | CO2M |
| COA | CoA |
| COAm | CoAM |
| CPAD5P | 1-(2-Carboxyphenylamino)-1-deoxy-D-ribulose 5-phosphate |
| CPP | Coproporphyrinogen |
| CTP | CTP |
| CTPm | CTPM |
| CYS | L-Cysteine |
| CYTD | Cytidine |
| CYTS | Cytosine |
| D45P1 | 1-Phosphatidyl-D-myo-inositol 4,5-bisphosphate |
| D6PGC | 6-Phospho-D-gluconate |
| D6PGL | D-Glucono-1,5-lactone 6-phosphate |
| D6RP5P | 2,5-Diamino-6-hydroxy-4-(5'-phosphoribosylamino)-pyrimidine |
| D8RL | 6,7-Dimethyl-8-(1-D-ribityl)lumazine |
| DA | Deoxyadenosine |
| DADP | dADP |
| DAGLY | Diacylglycerol |
| DAMP | dAMP |
| dAMP | dAMP |
| DANNA | 7,8-Diaminononanoate |
| DAPRP | 1,3-Diaminopropane |
| DATP | dATP |
| DB4P | L-3,4-Dihydroxy-2-butanone 4-phosphate |
| DC | Deoxycytidine |
| DCDP | dCDP |
| DCMP | dCMP |
| DCTP | dCTP |
| DFUC | alpha-D-Fucoside |
| DG | Deoxyguanosine |
| DGDP | dGDP |
| DGMP | dGMP |
| DGPP | Diacylglycerol pyrophosphate |
| DGTP | dGTP |
| DHF | Dihydrofolate |
| DHFm | DihydrofolateM |
| DHMVAm | (R)-2,3-dihydroxy-3-methylbutanoateM |
| DHP | 2-Amino-4-hydroxy-6-(D-erythro-1,2,3-trihydroxypropyl)-7,8-dihydropteridine |
| DHPP | Dihydroneopterin phosphate |
| DHPT | Dihydropteroate |
| DHSK | 3-Dehydroshikimate |
| DHSP | Sphinganine 1-phosphate |
| DHSPH | 3-Dehydrosphinganine |
| DHVALm | (R)-3-Hydroxy-3-methyl-2-oxobutanoateM |
| DIMGP | D-erythro-1-(Imidazol-4-yl)glycerol 3-phosphate |
| DIN | Deoxyinosine |
| DIPEP | Dipeptide |
| DISAC1P | 2,3-bis(3-hydroxytetradecanoyl)-D-glucosaminyl-1,6-beta-D-2,3-bis(3-hydroxytetradecanoyl)-beta-D-glucosaminyl 1-phosphate |
| DLIPOm | DihydrolipoamideM |
| DMPP | Dimethylallyl diphosphate |
| DMZYMST | 4,4-Dimethylzymosterol |
| DOL | Dolichol |
| DOLMANP | Dolichyl beta-D-mannosyl phosphate |
| DOLP | Dolichyl phosphate |
| DOLPP | Dehydrodolichol diphosphate |
| DOROA | (S)-Dihydroorotate |

TABLE 3-continued

| Abbreviation | Metabolite |
|---|---|
| DPCOA | Dephospho-CoA |
| DPCOAm | Dephospho-CoAM |
| DPTH | 2-[3-Carboxy-3-(methylammonio)propyl]-L-histidine |
| DQT | 3-Dehydroquinate |
| DR1P | Deoxy-ribose 1-phosphate |
| DR5P | 2-Deoxy-D-ribose 5-phosphate |
| DRIB | Deoxyribose |
| DSAM | S-Adenosylmethioninamine |
| DT | Thymidine |
| DTB | Dethiobiotin |
| DTBm | DethiobiotinM |
| DTDP | dTDP |
| DTMP | dTMP |
| DTP | 1-Deoxy-d-threo-2-pentulose |
| DTTP | dTTP |
| DU | Deoxyuridine |
| DUDP | dUDP |
| DUMP | dUMP |
| DUTP | dUTP |
| E4P | D-Erythrose 4-phosphate |
| EPM | Epimelibiose |
| EPST | Episterol |
| ER4P | 4-Phospho-D-erythronate |
| ERGOST | Ergosterol |
| ERTEOL | Ergosta-5,7,22,24(28)-tetraenol |
| ERTROL | Ergosta-5,7,24(28)-trienol |
| FTH | Ethanol |
| FTHm | EthanolM |
| FTHM | Ethanolamine |
| F1P | D-Fructose 1-phosphate |
| F26P | D-Fructose 2,6-bisphosphate |
| F6P | beta-D-Fructose 6-phosphate |
| FAD | FAD |
| FADH2m | FADH2M |
| FADm | FADM |
| FALD | Formaldehyde |
| FDP | beta-D-Fructose 1,6-bisphosphate |
| FERIm | Ferricytochrome cM |
| FEROm | Ferrocytochrome cM |
| FEST | Fecosterol |
| FGAM | 2-(Formamido)-N1-(5'-phosphoribosyl) acetamidine |
| FGAR | 5'-Phosphoribosyl-N-formylglycinamide |
| FGT | S-Formylglutathione |
| FKYN | L-Formylkynurenine |
| FMN | FMN |
| FMNm | FMNM |
| FMRNAm | N-Formylmethionyl-tRNAM |
| FOR | Formate |
| FORm | FormateM |
| FPP | trans,trans-Farnesyl diphosphate |
| FRU | D-Fructose |
| FTHF | 10-Formyltetrahydrofolate |
| FTHFm | 10-FormyltetrahydrofolateM |
| FUACAC | 4-Fumarylacetoacetate |
| FUC | beta-D-Fucose |
| FUM | Fumarate |
| FUMm | FumarateM |
| G1P | D-Glucose 1-phosphate |
| G6P | alpha-D-Glucose 6-phosphate |
| GA1P | D-Glucosamine 1-phosphate |
| GA6P | D-Glucosamine 6-phosphate |
| GABA | 4-Aminobutanoate |
| GABAL | 4-Aminobutyraldehyde |
| GABALm | 4-AminobutyraldehydeM |
| GABAm | 4-AminobutanoateM |
| GAL1P | D-Galactose 1-phosphate |
| GAR | 5'-Phosphoribosylglycinamide |
| GBAD | 4-Guanidino-butanamide |
| GBAT | 4-Guanidino-butanoate |
| GC | gamma-L-Glutamyl-L-cysteine |
| GDP | GDP |
| GDPm | GDPM |
| GDPMAN | GDPmannose |
| GGL | Galactosylglycerol |
| GL | Glycerol |
| GL3P | sn-Glycerol 3-phosphate |
| GL3Pm | sn-Glycerol 3-phosphateM |
| GLAC | D-Galactose |
| GLACL | 1-alpha-D-Galactosyl-myo-inositol |
| GLAL | Glycolaldehyde |
| GLAM | Glucosamine |
| GLC | alpha-D-Glucose |
| GLCN | Gluconate |
| GLN | L-Glutamine |
| GLP | Glycylpeptide |
| GLT | L-Glucitol |
| GLU | L-Glutamate |
| GLUGSAL | L-Glutamate 5-semialdehyde |
| GLUGSALm | L-Glutamate 5-semialdehydeM |
| GLUm | GlutamateM |
| GLUP | alpha-D-Glutamyl phosphate |
| GLX | Glyoxylate |
| GLY | Glycine |
| GLYCOGEN | Glycogen |
| GLYm | GlycineM |
| GLYN | Glycerone |
| GMP | GMP |
| GN | Guanine |
| GNm | GuanineM |
| GPP | Geranyl diphosphate |
| GSN | Guanosine |
| GSNm | GuanosineM |
| GTP | GTP |
| GTPm | GTPM |
| GTRNA | L-Glutamyl-tRNA(Glu) |
| GTRNAm | L-Glutamyl-tRNA(Glu)M |
| GTRP | P1,P4-Bis(5'-guanosyl)tetraphosphate |
| H2O2 | H2O2 |
| H2S | Hydrogen sulfide |
| H2SO3 | Sulfite |
| H3MCOA | (S)-3-Hydroxy-3-methylglutaryl-CoA |
| H3MCOAm | (S)-3-Hydroxy-3-methylglutaryl-CoAM |
| HACNm | But-1-ene-1,2,4-tricarboxylateM |
| HACOA | (3S)-3-Hydroxyacyl-CoA |
| HAN | 3-Hydroxyanthranilate |
| HBA | 4-Hydroxy-benzyl alcohol |
| HCIT | 2-Hydroxybutane-1,2,4-tricarboxylate |
| HCITm | 2-Hydroxybutane-1,2,4-tricarboxylateM |
| HCYS | Homocysteine |
| HFXT | H + EXT |
| HHTRNA | L-Histidyl-tRNA(His) |
| HIB | (S)-3-Hydroxyisobutyrate |
| HIBCOA | (S)-3-Hydroxyisobutyryl-CoA |
| HICITm | HomoisocitrateM |
| HIS | L-Histidine |
| HISOL | L-Histidinol |
| HISOLP | L-Histidinol phosphate |
| HKYN | 3-Hydroxykynurenine |
| Hm | H + M |
| HMB | Hydroxymethylbilane |
| HOMOGEN | Homogentisate |
| HPRO | trans-4-Hydroxy-L-proline |
| HSER | L-Homoserine |
| HTRNA | tRNA(His) |
| HYXAN | Hypoxanthine |
| IAC | Indole-3-acetate |
| IAD | Indole-3-acetamide |
| IBCOA | 2-Methylpropanoyl-CoA |
| ICIT | Isocitrate |
| ICITm | IsocitrateM |
| IDP | IDP |
| IDPm | IDPM |
| IGP | Indoleglycerol phosphate |
| IGST | 4,4-Dimethylcholesta-8,14,24-trienol |
| IIMZYMST | Intermediate_Methylzymosterol_II |
| IIZYMST | Intermediate_Zymosterol_II |
| ILE | L-Isoleucine |
| ILEm | L-IsoleucineM |
| IMACP | 3-(Imidazol-4-yl)-2-oxopropyl phosphate |
| IMP | IMP |
| IMZYMST | Intermediate_Methylzymosterol_I |
| INAC | Indoleacetate |
| INS | Inosine |

TABLE 3-continued

| Abbreviation | Metabolite |
|---|---|
| IPC | Inositol phosphorylceramide |
| IPPMAL | 2-Isopropylmalate |
| IPPMALm | 2-IsopropylmalateM |
| IPPP | Isopentenyl diphosphate |
| ISUCC | a-Iminosuccinate |
| ITCCOAm | Itaconyl-CoAM |
| ITCm | ItaconateM |
| ITP | ITP |
| ITPm | ITPM |
| IVCOA | 3-Methylbutanoyl-CoA |
| IZYMST | Intermediate__Zymosterol_I |
| K | Potassium |
| KYN | L-Kynurenine |
| LAC | (R)-Lactate |
| LACALm | (S)-LactaldehydeM |
| LACm | (R)-LactateM |
| LCCA | a Long-chain carboxylic acid |
| LLU | L-Leucine |
| LFUm | L-LeucineM |
| LGT | (R)-S-Lactoylglutathione |
| LGTm | (R)-S-LactoylglutathioneM |
| LIPIV | 2,3,2',3'-tetrakis(3-hydroxytetradecanoyl)-D-glucosaminyl-1,6-beta-D-glucosamine 1,4'-bisphosphate |
| LIPOm | LipoamideM |
| LIPX | Lipid X |
| LLACm | (S)-LactateM |
| LLCT | L-Cystathionine |
| LLTRNA | L-lysyl-tRNA(Lys) |
| LLTRNAm | L-lysyl-tRNA(Lys)M |
| LNST | Lanosterol |
| LIRNA | tRNA(Lys) |
| LIRNAm | tRNA(Lys)M |
| LYS | L-Lysine |
| LYSm | L-LysineM |
| MAACOA | a-Methylacetoacetyl-CoA |
| MACAC | 4-Maleylacetoacetate |
| MACOA | 2-Methylprop-2-enoyl-CoA |
| MAL | Malate |
| MALACP | Malonyl-[acyl-carrier protein] |
| MALACPm | Malonyl-[acyl-carrier protein]M |
| MALCOA | Malonyl-CoA |
| MALm | MalateM |
| MALT | Malonate |
| MALTm | MalonateM |
| MAN | alpha-D-Mannose |
| MANIP | alpha-D-Mannose 1-phosphate |
| MAN2PD | beta-D-Mannosyldiacetylchitobiosyldiphosphodolichol |
| MAN6P | D-Mannose 6-phosphate |
| MANNAN | Mannan |
| MBCOA | Methylbutyryl-CoA |
| MCCOA | 2-Methylbut-2-enoyl-CoA |
| MCRCOA | 2-Methylbut-2-enoyl-CoA |
| MDAP | Meso-diaminopimelate |
| MELI | Melibiose |
| MELT | Melibutol |
| MFT | L-Methionine |
| METH | Methanethiol |
| METHF | 5,10-Methenyltetrahydrofolate |
| METHFm | 5,10-MethenyltetrahydrofolateM |
| METTHF | 5,10-Methylenetetrahydrofolate |
| METTHFm | 5,10-MethylenetetrahydrofolateM |
| MGCOA | 3-Methylglutaconyl-CoA |
| MHIS | N(pai)-Methyl-L-histidine |
| MHVCOA | a-Methyl-b-hydroxyvaleryl-CoA |
| MI | myo-Inositol |
| MI1P | 1L-myo-Inositol 1-phosphate |
| MIP2C | Inositol-mannose-P-inositol-P-ceramide |
| MIPC | Mannose-inositol-P-ceramide |
| MK | Menaquinone |
| MLT | Maltose |
| MMCOA | Methylmalonyl-CoA |
| MMET | S-Methylmethionine |
| MMS | (S)-Methylmalonate semialdehyde |
| MNT | D-Mannitol |
| MNT6P | D-Mannitol 1-phosphate |
| MTHF | 5-Methyltetrahydrofolate |
| MTHFm | 5-MethyltetrahydrofolateM |
| MTHGXL | Methylglyoxal |
| MTHN | Methane |
| MTHNm | MethaneM |
| MTHPTGLU | 5-Methyltetrahydropteroyltri-L-glutamate |
| MTRNAm | L-Methionyl-tRNAM |
| MVL | (R)-Mevalonate |
| MVLm | (R)-MevalonateM |
| MYOI | myo-Inositol |
| MZYMST | 4-Methylzymsterol |
| N4HBZ | 3-Nonaprenyl-4-hydroxybenzoate |
| NA | Sodium |
| NAAD | Deamino-NAD+ |
| NAADm | Deamino-NAD + M |
| NAC | Nicotinate |
| NACm | NicotinateM |
| NAD | NAD+ |
| NADH | NADH |
| NADHm | NADHM |
| NADm | NAD + M |
| NADP | NADP+ |
| NADPH | NADPH |
| NADPHm | NADPHM |
| NADPm | NADP + M |
| NAG | N-Acetylglucosamine |
| NAGA1P | N-Acetyl-D-glucosamine 1-phosphate |
| NAGA6P | N-Acetyl-D-glucosamine 6-phosphate |
| NAGLUm | N-Acetyl-L-glutamateM |
| NAGLUPm | N-Acetyl-L-glutamate 5-phosphateM |
| NAGLUSm | N-Acetyl-L-glutamate 5-semialdehydeM |
| NAM | Nicotinamide |
| NAMm | NicotinamideM |
| NAMN | Nicotinate D-ribonucleotide |
| NAMNm | Nicotinate D-ribonucleotideM |
| NAORNm | N2-Acetyl-L-ornithineM |
| NH3 | NH3 |
| NH3m | NH3M |
| NH4 | NH4+ |
| NPP | all-trans-Nonaprenyldiphosphate |
| NPPm | all-trans-NonaprenyldiphosphateM |
| NPRAN | N-(5-Phospho-D-ribosyl)anthranilate |
| O2 | Oxygen |
| O2m | OxygenM |
| OA | Oxaloacetate |
| OACOA | 3-Oxoacyl-CoA |
| OAHSER | O-Acetyl-L-homoserine |
| OAm | OxaloacetateM |
| OBUT | 2-Oxobutanoate |
| OBUTm | 2-OxobutanoateM |
| OFP | Oxidized flavoprotein |
| OGT | Oxidized glutathione |
| OHB | 2-Oxo-3-hydroxy-4-phosphobutanoate |
| OHm | HO-M |
| OICAP | 3-Carboxy-4-methyl-2-oxopentanoate |
| OICAPm | 3-Carboxy-4-methyl-2-oxopentanoateM |
| OIVAL | (R)-2-Oxoisovalerate |
| OIVALm | (R)-2-OxoisovalerateM |
| OMP | Orotidine 5'-phosphate |
| OMVAL | 3-Methyl-2-oxobutanoate |
| OMVALm | 3-Methyl-2-oxobutanoateM |
| OPEP | Oligopeptide |
| ORN | L-Ornithine |
| ORNm | L-OrnithineM |
| OROA | Orotate |
| OSLHSER | O-Succinyl-L-homoserine |
| OSUC | Oxalosuccinate |
| OSUCm | OxalosuccinateM |
| OTHIO | Oxidized thioredoxin |
| OTHIOm | Oxidized thioredoxinM |
| OXA | Oxaloglutarate |
| OXAm | OxaloglutarateM |
| P5C | (S)-1-Pyrroline-5-carboxylate |
| P5Cm | (S)-1-Pyrroline-5-carboxylateM |
| P5P | Pyridoxine phosphate |
| PA | Phosphatidate |
| PABA | 4-Aminobenzoate |
| PAC | Phenylacetic acid |

TABLE 3-continued

| Abbreviation | Metabolite |
|---|---|
| PAD | 2-Phenylacetamide |
| PALCOA | Palmitoyl-CoA |
| PAm | PhosphatidateM |
| PANT | (R)-Pantoate |
| PANTm | (R)-PantoateM |
| PAP | Adenosine 3',5'-bisphosphate |
| PAPS | 3'-Phosphoadenylylsulfate |
| PBG | Porphobilinogen |
| PC | Phosphatidylcholine |
| PC2 | Sirohydrochlorin |
| PCHO | Choline phosphate |
| PDLA | Pyridoxamine |
| PDLA5P | Pyridoxamine phosphate |
| PDME | Phosphatidyl-N-dimethylethanolamine |
| PE | Phosphatidylethanolamine |
| PEm | PhosphatidylethanolamineM |
| PEP | Phosphoenolpyruvate |
| PEPD | Peptide |
| PEPm | PhosphoenolpyruvateM |
| PLPT | Peptide |
| PETHM | Ethanolamine phosphate |
| PGm | PhosphatidylglycerolM |
| PGPm | PhosphatidylglycerophosphateM |
| PHC | L-1-Pyrroline-3-hydroxy-5-carboxylate |
| PHE | L-Phenylalanine |
| PHEN | Prephenate |
| PHP | 3-Phosphonooxypyruvate |
| PHPYR | Phenylpyruvate |
| PHSER | O-Phospho-L-homoserine |
| PHSP | Phytosphingosine 1-phosphate |
| PHT | O-Phospho-4-hydroxy-L-threonine |
| PI | Orthophosphate |
| PIm | OrthophosphateM |
| PIME | Pimelic Acid |
| PINS | 1-Phosphatidyl-D-myo-inositol |
| PINS4P | 1-Phosphatidyl-1D-myo-inositol 4-phosphate |
| PINSP | 1-Phosphatidyl-1D-myo-inositol 3-phosphate |
| PL | Pyridoxal |
| PL5P | Pyridoxal phosphate |
| PMME | Phosphatidyl-N-methylethanolamine |
| PMVL | (R)-5-Phosphomevalonate |
| PNTO | (R)-Pantothenate |
| PPHG | Protoporphyrinogen IX |
| PPHGm | Protoporphyrinogen IXM |
| PPI | Pyrophosphate |
| PPIm | PyrophosphateM |
| PPIXm | ProtoporphyrinM |
| PPMAL | 2-Isopropylmaleate |
| PPMVL | (R)-5-Diphosphomevalonate |
| PRAM | 5-Phosphoribosylamine |
| PRBAMP | N1-(5-Phospho-D-ribosyl)-AMP |
| PRBATP | N1-(5-Phospho-D-ribosyl)-ATP |
| PRFICA | 1-(5'-Phosphoribosyl)-5-formamido-4-imidazolecarboxamide |
| PRFP | 5-(5-Phospho-D-ribosylaminoformimino)-1-(5-phosphoribosyl)-imidazole-4-carboxamide |
| PRLP | N-(5'-Phospho-D-1'-ribulosylformimino)-5-amino-1-(5"-phospho-D-ribosyl)-4-imidazolecarboxamide |
| PRO | L-Proline |
| PROm | L-ProlineM |
| PROPCOA | Propanoyl-CoA |
| PRPP | 5-Phospho-alpha-D-ribose 1-diphosphate |
| PRPPm | 5-Phospho-alpha-D-ribose 1-diphosphateM |
| PS | Phosphatidylserine |
| PSm | PhosphatidylserineM |
| PSPH | Phytosphingosine |
| PIHm | HemeM |
| PIRC | Putrescine |
| PTRSC | Putrescine |
| PUR15P | Pseudouridine 5'-phosphate |
| PYR | Pyruvate |
| PYRDX | Pyridoxine |
| PYRm | PyruvateM |
| Q | Ubiquinone-9 |
| QA | Pyridine-2,3-dicarboxylate |
| QAm | Pyridine-2,3-dicarboxylateM |
| QH2 | Ubiquinol |
| QH2m | UbiquinolM |
| Qm | Ubiquinone-9M |
| R1P | D-Ribose 1-phosphate |
| R5P | D-Ribose 5-phosphate |
| RADP | 4-(1-D-Ribitylamino)-5-amino-2,6-dihydroxypyrimidine |
| RAF | Raffinose |
| RFP | Reduced flavoprotein |
| RGT | Glutathione |
| RGTm | GlutathioneM |
| RIB | D-Ribose |
| RIBFLAVm | RiboflavinM |
| RIBOFLAV | Riboflavin |
| RIPm | alpha-D-Ribose 1-phosphateM |
| RL5P | D-Ribulose 5-phosphate |
| RMN | D-Rhamnose |
| RTHIO | Reduced thioredoxin |
| RTHIOm | Reduced thioredoxinM |
| S | Sulfur |
| S17P | Sedoheptulose 1,7-bisphosphate |
| S23E | (S)-2,3-Epoxysqualene |
| S7P | Sedoheptulose 7-phosphate |
| SACP | N6-(L-1,3-Dicarboxypropyl)-L-lysine |
| SAH | S-Adenosyl-L-homocysteine |
| SAHm | S-Adenosyl-L-homocysteineM |
| SAICAR | 1-(5'-Phosphoribosyl)-5-amino-4-(N-succinocarboxamide)-imidazole |
| SAM | S-Adenosyl-L-methionine |
| SAMm | S-Adenosyl-L-methionineM |
| SAMOB | S-Adenosyl-4-methylthio-2-oxobutanoate |
| SAPm | S-AminomethyldihydrolipoylproteinM |
| SER | L-Serine |
| SERm | L-SerineM |
| SLF | Sulfate |
| SLFm | SulfateM |
| SME | Shikimate |
| SME5P | Shikimate 3-phosphate |
| SOR | Sorbose |
| SOR1P | Sorbose 1-phosphate |
| SOT | D-Sorbitol |
| SPH | Sphinganine |
| SPMD | Spermidine |
| SPRM | Spermine |
| SPRMD | Spermidine |
| SQL | Squalene |
| SUC | Sucrose |
| SUCC | Succinate |
| SUCCm | SuccinateM |
| SUCCOAm | Succinyl-CoAM |
| SUCCSAL | Succinate semialdehyde |
| T3P1 | D-Glyceraldehyde 3-phosphate |
| T3P2 | Glycerone phosphate |
| T3P2m | Glycerone phosphateM |
| TAG16P | D-Tagatose 1,6-bisphosphate |
| TAG6P | D-Tagatose 6-phosphate |
| TAGLY | Triacylglycerol |
| TCOA | Tetradecanoyl-CoA |
| TGLP | N-Tetradecanoylglycylpeptide |
| THF | Tetrahydrofolate |
| THFG | Tetrahydrofolyl-[Glu](n) |
| THFm | TetrahydrofolateM |
| THIAMIN | Thiamin |
| THMP | Thiamin monophosphate |
| THPTGLU | Tetrahydropteroyltri-L-glutamate |
| THR | L-Threonine |
| THRm | L-ThreonineM |
| THY | Thymine |
| THZ | 5-(2-Hydroxyethyl)-4-methylthiazole |
| THZP | 4-Methyl-5-(2-phosphoethyl)-thiazole |
| TP1 | D-myo-inositol 1,4,5-trisphosphate |
| TPP | Thiamin diphosphate |
| TPPP | Thiamin triphosphate |
| TRE | alpha,alpha-Trehalose |
| TRE6P | alpha,alpha'-Trehalose 6-phosphate |
| TRNA | tRNA |
| TRNAG | tRNA(Glu) |
| TRNAGm | tRNA(Glu)M |
| TRNAm | tRNAM |

TABLE 3-continued

| Abbreviation | Metabolite |
|---|---|
| TRP | L-Tryptophan |
| TRPm | L-TryptophanM |
| TRPTRNAm | L-Tryptophanyl-tRNA(Trp)M |
| TYR | L-Tyrosine |
| UDP | UDP |
| UDPG | UDPglucose |
| UDPG23A | UDP-2,3-bis(3-hydroxytetradecanoyl)glucosamine |
| UDPG2A | UDP-3-O-(3-hydroxytetradecanoyl)-D-glucosamine |
| UDPG2AA | UDP-3-O-(3-hydroxytetradecanoyl)-N-acetylglucosamine |
| UDPGAL | UDP-D-galactose |
| UDPNAG | UDP-N-acetyl-D-galactosamine |
| UDPP | Undecaprenyl diphosphate |
| UGC | (−)-Ureidoglycolate |
| UMP | UMP |
| UPRG | Uroporphyrinogen III |
| URA | Uracil |
| UREA | Urea |
| UREAC | Urea-1-carboxylate |
| URI | Uridine |
| UTP | UTP |
| VAL | L-Valine |
| X5P | D-Xylose-5-phosphate |
| XAN | Xanthine |
| XMP | Xanthosine 5'-phosphate |
| XTSINE | Xanthosine |
| XTSN | Xanthosine |
| XUL | D-Xylulose |
| XYL | D-Xylose |
| ZYMST | Zymosterol |

Depending upon the particular environmental conditions being tested and the desired activity, a reaction network data structure can contain smaller numbers of reactions such as at least 200, 150, 100 or 50 reactions. A reaction network data structure having relatively few reactions can provide the advantage of reducing computation time and resources required to perform a simulation. When desired, a reaction network data structure having a particular subset of reactions can be made or used in which reactions that are not relevant to the particular simulation are omitted. Alternatively, larger numbers of reactions can be included in order to increase the accuracy or molecular detail of the methods of the invention or to suit a particular application. Thus, a reaction network data structure can contain at least 300, 350, 400, 450, 500, 550, 600 or more reactions up to the number of reactions that occur in or by S. cerevisiae or that are desired to simulate the activity of the full set of reactions occurring in S. cerevisiae. A reaction network data structure that is substantially complete with respect to the metabolic reactions of S. cerevisiae provides the advantage of being relevant to a wide range of conditions to be simulated, whereas those with smaller numbers of metabolic reactions are limited to a particular subset of conditions to be simulated.

A S. cerevisiae reaction network data structure can include one or more reactions that occur in or by S. cerevisiae and that do not occur, either naturally or following manipulation, in or by another prokaryotic organism, such as Escherichia coli, Haemophilus influenzae, Bacillus subtilis, Helicobacter pylori or in or by another eukaryotic organism, such as Homo sapiens. Examples of reactions that are unique to S. cerevisiae compared at least to Escherichia coli, Haemophilus influenzae, and Helicobacter pylori include those identified in Table 4. It is understood that a S. cerevisiae reaction network data structure can also include one or more reactions that occur in another organism. Addition of such heterologous reactions to a reaction network data structure of the invention can be used in methods to predict the consequences of heterologous gene transfer in S. cerevisiae, for example, when designing or engineering man-made cells or strains.

TABLE 4

Reactions specific to S. cerevisiae metabolic network glk1__3, hxk1__1, hxk2__1, hxk1__4, hxk2__4, pfk1__3, idh1, idp1__1, idp1__2, idp2__1, idp3__1, idp2__2, idp3__2, lsc1R, pyc1, pyc2, cyb2, dld1, ncp1, cytr__, cyto, atp1, pma1, pma2, pmp1, pmp2, cox1, rbk1__2, ach1__1, ach1__2, sfa1__1R, unkrx11R, pdc1, pdc5, pdc6, lys20, adh1R, adh3R, adh2R, adh4R, adh5R, sfa1__2R, psa1, pfk26, pfk27, fbp26, gal7R mel1__2, mel1__3, mel1__4R, mel1__5R, mel1__6R, mel1__7R, fsp2b, sor1, gsy1, gsy2, fks1, fks3, gsc2, tps1, tps3, tsl1, tps2, ath1, nth1, nth2, fdh1, tfo1a, tfo1b, dur1R, dur2, nit2, cyr1, guk1__3R, ade2R, pde1, pde2__1, pde2__2, pde2__3, pde2__4, pde2__5, apa2, apa1__1, apa1__3, apa1__2R, ura2__1, ura4R, ura1__1R, ura10R, ura5R, ura3, npkR, fur1, fcy1, tdk1, tdk2, urk1__1, urk1__2, urk1__3, deoa1R, deoa2R, cdd1__1, cdd1__2, cdc8R, dut1, cdc21, cmka2R, dcd1R, ura7__2, ura8__2, deg1R, pus1R, pus2R, pus4R, ura1__2R, ara1__1, ara1__2, gna1R, pcm1aR, qri1R, chs1, chs2, chs3, put2__1, put2, glt1, gdh2, cat2, yat1, mht1, sam4, ecm40__2, cpa2, ura2__2, arg3, spe3, spe4, amd, amd2__1, atrna, msr1, rnas, ded81, hom6__1, cys4, gly1, agtR, gcv2R, sah1, met6, cys3, met17__1, met17hR, dph5, met3, met14, met17__2, met17__3, lys21, lys20a, lys3R, lys4R, lys12R, lys12bR, amitR, lys2__1, lys2__2, lys9R, lys1aR, krs1, msk1, pro2__1, gps1R, gps2R, pro3__3, pro3__4, pro3__1, pro3__5, dal1R, dal2R, dal3R, his4__3, hts1, hmt1, tyr1, cta1, ctt1, ald6, ald4__2, ald5__1, tdo2, kfor__, kynu__1, kmo, kynu__2, bna1, aaaa, aaab, aaac, tyrdega, tyrdegb, tyrdegc, trydegd, msw1, amd2__2, amd2__3, spra, sprb, sprc, sprd, spre, dys1, leu4, leu1__2R, pclig, xapa1R, xapa2R, xapa3R, ynk1__6R, ynk1__9R, udpR, pyrh1R, pyrh2R, cmpg, usha1, usha2, usha5, usha6, usha11, gpx1R, gpx2R, hyr1R, ecm38, nit2__1, nit2__2, nmt1, nat1, nat2, bgl2, exg1, exg2, spr1, thi80__1, thi80__2, unkrxn8, pho11, fmn1__1, fmn1__2, pdx3__2R, pdx3__3R, pdx3__4R, pdx3__1, pdx3__5, bio1, fol1__4, ftfa, ftfb, fol3R, met7R, rma1R, met12, met13, mis1__2, ade3__2, mtd1, fmt1, TypeII__1, TypeII__2, TypeII__4, TypeII__3, TypeII__6, TypeII__5, TypeII__9, TypeII__8, TypeII__7, c100sn, c180sy, c182sy, faa1R, faa2R, faa3R, faa4R, fox2bR, pot1__1, erg10__1R, erg10__2R, Gat1__2, Gat2__2, ADHAPR, AGAT, slc1, Gat1__1, Gat2__1, cho1aR, cho1bR, cho2, opi3__1, opi3__2, cki1, pct1, cpt1, eki1, ect1, ept1R, ino1, impa1, pis1, tor1, tor2, vps34, pik1, sst4, fab1, mss4, plc1, pgs1R, crd1, dpp1, lpp1, hmgsR, hmg1R, hmg2R, erg12__1, erg12__2, erg12__3, erg12__4, erg8, mvd1, erg9, erg1, erg7, unkrxn3, unkrxn4, cdisoa, erg11__1, erg__24, erg25__1, erg26__1, erg11__2, erg25__2, erg26__2, erg11__3, erg6, erg2, erg3, erg5,

TABLE 4-continued

Reactions specific to *S. cerevisiae* metabolic network erg4, lcb1, lcb2, tsc10, sur2, csyna, csynb, scs7, aur1, csg2, sur1, ipt1, lcb4__1,
lcb5__1, lcb4__2, lcb5__2, lcb3, ysr3, dp11, sec59, dpm1, pmt1, pmt2, pmt3, pmt4,
pmt5, pmt6, kre2, ktr1, ktr2, ktr3, ktr4, ktr6, yur1, hor2, rhr2, cda1, cda2, daga,
dak1, dak2, gpd1, nadg1R, nadg2R, npt1, nadi, mnadphps, mnadg1R, mnadg2R,
mnpt1, mnadi, hem1, bet2, coq1, coq2, cox10, ram1, rer2, srt1, mo2R, mco2R,
methR, mmthnR, mnh3R, mthfR, mmthfR, mserR, mglyR, mcbhR, moicapR,
mproR, mcmpR, macR, macar__, mcar__, maclacR, mactcR, moiva1R, momva1R,
mpma1RR, ms1f, mthrR, maka, aac1, aac3, pet9, mir1aR, mir1dR, dic1__2R,
dic__1R, dic1__3, mm1tR, moabR, ctp1__1R, ctp1__2R, ctp1__3R, pyrcaR, mlacR,
gcaR, gcb, ort1R, crc1, gut2, gpd2, mt3p, mgl3p, mfad, mriboR, mdtbR, mmcoaR,
mmv1R, mpaR, mppntR, madR, mprppR, mdhfR, mqaR, moppR, msamR, msahR,
sfc1, odc1R, odc2R, hxt1__2, hxt10__2, hxt11__2, hxt13__2, hxt15__2, hxt16__2,
hxt17__2, hxt2__2, hxt3__2, hxt4__2, hxt5__2, hxt6__2, hxt7__2, hxt8__5, hxt9__2, sucup,
akmupR, sorupR, arbup1R, gltlupb, gal2__3, hxt1__1, hxt10__1, hxt11, hxt11__1,
hxt13__1, hxt15__1, hxt16__1, hxt17__1, hxt2__1, hxt3__1, hxt4, hxt4__1, hxt5__1, hxt6__1,
hxt7__1, hxt8__4, hxt9__1, stl1__1, gaupR, mmp1, mltup, mntup, nagup, rmnup, ribup,
treup__2, treup__1, xylupR, uga5, bap2__1R, bap3__1R, gap5R, gnp3R, tat7R, vap7R,
sam3, put7, uga4, dip9R, gap22R, gap7R, gnp1R, gap23R, gap9R, hip1R, vap6R,
bap2__4R, bap3__4R, gap13R, gap26R, gnp4R, mup1R, mup3R, bap2__5R, bap3__5R,
gap14R, gap29R, tat4R, ptrup, sprup1, ptr2, ptr3, ptr4, mnadd2, fcy2__3R,
fcy21__3R, fcy22__3R, gnupR, hyxnupR, nccup3, nccup4, nccup6, nccup7, ncgup4,
ncgup7, ncgup11, ncgup12, ncup4, ncup7, ncup11, ncup12, ethupR, su11, su12,
sulup, citupR, amgupR, atpmt, glaltxR, dal4, dal5, mthupR, papxR, thyxR,
ga6pupR, btupR, kapaupR, dapaupR, ogtup, sprmup, pimeup, thm1, thm2, thm3,
rflup, hnm1, ergupR, zymupR, hxt1__5, hxt10__3, hxt11__3, hxt13__3, hxt15__3,
hxt16__3, hxt17__3, hxt2__3, hxt3__3, hxt4__3, hxt5__3, hxt6__3, hxt7__3, hxt8__6, hxt9__3,
itr1, itr2, bio5a, agp2R, dttpxR, gltup A reaction network data structure or index of reactions used in the data structure such as that available in a metabolic reaction database, as described above, can be annotated to include information about a particular reaction. A reaction can be annotated to indicate, for example, assignment of the reaction to a protein, macromolecule or enzyme that performs the reaction, assignment of a gene(s) that codes for the protein, macromolecule or enzyme, the Enzyme Commission (EC) number of the particular metabolic reaction or Gene Ontology (GO) number of the particular metabolic reaction, a subset of reactions to which the reaction belongs, citations to references from which information was obtained, or a level of confidence with which a reaction is believed to occur in *S. cerevisiae*. A computer readable medium or media of the invention can include a gene database containing annotated reactions. Such information can be obtained during the course of building a metabolic reaction database or model of the invention as described below.

As used herein, the term "gene database" is intended to mean a computer readable medium or media that contains at least one reaction that is annotated to assign a reaction to one or more macromolecules that perform the reaction or to assign one or more nucleic acid that encodes the one or more macromolecules that perform the reaction. A gene database can contain a plurality of reactions some or all of which are annotated. An annotation can include, for example, a name for a macromolecule; assignment of a function to a macromolecule; assignment of an organism that contains the macromolecule or produces the macromolecule; assignment of a subcellular location for the macromolecule; assignment of conditions under which a macromolecule is being expressed or being degraded; an amino acid or nucleotide sequence for the macromolecule; or any other annotation found for a macromolecule in a genome database such as those that can be found in Saccharomyces Genome Database maintained by Stanford University, or Comprehensive Yeast Genome Database maintained by MIPS.

A gene database of the invention can include a substantially complete collection of genes and/or open reading frames in *S. cerevisiae* or a substantially complete collection of the macromolecules encoded by the *S. cerevisiae* genome. Alternatively, a gene database can include a portion of genes or open reading frames in *S. cerevisiae* or a portion of the macromolecules encoded by the *S. cerevisiae* genome. The portion can be at least 10%, 15%, 20%, 25%, 50%, 75%, 90% or 95% of the genes or open reading frames encoded by the *S. cerevisiae* genome, or the macromolecules encoded therein. A gene database can also include macromolecules encoded by at least a portion of the nucleotide sequence for the *S. cerevisiae* genome such as at least 10%, 15%, 20%, 25%, 50%, 75%, 90% or 95% of the *S. cerevisiae* genome. Accordingly, a computer readable medium or media of the invention can include at least one reaction for each macromolecule encoded by a portion of the *S. cerevisiae* genome.

An in silico *S. cerevisiae* model according to the invention can be built by an iterative process which includes gathering information regarding particular reactions to be added to a model, representing the reactions in a reaction network data structure, and performing preliminary simulations wherein a set of constraints is placed on the reaction network and the output evaluated to identify errors in the network. Errors in the network such as gaps that lead to non-natural accumulation or consumption of a particular metabolite can be identified as described below and simulations repeated until a desired performance of the model is attained. An exemplary method for iterative model construction is provided in Example I.

Thus, the invention provides a method for making a data structure relating a plurality of *S. cerevisiae* reactants to a plurality of *S. cerevisiae* reactions in a computer readable medium or media. The method includes the steps of: (a) identifying a plurality of *S. cerevisiae* reactions and a plurality of *S. cerevisiae* reactants that are substrates and products of the *S. cerevisiae* reactions; (b) relating the plurality of *S. cerevisiae* reactants to the plurality of *S. cerevisiae* reactions in a data structure, wherein each of the *S. cerevisiae* reactions includes a reactant identified as a substrate of the reaction, a reactant identified as a product of the reaction and a stoichiometric coefficient relating the substrate and the product; (c) making a constraint set for the plurality of *S. cerevisiae* reactions; (d) providing an objective function; (e) determining at least one flux distribution that minimizes or maximizes the objective function when the constraint set is applied to the data structure, and (f) if at least one flux distribution is not predictive of *S. cerevisiae* physiology, then adding a reaction to or deleting a reaction from the data structure and repeating step (e), if at least one flux distribution is predictive of *S. cerevisiae* physiology, then storing the data structure in a computer readable medium or media.

Information to be included in a data structure of the invention can be gathered from a variety of sources including, for example, the scientific literature or an annotated genome sequence of *S. cerevisiae* such as the GENBANK™, a site maintained by the NCBI (ncbi.nlm.gov), the CYGD database, a site maintained by MIPS, or the SGD database, a site maintained by the School of Medicine at Stanford University, etc.

In the course of developing an in silico model of *S. cerevisiae* metabolism, the types of data that can be considered include, for example, biochemical information which is information related to the experimental characterization of a chemical reaction, often directly indicating a protein(s) associated with a reaction and the stoichiometry of the reaction or indirectly demonstrating the existence of a reaction occurring within a cellular extract; genetic information which is information related to the experimental identification and genetic characterization of a gene(s) shown to code for a particular protein(s) implicated in carrying out a biochemical event; genomic information which is information related to the identification of an open reading frame and functional assignment, through computational sequence analysis, that is then linked to a protein performing a biochemical event; physiological information which is information related to overall cellular physiology, fitness characteristics, substrate utilization, and phenotyping results, which provide evidence of the assimilation or dissimilation of a compound used to infer the presence of specific biochemical event (in particular translocations); and modeling information which is information generated through the course of simulating activity of *S. cerevisiae* using methods such as those described herein which lead to predictions regarding the status of a reaction such as whether or not the reaction is required to fulfill certain demands placed on a metabolic network.

The majority of the reactions occurring in *S. cerevisiae* reaction networks are catalyzed by enzymes/proteins, which are created through the transcription and translation of the genes found on the chromosome(s) in the cell. The remaining reactions occur through non-enzymatic processes. Furthermore, a reaction network data structure can contain reactions that add or delete steps to or from a particular reaction pathway. For example, reactions can be added to optimize or improve performance of a *S. cerevisiae* model in view of empirically observed activity. Alternatively, reactions can be deleted to remove intermediate steps in a pathway when the intermediate steps are not necessary to model flux through the pathway. For example, if a pathway contains 3 nonbranched steps, the reactions can be combined or added together to give a net reaction, thereby reducing memory required to store the reaction network data structure and the computational resources required for manipulation of the data structure. An example of a combined reaction is that for fatty acid degradation shown in Table 2, which combines the reactions for acyl-CoA oxidase, hydratase-dehydrogenase-epimerase, and acetyl-CoA C-acyltransferase of beta-oxidation of fatty acids.

The reactions that occur due to the activity of gene-encoded enzymes can be obtained from a genome database that lists genes or open reading frames identified from genome sequencing and subsequent genome annotation. Genome annotation consists of the locations of open reading frames and assignment of function from homology to other known genes or empirically determined activity. Such a genome database can be acquired through public or private databases containing annotated *S. cerevisiae* nucleic acid or protein sequences. If desired, a model developer can perform a network reconstruction and establish the model content associations between the genes, proteins, and reactions as described, for example, in Covert et al. *Trends in Biochemical Sciences* 26:179-186 (2001) and Palsson, WO 00/46405.

As reactions are added to a reaction network data structure or metabolic reaction database, those having known or putative associations to the proteins/enzymes which enable/catalyze the reaction and the associated genes that code for these proteins can be identified by annotation. Accordingly, the appropriate associations for some or all of the reactions to their related proteins or genes or both can be assigned. These associations can be used to capture the non-linear relationship between the genes and proteins as well as between proteins and reactions. In some cases, one gene codes for one protein which then perform one reaction. However, often there are multiple genes which are required to create an active enzyme complex and often there are multiple reactions that can be carried out by one protein or multiple proteins that can carry out the same reaction. These associations capture the logic (i.e. AND or OR relationships) within the associations. Annotating a metabolic reaction database with these associations can allow the methods to be used to determine the effects of adding or eliminating a particular reaction not only at the reaction level, but at the genetic or protein level in the context of running a simulation or predicting *S. cerevisiae* activity.

A reaction network data structure of the invention can be used to determine the activity of one or more reactions in a plurality of *S. cerevisiae* reactions independent of any knowledge or annotation of the identity of the protein that performs the reaction or the gene encoding the protein. A model that is annotated with gene or protein identities can include reactions for which a protein or encoding gene is not assigned. While a large portion of the reactions in a cellular metabolic network are associated with genes in the organism's genome, there are also a substantial number of reactions included in a model for which there are no known genetic associations. Such reactions can be added to a reaction database based upon other information that is not necessarily related to genetics such as biochemical or cell based measurements or theoretical considerations based on observed biochemical or cellular activity. For example, there are many reactions that are not protein-enabled reactions. Furthermore, the occurrence of a particular reaction in a cell for which no associated proteins or genetics have been currently identified can be indicated during the course of model building by the iterative model building methods of the invention.

The reactions in a reaction network data structure or reaction database can be assigned to subsystems by annotation, if desired. The reactions can be subdivided according to biological criteria, such as according to traditionally identified metabolic pathways (glycolysis, amino acid metabolism and the like) or according to mathematical or computational criteria that facilitate manipulation of a model that incorporates or manipulates the reactions. Methods and criteria for subdividing a reaction database are described in further detail in Schilling et al., *J. Theor. Biol.* 203:249-283 (2000). The use of subsystems can be advantageous for a number of analysis methods, such as extreme pathway analysis, and can make the management of model content easier. Although assigning reactions to subsystems can be achieved without affecting the use of the entire model for simulation, assigning reactions to subsystems can allow a user to search for reactions in a particular subsystem, which may be useful in performing various types of analyses. Therefore, a reaction network data structure can include any number of desired subsystems including, for example, 2 or more subsystems, 5 or more subsystems, 10 or more subsystems, 25 or more subsystems or 50 or more subsystems.

The reactions in a reaction network data structure or metabolic reaction database can be annotated with a value indicating the confidence with which the reaction is believed to occur in *S. cerevisiae*. The level of confidence can be, for example, a function of the amount and form of supporting data that is available. This data can come in various forms including published literature, documented experimental results, or results of computational analyses. Furthermore, the data can provide direct or indirect evidence for the existence of a chemical reaction in a cell based on genetic, biochemical, and/or physiological data.

The invention further provides a computer readable medium, containing (a) a data structure relating a plurality of *S. cerevisiae* reactants to a plurality of *S. cerevisiae* reactions, wherein each of the *S. cerevisiae* reactions includes a reactant identified as a substrate of the reaction, a reactant identified as a product of the reaction and a stoichiometric coefficient relating the substrate and the product, and (b) a constraint set for the plurality of *S. cerevisiae* reactions.

Constraints can be placed on the value of any of the fluxes in the metabolic network using a constraint set. These constraints can be representative of a minimum or maximum allowable flux through a given reaction, possibly resulting from a limited amount of an enzyme present. Additionally, the constraints can determine the direction or reversibility of any of the reactions or transport fluxes in the reaction network data structure. Based on the in vivo environment where *S. cerevisiae* lives the metabolic resources available to the cell for biosynthesis of essential molecules for can be determined. Allowing the corresponding transport fluxes to be active provides the in silico *S. cerevisiae* with inputs and outputs for substrates and by-products produced by the metabolic network.

Returning to the hypothetical reaction network shown in FIG. 1, constraints can be placed on each reaction in the exemplary format, shown in FIG. 3, as follows. The constraints are provided in a format that can be used to constrain the reactions of the stoichiometric matrix shown in FIG. 2. The format for the constraints used for a matrix or in linear programming can be conveniently represented as a linear inequality such as $$\beta_j \leq v_j \leq \alpha_j; j=1 \ldots n \qquad (Eq. 1)$$

where $v_j$ is the metabolic flux vector, $\beta_j$ is the minimum flux value and $\alpha_j$ is the maximum flux value. Thus, $\alpha_j$ can take on a finite value representing a maximum allowable flux through a given reaction or $\beta_j$ can take on a finite value representing minimum allowable flux through a given reaction. Additionally, if one chooses to leave certain reversible reactions or transport fluxes to operate in a forward and reverse manner the flux may remain unconstrained by setting $\beta_j$ to negative infinity and $\alpha_j$ to positive infinity as shown for reaction $R_2$ in FIG. 3. If reactions proceed only in the forward reaction $\beta_j$ is set to zero while $\alpha_j$ is set to positive infinity as shown for reactions $R_1$, $R_3$, $R_4$, $R_5$, and $R_6$ in FIG. 3. As an example, to simulate the event of a genetic deletion or non-expression of a particular protein, the flux through all of the corresponding metabolic reactions related to the gene or protein in question are reduced to zero by setting $\alpha_j$ and $\beta_j$ to be zero. Furthermore, if one wishes to simulate the absence of a particular growth substrate, one can simply constrain the corresponding transport fluxes that allow the metabolite to enter the cell to be zero by setting $\alpha_j$ and $\beta_j$ to be zero. On the other hand if a substrate is only allowed to enter or exit the cell via transport mechanisms, the corresponding fluxes can be properly constrained to reflect this scenario.

The in silico *S. cerevisiae* model and methods described herein can be implemented on any conventional host computer system, such as those based on Intel.RTM. microprocessors and running Microsoft Windows operating systems. Other systems, such as those using the UNIX or LINUX operating system and based on IBM.RTM., DEC.RTM. or Motorola.RTM. microprocessors are also contemplated. The systems and methods described herein can also be implemented to run on client-server systems and wide-area networks, such as the Internet.

Software to implement a method or model of the invention can be written in any well-known computer language, such as JAVA™, C, C++, VISUAL BASIC™, FORTRAN or COBOL™ and compiled using any well-known compatible compiler. The software of the invention normally runs from instructions stored in a memory on a host computer system. A memory or computer readable medium can be a hard disk floppy disc, compact disc, magneto-optical disc, Random Access Memory, Read Only Memory or Plash Memory. The memory or computer readable medium used in the invention can be contained within a single computer or distributed in a network. A network can be any of a number of conventional network systems known in the art such as a local area network (LAN) or a wide area network (WAN). Client-server environments, database servers and networks that can be used in the invention are well known in the art. For example, the database server can run on an operating system such as UNIX™, running a relational database management system, a World Wide Web application and a World Wide Web server. Other types of memories and computer readable media are also contemplated to function within the scope of the invention.

A database or data structure of the invention can be represented in a markup language format including, for example, Standard Generalized Markup Language (SGML), Hypertext markup language (HTML) or Extensible Markup language (XML). Markup languages can be used to tag the information stored in a database or data structure of the invention, thereby providing convenient annotation and transfer of data between databases and data structures. In particular, an XML format can be useful for structuring the data representation of reactions, reactants and their annotations; for exchanging database contents, for example, over a network or internet; for updating individual elements using the document object model; or for providing differential access to multiple users for different information content of a data base or data structure of the invention. XML programming methods and editors for writing XML code are known in the art as described, for example, in Ray, *Learning XML* O'Reilly and Associates, Sebastopol, Calif. (2001).

A set of constraints can be applied to a reaction network data structure to simulate the flux of mass through the reaction network under a particular set of environmental conditions specified by a constraints set. Because the time constants characterizing metabolic transients and/or metabolic reactions are typically very rapid, on the order of milli-seconds to seconds, compared to the time constants of cell growth on the order of hours to days, the transient mass balances can be simplified to only consider the steady state behavior. Referring now to an example where the reaction network data structure is a stoichiometric matrix, the steady state mass balances can be applied using the following system of linear equations $$S \cdot v = 0 \quad (\text{Eq.2})$$

where S is the stoichiometric matrix as defined above and v is the flux vector. This equation defines the mass, energy, and redox potential constraints placed on the metabolic network as a result of stoichiometry. Together Equations 1 and 2 representing the reaction constraints and mass balances, respectively, effectively define the capabilities and constraints of the metabolic genotype and the organism's metabolic potential. All vectors, v, that satisfy Equation 2 are said to occur in the mathematical nullspace of S. Thus, the null space defines steady-state metabolic flux distributions that do not violate the mass, energy, or redox balance constraints. Typically, the number of fluxes is greater than the number of mass balance constraints, thus a plurality of flux distributions satisfy the mass balance constraints and occupy the null space. The null space, which defines the feasible set of metabolic flux distributions, is further reduced in size by applying the reaction constraints set forth in Equation 1 leading to a defined solution space. A point in this space represents a flux distribution and hence a metabolic phenotype for the network. An optimal solution within the set of all solutions can be determined using mathematical optimization methods when provided with a stated objective and a constraint set. The calculation of any solution constitutes a simulation of the model.

Objectives for activity of *S. cerevisiae* can be chosen to explore the improved use of the metabolic network within a given reaction network data structure. These objectives can be design objectives for a strain, exploitation of the metabolic capabilities of a genotype, or physiologically meaningful objective functions, such as maximum cellular growth. Growth can be defined in terms of biosynthetic requirements based on literature values of biomass composition or experimentally determined values such as those obtained as described above. Thus, biomass generation can be defined as an exchange reaction that removes intermediate metabolites in the appropriate ratios and represented as an objective function. In addition to draining intermediate metabolites this reaction flux can be formed to utilize energy molecules such as ATP, NADH and NADPH so as to incorporate any growth dependent maintenance requirement that must be met. This new reaction flux then becomes another constraint/balance equation that the system must satisfy as the objective function. Using the stoichiometric matrix of FIG. 2 as an example, adding such a constraint is analogous to adding the additional column $V_{growth}$ to the stoichiometric matrix to represent fluxes to describe the production demands placed on the metabolic system. Setting this new flux as the objective function and asking the system to maximize the value of this flux for a given set of constraints on all the other fluxes is then a method to simulate the growth of the organism.

Continuing with the example of the stoichiometric matrix applying a constraint set to a reaction network data structure can be illustrated as follows. The solution to equation 2 can be formulated as an optimization problem, in which the flux distribution that minimizes a particular objective is found. Mathematically, this optimization problem can be stated as:

$$\text{Minimize } Z \quad (\text{Eq. 3})$$

where $$z = \Sigma c_i \cdot v_i \quad (\text{Eq. 4})$$

where Z is the objective which is represented as a linear combination of metabolic fluxes $v_i$ using the weights $c_i$ in this linear combination. The optimization problem can also be stated as the equivalent maximization problem; i.e. by changing the sign on Z. Any commands for solving the optimization problem can be used including, for example, linear programming commands.

A computer system of the invention can further include a user interface capable of receiving a representation of one or more reactions. A user interface of the invention can also be capable of sending at least one command for modifying the data structure, the constraint set or the commands for applying the constraint set to the data representation, or a combination thereof. The interface can be a graphic user interface having graphical means for making selections such as menus or dialog boxes. The interface can be arranged with layered screens accessible by making selections from a main screen. The user interface can provide access to other databases useful in the invention such as a metabolic reaction database or links to other databases having information relevant to the reactions or reactants in the reaction network data structure or to *S. cerevisiae* physiology. Also, the user interface can display a graphical representation of a reaction network or the results of a simulation using a model of the invention.

Once an initial reaction network data structure and set of constraints has been created, this model can be tested by preliminary simulation. During preliminary simulation, gaps in the network or "dead-ends" in which a metabolite can be produced but not consumed or where a metabolite can be consumed but not produced can be identified. Based on the results of preliminary simulations areas of the metabolic reconstruction that require an additional reaction can be identified. The determination of these gaps can be readily calculated through appropriate queries of the reaction network data structure and need not require the use of simulation strategies, however, simulation would be an alternative approach to locating such gaps.

In the preliminary simulation testing and model content refinement stage the existing model is subjected to a series of functional tests to determine if it can perform basic requirements such as the ability to produce the required biomass constituents and generate predictions concerning the basic physiological characteristics of the particular organism strain being modeled. The more preliminary testing that is conducted the higher the quality of the model that will be generated. Typically the majority of the simulations used in this stage of development will be single optimizations. A single optimization can be used to calculate a single flux distribution demonstrating how metabolic resources are routed determined from the solution to one optimization problem. An optimization problem can be solved using linear programming as demonstrated in the Examples below. The result can be viewed as a display of a flux distribution on a reaction map. Temporary reactions can be added to the network to determine if they should be included into the model based on modeling/simulation requirements.

Once a model of the invention is sufficiently complete with respect to the content of the reaction network data structure according to the criteria set forth above, the model can be used to simulate activity of one or more reactions in a reaction network. The results of a simulation can be displayed in a variety of formats including, for example, a table, graph, reaction network, flux distribution map or a phenotypic phase plane graph.

Thus, the invention provides a method for predicting a *S. cerevisiae* physiological function. The method includes the steps of (a) providing a data structure relating a plurality of *S. cerevisiae* reactants to a plurality of *S. cerevisiae* reactions, wherein each of the *S. cerevisiae* reactions includes a reactant identified as a substrate of the reaction, a reactant identified as a product of the reaction and a stoichiometric coefficient relating said substrate and said product; (b) providing a constraint set for the plurality of *S. cerevisiae* reactions; (c) providing an objective function, and (d) determining at least one flux distribution that minimizes or maximizes the objective function when the constraint set is applied to the data structure, thereby predicting a *S. cerevisiae* physiological function.

As used herein, the term "physiological function," when used in reference to *S. cerevisiae*, is intended to mean an activity of a *S. cerevisiae* cell as a whole. An activity included in the term can be the magnitude or rate of a change from an initial state of a *S. cerevisiae* cell to a final state of the *S. cerevisiae* cell. An activity can be measured qualitatively or quantitatively. An activity included in the term can be, for example, growth, energy production, redox equivalent production, biomass production, development, or consumption of carbon, nitrogen, sulfur, phosphate, hydrogen or oxygen. An activity can also be an output of a particular reaction that is determined or predicted in the context of substantially all of the reactions that affect the particular reaction in a *S. cerevisiae* cell or substantially all of the reactions that occur in a *S. cerevisiae* cell. Examples of a particular reaction included in the term are production of biomass precursors, production of a protein, production of an amino acid, production of a purine, production of a pyrimidine, production of a lipid, production of a fatty acid, production of a cofactor, or transport of a metabolite. A physiological function can include an emergent property which emerges from the whole but not from the sum of parts where the parts are observed in isolation (see for example, Palsson *Nat. Biotech* 18:1147-1150 (2000)).

A physiological function of *S. cerevisiae* reactions can be determined using phase plane analysis of flux distributions. Phase planes are representations of the feasible set which can be presented in two or three dimensions. As an example, two parameters that describe the growth conditions such as substrate and oxygen uptake rates can be defined as two axes of a two-dimensional space. The optimal flux distribution can be calculated from a reaction network data structure and a set of constraints as set forth above for all points in this plane by repeatedly solving the linear programming problem while adjusting the exchange fluxes defining the two-dimensional space. A finite number of qualitatively different metabolic pathway utilization patterns can be identified in such a plane, and lines can be drawn to demarcate these regions. The demarcations defining the regions can be determined using shadow prices of linear optimization as described, for example in Chvatal, *Linear Programming* New York, W.H. Freeman and Co. (1983). The regions are referred to as regions of constant shadow price structure. The shadow prices define the intrinsic value of each reactant toward the objective function as a number that is either negative, zero, or positive and are graphed according to the uptake rates represented by the x and y axes. When the shadow prices become zero as the value of the uptake rates are changed there is a qualitative shift in the optimal reaction network.

One demarcation line in the phenotype phase plane is defined as the line of optimality (LO). This line represents the optimal relation between respective metabolic fluxes. The LO can be identified by varying the x-axis flux and calculating the optimal y-axis flux with the objective function defined as the growth flux. From the phenotype phase plane analysis the conditions under which a desired activity is optimal can be determined. The maximal uptake rates lead to the definition of a finite area of the plot that is the predicted outcome of a reaction network within the environmental conditions represented by the constraint set. Similar analyses can be performed in multiple dimensions where each dimension on the plot corresponds to a different uptake rate. These and other methods for using phase plane analysis, such as those described in Edwards et al., *Biotech Bioeng.* 77:27-36(2002), can be used to analyze the results of a simulation using an in silico *S. cerevisiae* model of the invention.

Figure 4:
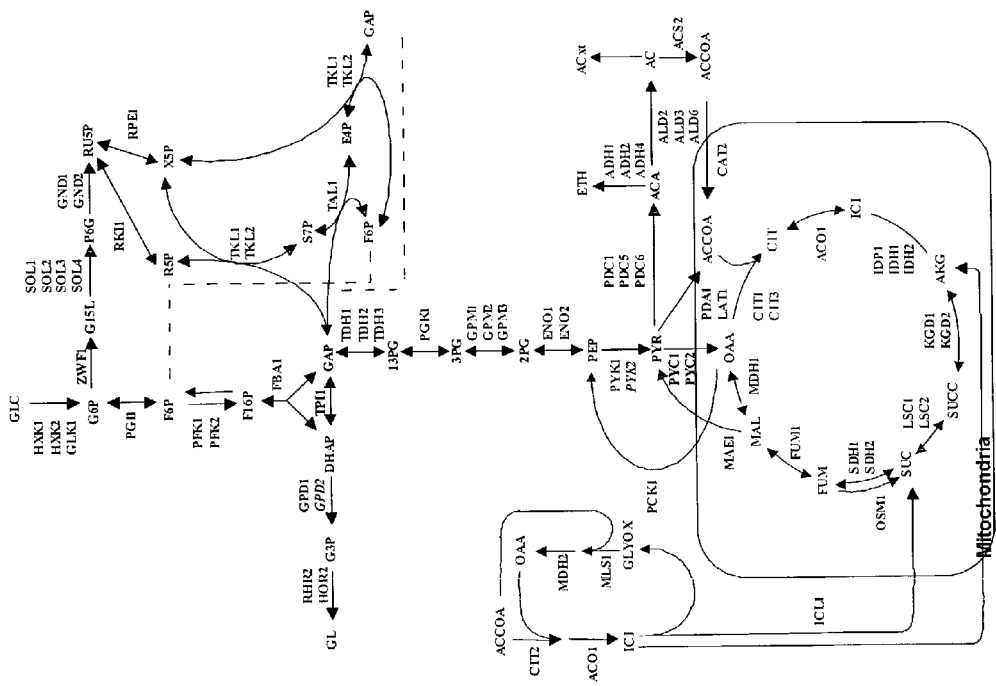
FIG. 4 shows an exemplary metabolic reaction network in *S. cerevisiae*.

A physiological function of *S. cerevisiae* can also be determined using a reaction map to display a flux distribution. A reaction map of *S. cerevisiae* can be used to view reaction networks at a variety of levels. In the case of a cellular metabolic reaction network a reaction map can contain the entire reaction complement representing a global perspective. Alternatively, a reaction map can focus on a particular region of metabolism such as a region corresponding to a reaction subsystem described above or even on an individual pathway or reaction. An example of a reaction map showing a subset of reactions in a reaction network of *S. cerevisiae* is shown in FIG. 4.

The invention also provides an apparatus that produces a representation of a *S. cerevisiae* physiological function, wherein the representation is produced by a process including the steps of: (a) providing a data structure relating a plurality of *S. cerevisiae* reactants to a plurality of *S. cerevisiae* reactions, wherein each of the *S. cerevisiae* reactions includes a reactant identified as a substrate of the reaction, a reactant identified as a product of the reaction and a stoichiometric coefficient relating said substrate and said product; (b) providing a constraint set for the plurality of *S. cerevisiae* reactions; (c) providing an objective function; (d) determining at least one flux distribution that minimizes or maximizes the objective function when the constraint set is applied to the data structure, thereby predicting a *S. cerevisiae* physiological function, and (e) producing a representation of the activity of the one or more *S. cerevisiae* reactions.

The methods of the invention can be used to determine the activity of a plurality of *S. cerevisiae* reactions including, for example, biosynthesis of an amino acid, degradation of an amino acid, biosynthesis of a purine, biosynthesis of a pyrimidine, biosynthesis of a lipid, metabolism of a fatty acid, biosynthesis of a cofactor, transport of a metabolite and metabolism of an alternative carbon source. In addition, the methods can be used to determine the activity of one or more of the reactions described above or listed in Table 2.

The methods of the invention can be used to determine a phenotype of a *S. cerevisiae* mutant. The activity of one or more *S. cerevisiae* reactions can be determined using the methods described above, wherein the reaction network data structure lacks one or more gene-associated reactions that occur in *S. cerevisiae*. Alternatively, the methods can be used to determine the activity of one or more *S. cerevisiae* reactions when a reaction that does not naturally occur in *S. cerevisiae* is added to the reaction network data structure. Deletion of a gene can also be represented in a model of the invention by constraining the flux through the reaction to zero, thereby allowing the reaction to remain within the data structure. Thus, simulations can be made to predict the effects of adding or removing genes to or from *S. cerevisiae*. The methods can be particularly useful for determining the effects of adding or deleting a gene that encodes for a gene product that performs a reaction in a peripheral metabolic pathway.

A drug target or target for any other agent that affects *S. cerevisiae* function can be predicted using the methods of the invention. Such predictions can be made by removing a reaction to simulate total inhibition or prevention by a drug or agent. Alternatively, partial inhibition or reduction in the activity a particular reaction can be predicted by performing the methods with altered constraints. For example, reduced activity can be introduced into a model of the invention by altering the $\alpha_j$ or $\beta_j$ values for the metabolic flux vector of a target reaction to reflect a finite maximum or minimum flux value corresponding to the level of inhibition. Similarly, the effects of activating a reaction, by initiating or increasing the activity of the reaction, can be predicted by performing the methods with a reaction network data structure lacking a particular reaction or by altering the $\alpha_j$ or $\beta_j$ values for the metabolic flux vector of a target reaction to reflect a maximum or minimum flux value corresponding to the level of activation. The methods can be particularly useful for identifying a target in a peripheral metabolic pathway.

Once a reaction has been identified for which activation or inhibition produces a desired effect on *S. cerevisiae* function, an enzyme or macromolecule that performs the reaction in *S. cerevisiae* or a gene that expresses the enzyme or macromolecule can be identified as a target for a drug or other agent. A candidate compound for a target identified by the methods of the invention can be isolated or synthesized using known methods. Such methods for isolating or synthesizing compounds can include, for example, rational design based on known properties of the target (see, for example, DeCamp et al., *Protein Engineering Principles and Practice*, Ed. Cleland and Craik, Wiley-Liss, New York, pp. 467-506 (1996)), screening the target against combinatorial libraries of compounds (see for example, Houghten et al., *Nature*, 354, 84-86 (1991); Dooley et al., *Science*, 266, 2019-2022 (1994), which describe an iterative approach, or R. Houghten et al. PCT/US91/08694 and U.S. Pat. No. 5,556,762 which describe a positional-scanning approach), or a combination of both to obtain focused libraries. Those skilled in the art will know or will be able to routinely determine assay conditions to be used in a screen based on properties of the target or activity assays known in the art.

A candidate drug or agent, whether identified by the methods described above or by other methods known in the art, can be validated using an in silico *S. cerevisiae* model or method of the invention. The effect of a candidate drug or agent on *S. cerevisiae* physiological function can be predicted based on the activity for a target in the presence of the candidate drug or agent measured in vitro or in vivo. This activity can be represented in an in silico *S. cerevisiae* model by adding a reaction to the model, removing a reaction from the model or adjusting a constraint for a reaction in the model to reflect the measured effect of the candidate drug or agent on the activity of the reaction. By running a simulation under these conditions the holistic effect of the candidate drug or agent on *S. cerevisiae* physiological function can be predicted.

The methods of the invention can be used to determine the effects of one or more environmental components or conditions on an activity of *S. cerevisiae*. As set forth above, an exchange reaction can be added to a reaction network data structure corresponding to uptake of an environmental component, release of a component to the environment, or other environmental demand. The effect of the environmental component or condition can be further investigated by running simulations with adjusted $\alpha_j$ or $\beta_j$ values for the metabolic flux vector of the exchange reaction target reaction to reflect a finite maximum or minimum flux value corresponding to the effect of the environmental component or condition. The environmental component can be, for example an alternative carbon source or a metabolite that when added to the environment of *S. cerevisiae* can be taken up and metabolized. The environmental component can also be a combination of components present for example in a minimal medium composition. Thus, the methods can be used to determine an optimal or minimal medium composition that is capable of supporting a particular activity of *S. cerevisiae*.

The invention further provides a method for determining a set of environmental components to achieve a desired activity for *S. cerevisiae*. The method includes the steps of (a) providing a data structure relating a plurality of *S. cerevisiae* reactants to a plurality of *S. cerevisiae* reactions, wherein each of the *S. cerevisiae* reactions includes a reactant identified as a substrate of the reaction, a reactant identified as a product of the reaction and a stoichiometric coefficient relating the substrate and the product; (b) providing a constraint set for the plurality of *S. cerevisiae* reactions; (c) applying the constraint set to the data representation, thereby determining the activity of one or more *S. cerevisiae* reactions (d) determining the activity of one or more *S. cerevisiae* reactions according to steps (a) through (c), wherein the constraint set includes an upper or lower bound on the amount of an environmental component and (e) repeating steps (a) through (c) with a changed constraint set, wherein the activity determined in step (e) is improved compared to the activity determined in step (d).

The following examples are intended to illustrate but not limit the present invention.

Example I

Reconstruction of the Metabolic Network of *S. Cerevisiae*

This example shows how the metabolic network of *S. cerevisiae* can be reconstructed.

Figure 5:
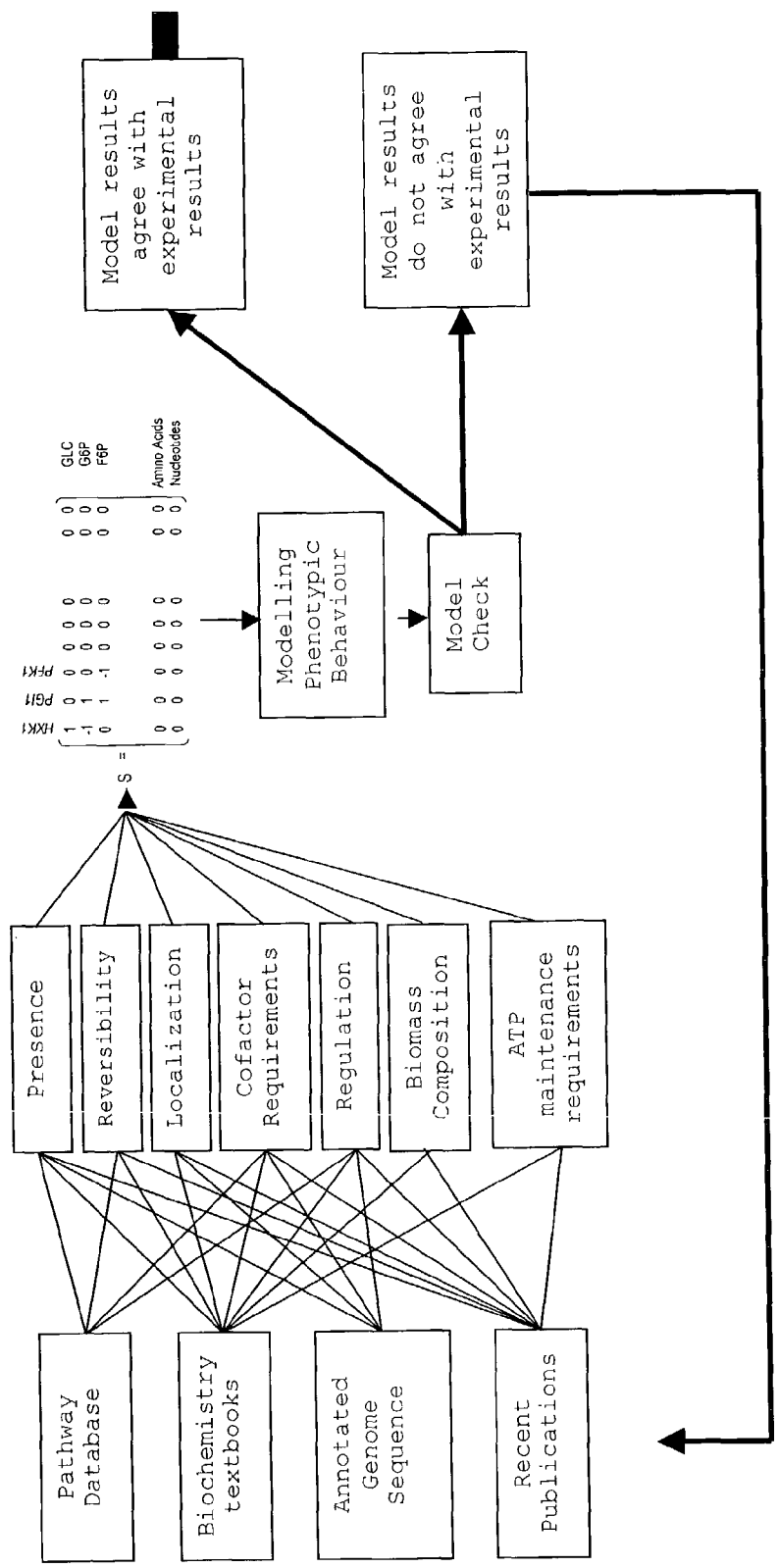
FIG. 5 shows a method for reconstruction of the metabolic network of *S. cerevisiae*. Based on the available information from the genome annotation, biochemical pathway databases, biochemistry textbooks and recent publications, a genome-scale metabolic network for *S. cerevisiae* was designed. Additional physiological constraints were considered and modeled, such as growth, non-growth dependent ATP requirements and biomass composition.

The reconstruction process was based on a comprehensive search of the current knowledge of metabolism in *S. cerevisiae* as shown in FIG. 5. A reaction database was built using the available genomic and metabolic information on the presence, reversibility, localization and cofactor requirements of all known reactions. Furthermore, information on non-growth-dependent and growth-dependent ATP requirements and on the biomass composition was used.

For this purpose different online reaction databases, recent publications and review papers (Table 5 and 9), and established biochemistry textbooks (Zubay, *Biochemistry* Wm.C. Brown Publishers, Dubuque, Iowa (1998); Stryer, *Biochemistry* W.H. Freeman, New York, N.Y. (1988)) were consulted. Information on housekeeping genes of *S. cerevisiae* and their functions were taken from three main yeast on-line resources:

The MIPS Comprehensive Yeast Genome Database (CYGD) (Mewes et al., *Nucleic Acids Research* 30(1): 31-34 (2002));

The Saccharomyces Genome Database (SGD) (Cherry et al., *Nucleic Acids Research* 26(1): 73-9 (1998));

The Yeast Proteome Database (YPD) (Costanzo et al., *Nucleic Acids Research* 29(1): 75-9 (2001)).

The following metabolic maps and protein databases (available online) were investigated:

Kyoto Encyclopedia of Genes and Genomes database (KEGG) (Kanehisa et al., *Nucleic Acids Research* 28(1): 27-30 (2000));

The Biochemical Pathways database of the Expert Protein Analysis System database (ExPASy) (Appel et al., *Trends Biochem Sci.* 19(6): 258-260 (1994));

ERGO from Integrated Genomics (www.integratedgenomics.com)

SWISS-PROT Protein Sequence database (Bairoch et al., *Nucleic Acids Research* 28(1): 45-48 (2000)).

Table 5 lists additional key references that were consulted for the reconstruction of the metabolic network of *S. cerevisiae*.

TABLE 5

Amino acid biosynthesis

Strathern et al., The Molecular biology of the yeast *Saccharomyces*: metabolism and gene expression Cold Spring Harbor Laboratory, Cold Spring Harbor, N.Y. (1982))
Lipid synthesis Daum et al., Yeast 14(16): 1471-510 (1998);
Dickinson et al., The metabolism and molecular physiology of *Saccharomyces cerevisiae* Taylor & Francis, London; Philadelphia (1999);
Dickson et al., Methods Enzymol. 311: 3-9 (2000);
Dickson, Annu Rev Biochem 67: 27-48 (1998);
Parks, CRC Crit Rev Microbiol 6(4): 301-41 (1978))
Nucleotide Metabolism Strathern et al., supara (1982))
Oxidative phosphorylation and electron transport (Verduyn et al., Antonie Van Leeuwenhoek 59(1): 49-63 (1991);
Overkamp et al., J. of Bacteriol 182(10): 2823-2830 (2000))
Primary Metabolism Zimmerman et al., Yeast sugar metabolism: biochemistry, genetics, biotechnology, and applications Technomic Pub., Lancaster, PA (1997);
Dickinson et al., supra (1999);
Strathern et al., supra (1982))
Transport across the cytoplasmic membrane Paulsen et al., FEBS Lett 430(1-2): 116-125 (1998);
Wieczorke et al., FEBS Lett 464(3): 123-128 (1999);
Regenberg et al., Curr Genet 36(6): 317-328 (1999);
Andre, Yeast 11(16): 1575-1611 (1995))
Transport across the mitochondrial membrane Palmieri et al., J. Bioenerg Biomembr 32(1): 67:77 (2000);
Palmieri et al., Biochim Biophys Acta 1459(2-3): 363-369 (2000);
Palmieri et al., J. Biol Chem 274(32): 22184-22190 (1999);
Palmieri et al., FEBS Lett 417(1): 114-118 (1997);
Paulsen et al., supra (1998);
Pallotta et al., FEBS Lett 428(3): 245-249 (1998);
Tzagologg et al. Mitochondria Plenum Press, New York (1982); Andre Yeast 11(16): 1575-611 (1995))

All reactions are localized into the two main compartments, cytosol and mitochondria, as most of the common metabolic reactions in *S. cerevisiae* take place in these compartments. Optionally, one or more additional compartments can be considered. Reactions located in vivo in other compartments or reactions for which no information was available regarding localization were assumed to be cytosol. All corresponding metabolites were assigned appropriate localization and a link between cytosol and mitochondria was established through either known transport and shuttle systems or through inferred reactions to meet metabolic demands.

After the initial assembly of all the metabolic reactions the list was manually examined for resolution of detailed biochemical issues. A large number of reactions involve cofactors utilization, and for many of these reactions the cofactor requirements have not yet been completely elucidated. For example, it is not clear whether certain reactions use only NADH or only NADPH as a cofactor or can use both cofactors, whereas other reactions are known to use both cofactors. For example, a mitochondrial aldehyde dehydrogenase encoded by ALD4 can use both NADH and NADPH as a cofactor (Remize et al. *Appl Environ Microbiol* 66(8): 3151-3159 (2000)). In such cases, two reactions are included in the reconstructed metabolic network.

Further considerations were taken into account to preserve the unique features of *S. cerevisiae* metabolism. *S. cerevisiae* lacks a gene that encodes the enzyme transhydrogenase. Insertion of a corresponding gene from Azetobacter vinelandii in *S. cerevisiae* has a major impact on its phenotypic behavior, especially under anaerobic conditions (Niessen et al. *Yeast* 18(1): 19-32 (2001)). As a result, reactions that create a net transhydrogenic effect in the model were either constrained to zero or forced to become irreversible. For instance, the flux carried by NADH dependent glutamate dehydrogenase (Gdh2p) was constrained to zero to avoid the appearance of a net transhydrogenase activity through coupling with the NADPH dependent glutamate dehydrogenases (Gdh1p and Gdh3p).

Once a first generation model is prepared, microbial behavior can be modeled for a specific scenario, such as anaerobic or aerobic growth in continuous cultivation using glucose as a sole carbon source. Modeling results can then be compared to experimental results. If modeling and experimental results are in agreement, the model can be considered as correct, and it is used for further modeling and predicting *S. cerevisiae* behavior. If the modeling and experimental results are not in agreement, the model has to be evaluated and the reconstruction process refined to determine missing or incorrect reactions, until modeling and experimental results are in agreement. This iterative process is shown in FIG. 5 and exemplified below.

Example II

Calculation of the P/O Ratio

This example shows how the genome-scale reconstructed metabolic model of *S. cerevisiae* was used to calculate the P/O ratio, which measures the efficiency of aerobic respiration. The P/O ratio is the number of ATP molecules produced per pair of electrons donated to the electron transport system (ETS).

Linear optimization was applied, and the in silico P/O ratio was calculated by first determining the maximum number of ATP molecules produced per molecule of glucose through the electron transport system (ETS), and then interpolating the in silico P/O ratio using the theoretical relation (i.e. in *S. cerevisiae* for the P/O ratio of 1.5, 18 ATP molecules are produced).

Experimental studies of isolated mitochondria have shown that *S. cerevisiae* lacks site I proton translocation (Verduyn et al., *Antonie Van Leeuwenhoek* 59(1): 49-63 (1991)). Consequently, estimation of the maximum theoretical or "mechanistic" yield of the ETS alone gives a P/O ratio of 1.5 for oxidation of NADH in *S. cerevisiae* grown on glucose (Verduyn et al., supra (1991)). However, based on experimental measurements, it has been determined that the net in vivo P/O ratio is approximately 0.95 (Verduyn et al., supra (1991)). This difference is generally thought to be due to the use of the mitochondrial transmembrane proton gradient needed to drive metabolite exchange, such as the proton-coupled translocation of pyruvate, across the inner mitochondrial membrane. Although simple diffusion of protons (or proton leakage) would be surprising given the low solubility of protons in the lipid bilayer, proton leakage is considered to contribute to the lowered P/O ratio due to the relatively high electrochemical gradient across the inner mitochondrial membrane (Westerhoff and van Dam, *Thermodynamics and control of biological free-energy transduction* Elsevier, New York, N.Y. (1987)).

Using the reconstructed network, the P/O ratio was calculated to be 1.04 for oxidation of NADH for growth on glucose by first using the model to determine the maximum number of ATP molecules produced per molecule of glucose through the electron transport system (ETS) (YATP,max=12.5 ATP molecules/glucose molecule via ETS in silico). The in silico P/O ratio was then interpolated using the theoretical relation (i.e. 18 ATP molecules per glucose molecule are produced theoretically when the P/O ratio is 1.5). The calculated P/O ratio was found to be close to the experimentally determined value of 0.95. Proton leakage, however, was not included in the model, which suggests that the major reason for the lowered P/O ratio is the use of the proton gradient for solute transport across the inner mitochondrial membrane. This result illustrates the importance of including the complete metabolic network in the analysis, as the use of the proton gradient for solute transport across the mitochondrial membrane contributes significantly to the operational P/O ratio.

Example III

Phenotypic Phase Plane Analysis

This example shows how the *S. cerevisiae* metabolic model can be used to calculate the range of characteristic phenotypes that the organism can display as a function of variations in the activity of multiple reactions.

For this analysis, $O_2$ and glucose uptake rates were defined as the two axes of the two-dimensional space. The optimal flux distribution was calculated using linear programming (LP) for all points in this plane by repeatedly solving the LP problem while adjusting the exchange fluxes defining the two-dimensional space. A finite number of quantitatively different metabolic pathway utilization patterns were identified in the plane, and lines were drawn to demarcate these regions. One demarcation line in the phenotypic phase plane (PhPP) was defined as the line of optimality (LO), and represents the optimal relation between the respective metabolic fluxes. The LO was identified by varying the x-axis (glucose uptake rate) and calculating the optimal y-axis ($O_2$ uptake rate), with the objective function defined as the growth flux. Further details regarding Phase-Plane Analysis are provided in Edwards et al., *Biotechnol. Bioeng.* 77:27-36 (2002) and Edwards et al., *Nature Biotech.* 19:125-130 (2001)).

Figure 6:
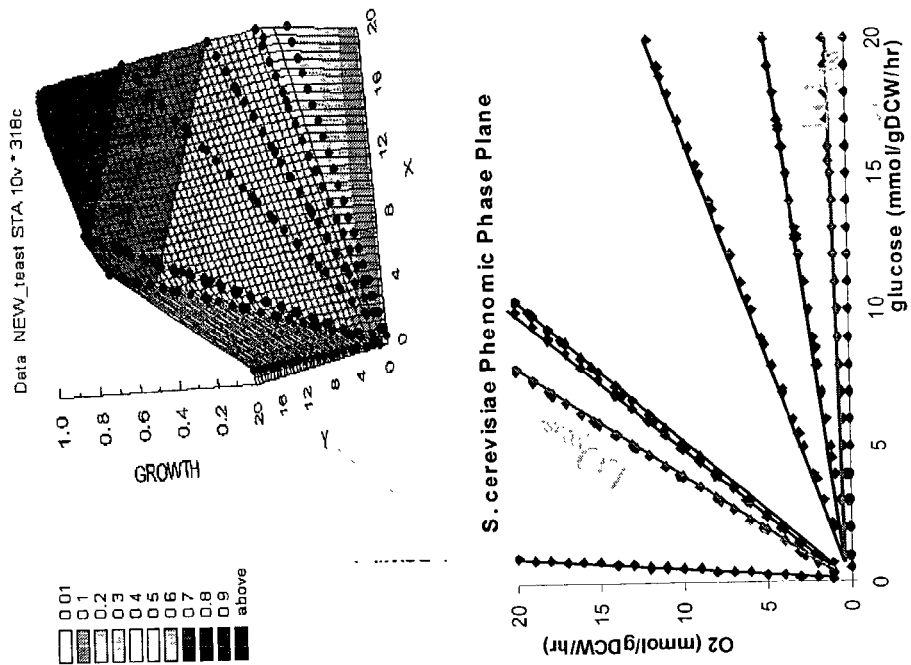
FIG. 6 shows a Phenotypic Phase Plane (PhPP) diagram for *S. cerevisiae* revealing a finite number of qualitatively distinct patterns of metabolic pathway utilization divided into discrete phases. The characteristics of these distinct phases are interpreted using ratios of shadow prices in the form of isoclines. The isoclines can be used to classify these phases into futile, single and dual substrate limitation and to define the line of optimality. The upper part of the figure shows a 3-dimensional *S. cerevisiae* Phase Plane diagram. The bottom part shows a 2-dimensional Phase Plane diagram with the line of optimality (LO) indicated.

As illustrated in FIG. 6, the *S. cerevisiae* PhPP contains 8 distinct metabolic phenotypes. Each region (P1-P8) exhibits unique metabolic pathway utilization that can be summarized as follows:

The left-most region is the so-called "infeasible" steady state region in the PhPP, due to stoichiometric limitations.

From left to right:

P1: Growth is completely aerobic. Sufficient oxygen is available to complete the oxidative metabolism of glucose to support growth requirements. This zone represents a futile cycle. Only $CO_2$ is formed as a metabolic by-product. The growth rate is less than the optimal growth rate in region P2. The P1 upper limit represents the locus of points for which the carbon is completely oxidized to eliminate the excess electron acceptor, and thus no biomass can be generated.

P2: Oxygen is slightly limited, and all biosynthetic cofactor requirements cannot be optimally satisfied by oxidative metabolism. Acetate is formed as a metabolic by-product enabling additional high-energy phosphate bonds via substrate level phosphorylation. With the increase of $O_2$ supply, acetate formation eventually decreases to zero.

P3: Acetate is increased and pyruvate is decreased with increase in oxygen uptake rate.

P4: Pyruvate starts to increase and acetate is decreased with increase in oxygen uptake rate. Ethanol production eventually decreases to zero.

P5: The fluxes towards acetate formation are increasing and ethanol production is decreasing.

P6: When the oxygen supply increases, acetate formation increases and ethanol production decreases with the carbon directed toward the production of acetate. Besides succinate production, malate may also be produced as metabolic by-product.

P7: The oxygen supply is extremely low, ethanol production is high and succinate production is decreased. Acetate is produced at a relatively low level.

P8: This region is along the Y-axis and the oxygen supply is zero. This region represents completely anaerobic fermentation. Ethanol and glycerol are secreted as a metabolic by-product. The role of NADH-consuming glycerol formation is to maintain the cytosol redox balance under anaerobic conditions (Van Dijken and Scheffers *Yeast* 2(2): 123-7 (1986)).

Line of Optimality: Metabolically, the line of optimality (LO) represents the optimal utilization of the metabolic pathways without limitations on the availability of the substrates. On an oxygen/glucose phenotypic phase plane diagram, LO represents the optimal aerobic glucose-limited growth of *S. cerevisiae* metabolic network to produce biomass from unlimited oxygen supply for the complete oxidation of the substrates in the cultivation processes. The line of optimality therefore represents a completely respiratory metabolism, with no fermentation by-product secretion and the futile cycle fluxes equals zero.

Thus, this example demonstrates that Phase Plane Analysis can be used to determine the optimal fermentation pattern for *S. cerevisiae*, and to determine the types of organic byproducts that are accumulated under different oxygenation conditions and glucose uptake rates.

Example IV

Calculation of Line of Optimality and Respiratory Quotient

This example shows how the *S. cerevisiae* metabolic model can be used to calculate the oxygen uptake rate (OUR), the carbon dioxide evolution rate (CER) and the respiration quotient (RQ), which is the ratio of CER over OUR.

Figure 7:
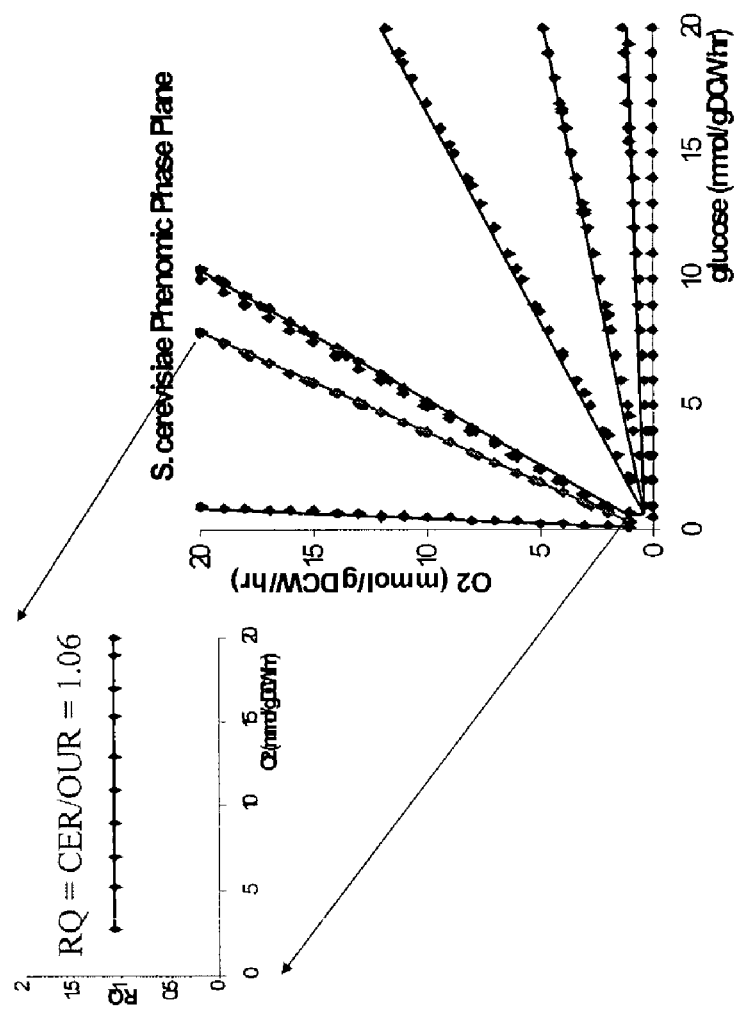
FIG. 7 shows the respiratory quotient (RQ) versus oxygen uptake rate (mmole/g-DW/hr) (upper left) on the line of optimality. The phenotypic phase plane (PhPP) illustrates that the predicted RQ is a constant of value 1.06

The oxygen uptake rate (OUR) and the carbon dioxide evolution rate (CER) are direct indicators of the yeast metabolic activity during the fermentation processes. RQ is a key metabolic parameter that is independent of cell number. As illustrated in FIG. 7, if the *S. cerevisiae* is grown along the line of optimality, LO, its growth is at optimal aerobic rate with all the carbon sources being directed to biomass formation and there are no metabolic by-products secreted except $CO_2$. The calculated RQ along the LO is a constant value of 1.06; the RQ in P1 region is less than 1.06; and the RQ in the remaining regions in the yeast PhPP are greater than 1.06. The RQ has been used to determine the cell growth and metabolism and to control the glucose feeding for optimal biomass production for decades (Zeng et al. *Biotechnol. Bioeng.* 44:1107-1114

(1994)). Empirically, several researchers have proposed the values of 1.0 (Zigova, *J Biotechnol* 80: 55-62 (2000). Journal of Biotechnology), 1.04 (Wang et al., *Biotechnol & Bioeng* 19:69-86 (1977)) and 1.1 (Wang et al., *Biotechnol. & Bioeng.* 21:975-995 (1979)) as optimal RQ which should be maintained in fed-batch or continuous production of yeast's biomass so that the highest yeast biomass could be obtained (Dantigny et al., *Appl. Microbiol. Biotechnol.* 36:352-357 (1991)). The constant RQ along the line of optimality for yeast growth by the metabolic model is thus consistent with the empirical formulation of the RQ through on-line measurements from the fermentation industry.

Example V

Computer Simulations

This example shows computer simulations for the change of metabolic phenotypes described by the yeast PHPP.

Figure 8:
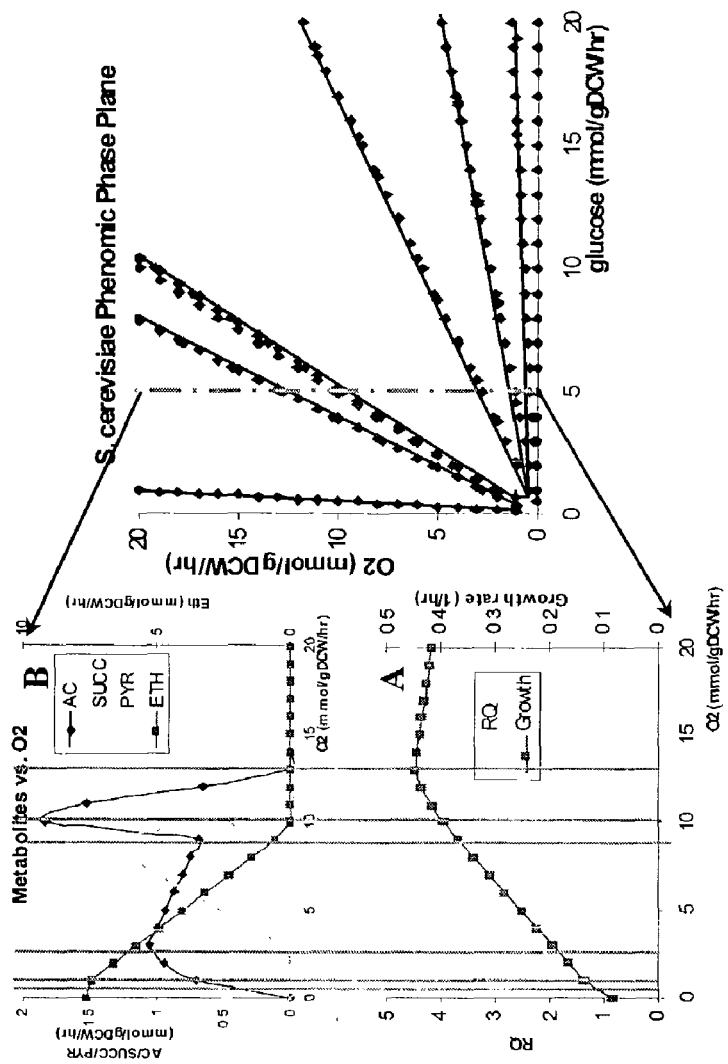
FIG. 8 shows phases of metabolic phenotype associated with varying oxygen availability, from completely anaerobic fermentation to aerobic growth in *S. cerevisiae*. The glucose uptake rate was fixed under all conditions, and the resulting optimal biomass yield, as well as respiratory quotient, RQ, are indicated along with the output fluxes associated with four metabolic by-products: acetate, succinate, pyruvate, and ethanol.

A piece-wise linearly increasing function was used with the oxygen supply rates varying from completely anaerobic to fully aerobic conditions (with increasing oxygen uptake rate from 0 to 20 mmol per g cell-hour). A glucose uptake rate of 5 mmol of glucose per g (dry weight)-hour was arbitrarily chosen for these computations. As shown in FIG. 8A, the biomass yield of the in silico *S. cerevisiae* strain was shown to increase from P8 to P2, and become optimal on the LO. The yield then started to slowly decline in P1 (futile cycle region). At the same time, the RQ value declines in relation to the increase of oxygen consumption rate, reaching a value of 1.06 on the LO1 and then further declining to become less than 1.

FIG. 8B shows the secretion rates of metabolic by-products; ethanol, succinate, pyruvate and acetate with the change of oxygen uptake rate from 0 to 20 mmol of oxygen per g (dry weight)-h. Each one of these by-products is secreted in a fundamentally different way in each region. As oxygen increases from 0 in P7, glycerol production (data not shown in this figure) decreases and ethanol production increases. Acetate and succinate are also secreted.

Example VI

Modeling of Phenotypic Behavior in Chemostat Cultures

This example shows how the *S. cerevisiae* metabolic model can be used to predict optimal flux distributions that would optimize fermentation performance, such as specific product yield or productivity. In particular, this example shows how flux based analysis can be used to determine conditions that would minimize the glucose uptake rate of *S. cerevisiae* grown on glucose in a continuous culture under anaerobic and under aerobic conditions.

In a continuous culture, growth rate is equivalent to the dilution rate and is kept at a constant value. Calculations of the continuous culture of *S. cerevisiae* were performed by fixing the in silico growth rate to the experimentally determined dilution rate, and minimizing the glucose uptake rate. This formulation is equivalent to maximizing biomass production given a fixed glucose uptake value and was employed to simulate a continuous culture growth condition. Furthermore, a non growth dependent ATP maintenance of 1 mmol/gDW, a systemic P/O ratio of 1.5 (Verduyn et al. *Antonie Van Leeuwenhoek* 59(1): 49-63 (1991)), a polymerization cost of 23.92 mmol ATP/gDW, and a growth dependent ATP maintenance of 35.36 mmol ATP/gDW, which is simulated for a biomass yield of 0.51 gDW/h, are assumed. The sum of the latter two terms is included into the biomass equation of the genome-scale metabolic model.

Figure 9:
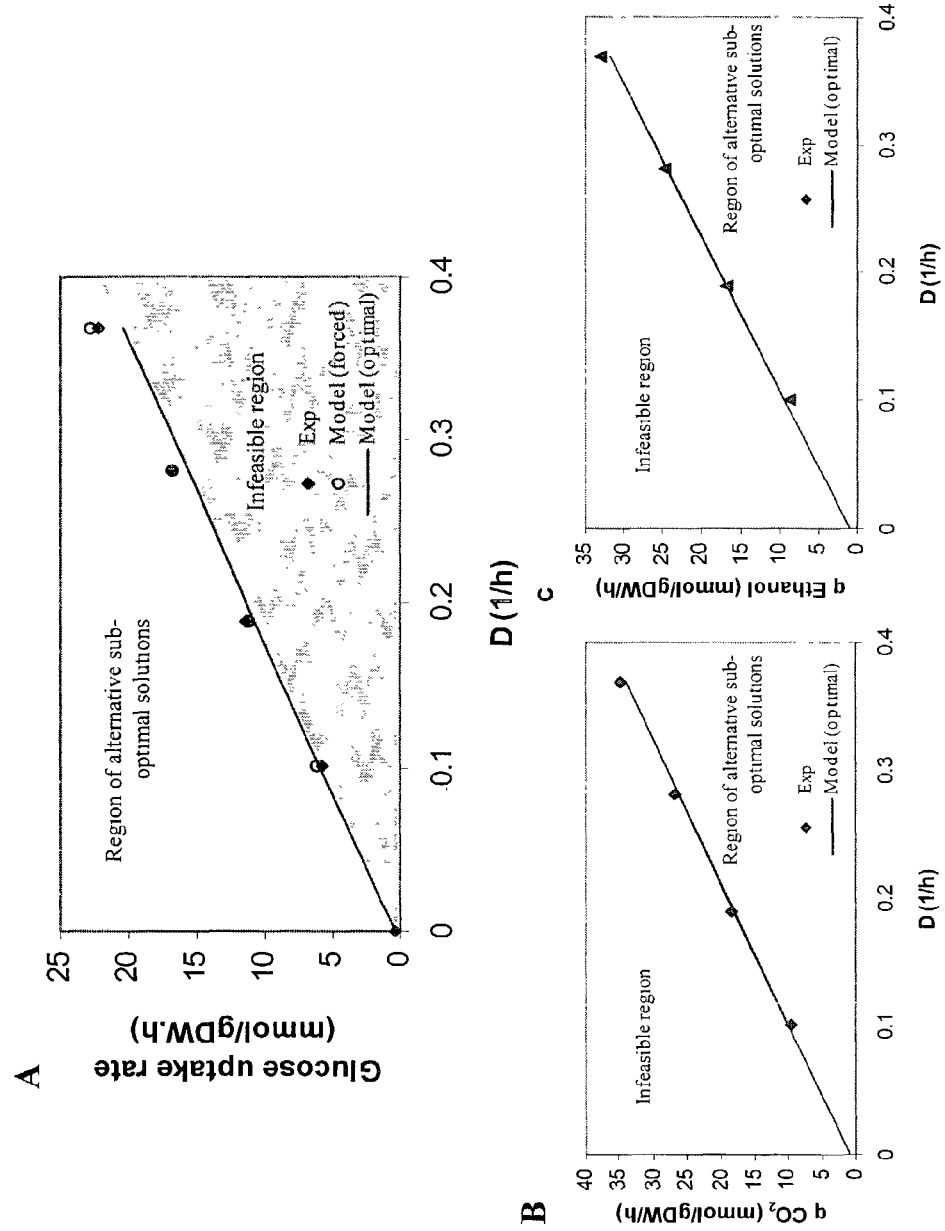
FIG. 9 shows anaerobic glucose limited continuous culture of *S. cerevisiae*.

Optimal growth properties of *S. cerevisiae* were calculated under anaerobic glucose-limited continuous culture at dilution rates varying between 0.1 and 0.4 $h^{-1}$. The computed by-product secretion rates were then compared to the experimental data (Nissen et al. *Microbiology* 143(1): 203-18 (1997)). The calculated uptake rates of glucose and the production of ethanol, glycerol, succinate, and biomass are in good agreement with the independently obtained experimental data (FIG. 9). The relatively low observed acetate and pyruvate secretion rates were not predicted by the iii silico model since the release of these metabolites does not improve the optimal solution of the network.

It is possible to constrain the in silico model further to secrete both, pyruvate and acetate at the experimental level and recompute an optimal solution under these additional constraints. This calculation resulted in values that are closer to the measured glucose uptake rates (FIG. 9A). This procedure is an example of an iterative data-driven constraint-based modeling approach, where the successive incorporation of experimental data is used to improve the in silico model. Besides the ability to describe the overall growth yield, the model allows further insight into how the metabolism operates. From further analysis of the metabolic fluxes at anaerobic growth conditions the flux through the glucose-6-phosphate dehydrogenase was found to be 5.32% of the glucose uptake rate at dilution rate of 0.1 $h^{-1}$, which is consistent with experimentally determined value (6.34%) for this flux when cells are operating with fermentative metabolism (Nissen et al., *Microbiology* 143(1): 203-218 (1997)).

Figure 10:
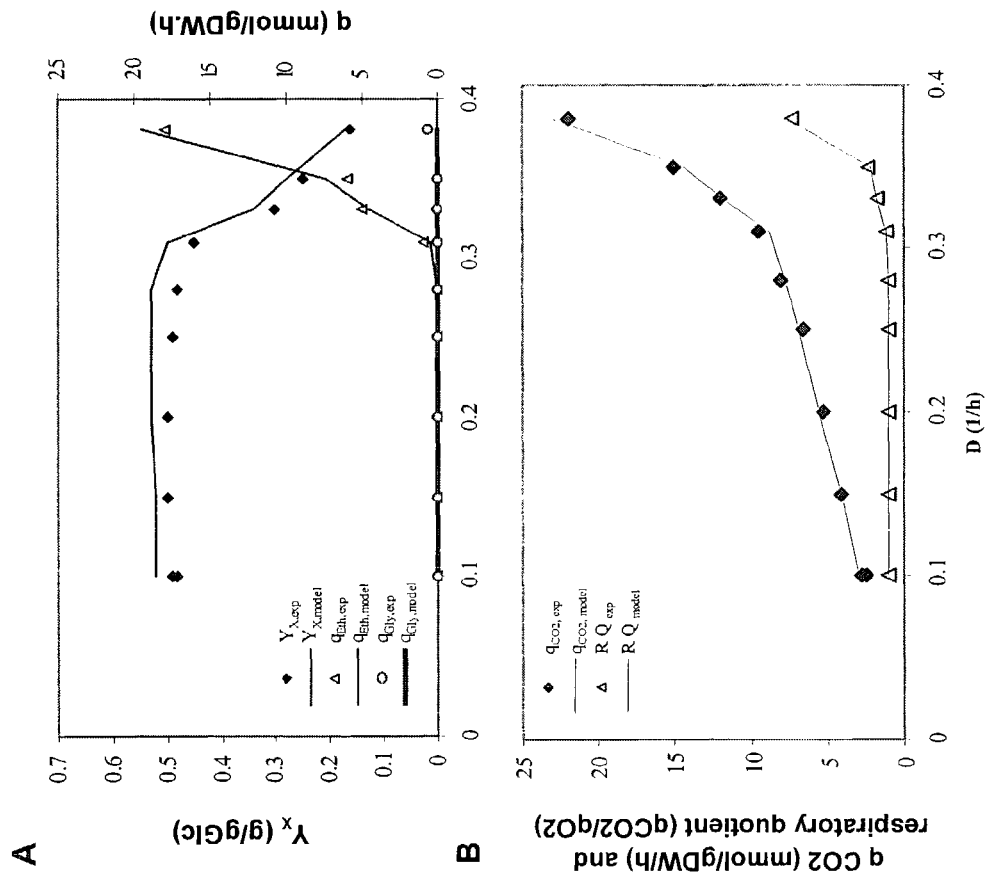
FIG. 10 shows aerobic glucose-limited continuous culture of *S. cerevisiae* in vivo and in silico.

Optimal growth properties of *S. cerevisiae* were also calculated under aerobic glucose-limited continuous culture in which the Crabtree effect plays an important role. The molecular mechanisms underlying the Crabtree effect in *S. cerevisiae* are not known. The regulatory features of the Crabtree effect (van Dijken et al. *Antonie Van Leeuwenhoek* 63(3-4):343-52 (1993)) can, however, be included in the in silico model as an experimentally determined growth rate-dependent maximum oxygen uptake rate (Overkamp et al. *J. of Bacteriol* 182(10): 2823-30 (2000))). With this additional constraint and by formulating growth in a chemostat as described above, the in silico model makes quantitative predictions about the respiratory quotient, glucose uptake, ethanol, CO2, and glycerol secretion rates under aerobic glucose-limited continuous condition (FIG. 10).

Example VII

Analysis of Deletion of Genes Involved in Central Metabolism in S. Cerevsiae

This example shows how the *S. cerevisiae* metabolic model can be used to determine the effect of deletions of individual reactions in the network.

Gene deletions were performed in silico by constraining the flux(es) corresponding to a specific gene to zero. The impact of single gene deletions on growth was analysed by simulating growth on a synthetic complete medium containing glucose, amino acids, as well as purines and pyrimidines.

In silico results were compared to experimental results as supplied by the Saccharomyces Genome Database (SGD) (Cherry et al., *Nucleic Acids Research* 26(1):73-79 (1998)) and by the Comprehensive Yeast Genome Database (Mewes et al., *Nucleic Acids Research* 30(1):31-34 (2002)). In 85.6% of all considered cases (499 out of 583 cases), the in silico prediction was in qualitative agreement with experimental results. An evaluation of these results can be found in Example VIII. For central metabolism, growth was predicted under various experimental conditions and 81.5% (93 out of 114 cases) of the in silico predictions were in agreement with in vivo phenotypes.

Table 6 shows the impact of gene deletions on growth in *S. cerevisiae*. Growth on different media was considered, including defined complete medium with glucose as the carbon source, and minimal medium with glucose, ethanol or acetate as the carbon source. The complete reference citations for Table 6 can be found in Table 9.

Thus, this example demonstrates that the in silico model can be used to uncover essential genes to augment or circumvent traditional genetic studies.

TABLE 6

| Defined Medium Carbon Source Gene | Complete Glucose in silico/in vivo | Minimal Glucose in silico/in vivo | Minimal Acetate in silico/in vivo | Minimal Ethanol in silico/in vivo | References: (Minimal media) |
|---|---|---|---|---|---|
| ACO1 | +/+ | −/− | | | (Gangloff et al., 1990) |
| CDC19# | +/+ | +/− | | | (Boles et al., 1998) |
| CIT1 | +/+ | +/+ | | | (Kim et al., 1986) |
| CIT2 | +/+ | +/+ | | | (Kim et al., 1986) |
| CIT3 | +/+ | | | | |
| DAL7 | +/+ | +/+ | +/+ | +/+ | (Hartig et al., 1992) |
| ENO1 | +/+ | | | | |
| ENO2$^{\$\$}$ | +/− | +/− | | | |
| FBA1* | +/− | +/− | | | |
| FBP1 | +/+ | +/+ | | +/− | (Sedivy and Fraenkel, 1985; Gancedo and Delgado, 1984) |
| FUM1 | +/+ | | | | |
| GLK1 | +/+ | | | | |
| GND1## | +/− | +/− | | | |
| GND2 | +/+ | | | | |
| GPM1$^{\|}$ | +/− | +/− | | | |
| GPM2 | +/+ | | | | |
| GPM3 | +/+ | | | | |
| HXK1 | +/+ | | | | |
| HXK2 | +/+ | | | | |
| ICL1 | +/+ | +/+ | | | (Smith et al., 1996) |
| IDH1 | +/+ | +/+ | | | (Cupp and McAlister-Henn, 1992) |
| IDH2 | +/+ | +/+ | | | (Cupp and McAlister-Henn, 1992) |
| IDP1 | +/+ | +/+ | | | (Loftus et al., 1994) |
| IDP2 | +/+ | +/+ | | | (Loftus et al., 1994) |
| IDP3 | +/+ | | | | |
| KGD1 | +/+ | +/+ | | | (Repetto and Tzagoloff, 1991) |
| KGD2 | +/+ | +/+ | | | (Repetto and Tzagoloff, 1991) |
| LPD1 | +/+ | | | | |
| LSC1 | +/+ | | +/+ | +/+ | (Przybyla-Zawislak et al., 1998) |
| LSC2 | +/+ | | +/+ | +/+ | (Przybyla-Zawislak et al., 1998) |
| MAE1 | +/+ | +/+ | | +/+ | (Boles et al., 1998) |
| MDH1 | +/+ | +/+ | +/− | | (McAlister-Henn and Thompson, 1987) |
| MDH2 | +/+ | +/+ | +/+ | +/− | (McAlister-Henn and Thompson, 1987) |
| MDH3 | +/+ | | | | |
| MLS1 | +/+ | +/+ | +/+ | +/+ | (Hartig et al., 1992) |
| OSM1 | +/+ | | | | |
| PCK1 | +/+ | | | | |
| PDC1 | +/+ | +/+ | | | (Flikweert et al., 1996) |
| PDC5 | +/+ | +/+ | | | (Flikweert et al., 1996) |
| PDC6 | +/+ | +/+ | | | (Flikweert et al., 1996) |
| PFK1 | +/+ | +/+ | | | (Clifton and Fraenkel, 1982) |
| PFK2 | +/+ | +/+ | | | (Clifton and Fraenkel, 1982) |
| PGI1*, & | +/− | +/− | | | (Clifton et al., 1978) |
| PGK1* | +/− | +/− | | | |
| PGM1 | +/+ | +/+ | | | (Boles et al., 1994) |
| PGM2 | +/+ | +/+ | | | (Boles et al., 1994) |
| PYC1 | +/+ | +/+ | +/− | +/− | (Wills and Melham, 1985) |
| PYC2 | +/+ | | | | |
| PYK2 | +/+ | +/+ | | +/+ | (Boles et al., 1998; McAlister-Henn and Thompson, 1987) |
| RKI1 | −/− | | | | |
| RPE1 | +/+ | | | | |
| SOL1 | +/+ | | | | |
| SOL2 | +/+ | | | | |
| SOL3 | +/+ | | | | |
| SOL4 | +/+ | | | | |
| TAL1 | +/+ | +/+ | | | (Schaaff-Gerstenschläger and Zimmermann, 1993) |
| TDH1 | +/+ | | | | |
| TDH2 | +/+ | | | | |

TABLE 6-continued

| Defined Medium Carbon Source Gene | Complete Glucose in silico/in vivo | Minimal Glucose in silico/in vivo | Minimal Acetate in silico/in vivo | Minimal Ethanol in silico/in vivo | References: (Minimal media) |
|---|---|---|---|---|---|
| TDH3 | +/+ | | | | |
| TKL1 | +/+ | +/+ | | | (Schaff-Gerstenschläger and Zimmermann, 1993) |
| TKL2 | +/+ | | | | |
| TPI1*, $ | +/− | | | | |
| ZWF1 | +/+ | +/+ | | | (Schaaff-Gerstenschläger and Zimmermann, 1993) |

+/− Growth/no growth
The isoenyzme Pyk2p is glucose repressed, and cannot sustain growth on glucose.
*Model predicts single deletion mutant to be (highly) growth retarded.
$Growth of single deletion mutant is inhibited by glucose.
&Different hypotheses exist for why Pgi1p deficient mutants do not grow on glucose, e.g. the pentose phosphate pathway in S. cerevisiae is insufficient to support growth and cannot supply the EMP pathway with sufficient amounts of fructose-6-phosphate and glyceraldehydes-3-phosphate (Boles, 1997).
‖The isoenzymes Gpm2p and Gpm3p cannot sustain growth on glucose. They only show residual in vivo activity when they are expressed from a foreign promoter (Heinisch et al., 1998).
Gnd1p accounts for 80% of the enzyme activity. A mutant deleted in GND1 accumulates gluconate-6-phosphate, which is toxic to the cell (Schaaff-Gerstenschläger and Miosga, 1997).
$$ENO1 plays central role in gluconeogenesis whereas ENO2 is used in glycolysis (Müller and Entian, 1997).

Example VIII

Large-Scale Gene Deletion Analysis in S. Cerevisiae

A large-scale in silico evaluation of gene deletions in S. cerevisiae was conducted using the genome-scale metabolic model. The effect of 599 single gene deletions on cell viability was simulated in silico and compared to published experimental results. In 526 cases (87.8%), the in silico results were in agreement with experimental observations when growth on synthetic complete medium was simulated. Viable phenotypes were predicted in 89.4% (496 out of 555) and lethal phenotypes are correctly predicted in 68.2% (30 out of 44) of the cases considered.

The failure modes were analyzed on a case-by-case basis for four possible inadequacies of the in silico model: 1) incomplete media composition; 2) substitutable biomass components; 3) incomplete biochemical information; and 4) missing regulation. This analysis eliminated a number of false predictions and suggested a number of experimentally testable hypotheses. The genome-scale in silico model of S. cerevisiae can thus be used to systematically reconcile existing data and fill in knowledge gaps about the organism.

Growth on complete medium was simulated under aerobic condition. Since the composition of a complete medium is usually not known in detail, a synthetic complete medium containing glucose, twenty amino acids (alanine, arginine, asparagine, aspartate, cysteine, glutamine, glutamate, glycine, histidine, isoleucine, leucine, lysine, methionine, phenylalanine, proline, serine, threonine, tryptophane, tyrosine, valine) and purines (adenine and guanine) as well as pyrimidines (cytosine and thymine) was defined for modeling purposes. Furthermore, ammonia, phosphate, and sulphate were supplied. The in silico results were initially compared to experimental data from a competitive growth assay (Winzeler et al., Science 285:901-906 (1999)) and to available data from the MIPS and SGD databases (Mewes et al., Nucleic Acids Research 30(1):31-34 (2002); Cherry et al., Nucleic Acids Research 26(1):73-79 (1998)). Gene deletions were simulated by constraining the flux through the corresponding reactions to zero and optimizing for growth as previously described (Edwards and Palsson, Proceedings of the National Academy of Sciences 97(10):5528-5533 (2000)). For this analysis, a viable phenotype was defined as a strain that is able to meet all the defined biomass requirements and thus grow. Single gene deletion mutants that have a reduced growth rate compared to the wild type simulation are referred to as growth retarded mutants.

The analysis of experimental data was approached in three steps:

The initial simulation using the synthetic medium described above, referred to as simulation 1.

False predictions of simulation 1 were subsequently examined to determine if the failure was due to incomplete information in the in silico model, such as missing reactions, the reversibility of reactions, regulatory events, and missing substrates in the synthetic complete medium. In simulation 2, any such additional information was introduced into the in silico model and growth was re-simulated for gene deletion mutants whose in silico phenotype was not in agreement with its in vivo phenotype.

A third simulation was carried out, in which dead end pathways (i.e. pathways leading to intracellular metabolites that were not further connected into the overall network), were excluded from the analysis (simulation 3).

The effect of single gene deletions on the viability of S. cerevisiae was investigated for each of the 599 single gene deletion mutants. The in silico results were categorized into four groups:

1. True negatives (correctly predicted lethal phenotype);
2. False negatives (wrongly predicted lethal phenotype);
3. True positives (correctly predicted viable phenotypes);
4. False positives (wrongly predicted viable phenotypes).

In simulation 1, 509 out of 599 (85%) simulated phenotypes were in agreement with experimental data. The number of growth retarding genes in simulation 1 was counted to be 19, a surprisingly low number. Only one deletion, the deletion of TPI1, had a severe impact on the growth rate. Experimentally, a deletion in TPI1 is lethal (Ciriacy and Breitenbach, J Bacteriol 139(1):152-60 (1979)). In silico, a tpi1 mutant could only sustain a specific growth rate of as low as 17% of the wild type. All other growth retarding deletions sustained approximately 99% of wild type growth, with the exception of a deletion of the mitochondrial ATPase that resulted in a specific growth rate of approximately 90% of wild type.

Predictions of simulation 1 were evaluated in a detailed manner on a case-by-case basis to determine whether the false predictions could be explained by:

1. Medium composition used for the simulation;
2. The biomass composition used in the simulation;

3. Incomplete biochemical information; and
4. Effects of gene regulation.

Analysis of the false predictions from simulation 1 based on these possible failure modes resulted in model modifications that led to 526 out of 599 correctly predicted phenotypes (87.8%), i.e. simulation 2.

Simulation 3 uncovered some 220 reactions in the reconstructed network that are involved in dead end pathways. Removing these reactions and their corresponding genes from the genome-scale metabolic flux balance model, simulation 3 resulted in 473 out of 530 (89.6%) correctly predicted phenotypes of which 91.4% are true positive and 69.8% are true negative predictions.

Table 7 provides a summary of the large-scale evaluation of the effect of in silico single gene deletions in S. cerevisiae on viability.

TABLE 7

| Simulation | 1 | 2 | Genes involved in dead end pathways | 3 |
|---|---|---|---|---|
| Number of deletion | 599 | 599 |  | 530 |
| Predicted Total | 509 | 526 |  | 475 |
| True positive | 481 | 496 | 51 | 445 |

TABLE 7-continued

| Simulation | 1 | 2 | Genes involved in dead end pathways | 3 |
|---|---|---|---|---|
| True negative | 28 | 30 | 0 | 30 |
| False positive | 63 | 59 | 17 | 42 |
| False negative | 27 | 14 | 1 | 13 |
| Overall Prediction | 85.0% | 87.8% |  | 89.6% |
| Positive Prediction | 88.4% | 89.4% |  | 91.4% |
| Negative Prediction | 50.9% | 68.2% |  | 69.8% |

A comprehensive list of all the genes used in the in silico deletion studies and results of the analysis are provided in Table 8. Table 8 is organized according to the categories true negative, false negative, true positive and false positive predictions. Genes highlighted in grey boxes, such as *INO1* corresponded initially to false predictions (simulation 1); however, evaluation of the false prediction and simulation 2 identified these cases as true predictions. ORFs or genes that are in an open box, such as *TRR2* were excluded in simulation 3, as the corresponding reactions catalysed steps in dead end pathways.

TABLE 8

False Positive

ACS2 AUR1 BET2 CDC19 CDC21 CDC8 CYR1 DED81 DFR1 DIM1 DUT1 DYS1 ENO2 ERG10 ERG13 FAD1 FMN1 FOL1 FOL2 FOL3 GFA1 GPM1 HEM1 HEM12 HEM13 HEM15 HEM2 HEM3 HEM4 HIP1 HTS1 ILV3 ILV5 KRS1 LCB1 LCB2 MSS4 NAT2 NCP1 NMT1 PCM1 PET9 PGS1 PIK1 PMA1 PRO3 QNS1 QRI1 RER2 RIB5 SEC59 STT4 THI80 TOR2 TPI TSC10 UGP1 URA6 YDR341C YGL245W

False Negative

ADE3 ADK1 CHO1 CHO2 DPP1 ERG3 ERG4 ERG5 ERG6 INM1 MET6 OPI3 PPT2 YNK1

True Negative

ACC1 ADE13 CDS1 DPM1 ERG1 ERG7 ERG8 ERG9 ERG11 ERG12 ERG20 ERG25 ERG26 ERG27 FBA1 GLN1 GUK1 IDI1 IPP1 MVD1 PGI1 PGK1 PIS1 PMI40 PSA1 RKI1 SAH1 SEC53 TRR1 YDR531W

True Positive

AAC1 AAC3 AAH1 AAT1 AAT2 ABZ1 ACO1 ACS1 ADE1 ADE12 ADE16 ADE17 ADE2 ADE4 ADE5 ADE6 ADE7 ADE8 ADH1 ADH2 ADH3 ADH4 ADH5 ADK2 AGP1 AGP2 AGP3 ALD2 ALD3 ALD4 ALD5 ALD6 ALP1 ASP1 ATH1 ATP1 BAP2 BAP3 BAT1 BAT2 BGL2 BIO2 BIO3 BIO4 BIO5 BNA1 CAN1 CAR1 CAR2 CAT2 CDA1 CDA2
CDD1 CEM1 CHA1 CHS1 CHS2 CHS3 CIT1 CIT2 CIT3 CKI1 COQ1 COQ2 COQ3 COQ5 COQ6 COX1 COX10 CPA2 CPT1 CRC1 CRD1 CSG2 CTA1 CTP1 CTT1 CYB2 CYS3 CYS4 DAK1 DAK2 DAL1 DAL2 DAL3 DAL4 DAL5 DAL7 DCD1 DEG1 DIC1 DIP5 DLD1 DPH5 DPL1 DUR1 DUR3
ECM17 ECM31 ECM40 ECT1 EKI1 ENO1 EPT1 ERG2 ERG24 ERR1 ERR2 EXG1 EXG2 FAA1 FAA2 FAA3 FAA4 FAB1 FAS1 FBP1 FBP26 FCY1 FCY2 FKS1 FKS3 FLX1 FMT1 FOX2 FRDS FUI1 FUM1 FUN63 FUR1 FUR4 GAD1 GAL1 GAL10 GAL2 GAL7 GAP1 GCV1 GCV2 GDH1 GDH2 GDH3 GLC3 GLK1 GLO1 GLO2 GLO4 GLR1 GLT1 GLY1 GNA1 GND1 GND2 GNP1 GPD1 GPD2 GPH1 GPM2 GPM3 GPX1 GPX2 GSC2 GSH1 GSH2 GSY1 GSY2 GUA1 GUT1 GUT2
HEM14 HIS1 HIS2 HIS3 HIS4 HIS5 HIS6 HIS7 HMG1 HMG2 HMT1 HNM1 HOM2 HOM3 HOM6 HOR2 HPT1 HXK1 HXK2 HXT1 HXT10 HXT11 HXT13 HXT14 HXT15 HXT16 HXT17 HXT2 HXT3 HXT4 HXT5 HXT6 HXT7 HXT8 HXT9 HYR1 ICL1 ICL2 IDH1 IDP1 IDP2 IDP3 ILV1 ILV2 INO1 IPT1 ITR1 ITR2 JEN1 KGD1 KRE2 KTR1 KTR2 KTR3 KTR4 KTR6 LCB3 LCB4 LCB5 LEU1 LEU2 LEU4 LPD1 LPP1 LSC1 LSC2 LYP1 LYS1 LYS12 LYS2 LYS20 LYS21 LYS4 LYS9 MAE1 MAK3 MAL12 MAL31 MAL32 MDH1 MDH2 MDH3 MEL1 MEP1 MEP2 MEP3 MET1 MET10 MET12 MET13 MET14 MET16 MET17 MET2 MET22 MET3 MET7 MHT1 MIR1 MIS1 MLS1 MMP1 MSE1 MSK1 MSR1 MSW1 MTD1 MUP1 MUP3 NAT1 NDH1 NDH2 NDI1 NHA1 NIT2 NPT1 NTA1 NTH1 NTH2 OAC1 ODC1 ODC2 ORT1 OSM1 PAD1 PCK1 PCT1 PDA1 PDC2 PDC5 PDC6 PDE1 PDE2 PDX3 PFK1 PFK2 PFK26 PFK27 PGM1 PGM2 PHA2 PHO8 PHO11 PHO84 PLC1 PMA2 PMP1 PMP2 PMT1 PMT2 PMT3 PMT4 PMT5 PMT6 PNC1 PNP1 POS5 POT1 PPA2 PRM4 PRM5 PRM6 PRO1 PRO2 PRS1 PRS2 PRS3 PRS4 PRS5 PSD1 PSD2 PTR2 PUR5 PUS1 PUS2 PUS4 PUT1 PUT2 PUT4 PYC1 PYC2 PYK1 QPT1 RAM1 RBK1 RHR2 RIB1 RIB4 RIB7 RMA1 RNR1 RNR3 RPE1 SAM1 SAM2 SAM3 SAM4 SCS7 SDH3 SER1 SER2 SER3 SER33 SFA1 SFC1 SHM1 SHM2 SLC1 SOL1 SOL2 SOL3 SOL4 SOR1 SPE1 SPE2 SPE3 SPE4 SPR1 SRT1 STL1 SUC2 SUL1 SUL2 SUR1 SUR2

TABLE 8-continued

TAL1 TAT1 TAT2 TDH1 TDH2 TDH3 THI20 THI21 THI22 THI6 THI7 THM2 THM3 THR1 THR4
TKL1 TKL2 TOR1 TPS1 TPS2 TPS3 |TRK1|TRP1 TRP2 TRP3 TRP4 TRP5 |TRR2|TSL1 TYR1 UGA1
UGA4 URA1 URA2 URA3 URA4 URA5 URA7 URA8 URA10 URH1 URK1 UTR1 VAP1 VPS34 XPT1
YAT1 YSR3 YUR1 ZWF1 |YBL098W|YBR006W YBR284W YDL100C YDR111C YEL041W YER053C
YFL030W YFR055W YGR012W YGR043C YGR125W YGR287C YIL145C YIL167W YJL070C
YJL200C YJL216C YJL218W YJR078W |YLR089C|YLR231C YLR328W |YML082W|YMR293C

The following text describes the analysis of the initially false predictions of simulation 1 that were performed, leading to simulation 2 results.

Influence of Media Composition on Simulation Results:

A rather simple synthetic complete medium composition was chosen for simulation 1. The in silico medium contained only glucose, amino acids and nucleotides as the main components. However, complete media often used for experimental purposes, e.g. the YPD medium containing yeast extract and peptone, include many other components, which are usually unknown.

False negative predictions: The phenotype of the following deletion mutants: ecm1Δ, yil145cΔ, erg2 Δ, erg24 Δ, fas1 Δ, ura1 Δ, ura2 Δ, ura3 Δ and ura4 Δ were falsely predicted to be lethal in simulation 1. In simulation 2, an additional supplement of specific substrate could rescue a viable phenotype in silico and as the supplemented substrate may be assumed to be part of a complex medium, the predictions were counted as true positive predictions in simulation 2. For example, both Ecm1 and Yil145c are involved in pantothenate synthesis. Ecm1 catalyses the formation of dehydropantoate from 2-oxovalerate, whereas Yil145c catalyses the final step in pantothenate synthesis from β-alanine and panthoate. In vivo, ecm1 Δ, and yil145c a mutants require pantothenate for growth (White et al., *J Biol Chem* 276(14): 10794-10800 (2001)). By supplying pantothenate to the synthetic complete medium in silico, the model predicted a viable phenotype and the growth rate was similar to in silico wild type *S. cerevisiae*.

Similarly other false predictions could be traced to medium composition:

Mutants deleted in ERG2 or ERG24 are auxotroph for ergosterol (Silve et al., *Mol Cell Biol* 16(6): 2719-2727 (1996); Bourot and Karst, Gene 165(1): 97-102 (1995)). Simulating growth on a synthetic complete medium supplemented with ergosterol allowed the model to accurately predict viable phenotypes.

A deletion of FAS1 (fatty acid synthase) is lethal unless appropriate amounts of fatty acids are provided, and by addition of fatty acids to the medium, a viable phenotype was predicted.

Strains deleted in URA1, URA2, URA3, or URA4 are auxotroph for uracil (Lacroute, *J Bacteriol* 95(3): 824-832 (1968)), and by supplying uracil in the medium the model predicted growth.

The above cases were initially false negative predictions, and simulation 2 demonstrated that these cases were predicted as true positive by adjusting the medium composition.

False positive predictions: Simulation 1 also contained false positive predictions, which may be considered as true negatives or as true positives. Contrary to experimental results from a competitive growth assay (Winzeler et al., *Science* 285: 901-906 (1999)), mutants deleted in ADEJ3 are viable in vivo on a rich medium supplemented with low concentrations of adenine, but grow poorly (Guetsova et al., *Genetics* 147(2): 383-397 (1997)). Adenine was supplied in the in silico synthetic complete medium. By not supplying adenine, a lethal mutant was predicted. Therefore, this case was considered as a true negative prediction.

A similar case was the deletion of GLN1, which codes a glutamine synthase, the only pathway to produce glutamine from ammonia. Therefore, gln1Δ mutants are glutamine auxotroph (Mitchell, *Genetics* 111(2):243-58 (1985)). In a complex medium, glutamine is likely to be deaminated to glutamate, particularly during autoclaving. Complex media are therefore likely to contain only trace amounts of glutamine, and gln1Δ mutants are therefore not viable. However, in silico, glutamine was supplied in the complete synthetic medium and growth was predicted. By not supplying glutamine to the synthetic complete medium, the model predicted a lethal phenotype resulting in a true negative prediction.

Ilv3 and Ilv5 are both involved in branched amino acid metabolism. One may expect that a deletion of ILV3 or ILV5 could be rescued with the supply of the corresponding amino acids. For this, the model predicted growth. However, contradictory experimental data exists. In a competitive growth assay lethal phenotypes were reported. However, earlier experiments showed that ilv3Δ and ilv5Δ mutants could sustain growth when isoleucine and valine were supplemented to the medium, as for the complete synthetic medium. Hence, these two cases were considered to be true positive predictions.

Influence of the Definition of the Biomass Equation

The genome-scale metabolic model contains the growth requirements in the form of biomass composition. Growth is defined as a drain of building blocks, such as amino acids, lipids, nucleotides, carbohydrates, etc., to form biomass. The number of biomass components is 44 (see Table 1). These building blocks are essential for the formation of cellular components and they have been used as a fixed requirement for growth in the in silico simulations. Thus, each biomass component had to be produced by the metabolic network otherwise the organism could not grow in silico. In vivo, one often finds deletion mutants that are not able to produce the original biomass precursor or building block; however, other metabolites can replace these initial precursors or building blocks. Hence, for a number of strains a wrong phenotype was predicted in silico for this reason.

Phosphatidylcholine is synthesized by three methylation steps from phosphatidylethanolamine (Dickinson and Schweizer, *The metabolism and molecular physiology of Saccharomyces cerevisiae* Taylor & Francis, London; Philadelphia (1999)). The first step in the synthesis of phosphatidylcholine from phosphatidylethanolamine is catalyzed by a methyltransferase encoded by CHO2 and the latter two steps are catalyzed by phospholipid methyltransferase encoded by OPI3. Strains deleted in CHO2 or OPI3 are viable (Summers et al., *Genetics* 120(4): 909-922 (1988); Daum et al., *Yeast* 14(16): 1471-1510 (1998)); however, either null mutant accumulates mono- and dimethylated phosphatidylethanolamine under standard conditions and display greatly reduced levels of phosphatidylcholine (Daum et al., *Yeast* 15(7): 601-614

(1999)). Hence, phosphatidylethanolamine can replace phosphatidylcholine as a biomass component. In silico, phosphatidylcholine is required for the formation of biomass. One may further speculate on whether an alternative pathway for the synthesis of phosphatidylcholine is missing in the model, since Daum et al., supra (1999) detected small amounts of phosphatidylcholine in cho2Δ mutants. An alternative pathway, however, was not included in the in silico model.

Deletions in the ergosterol biosynthetic pathways of ERG3, ERG4, ERG5 or ERG6 lead in vivo to viable phenotypes. The former two strains accumulate ergosta-8, 22,24 (28)-trien-3-beta-ol (Bard et al., *Lipids* 12(8): 645-654 (1977); Zweytick et al., *FEBS Lett* 470(1): 83-87 (2000)), whereas the latter two accumulate ergosta-5,8-dien-3beta-ol (Hata et al., *J Biochem (Tokyo)* 94(2): 501-510 (1983)), or zymosterol and smaller amounts of cholesta-5,7,24-trien-3-beta-ol and cholesta-5,7,22,24-trien-3-beta-ol (Bard et al., supra (1977); Parks et al., *Crit Rev Biochem Mol Biol* 34(6): 399-404 (1999)), respectively, components that were not included in the biomass equations.

The deletion of the following three genes led to false positive predictions: RER2, SEC59 and QIR1. The former two are involved in glycoprotein synthesis and the latter is involved in chitin metabolism. Both chitin and glycoprotein are biomass components. However, for simplification, neither of the compounds was considered in the biomass equation. Inclusion of these compounds into the biomass equation may improve the prediction results.

Incomplete Biochemical Information

For a number of gene deletion mutants (inm1Δ, met6Δ, ynk1Δ, pho84Δ psd2Δ, tps2Δ), simulation 1 produced false predictions that could not be explained by any of the two reasons discussed above nor by missing gene regulation (see below). Further investigation of the metabolic network including an extended investigation of biochemical data from the published literature showed that some information was missing initially in the in silico model or information was simply not available.

Inm1 catalyses the ultimate step in inositol biosynthesis from inositol 1-phosphate to inositol (Murray and Greenberg, *Mol Microbiol* 36(3): 651-661 (2000)). Upon deleting INM1, the model predicted a lethal phenotype in contrary to the experimentally observed viable phenotype. An isoenzyme encoded by IMP2 was initially not included in the model, which may take over the function of INM1 and this addition would have led to a correct prediction. However, an inm1Δimp2Δ in vivo double deletion mutant is not inositol auxotroph (Lopez et al., *Mol Microbiol* 31(4): 1255-1264 (1999)). Hence, it appears that alternative routes for the production of inositol probably exist. Due to the lack of comprehensive biochemical knowledge, effects on inositol biosynthesis and the viability of strains deleted in inositol biosynthetic genes could not be explained.

Met6Δ mutants are methionine auxotroph (Thomas and Surdin-Kerjan, *Microbiol Mol Biol Rev* 61(4):503-532 (1997)), and growth may be sustained by the supply of methionine or S-adenosyl-L-methionine. In silico growth was supported neither by the addition of methionine nor by the addition of S-adenosyl-L-methionine. Investigation of the metabolic network showed that deleting MET6 corresponds to deleting the only possibility for using 5-methyltetrahydrofolate. Hence, the model appears to be missing certain information. A possibility may be that the carbon transfer is carried out using 5-methyltetrahydropteroyltri-L-glutamate instead of 5-methyltetrahydrofolate. A complete pathway for such a by-pass was not included in the genome-scale model.

The function of Ynk1p is the synthesis of nucleoside triphosphates from nucleoside diphosphates. YNK1Δ mutants have a 10-fold reduced Ynk1p activity (Fukuchi et al., *Genes* 129(1):141-146 (1993)), though this implies that there may either be an alternative route for the production of nucleoside triphosphates or a second nucleoside diphosphate kinase, even though there is no ORF in the genome with properties that indicates that there is a second nucleoside diphosphate kinase. An alternative route for the production of nucleoside triphosphate is currently unknown (Dickinson et al., supra (1999)), and was therefore not included in the model, hence a false negative prediction.

PHO84 codes for a high affinity phosphate transporter that was the only phosphate transporter included in the model. However, at least two other phosphate transporters exist, a second high affinity and $Na^+$ dependent transporter Pho89 and a low affinity transporter (Persson et al., *Biochim Biophys Acta* 1422(3): 255-72 (1999)). Due to exclusion of these transporters a lethal pho84☐ mutant was predicted. Including PHO89 and a third phosphate transporter, the model predicted a viable deletion mutant.

In a null mutant of PSD2, phosphatidylethanolamine synthesis from phosphatidylserine is at the location of Psd1 (Trotter et al., *J Biol Chem* 273(21): 13189-13196 (1998)), which is located in the mitochondria. It has been postulated that phosphatidylserine can be transported into the mitochondria and phosphatidylethanolamine can be transported out of the mitochondria. However, transport of phosphatidylethanolamine and phosphatidylserine over the mitochondrial membrane was initially not included in the model. Addition of these transporters to the genome-scale flux balance model allowed in silico growth of a PSD2 deleted mutant.

Strains deleted in TPS2 have been shown to be viable when grown on glucose (Bell et al., *J Biol Chem* 273(50): 33311-33319 (1998)). The reaction carried out by Tps2p was modeled as essential and as the final step in trehalose synthesis from trehalose 6-phosphate. However, the in vivo viable phenotype shows that other enzymes can take over the hydrolysis of trehalose 6-phosphate to trehalose from Tps2p (Bell et al., supra (1998)). The corresponding gene(s) are currently unknown. Inclusion of a second reaction catalyzing the final step of trehalose formation allowed for the simulation of a viable phenotype.

Strains deleted in ADE3 (C1-tetrahydrofolate synthase) and ADK1 (Adenylate kinase) could not be readily explained. It is possible that alternative pathways or isoenzyme-coding genes for both functions exist among the many orphan genes still present in the *S. cerevisiae*.

The reconstruction process led to some incompletely modeled parts of metabolism. Hence, a number of false positive predictions may be the result of gaps (missing reactions) within pathways or between pathways, which prevent the reactions to completely connect to the overall pathway structure of the reconstructed model. Examples include:

Sphingolipid metabolism. It has not yet been fully elucidated and therefore was not included completely into the model nor were sphingolipids considered as building blocks in the biomass equation.

Formation of tRNA. During the reconstruction process some genes were included responsible for the synthesis of tRNA (DED81, HTS1, KRS1, YDR41C, YGL245H). However, pathways of tRNA synthesis were not fully included.

Heme synthesis was considered in the reconstructed model (HEM1, HEM12, HEM13, HEM15, HEM2, HEM3, HEM4). However no reaction was included that metabolized heme in the model.

Hence, the incomplete structure of metabolic network may be a reason for false prediction of the phenotype of aur1Δ, lcb1Δ, lcb2Δ, tsc10Δ, ded81Δ, hts1Δ, krs1Δ, ydr41Δ, yg1245wΔ, hem1Δ, hem12Δ, hem13Δ, hem15Δ, hem2Δ, hem3Δ, and hem4Δ deletion mutants. Reaction reversibility. The CHO1 gene encodes a phosphatidylserine synthase, an integral membrane protein that catalyses a central step in cellular phospholipid biosynthesis. In vivo, a deletion in CHO1 is viable (Winzeler et al., *Science* 285: 901-906 (1999)). However, mutants are auxotrophic for choline or ethanolamine on media containing glucose as the carbon source (Bimer et al., *Mol Biol Cell* 12(4): 997-1007 (2001)).

Nevertheless, the model did not predict growth when choline and/or ethanolamine were supplied. Further investigation of the genome-scale model showed that this might be due to defining reactions leading from phosphatidylserine to phosphatidylcholine via phosphatidylethanolamine exclusively irreversible. By allowing these reactions to be reversible, either supply of choline and ethanolamine could sustain growth in silico.

Gene Regulation

Whereas many false negative predictions could be explained by either simulation of growth using the incorrect in silico synthetic complete medium or by initially missing information in the model, many false positives may be explained by in vivo catabolite expression, product inhibition effects or by repressed isoenzymes, as kinetic and other regulatory constraints were not included in the genome-scale metabolic model.

A total of 17 false positive predictions could be related to regulatory events. For a deletion of CDC19, ACS2 or ENO2 one may usually expect that the corresponding isoenzymes may take over the function of the deleted genes. However, the corresponding genes, either PYK2, ACS1 or ENO1, respectively, are subject to catabolite repression (Boles et al., *J Bacteriol* 179(9): 2987-2993 (1997); van den Berg and Steensma, *Eur J Biochem* 231(3): 704-713 (1995); Zimmerman et al., *Yeast sugar metabolism: biochemistry, genetics, biotechnology, and applications* Technomic Pub., Lancaster, Pa. (1997)). A deletion of GPM1 should be replaced by either of the two other isoenzymes, Gpm2 and Gpm3; however for the two latter corresponding gene products usually no activity is found (Heinisch et al., *Yeast* 14(3): 203-13 (1998)).

Falsely predicted growth phenotypes can often be explained when the corresponding deleted metabolic genes are involved in several other cell functions such as cell cycle, cell fate, communication, cell wall integrity, etc. The following genes whose deletions yielded false positive predictions were found to have functions other than just metabolic function: ACS2, BET2, CDC19, CDC8, CYR1, DIM1, ENO2, FAD1, GFA1, GPM1, HIP1, MSS4, PET9, PIK1, PMA1, STT4, TOR2. Indeed, a statistical analysis of the MIPS functional catalogue (found at the URL mips.gsf.de/proj/yeast/) showed that in general it was more likely to have a false prediction when the genes that had multiple functions were involved in cellular communication, cell cycling and DNA processing or control of cellular organization.

TABLE 9

Reference list for Table 2

Boles, E., Liebetrau, W., Hofmann, M. & Zimmermann, F. K. A family of hexosephosphate mutases in *Saccharomyces cerevisiae*. Eur. J. Biochem. 220, 83-96 (1994).

TABLE 9-continued

Reference list for Table 2

Boles, E. Yeast sugar metabolism. Zimmermann, F. K. & Entian, K.-D. (eds.), pp. 81-96 (Technomic Publishing CO., INC., Lancaster, 1997).
Boles, E., Jong-Gubbels, P. & Pronk, J. T. Identification and characterization of MAE1, the *Saccharomyces cerevisiae* structural gene encoding mitochondrial malic enzyme. J. Bacteriol. 180, 2875-2882 (1998).
Clifton, D., Weinstock, S. B. & Fraenkel, D. G. Glycolysis mutants in *Saccharomyces cerevisiae*. Genetics 88, 1-11 (1978).
Clifton, D. & Fraenkel, D. G. Mutant studies of yeast phosphofructokinase. Biochemistry 21, 1935-1942 (1982).
Cupp, J. R. & McAlister-Henn, L. Cloning and Characterization of the gene encoding the IDH1 subunit of NAD(+)-dependent isocitrate dehydrogenase from *Saccharomyces cerevisiae*. J. Biol. Chem. 267, 16417-16423 (1992).
Flikweert, M. T. et al. Pyruvate decarboxylase: an indispensable enzyme for growth of *Saccharomyces cerevisiae* on glucose. Yeast 12, 247-257 (1996).
Gancedo, C. & Delgado, M. A. Isolation and characterization of a mutant from *Saccharomyces cerevisiae* lacking fructose 1,6-bisphosphatase. Eur. J. Biochem. 139, 651-655 (1984).
Gangloff, S. P., Marguet, D. & Lauquin, G. J. Molecular cloning of the yeast mitochondrial aconitase gene (ACO1) and evidence of a synergistic regulation of expression by glucose plus glutamate. Mol Cell Biol 10, 3551-3561 (1990).
Hartig, A. et al. Differentially regulated malate synthase genes participate in carbon and nitrogen metabolism of *S. cerevisiae*. Nucleic Acids Res. 20, 5677-5686 (1992).
Heinisch, J. J., Muller, S., Schluter, E., Jacoby, J. & Rodicio, R. Investigation of two yeast genes encoding putative isoenzymes of phosphoglycerate mutase. Yeast 14, 203-213 (1998).
Kim, K. S., Rosenkrantz, M. S. & Guarente, L. *Saccharomyces cerevisiae* contains two functional citrate synthase genes. Mol. Cell Biol. 6, 1936-1942 (1986).
Loftus, T. M., Hall, L. V., Anderson, S. L. & McAlister-Henn, L. Isolation, characterization, and disruption of the yeast gene encoding cytosolic NADP-specific isocitrate dehydrogenase. Biochemistry 33, 9661-9667 (1994).
McAlister-Henn, L. & Thompson, L.M. Isolation and expression of the gene encoding yeast mitochondrial malate dehydrogenase. J. Bacteriol. 169, 5157-5166 (1987).
Müller, S. & Entian, K.-D. Yeast sugar metabolism. Zimmermann, F. K. & Entian, K.-D. (eds.), pp. 157-170 (Technomic Publishing CO., INC., Lancaster, 1997).
Ozcan, S., Freidel, K., Leuker, A. & Ciriacy, M. Glucose uptake and catabolite repression in dominant HTR1 mutants of *Saccharomyces cerevisiae*. J. Bacteriol. 175, 5520-5528 (1993).
Przybyla-Zawislak, B., Dennis, R. A., Zakharkin, S. O. & McCammon, M. T. Genes of succinyl-CoA ligase from *Saccharomyces cerevisiae*. Eur. J. Biochem. 258, 736-743 (1998).
Repetto, B. & Tzagoloff, A. In vivo assembly of yeast mitochondrial alphaketoglutarate dehydrogenase complex. Mol. Cell Biol. 11, 3931-3939 (1991).
Schaaff-Gerstenschlager, I. & Zimmermann, F. K. Pentose-phosphate pathway in *Saccharomyces cerevisiae*: analysis of deletion mutants for transketolase, transaldolase, and glucose 6-phosphate dehydrogenase. Curr. Genet. 24, 373-376 (1993).
Schaaff-Gerstenschlager, I. & Miosga, T. Yeast sugar metabolism. Zimmermann, F. K. & Entian, K.-D. (eds.), pp. 271-284 (Technomic Publishing CO., INC., Lancaster, 1997).
Sedivy, J. M. & Fraenkel, D. G. Fructose bisphosphatase of *Saccharomyces cerevisiae*. Cloning, disruption and regulation of the FBP1 structural gene. J. Mol. Biol. 186, 307-319 (1985).
Smith, V., Chou, K. N., Lashkari, D., Botstein, D. & Brown, P. O. Functional analysis of the genes of yeast chromosome V by genetic footprinting. Science 274, 2069-2074 (1996).
Swartz, J. A PURE approach to constructive biology. Nat. Biotechnol. 19, 732-733 (2001).
Wills, C. & Melham, T. Pyruvate carboxylase deficiency in yeast: a mutant affecting the interaction between the glyoxylate and Krebs cycles. Arch. Biochem. Biophys. 236, 782-791 (1985).

Throughout this application various publications have been referenced. The disclosures of these publications in their entireties are hereby incorporated by reference in this application in order to more fully describe the state of the art to which this invention pertains.

Although the invention has been described with reference to the examples provided above, it should be understood that various modifications can be made without departing from the spirit of the invention. Accordingly, the invention is only limited by the claims.

What is claimed is:

1. A computer readable storage medium or media, comprising:
    (a) a data structure contained on a computer readable storage medium or media that is read by a computer, said data structure comprising a stoichiometric matrix relating a plurality of *Saccharomyces cerevisiae* reactants to a plurality of *Saccharomyces cerevisiae* reactions, wherein each of said *Saccharomyces cerevisiae* reactions comprises a reactant identified as a substrate of the reaction, a reactant identified as a product of the reaction and a stoichiometric coefficient relating said substrate and said product, wherein at least one of said *Saccharomyces cerevisiae* reactions is annotated to indicate an associated gene, and wherein a plurality of chemically and electrochemically balanced reactions are assigned to a plurality of different membranous compartments;
    (b) a gene database comprising information characterizing said associated gene;
    (c) a constraint set for said plurality of *Saccharomyces cerevisiae* reactions;
    (d) a program contained on said computer readable storage medium or media comprising executable commands using said data structure for determining at least one flux distribution for said plurality of chemically and electrochemically balanced reactions across said plurality of different membranous compartments that minimizes or maximizes an objective function when said constraint set is applied to said data structure, wherein said at least one flux distribution is predictive of a *Saccharomyces cerevisiae* physiological function, and
    (e) said program contained on said computer readable storage medium or media comprising executable commands for visually displaying said at least one resulting flux distribution to a user.

2. The computer readable storage medium or media of claim 1, wherein said plurality of reactions comprises at least one reaction from a peripheral metabolic pathway.

3. The computer readable storage medium or media of claim 2, wherein said peripheral metabolic pathway is selected from the group consisting of amino acid biosynthesis, amino acid degradation, purine biosynthesis, pyrimidine biosynthesis, lipid biosynthesis, fatty acid metabolism, cofactor biosynthesis, cell wall metabolism and transport processes.

4. The computer readable storage medium or media of claim 1, wherein said *Saccharomyces cerevisiae* physiological function is selected from the group consisting of growth, energy production, redox equivalent production, biomass production, production of biomass precursors, production of a protein, production of an amino acid, production of a purine, production of a pyrimidine, production of a lipid, production of a fatty acid, production of a cofactor, production of a cell wall component, transport of a metabolite, and consumption of carbon, nitrogen, sulfur, phosphate, hydrogen or oxygen.

5. The computer readable medium or media of claim 1, wherein said *Saccharomyces cerevisiae* physiological function is selected from the group consisting of degradation of a protein, degradation of an amino acid, degradation of a purine, degradation of a pyrimidine, degradation of a lipid, degradation of a fatty acid, degradation of a cofactor and degradation of a cell wall component.

6. The computer readable medium or media of claim 1, wherein said data structure comprises a set of linear algebraic equations.

7. The computer readable storage medium or media of claim 1, wherein said commands comprise an optimization problem.

8. The computer readable medium or media of claim 1, wherein said commands comprise a linear program.

9. The computer readable storage medium or media of claim, wherein a first substrate or product in said plurality of *Saccharomyces cerevisiae* reactions is assigned to a first compartment and a second substrate or product in said plurality of *Saccharomyces cerevisiae* reactions is assigned to a second compartment.

10. The computer readable storage medium or media of claim 1, wherein a plurality of said *Saccharomyces cerevisiae* reactions is annotated to indicate a plurality of associated genes and wherein said gene database comprises information characterizing said plurality of associated genes.

11. A computer readable medium or media, comprising:
    (a) a data structure relating a plurality of *Saccharomyces cerevisiae* reactants to a plurality of *Saccharomyces cerevisiae* reactions, wherein each of said *Saccharomyces cerevisiae* reactions comprises a reactant identified as a substrate of the reaction, a reactant identified as a product of the reaction and a stoichiometric coefficient relating said substrate and said product;
    (b) a constraint set for said plurality of *Saccharomyces cerevisiae* reactions, and
    (c) commands for determining at least one flux distribution that minimizes or maximizes an objective function when said constraint set is applied to said data representation, wherein said at least one flux distribution is predictive of *Saccharomyces cerevisiae* growth.

12. A method for predicting a *Saccharomyces cerevisiae* physiological function, comprising:
    (a) storing in a computer a data structure relating a plurality of *Saccharomyces cerevisiae* reactants to a plurality of reactions, wherein each of said *Saccharomyces cerevisiae* reactions comprises a reactant identified as a substrate of the reaction, a reactant identified as a product of the reaction and a stoichiometric coefficient relating said substrate and said product, wherein at least one of said *Saccharomyces cerevisiae* reactions is annotated to indicate an associated gene, and wherein a plurality of chemically and electrochemically balanced reactions are assigned to a plurality of different membranous compartments;
    (b) providing a constraint set for said plurality of *Saccharomyces cerevisiae* reactions;
    (c) providing an objective function;
    (d) executing commands in a suitably programmed computer using said stored data structure for determining at least one flux distribution for said plurality of chemically and electrochemically balanced reactions across said plurality of different membranous compartments that minimizes or maximizes said objective function when said constraint set is applied to said data structure, wherein said at least one flux distribution is predictive of a *Saccharomyces cerevisiae* physiological function related to said gene, and
    (e) visually displaying said at least one resulting flux distribution to a user.

13. The method of claim 12, wherein said plurality of *Saccharomyces cerevisiae* reactions comprises at least one reaction from a peripheral metabolic pathway.

14. The method of claim 12, wherein said peripheral metabolic pathway is selected from the group consisting of amino acid biosynthesis, amino acid degradation, purine biosynthesis, pyrimidine biosynthesis, lipid biosynthesis, fatty acid metabolism, cofactor biosynthesis, cell wall metabolism and transport processes.

15. The method of claim 12, wherein said *Saccharomyces cerevisiae* physiological function is selected from the group consisting of growth, energy production, redox equivalent production, biomass production, production of biomass precursors, production of a protein, production of an amino acid, production of a purine, production of a pyrimidine, production of a lipid, production of a fatty acid, production of a cofactor, production of a cell wall component, transport of a metabolite, and consumption of carbon, nitrogen, sulfur, phosphate, hydrogen or oxygen.

16. The method of claim 12, wherein said *Saccharomyces cerevisiae* physiological function is selected from the group consisting of glycolysis, the TCA cycle, pentose phosphate pathway, respiration, biosynthesis of an amino acid, degradation of an amino acid, biosynthesis of a purine, biosynthesis of a pyrimidine, biosynthesis of a lipid, metabolism of a fatty acid, biosynthesis of a cofactor, metabolism of a cell wall component, transport of a metabolite and metabolism of a carbon source, nitrogen source, oxygen source, phosphate source, hydrogen source or sulfur source.

17. The method of claim 12, wherein said data structure comprises a set of linear algebraic equations.

18. The method of claim 12, wherein said data structure comprises a matrix.

19. The method of claim 12, wherein said flux distribution is determined by linear programming.

20. The method of claim 12, further comprising:
(f) providing a modified data structure, wherein said modified data structure comprises at least one added reaction, compared to the data structure of part (a), and
(f) determining at least one flux distribution that minimizes or maximizes said objective function when said constraint set is applied to said modified data structure, thereby predicting a *Saccharomyces cerevisiae* physiological function.

21. The method of claim 20, further comprising identifying at least one participant in said at least one added reaction.

22. The method of claim 21, wherein said identifying at least one participant comprises associating a *Saccharomyces cerevisiae* protein with said at least one reaction.

23. The method of claim 22, further comprising identifying at least one gene that encodes said protein.

24. The method of claim 21, further comprising identifying at least one compound that alters the activity or amount of said at least one participant, thereby identifying a candidate drug or agent that alters a *Saccharomyces cerevisiae* physiological function.

25. The method of claim 12, further comprising:
(f) providing a modified data structure, wherein said modified data structure lacks at least one reaction compared to the data structure of part (a), and
(g) determining at least one flux distribution that minimizes or maximizes said objective function when said constraint set is applied to said modified data structure, thereby predicting a *Saccharomyces cerevisiae* physiological function.

26. The method of claim 25, further comprising identifying at least one participant in said at least one reaction.

27. The method of claim 26, wherein said identifying at least one participant comprises associating a *Saccharomyces cerevisiae* protein with said at least one reaction.

28. The method of claim 27, further comprising identifying at least one gene that encodes said protein that performs said at least one reaction.

29. The method of claim 26, further comprising identifying at least one compound that alters the activity or amount of said at least one participant, thereby identifying a candidate drug or agent that alters a *Saccharomyces cerevisiae* physiological function.

30. The method of claim 12, further comprising:
(f) providing a modified constraint set, wherein said modified constraint set comprises a changed constraint for at least one reaction compared to the constraint for said at least one reaction in the data structure of part (a), and
(g) determining at least one flux distribution that minimizes or maximizes said objective function when said modified constraint set is applied to said data structure, thereby predicting a *Saccharomyces cerevisiae* physiological function.

31. The method of claim 30, further comprising identifying at least one participant in said at least one reaction.

32. The method of claim 31, wherein said identifying at least one participant comprises associating a *Saccharomyces cerevisiae* protein with said at least one reaction.

33. The method of claim 32, further comprising identifying at least one gene that encodes said protein.

34. The method of claim 31, further comprising identifying at least one compound that alters the activity or amount of said at least one participant, thereby identifying a candidate drug or agent that alters a *Saccharomyces cerevisiae* physiological function.

35. The method of claim 12, further comprising providing a gene database relating one or more reactions in said data structure with one or more genes or proteins in *Saccharomyces cerevisiae*.

36. A method for predicting *Saccharomyces cerevisiae* growth, comprising:
(a) storing in a computer a data structure relating a plurality of *Saccharomyces cerevisiae* reactants to a plurality of *Saccharomyces cerevisiae* reactions, wherein each of said *Saccharomyces cerevisiae* reactions comprises a reactant identified as a substrate of the reaction, a reactant identified as a product of the reaction and a stoichiometric coefficient relating said substrate and said product;
(b) providing a constraint set for said plurality of *Saccharomyces cerevisiae* reactions;
(c) providing an objective function, and
(d) executing commands in a suitably programmed computer using said stored data structure to determine at least one flux distribution that minimizes or maximizes said objective function when said constraint set is applied to said data structure, thereby predicting *Saccharomyces cerevisiae* growth.

\* \* \* \* \*